(12) United States Patent
Naghavi et al.

(10) Patent No.: US 8,551,008 B2
(45) Date of Patent: Oct. 8, 2013

(54) METHOD AND APPARATUS FOR DETERMINING VASCULAR HEALTH CONDITIONS

(76) Inventors: Morteza Naghavi, Houston, TX (US); Nachiket Kharalkar, Austin, TX (US); Timothy J. O'Brien, Anoka, MN (US)

( * ) Notice: Subject to any disclaimer, the term of this patent is extended or adjusted under 35 U.S.C. 154(b) by 504 days.

(21) Appl. No.: 11/871,901

(22) Filed: Oct. 12, 2007

(65) Prior Publication Data

US 2008/0255471 A1 Oct. 16, 2008

Related U.S. Application Data

(63) Continuation of application No. 11/563,676, filed on Nov. 27, 2006, now abandoned, which is a continuation-in-part of application No. PCT/US2005/018437, filed on May 25, 2005, application No. 11/871,901, which is a continuation-in-part of application No. 10/525,255, filed as application No. PCT/US03/26238 on Aug. 22, 2003, now abandoned.

(60) Provisional application No. 60/585,773, filed on Jul. 6, 2004, provisional application No. 60/574,255, filed on May 26, 2004, provisional application No. 60/626,006, filed on Nov. 8, 2004, provisional application No. 60/628,173, filed on Nov. 15, 2004, provisional application No. 60/405,352, filed on Aug. 23, 2002.

(51) Int. Cl.
*A61B 5/02* (2006.01)

(52) U.S. Cl.
USPC .......................... 600/504; 600/481; 600/549

(58) Field of Classification Search
USPC ................. 600/474, 479–481, 485, 490–492, 600/504, 549, 555, 561
See application file for complete search history.

(56) References Cited

U.S. PATENT DOCUMENTS

| | | |
|---|---|---|
| 3,463,854 A | 8/1969 | Kopjas |
| RE30,317 E | 7/1980 | Lübbers et al. |
| 4,321,929 A * | 3/1982 | Lemelson et al. ............ 600/301 |
| 4,332,566 A | 6/1982 | Mazeski et al. |
| 4,379,461 A | 4/1983 | Nilsson et al. |
| 4,428,382 A | 1/1984 | Walsall et al. |

(Continued)

FOREIGN PATENT DOCUMENTS

| | | |
|---|---|---|
| WO | 00/74551 A2 | 12/2000 |
| WO | 02/34105 A2 | 5/2002 |

(Continued)

OTHER PUBLICATIONS

Aboyans, et al., "[Abstract] [*Ankle-Brachial Index: A Marker of Atherosclerosis and Cardiovascular Prognosis*]," Arch Mal Coeur Vaiss, Feb. 2004, 139-46, vol. 97 (2).

(Continued)

*Primary Examiner* — Rene Towa
(74) *Attorney, Agent, or Firm* — David McEwing

(57) ABSTRACT

The present invention relates to assessing and measuring vascular and endothelial function. A vasostimulant is provided to a patient to stimulate hemodynamic activity in a selected extremity and vascular function is assessed by monitoring a change in a blood flow, skin temperature and/or blood oxygen content at the selected extremity and assessing the patient's vascular function based upon the monitoring.

16 Claims, 37 Drawing Sheets

(56) References Cited

U.S. PATENT DOCUMENTS

| | | | |
|---|---|---|---|
| 4,450,843 A | 5/1984 | Barney et al. | |
| 4,494,550 A * | 1/1985 | Blazek et al. | 600/473 |
| 4,569,355 A | 2/1986 | Bitterly | |
| 4,883,063 A | 11/1989 | Bernard et al. | |
| 5,050,612 A | 9/1991 | Matsumura | |
| 5,064,410 A | 11/1991 | Frenkel et al. | |
| 5,553,610 A | 9/1996 | Lodder | |
| 5,634,468 A | 6/1997 | Platt et al. | |
| 5,694,939 A | 12/1997 | Cowings | |
| 5,755,229 A | 5/1998 | Amano et al. | |
| 5,769,784 A | 6/1998 | Barnett et al. | |
| 5,771,261 A | 6/1998 | Anbar | |
| 5,964,701 A | 10/1999 | Asada et al. | |
| 5,973,011 A | 10/1999 | Noack et al. | |
| 5,991,654 A * | 11/1999 | Tumey et al. | 600/479 |
| 6,077,228 A | 6/2000 | Schonberger | |
| 6,090,050 A | 7/2000 | Constantinides | |
| 6,102,846 A | 8/2000 | Patton et al. | |
| 6,117,075 A * | 9/2000 | Barnea | 600/300 |
| 6,152,881 A | 11/2000 | Raines et al. | |
| 6,221,025 B1 | 4/2001 | Skoletsky | |
| 6,240,306 B1 | 5/2001 | Rohrscheib et al. | |
| 6,248,066 B1 * | 6/2001 | Barnett et al. | 600/363 |
| 6,293,915 B1 | 9/2001 | Amano et al. | |
| 6,322,515 B1 | 11/2001 | Goor et al. | |
| 6,332,867 B1 | 12/2001 | Chen et al. | |
| 6,338,719 B1 | 1/2002 | Drzewiecki et al. | |
| 6,374,129 B1 | 4/2002 | Chin et al. | |
| 6,402,690 B1 | 6/2002 | Rhee et al. | |
| 6,403,643 B1 | 6/2002 | Esteve-Soler | |
| 6,413,223 B1 | 7/2002 | Yang et al. | |
| 6,445,945 B1 | 9/2002 | Arsenault | |
| 6,447,460 B1 * | 9/2002 | Zheng et al. | 600/549 |
| 6,488,623 B1 | 12/2002 | Ozarowski et al. | |
| 6,488,633 B1 | 12/2002 | Schnall | |
| 6,520,921 B1 | 2/2003 | Patton et al. | |
| 6,540,687 B2 | 4/2003 | Chio | |
| 6,547,745 B1 | 4/2003 | Rubinstein | |
| 6,596,708 B1 | 7/2003 | Petrus | |
| 6,614,521 B2 | 9/2003 | Samsoondar et al. | |
| 6,654,628 B1 | 11/2003 | Silber et al. | |
| 6,656,116 B2 | 12/2003 | Kim et al. | |
| 6,662,033 B2 | 12/2003 | Casciani et al. | |
| 6,676,608 B1 | 1/2004 | Keren | |
| 6,730,035 B2 | 5/2004 | Stein | |
| 6,743,182 B2 | 6/2004 | Miller et al. | |
| 6,846,106 B1 | 1/2005 | Chen et al. | |
| 6,847,913 B2 | 1/2005 | Wigley et al. | |
| 6,904,408 B1 | 6/2005 | McCarthy et al. | |
| 6,908,436 B2 | 6/2005 | Chowienczyk et al. | |
| 6,916,289 B2 | 7/2005 | Schnall | |
| 6,921,367 B2 | 7/2005 | Mills | |
| 6,939,304 B2 | 9/2005 | Schnall et al. | |
| 7,024,234 B2 | 4/2006 | Margulies et al. | |
| 7,029,628 B2 | 4/2006 | Tam et al. | |
| 7,090,648 B2 | 8/2006 | Sackner et al. | |
| 2002/0072681 A1 | 6/2002 | Schnali | |
| 2002/0082489 A1 | 6/2002 | Casciani et al. | |
| 2002/0173731 A1 | 11/2002 | Martin et al. | |
| 2003/0004423 A1 | 1/2003 | Lavie et al. | |
| 2003/0049250 A1 | 3/2003 | Karvonen et al. | |
| 2003/0191395 A1 * | 10/2003 | Bowman et al. | 600/474 |
| 2003/0215430 A1 | 11/2003 | Petrus | |
| 2003/0219719 A1 | 11/2003 | Bowman et al. | |
| 2003/0229288 A1 * | 12/2003 | Chowienczyk et al. | 600/500 |
| 2003/0233048 A1 | 12/2003 | Silverman et al. | |
| 2004/0019269 A1 | 1/2004 | Schaefer et al. | |
| 2004/0022778 A1 | 2/2004 | Watts et al. | |
| 2004/0059234 A1 | 3/2004 | Martin et al. | |
| 2004/0116377 A1 | 6/2004 | Daniels | |
| 2005/0177047 A1 | 8/2005 | Harpas et al. | |
| 2005/0228303 A1 | 10/2005 | Hayano et al. | |
| 2005/0283086 A1 | 12/2005 | Satoh et al. | |
| 2006/0015032 A1 | 1/2006 | Gordon | |
| 2006/0057072 A1 | 3/2006 | Finkel et al. | |
| 2006/0165596 A1 | 7/2006 | Kharalkar et al. | |
| 2007/0173727 A1 | 7/2007 | Naghavi et al. | |
| 2007/0225606 A1 | 9/2007 | Naghavi et al. | |
| 2007/0225614 A1 | 9/2007 | Naghavi et al. | |
| 2008/0081963 A1 | 4/2008 | Naghavi et al. | |

FOREIGN PATENT DOCUMENTS

| | | |
|---|---|---|
| WO | 02/080752 A2 | 10/2002 |
| WO | 2004/006748 A2 | 1/2004 |
| WO | 2004/017905 A2 | 3/2004 |
| WO | 2004/041079 A1 | 5/2004 |
| WO | 2004/075928 A2 | 9/2004 |
| WO | 2005/069740 A2 | 8/2005 |
| WO | 2005/079189 A2 | 9/2005 |
| WO | 2005/099572 A1 | 10/2005 |
| WO | 2005/118516 A2 | 12/2005 |

OTHER PUBLICATIONS

Akosah, et al., "Preventing Myocardial Infarction in the Young Adult in the First Place: How Do the National Cholesterol Education Panel Iii Guidelines Perform?," J Am Coll Cardiol, May 7, 2003, 1475-9, vol. 41 (9).

Allen, et al, "Vasomotor Innervation Fields of Peripheral Nerves Supplying the Hand: Differences Between Neurovascular and Somatosensory Patterns." Journal of Neurologic Physical Therapy, Jun. 2004, vol. 28(2) 58-62.

Anderson, et al, "Digital iontophoresis of vasoactive substances as measured by laser Doppler imaging—a non-invasive technique by which to measure microvascular dysfunction in Raynaud's phenomenon." Rheumatology vol. 43, No. 8, Jun. 2004, 986-991.

Anderson, "Prognostic Significance of Brachial Flow-Mediated Vasodilation," Circulation, May 8, 2007, 2373-5, vol. 115 (18).

Asahara, et al. (1997). "Isolation of putative progenitor endothelial cells for angiogenesis." Science 275, 964-7.

Bastuji-Garin, et al., "The Framingham Prediction Rule Is Not Valid in a European Population of Treated Hypertensive Patients," J Hypertens, (2002) 1973-80, vol. 20 (10).

Behrendt, et al., "Endothelial Function. From Vascular Biology to Clinical Applications," Am J Cardiol, (2002) 40L-48L, vol. 90 (10C).

Benzaquen, et al., "High Sensitivity C-Reactive Protein: An Emerging Role in Cardiovascular Risk Assessment," Crit Rev Clin Lab Sci, (2002) 459-97, vol. 39 (4-5).

Berry, et al., "Framingham Risk Score and Prediction of Coronary Heart Disease Death in Young Men," Am Heart J, Jul. 2007, 80-6, vol. 154 (1).

Berry, et al., "Occlusion Cuff Position Is an Important Determinant of the Time Course and Magnitude-of Human Brachial Artery Flow-Mediated Dilation," Clin Sci (Lond), Oct. 2000, 261-7, vol. 99 (4).

Bonetti, et al., "Noninvasive Identification of Patients with Early Coronary Atherosclerosis by Assessment of Digital Reactive Hyperemia," J Am Coll Cardiol, Dec. 7, 2004, 2137-41, vol. 44 (11).

Bots, et al., "Assessment of Flow-Mediated Vasodilatation (Fmd) of the Brachial Artery: Effects of Technical Aspects of the Fmd Measurement on the Fmd Response," Eur Heart J, Feb. 2005, 363-8, vol. 26 (4) (pub. ahead of print doi:10.1093/eurheasrt/ehi017).

Brevetti, et al., "Endothelial Dysfunction and Cardiovascular Risk Prediction in Peripheral Arterial Disease: Additive Value of Flow-Mediated Dilation to Ankle-Brachial Pressure Index," Circulation, Oct. 28, 2003, 2093-8 Epub 03 Oct. 6, vol. 108 (17).

Brindle, et al., "Predictive Accuracy of the Framingham Coronary Risk Score in British Men: Prospective Cohort Study," Bmj, Nov. 29, 2003, 1267, vol. 327 (7426) (epub p. 1-6).

Buchele, et al., "How Microcirculation Data Have Changed My Clinical Practice," Curr Opin Crit Care, Jun. 2007, 324-31, vol. 13 (3).

Bugiardini, et al., "Endothelial Function Predicts Future Development of Coronary Artery Disease: A Study of Women with Chest Pain and Normal Coronary Angiograms," Circulation, Jun. 1, 2004, 2518-23, vol. 109 (21).

Caballero, et al, "Microvascular and Macrovascular Reactivity Is Reduced in Subjects at Risk for Type 2 Diabetes." Diabetes, vol. 48, Sep. 1999, 1856-1862.

Carney, et al., "*Change in Heart Rate and Heart Rate Variability During Treatment for Depression in Patients with Coronary Heart Disease*," Psychosom Med, Sep. 1, 2000, 2000, 639-47, vol. 62 (5).

Carreiro-Lewandowski, "*Update on Selected Markers Used in Risk Assessment for Vascular Disease*," Clin Lab Sci, Winter, 2004, 43-9, vol. 17 (1).

Charbonneau, "[Abstract] *Use of Measures of Endothelial Function to Stratify Risk*," Can J Cardiol, May 2001, 18A-21A, vol. 17 (Suppl A).

Chenzbraun, et al., "*The Peripheral Vascular Response to Exercise Is Impaired in Patients with Risk Factors for Coronary Artery Disease*" Cardiology, 2001, 126-30, vol. 95 (3).

Cohn, et al., "*Surrogate Markers for Cardiovascular Disease: Functional Markers*," Circulation, Jun. 29, 2004, IV31-46, vol. 109 (25 Suppl 1).

Cracowski, et al., "*Methodological Issues in the Assessment of Skin Microvascular Endothelial Function in Humans*," Trends Pharmacol Sci, Sep. 2006, 503-8, vol. 27 (9).

Danesh, et al., "*C-Reactive Protein and Other Circulating Markers of Inflammation in the Prediction of Coronary Heart Disease*," N Engl J Med, Apr. 1, 2004, 1387-97, vol. 350 (14).

Deanfield, et al., "*Endothelial Function and Dysfunction: Testing and Clinical Relevance*," Circulation, Mar. 13, 2007, 1285-95, vol. 115 (10).

Diehm, et al., "[*Importance of the Ankle-Brachial Index (Abi) in the Prevention of Cardiovascular Diseases. Ten Questions and Answers*]," Herz, Aug. 2007, 404-9, vol. 32 (5).

Djuric, et al., "[Abstract]*Age-Related Progressive Brachial Artery Endothelial Dysfunction Precedes the Changed Carotid and Left Ventricular Geometry in Healthy Humans*," Angiology, Jul. 1999, 555-61, vol. 50 (7).

Donald, et al., "*Non-Invasive Assessment of Endothelial Function: Which Technique?*," J Am Coll Cardiol, Nov. 7, 2006, 1846-50, vol. 48 (9).

Dupuis, et al, "*Quantitative Hyperemic Reactivity in Opposed Limbs During Myocardial Perfusion Imaging.*" J. Am. Coll. Cardiol., vol. 44, No. 7, 2004.

Empana, et al., "*Are the Framingham and Procam Coronary Heart Disease Risk Functions Applicable to Different European Populations? The Prime Study*," Eur Heart J, Nov. 2003, 1903-11, vol. 24 (21).

ENDO-PATH 2000 [Brochure], *Non-invasive Endothelia Dysfunction Research Package*. Itamar Medical Ltd. Aug. 2004.

Farkas, et al., "*Non-Invasive Assessment of Microvascular Endothelial Function by Laser Doppler Flowmetry in Patients with Essential Hypertension*," Atherosclerosis, Mar. 2004, 97-102, vol. 173 (1).

Fazel, et al, "*A Novel Technique to Assess Flow-Mediate Vasodilation.*" [Editorial Comment] Am. Coll. Cardiol., vol. 44, No. 7, 2004, 1478-1480.

Feldt-Rasmussen, "*Microalbuminuria, Endothelial Dysfunction and Cardiovascular Risk*," Diabetes Metab, Jul. 2000, 64-6, vol. 26 (Suppl 4).

Fichtlscherer, et al., "*Elevated C-Reactive Protein Levels and Impaired Endothelial Vasoreactivity in Patients with Coronary Artery Disease*," Circulation, Aug. 29, 2000, 1000-6, vol. 102 (9).

Fichtlscherer, et al., "*Endothelial Dysfunction in Acute Coronary Syndromes: Association with Elevated C-Reactive Protein Levels*," Ann Med, Nov. 2000, 515-8, vol. 32 (8).

Fichtlscherer, et al., "*Prognostic Value of Systemic Endothelial Dysfunction in Patients with Acute Coronary Syndromes: Further Evidence for the Existence of the "Vulnerable" Patient*," Circulation, Oct. 5, 2004, 1926-32, vol. 110 (14).

Folsom, et al., "*An Assessment of Incremental Coronary Risk Prediction Using C-Reactive Protein and Other Novel Risk Markers: The Atherosclerosis Risk in Communities Study*," Arch Intern Med, Jul. 10, 2006, 1368-73, vol. 166 (13).

Ganz, et al., "*Testing Endothelial Vasomotor Function: Nitric Oxide, a Multipotent Molecule*," Circulation, Oct. 28, 2003, 2049-53, vol. 108 (17).

Gazelius, "*Iontophoresis-theory.*" Perimed Jan. 12, 1999.

Gibbons, et al, "*The Emerging Concept of Vascular Remodeling.*" The New England Journal of Medicine [Review Article] vol. 330:1431-1438, No. 20, May 19, 1994.

Gokce, et al, "*Predictive Value of Noninvasively Determine Endothelia Dysfunction for Long-Term Cardiovascular Events in Patients with Peripheral Vascular Disease.*" J. Am. Coll. of Cardiol., vol. 41, No. 10, 2003.

Gonzalez, et al., "*Endothelial Function, Inflammation, and Prognosis in Cardiovascular Disease*," Am J Med, Dec. 8, 2003, 99S-106S, vol. 115 (Suppl 8A).

Grover, et al. (2007). "*Patient Knowledge of Coronary Risk Profile Improves the Effectiveness of Dyslipidemia Therapy: The CHECK-UP Study: A Randomized Controlled Trial*" Arch Intern Med 167(21): 2296-2303.

Grundy, (2001). "*Coronary plaque as a replacement for age as a risk factor in global risk assessment.*" Am J Cardiol 88(2A): 8E-11E.

Guerci, et al., "*Endothelial Dysfunction and Type 2 Diabetes. Part 2: Altered Endothelial Function and the Effects of Treatments in Type 2 Diabetes Mellitus*," Diabetes Metab, Sep. 2001, 436-47, vol. 27 (4 Pt 1).

Halcox, et al, "*Child origins of endothelial dysfunction.*" [Mini-Symposium] Heart 2005; 91:1272-1274.

Hamburg, et al, "*Cross-Sectional Relations of Digital Vascular Function to Cardiovascular Risk Factors in the Framingham Heart Study.*" Circulation. 2008; 117-2467-2474.

Hänsel, et al, "*Endothelial dysfunction in young patients with long-term rheumatoid arthritis and low disease activity.*" Atherosclerosis 170 (2003) 177-180.

Hashimoto, et al., "*Correlation between Flow-Mediated Vasodilation of the Brachial Artery and Intima-Media Thickness in the Carotid Artery in Men*," Arterioscler Thromb Vasc Biol, Nov. 1999, 2795-800, vol. 19 (11).

Hashimoto, et al., "*New Methods to Evaluate Endothelial Function: Non-Invasive Method of Evaluating Endothelial Function in Humans*," J Pharmacol Sci, Dec. 2003, 405-8, vol. 93 (4).

Heiss, et al, "*Impaired Progenitor Cell Activity in Age-Related Endothelial Dysfunction.*" J. Am. Coll. Cardiol. vol. 45, No. 9, (2005) 1441-1448.

Heitzer, et al., "*Endothelial Dysfunction, Oxidative Stress, and Risk of Cardiovascular Events in Patients with Coronary Artery Disease*," Circulation, Nov. 27, 2001, 2673-8, vol. 104 (22).

Higashi, et al., "*New Methods to Evaluate Endothelial Function: Method for Assessing Endothelial Function in Humans Using a Strain-Gauge Plethysmography: Nitric Oxide-Dependent and -Independent Vasodilation*," J Pharmacol Sci, Dec. 2003, 399-404, vol. 93 (4).

Hsueh, et al., "*Role of Endothelial Dysfunction in Insulin Resistance*," Am J Cardiol, Aug. 18, 2003, 10J-17J, vol. 92 (4A).

Huang, et al., "*Predictive Value of Reactive Hyperemia for Cardiovascular Events in Patients with Peripheral Arterial Disease Undergoing Vascular Surgery*," Arterioscler Thromb Vasc Biol, Oct. 2007, 2113-9, vol. 27 (10).

IMDP, Inc., "*Cardio Vision, MS-2000 Framingham Risk Analysis.*" IMDP, Inc.

Ip, et al., "*Endothelial Function in Obstructive Sleep Apnea and Response to Treatment*," Am J Respir Crit Care Med, Feb. 1, 2004, 348-53, vol. 169 (3).

Ishibashi, et al., "*Short Duration of Reactive Hyperemia in the Forearm of Subjects with Multiple Cardiovascular Risk Factors*," Circ J, Jan. 2006, 115-23, vol. 70 (1).

Jadhav, et al., "*Noninvasive Assessment of Endothelial Dysfunction by Brachial Artery Flow-Mediated Dilatation in Prediction of Coronary Artery Disease in Indian Subjects*," Indian Heart J, Jan.-Feb. 2003, 44-8, vol. 55 (1).

Juonala, et al., "*Young Adults with Family History of Coronary Heart Disease Have Increased Arterial Vulnerability to Metabolic Risk Factors: The Cardiovascular Risk in Young Finns Study*," Arterioscler Thromb Vasc Biol, Jun. 2006, 1376-82, vol. 26 (6).

Kimura, et al., "[Abstract] *Impaired Endothelial Function in Hypertensive Elderly Patients Evaluated by High Resolution Ultrasonography*," Can J Cardiol, May 1999, 563-8, vol. 15 (5).

Kuvin, et al., (2003). "*Clinical utility of endothelial function testing: ready for prime time?*" Circulation 107(25): 3243-7.

Lengele, et al., "*Cardiovascular Risk Assessment in Hypertensive Patients: Major Discrepancy According to Esh and Score Strategies*," J Hypertens, Apr. 2007, 757-62, vol. 25 (4).

Lerman, "*Non-invasive Diagnosis of Endothelial Dysfunction: Practicality and Clinical Implications*." [Presentation] Mayo Clinic, Rochester, MN.

Linke, et al, "*Flow-mediated vasodilation partially reflects nitric oxide-mediated endothelial function*." [Point:Counterpoint Comments] J Appl Physiol 99: 1622, 2005.

Liu, et al., "*Predictive Value for the Chinese Population of the Framingham Chd Risk Assessment Tool Compared with the Chinese Multi-Provincial Cohort Study*," JAMA, Jun. 2, 2004, 2591-9, vol. 291 (21).

London, et al., "*Forearm Reactive Hyperemia and Mortality in End-Stage Renal Disease*," Kidney Int, Feb. 2004, 700-4, vol. 65 (2).

Lupattelli, et al., "*Mechanisms of High-Density Lipoprotein Cholesterol Effects on the Endothelial Function in Hyperlipemia*," Metabolism, Sep. 2003, 1191-5, vol. 52 (9).

Maltz, et al, "*Instrument for the non-invasive evaluation of human arterial endothelial function via measurement of changes in the transit time of an artificial pulse*." Department of Nuclear Medicine and Functional Imaging, Berkeley Lab, University of California, Berkeley 2004.

McGinnis, et al., "*Biofeedback-Assisted Relaxation in Type 2 Diabetes*," Diabetes Care, Sep. 1, 2005, 2145-49, vol. 28 (9).

Medow, et al, "*Decreased Microvascular Nitric Oxide-Dependent Vasodilation in Postural Tachycardia Syndrome*." Circulation 2005; 112:2611-2618.

Meco, et al., "*Improvement in Endothelial Dysfunction in Patients with Hypoalphalipoproteinemia and Coronary Artery Disease Treated with Bezafibrate*," J Cardiovasc Pharmacol, Aug. 2001, 250-8, vol. 38 (2).

Meigs, et al, "*Biomarkers of Endothelial Dysfunction and Risk of Type 2 Diabetes Mellitus*." JAMA, Apr. 28, 2004—vol. 291, No. 16:1978-1986.

MIC2, *Transdermal Drug Delivery by Iontophoresis*. [Brochure] Moor Instruments.

Micro Medical, "*Pulse Trace 1000*." [Brochure].

Milkiewicz, M., E. Ispanovic, et al. (2006). "*Regulators of angiogenesis and strategies for their therapeutic manipulation*." Int J Biochem Cell Biol 38(3): 333-57.

Mitani, Y., et al., "*Evaluation of Psychophysiological Asymmetry in Patients with Fibromyalgia Syndrome*," Appl Psychophysiol Biofeedback, Sep. 2006, 217-25, vol. 31 (3).

Mitchell, et al, "*Local Shear Stress and Brachial Artery Flow-Mediated Dilation. The Framingham Heart Study*." Hypertension 2004; 44:134-139.

Moor Instruments, *Tissue Blood-Flow and Pressure Monitoring with DRT4-PRM2*. [Brochure].

Naghavi, et al. (2003). "*From vulnerable plaque to vulnerable patient: a call for new definitions and risk assessment strategies: Part I*." Circulation 108(14): 1664-72.

Naghavi, et al. (2003). "*From vulnerable plaque to vulnerable patient: a call for new definitions and risk assessment strategies: Part II*." Circulation 108(15): 1772-8.

Naghavi, et al., "*From Vulnerable Plaque to Vulnerable Patient—Part Iii: Executive Summary of the Screening for Heart Attack Prevention and Education (Shape) Task Force Report*," Am J Cardiol, Jul. 17, 2006, 2H-15H, vol. 98 (2A).

Nagoshi, et al., "*Effects of C-Reactive Protein on Atherogenic Mediators and Adrenomedullin in Human Coronary Artery Endothelial and Smooth Muscle Cells*," Biochem Biophys Res Commun, Feb. 20, 2004, 1057-63, vol. 314 (4).

Naka, et al, "*Flow-mediated changes in pulse wave velocity: a new clinical measure of endothelial function*." European Heart Journal, Nov. 2, 2005 epub doi:10.1093/eurheartj/ehi619).

Nakano, et al., "*[Abstract] Measurement of Ankle Brachial Index for Assessment of Atherosclerosis in Patients with Stroke*," Cerebrovasc Dis, 2004, 212-7 Epub Dec. 29, 2003 vol. 17 (2-3).

Nasir, et al., "*Detection of High-Risk Young Adults and Women by Coronary Calcium and National Cholesterol Education Program Panel III Guidelines*," J. Am. Coll. Cardiol., Nov. 15, 2005, 1931-6, vol. 46 (10).

Neuhauser, et al., "*A Comparison of Framingham and Score-Based Cardiovascular Risk Estimates in Participants of the German National Health Interview and Examination Survey 1998*," Eur J Cardiovasc Prev Rehabil, Oct. 2005, 442-50, vol. 12 (5).

Nitenberg, et al., "*Epicardial Coronary Artery Constriction to Cold Pressor Test Is Predictive of Cardiovascular Events in Hypertensive Patients with Angiographically Normal Coronary Arteries and without Other Major Coronary Risk Factor*," Atherosclerosis, Mar. 2004, 115-23, vol. 173 (1).

Nohria, et al, "*Role of nitric oxide in the regulation of digital pulse volume amplitude in humans*." J Appl Physiol 101: 545-548, 2006.

Otto, et al., "*Early Morning Attenuation of Endothelial Function in Healthy Humans*," Circulation, Jun. 1, 2004, 2507-10, vol. 109 (21).

Parameswaran, et al., "*Pulse Oximetry as a Potential Screening Tool for Lower Extremity Arterial Disease in Asymptomatic Patients with Diabetes Mellitus*," Arch Intern Med, Feb. 28, 2005, 442-6, vol. 165 (4).

Pasternak, et al., "*34th Bethesda Conference: Task Force #1—Identification of Coronary Heart Disease Risk: Is There a Detection Gap?,* " J Am Coll Cardiol, Jun. 4, 2003, 1863-74, vol. 41 (11).

Philpott, et al., "*Reactive Hyperemia and Cardiovascular Risk*," Arterioscler Thromb Vasc Biol, Oct. 2007, 2065-7, vol. 27 (10).

Prasad, et al., "*Abnormal Coronary Microvascular Endothelial Function in Humans with Asymptomatic Left Ventricular Dysfunction*," Am Heart J, Sep. 2003, 549-54, vol. 146 (3).

Pyke, et al., "*The Relationship between Shear Stress and Flow-Mediated Dilatation: Implications for the Assessment of Endothelial Function*," J Physiol, Oct. 15, 2005, 357-69, vol. 568 (Pt 2).

Quyyumi, et al., "*Vasodilation by Hyperpolarization: Beyond No*," Hypertension, Dec. 2006, 1023-5, vol. 48 (6).

Ijzerman, et al., "*Individuals at Increased Coronary Heart Disease Risk Are Characterized by an Impaired Microvascular Function in Skin*," Eur J Clin Invest, Jul. 2003, 536-42, vol. 33 (7).

Robinson, et al., "*The Effects of Physical and Mental Stress on Cardiovascular Reactivity in a Group of African American Female College Students*," Journal of Anxiety Disorders, 1996, 543-53, vol. 10 (6).

Rodriguez-Porcel, et al., "*Hypercholesterolemia and Hypertension Have Synergistic Deleterious Effects on Coronary Endothelial Function*," Arterioscler Thromb Vasc Biol, May 1, 2003, 885-91 Epub Mar. 27, 2003 vol. 23 (5).

Rosamond, et al., "*Heart Disease and Stroke Statistics—2007 Update: A Report from the American Heart Association Statistics Committee and Stroke Statistics Subcommittee*," Circulation, Feb. 6, 2007, e69-171, vol. 115 (5).

Rossi, et al, "*The investigation of skin blood flowmotion: a new approach to study the microcirculatory impairment in vascular diseases?*" [Short review] Biomedicine & Pharmacotherapy 60 (2006) 437-442.

Schisterman, et al. (2004). "*Coronary age as a risk factor in the modified Framingham risk score*." BMC Med Imaging 4(1): 1-6.

Sharma, et al., "*[Abstract] Endothelial Function as a Therapeutic Target in Coronary Artery Disease*," Curr Atheroscler Rep, Jul. 2000, 303-7, vol. 2 (4).

Shimbo, et al., "*The Association between Endothelial Dysfunction and Cardiovascular Outcomes in a Population-Based Multi-Ethnic Cohort*," Atherosclerosis, May 2007, 197-203, vol. 192 (1).

Shusterman, et al., "*[Abstract] Spectral Characteristics of Skin Temperature Indicate Peripheral Stress-Response*" Biofeedback Self Regul., Dec. 1995, 357-67, vol. 20 (4).

Shusterman, et al., "*Sympathetic Nervous System Activity in Stress and Biofeedback Relaxation*," Engineering in Medicine and Biology Magazine, IEEE, 2005, 52-57, vol. 24 (2).

Silber, et al, "*Why is flow-mediate dilation dependent on arterial size? Assessment of the shear stimulus using phase-contrast magnetic resonance imaging*." A J Physiol Heart Circ Physiol 288: YH822-H828, 2005.

Sorensen, et al., "*Atherosclerosis in the Human Brachial Artery*," J Am Coll Cardiol, Feb. 1997, 318-22, vol. 29 (2).

Spieker, et al., "*Mental Stress Induces Prolonged Endothelial Dysfunction Via Endothelin-a Receptors*," Circulation, Jun. 18, 2002, 2817-20, vol. 105 (24).

Stein, et al. (2004). "*Vascular age: integrating carotid intima-media thickness measurements with global coronary risk assessment.*" Clin Cardiol 27(7): 388-92.

Stirban, et al, "*Benfotiamine Prevents Macro- and Microvascular Endothelial Dysfunction and Oxidative Stress Following a Meal Rich in Advanced Glycation End Products in Individuals With Type 2 Diabetes.*" Diabetes Care 29:2064-2071, 2006.

Struijker-Doudier, et al, *Evaluation of the microcirculation in hypertension and cardiovascular disease.* European Heart Journal (2007) 28: 2834-2840.

Takase, et al, "*Close relationship between the vasodilator response to acetylcholine in the brachial and coronary artery in suspected coronary artery disease.*" International Journal of Cardiology 105 (2005) 58-66.

Targonski, et al., "*Coronary Endothelial Dysfunction Is Associated with an Increased Risk of Cerebrovascular Events,*" Circulation, Jun. 10, 2003, 2805-9 Epub 003 May 27, vol. 107 (22).

Tarján et al., "*Flow Mediated Change of Finger-Tip-Temperature in Patients with High Cardiovascular Risk,*" Cardiologia Hungarica, 2005, 11-16, vol. 35.

Taylor, et al., "*Do Conventional Risk Factors Predict Subclinical Coronary Artery Disease? Results from the Prospective Army Coronary Calcium Project,*" Am Heart J, Mar. 2001, 463-8, vol. 141 (3).

Thomas, "*Flow-mediated dilation and biological variability.*" [Point:Counterpoint Comments] J Appl Physiol 99: 1626, 2005.

Tillin, et al, "*Measurement of pulse wave velocity: site matters.*" Journal of Hypertension 2007, 25:383-389.

Tomiyama, et al, "*Discrepancy between improvement of insulin sensitivity and that of arterial endothelial function in patients receiving antihypertensive medication.*" Journal of Hypertension 2007, 25:883-889.

Tzemos, et al., "*Is Exercise Blood Pressure a Marker of Vascular Endothelial Function?,*" QJM, Jul. 1, 2002, 2002, 423-29, vol. 95 (7).

Vallbo, et al., "*Microneurography: How the Technique Developed and Its Role in the Investigation of the Sympathetic Nervous System,*" J Appl Physiol, Apr. 2004, 1262-9, vol. 96 (4).

Van Den Berg, et al., "[Abstract] *Hyperhomocysteinaemia and Endothelial Dysfunction in Young Patients with Peripheral Arterial Occlusive Disease,*" Eur J Clin Invest, Mar. 1995, 176-81, vol. 25 (3).

Vinik, et al, "*Diabetic Cardiovascular Autonomic Neuropathy.*" Circulation 2007; 115:387-397.

Vink, et al, "*Morphometric and immunohistochemical characterization of the intimal layer throughout the arterial system of elderly humans.*" J. Anat. (2002) 200, pp. 97-103.

Vita, et al., "*Brachial Artery Vasodilator Function and Systemic Inflammation in the Framingham Offspring Study,*" Circulation, Dec. 7, 2004, 3604-9, vol. 110 (23).

Vita, et al., "*Endothelial Function: A Barometer for Cardiovascular Risk?,*" Circulation, Aug. 6, 2002, 2002, 640-42, vol. 106 (6).

Vita, "*Endothelial function and clinical outcome.*" [Mini-symposium] Heart 2005; 91:1278-1279.

Vitale, et al., "[Abstract] *in Patients with Coronary Artery Disease Endothelial Function Is Associated with Plasma Levels of C-Reactive Protein and Is Improved by Optimal Medical Therapy,*" Ital Heart J, Sep. 2003, 627-32, vol. 4 (9).

Vuilleumier, et al., "*Postischemic Forearm Skin Reactive Hyperemia Is Related to Cardiovascular Risk Factors in a Healthy Female Population,*" J Hypertens, Sep. 2002, 1753-7, vol. 20 (9).

Wang, et al., "*Multiple Biomarkers for the Prediction of First Major Cardiovascular Events and Death,*" N Engl J Med, Dec. 21, 2006, 2631-9, vol. 355 (25).

Widlansky, et al., "*The Clinical Implications of Endothelial Dysfunction,*" J Am Coll Cardiol, Oct. 1, 2003, 1149-60, vol. 42 (7).

Wilson, *Are vascular function measurements ready for the clinic?* European Heart Journal (2006) 27, 255-257.

Wray, et al, "*In FMD, NO is actually "The middle man".*" [Point:Counterpoint Comments] J Appl Physiol 99: 1624, 2005.

Yeboah, et al., "*Brachial Flow-Mediated Dilation Predicts Incident Cardiovascular Events in Older Adults: The Cardiovascular Health Study,*" Circulation, May 8, 2007, 2390-7, vol. 115 (18).

Yu, et al, "*Tissue Doppler Imaging. A New Prognosticator for Cardiovascular Diseases.*" J. Am. Coll. Of Cardiol., vol. 49, No. 19, 2007.

Yufu, et al., "*Brachial Arterial Stiffness Predicts Coronary Atherosclerosis in Patients at Risk for Cardiovascular Diseases,*" Jpn Heart J, Mar. 2004, 231-42, vol. 45 (2).

Yvonne-Tee, et al. (2006). "*Noninvasive assessment of cutaneous vascular function in vivo using capillaroscopy, plethysmography and laser-Doppler instruments: its strengths and weaknesses.*" Clin Hemorheol Microcirc 34(4): 457-73.

Zheng, et al., "*Associations of Ankle-Brachial Index with Clinical Coronary Heart Disease, Stroke and Preclinical Carotid and Popliteal Atherosclerosis: The Atherosclerosis Risk in Communities (Aric) Study,*" Atherosclerosis, May 1997, 115-25, vol. 131 (1).

G.T. Martin; H.F. Bowman, Validation of real-time continuous perfusion measurement, Medical & Biological Engineering & Computing, 2000, p. 319-325, vol. 38.

Georges Delhomme, Thermal Diffusion Probe and Instrument System for Tissue Blood Flow . . . , IEEE Transaction on Biomedical Engineering, Jul. 1994, p. 656-662 vol 41, No. 7.

"*Third Report of the National Cholesterol Education Program (NCEP) Expert Panel on Detection, Evaluation, and Treatment of High Blood Cholesterol in Adults (Adult Treatment Panel III) Final Report,*" Circulation, Dec. 17, 2002, 3143-421, vol. 106 (25).

Agewall, et al., "*Comparison of Ultrasound Assessment of Flow-Mediated Dilatation in the Radial and Brachial Artery with Upper and Forearm Cuff Positions,*" Clin Physiol, Jan. 2001, 9-14, vol. 21 (1).

Allen, et al., "*Microvascular Blood Flow and Skin Temperature Changes in the Fingers Following a Deep Inspiratory Gasp,*" Physiol Meas, Mar. 2002, 365-73, vol. 23 (2).

Anderson, et al., "*Close Relation of Endothelial Function in the Human Coronary and Peripheral Circulations,*" J Am Coll Cardiol, Nov. 1, 1995, 1235-41, vol. 26 (5).

Andersson, S.E., et al, [Abstract] "*Cutaneous vascular reactivity is reduced in aging and in heart failure: association with inflammation.*" Clinical Science (2003) 105, 699-707.

Asada, et al, "*Mobile Monitoring with Wearable Photoplethysmographic Biosensors.*" IEEE Engineering in Medicine and Biology Magazine, May/Jun. 2003, 28-40.

Asada, et al. "*Photoplethysmograph fingernail sensors for measuring finger forces without haptic obstruction*" IEEE Transactions vol. 17, Issue 5, Oct. 2001 p. 698. Abstract only.

Bae, "[Abstract] *Noninvasive Evaluation of Endothelial Function,*" J Cardiol, 2001, 89-92, vol. 37 (Suppl 1).

Bank, et al, "*In Vivo Human Brachial Artery Elastic Mechanics. Effects of Smooth Muscle Relaxation.*" Circulation 100 (1999) 41-47.

Behrendt, et al., "*Endothelial Function. From Vascular Biology to Clinical Applications*" Am J Cardiol, (2002) 40L-48L, vol. 90 (10C).

Bell, D. M., et al., "*Endothelial Dysfunction: Implications for Therapy of Cardiovascular Diseases,*" Ann Pharmacother, Apr. 1998, 459-70, vol. 32 (4).

Berardesca, et al., "*Eemco Guidance for the Measurement of Skin Microcirculation,*" Skin Pharmacol Appl Skin Physiol, Nov.-Dec. 2002, 442-56, vol. 15 (6).

Berry, et al., "*Occlusion Cuff Position Is an Important Determinant of the Time Course and Magnitude of Human Brachial Artery Flow-Mediated Dilation,*" Clin Sci (Lond), Oct. 2000, 261-7, vol. 99 (4).

Binggeli, et al., "*Statins Enhance Postischemic Hyperemia in the Skin Circulation of Hypercholesterolemic Patients: A Monitoring Test of Endothelial Dysfunction for Clinical Practice?,*" J Am Coll Cardiol, Jul. 2, 2003, 71-7, vol. 42 (1).

Blum, et al, "*Endothelial Dysfunction in Preeclampsia and Eclampsia: Current Etiology and Future Non-Invasive Assessment.*" IMAJ 2003; 5:724-726.

Bonetti, et al., "*Endothelial Dysfunction: A Marker of Atherosclerotic Risk,*" Arterioscler Thromb Vasc Biol, Feb. 1, 2003, 168-75, vol. 23 (2).

Bonetti, et al, "*Enhanced External Counterpulsation Improves Endothelial Function in Patients With Symptomatic Coronary Artery Disease.*" Journal of the American College of Cardiology, vol. 41, No. 10 (2003) 1761-1768.

Bornmyr, et al., "*Skin Temperature Changes and Changes in Skin Blood Flow Monitored with Laser Doppler Flowmetry and Imaging: A Methodological Study in Normal Humans,*" Clin Physiol, Jan. 1997, 71-81, vol. 17 (1).

Bystrom, et al., "*Ultrasound-Doppler Technique for Monitoring Blood Flow in the Brachial Artery Compared with Occlusion Plethysmography of the Forearm*," Scandinavian Journal of Clinical and Laboratory Investigation, 1998, 569-76, vol. 58 (7).

Caballero, et al, "*Microvascular and Macrovascular Reactivity Is Reduced in Subjects at Risk for Type 2 Diabetes*." Diabetes, vol. 48, Sep. 1999, 1856-1862.

Campuzano, et al., "*Endothelial Dysfunction and Intima-Media Thickness in Relation to Cardiovascular Risk Factors in Patients without Clinical Manifestations of Atherosclerosis*," Rev Esp Cardiol, Jun. 2003, 546-54, vol. 56 (6).

Celermajer, et al., "*Non-Invasive Detection of Endothelial Dysfunction in Children and Adults at Risk of Atherosclerosis*," Lancet, Nov. 7, 1992, 1111-5, vol. 340 epub p. 1-6.

Ceravolo, et al., "*Pulse Pressure and Endothelial Dysfunction in Never-Treated Hypertensive Patients*," J Am Coll Cardiol, May 21, 2003, 1753-8, vol. 41 (10).

Charbonneau, "[Abstract] *Use of Measures of Endothelial Function to Stratify Risk*," Can J Cardiol, May, 2001, 18A-21A, vol. 17 (Suppl A).

Chenzbraun, et al., "*The Peripheral Vascular Response to Exercise Is Impaired in Patients with Risk Factors for Coronary Artery Disease*" Cardiology, 2001, 126-30, vol. 95 (3).

Cleland, et al, "*Endothelial dysfunction as a possible link between C-reactive protein levels and cardiovascular disease*." Clinical Science (2000) 98, 531-535.

Corretti, et al., "*Guidelines for the Ultrasound Assessment of Endothelial-Dependent Flow-Mediated Vasodilation of the Brachial Artery: A Report of the International Brachial Artery Reactivity Task Force*," J Am Coll Cardiol, Jan. 16, 2002, 257-65, vol. 39 (2).

Djuric, et al., "[Abstract] *Age-Related Progressive Brachial Artery Endothelial Dysfunction Precedes the Changed Carotid and Left Ventricular Geometry in Healthy Humans*," Angiology, Jul. 1999, 555-61, vol. 50 (7).

Doshi, et al., "*Flow-Mediated Dilatation Following Wrist and Upper Arm Occlusion in Humans: The Contribution of Nitric Oxide*," Clin Sci (Lond), Dec. 2001, 629-35, vol. 101 (6).

Fichtlscherer, et al., "*Elevated C-Reactive Protein Levels and Impaired Endothelial Vasoreactivity in Patients with Coronary Artery Disease*," Circulation, Aug. 29, 2000, 1000-6, vol. 102 (9).

Gokce, et al., "*Risk Stratification for Postoperative Cardiovascular Events Via Noninvasive Assessment of Endothelial Function: A Prospective Study*," Circulation, Apr. 2, 2002, 1567-72, vol. 105 (13).

Guerci, et al., "*Endothelial Dysfunction and Type 2 Diabetes. Part 1: Physiology and Methods for Exploring the Endothelial Function*," Diabetes Metab, Sep. 2001, 425-34, vol. 27 (4 Pt 1).

Hambrecht, et al, "*Effect on exercise on coronary endothelial function in patients with coronary artery disease*." The New England Journal of Medicine, Feb. 17, 2000.454-460.

Hashimoto, et al., "*Association of Coronary Risk Factors and Endothelium-Dependent Flow-Mediated Dilatation of the Brachial Artery*," Hypertens Res, May 2000, 233-8, vol. 23 (3).

Hayoz, et al, "*Postischemic Blood Flow Response to Hypercholesterolemic Patients*." Hypertension 1995;26:497-502.

Hokanson, et al., "*An Electrically Calibrated Plethysmograph for Direct Measurement of Limb Blood Flow*," IEEE Trans Biomed Eng, Jan. 1975, 25-9, vol. 22 (1).

House, et al, "*Response to Sessler Letter*." Eur J Appl Physiol (2003) 89:403-404.

Hughes, et al, "*Wearing your heart in your sleeve?*" [Editorial] European Heart Journal (2001) 22, 1071-1073.

Husain, et al, "*Aspirin Improves Endothelial Dysfunction in Atherosclerosis*." Circulation (1998) 97:716-720.

Hypertension Diagnostics, "*Hypertension Diagnostics CVProfilor. CardioVascular Profiling System Clinical Trial*." Apr. 2003.

Hypertension Diagnostics, Inc., "*Clinical Application of the CVProfilor. The Value of Arterial Elasticity Assessment in Clinical Practice*." Hypertension Diagnostics, Inc., Jun. 2002.

Ijzerman, et al, "*Individuals at increased coronary heart disease risk are characterized by an impaired microvascular function in skin*." European Journal of Clinical Investigation (2003) 33, 536-542.

Jamieson, et al., "[Abstract] *Ambulatory Blood Pressure in Heart Failure*," Eur J Clin Invest, 2001, 18-25, vol. 31 Suppl 2.

Jennings, et al., "*A Thermal Vascular Test for Distinguishing between Patients with Raynaud's Phenomenon and Healthy Controls. Raynaud's Treatment Study Investigators*," Health Psychol, Jul. 1999, 421-6, vol. 18 (4).

Joannides, et al., "*Nitric Oxide Is Responsible for Flow-Dependent Dilatation of Human Peripheral Conduit Arteries in Vivo*," Circulation, Mar. 1, 1995, 1314-9, vol. 91 (5).

Kang, et al., "*Relation of Vasodilator Response of the Brachial Artery to Inflammatory Markers in Patients with Coronary Artery Disease*," Echocardiography, Nov. 2002, 661-7, vol. 19 (8).

Kelly, et al, "*Noninvasive Determination of Age-Related Changes in the Human Arterial Pulse*." Circulation, vol. 80 (1989) 1652-1659.

Kharalkar et al., "*Novel Temperature Based Technique for Measurement of Endothelial Dysfunction*" Engineering in Medicine and Biology Society, 2003. Proceedings of the 25th Annual International Conference of the IEEE 2003, vol. 1, 308-311.

Kimura, et al., "[Abstract] *Impaired Endothelial Function in Hypertensive Elderly Patients Evaluated by High Resolution Ultrasonography*,"Can J Cardiol, May 1999, 563-8, vol. 15 (5).

Kuvin, et al., "*Clinical utility of endothelial function testing: ready for prime time?*" Circulation 107(25) (2003) 3243-7.

Kuvin, et al., "*Assessment of Peripheral Vascular Endothelial Function with Finger Arterial Pulse Wave Amplitude*," Am Heart J, Jul. 2003, 168-74, vol. 146 (1).

Kuvin, et al., "*Relation between High-Density Lipoprotein Cholesterol and Peripheral Vasomotor Function*," Am J Cardiol, Aug. 1, 2003, 275-9, vol. 92 (3).

LaFontaine et al. "*Atherosclerosis, Endothelial Function, and Exercise in Coronary Artery Disease Patients*" American College of Sports Medicine, ACSM's Certified News, 2002, 12:1, p. 1-5.

Lambert, et al., "*Familial Hyperhomocysteinaemia and Endothelium-Dependent Vasodilatation and Arterial Distensibility of Large Arteries*," Cardiovasc Res, Jun. 1999, 743-51, vol. 42 (3).

Laurent, et al, "*Heart Rate and Pulse Pressure Amplification in Hypertensive Subjects*." AJH 2003; 16:363-370.

Lekakis, et al., "*Peripheral Vascular Endothelial Dysfunction in Patients with Angina Pectoris and Normal Coronary Arteriograms*," J Am Coll Cardiol, Mar. 1, 1998, 541-6, vol. 31 (3).

Lerman, et al, "*Endothelial Function Under Pressure*." [Editorial Comment] Journal of the American College of Cardiology, vol. 41, No. 10, 2003.

Libby, et al., "*Lipid Lowering Improves Endothelial Functions*," Int J Cardiol, Jun. 30, 2000, S3-S10, vol. 74 Suppl 1 (74).

L'Ltalien, et al., "*The Cardiovascular Event Reduction Tool (Cert)—a Simplified Cardiac Risk Prediction Model Developed from the West of Scotland Coronary Prevention Study (Woscops)*," Am J Cardiol, Mar. 15, 2000, 720-4, vol. 85 (6).

Lu, et al., "*Post-Occlusive Reactive Hyperemia in Single Nutritive Capillaries of the Nail Fold: Methodological Considerations*," Scand J Clin Lab Invest, 2002, 537-9, vol. 62 (7).

McVeigh, et al., "[Abstract] *Endothelial Dysfunction and the Metabolic Syndrome*," Curr Diab Rep, Feb. 2003, 87-92, vol. 3 (1).

McVeigh, et al, "*Evaluation of mechanical arterial properties: clinical, experimental and therapeutic aspects*." [Review] Clinical Science (2002) 102, 51-67.

Meng, et al., "*Elevated C-Reactive Protein Levels Are Associated with Endothelial Dysfunction in Chronic Cocaine Users*," Int J Cardiol, Apr. 2003, 191-8, vol. 88 (2-3).

Meredith, et al., "[Abstract] *Postischemic Vasodilation in Human Forearm Is Dependent on Endothelium-Derived Nitric Oxide*," Am J Physiol, Apr. 1996, H1435-40, vol. 270 (4 Pt 2).

Micro Medical, "*Pulse Contour Analysis for the rapid assessment of arterial stiffness and endothelial function*." [Brochure] May 2003.

Minson, et al., "*Nitric Oxide and Neurally Mediated Regulation of Skin Blood Flow During Local Heating*," J Appl Physiol, Oct. 2001, 1619-26, vol. 91 (4).

Mittleman, et al., "*Triggering of Acute Myocardial Infarction Onset by Episodes of Anger*," Circulation, Oct. 1, 1995, 1720-25, vol. 92 (7).

Mullen, et al, "*Heterogenous Nature of Flow-Mediated Dilatation in Human Conduit Arteries in Vivo. Relevant to Endothelial Dysfunction in Hypercholesterolemia*." Cir. Res. 2001; 88:145-151.

Myerburg, et al., "*Frequency of Sudden Cardiac Death and Profiles of Risk*," Am J Cardiol, Sep. 11, 1997, 10E-19F, vol. 80 (5B).

Nabel, et al, "*Dilation of normal and constriction of atherosclerotic coronary arteries caused by the cold pressor test.*" Circulation, vol. 77, No. 1, 43-52, 1988.

Neunteufl, et al., "*Late Prognostic Value of Flow-Mediated Dilation in the Brachial Artery of Patients with Chest Pain,*" Am J Cardiol, Jul. 15, 2000, 207-10, vol. 86 (2).

Neunteufl, et al., "*Systemic Endothelial Dysfunction Is Related to the Extent and Severity of Coronary Artery Disease,*" Atherosclerosis, Feb. 28, 1997, 111-8, vol. 129 (1).

Nigam, et al., "*Relation between Conduit Vessel Stiffness (Assessed by Tonometry) and Endothelial Function (Assessed by Flow-Mediated Dilatation) in Patients with and without Coronary Heart Disease,*" Am J Cardiol, Aug. 15, 2003, 395-9, vol. 92 (4).

Ninet, et al, "*Cutaneous Postocclusive Reactive Hyperemia Monitored by Laser Doppler Flux Metering and Skin Temperature.*" Microvascular Research 30, 125-132 (1985).

Ninet, et al., "*[Abstract] Cutaneous Postocclusive Reactive Hyperemia Monitored by Laser Doppler Flux Metering and Skin Temperature,*" Microvasc Res, Jul. 1985, 125-32, vol. 30 (1).

Noon, et al., "*Local Inhibition of Nitric Oxide Generation in Man Reduces Blood Flow in Finger Pulp but Not in Hand Dorsum Skin,*" J Physiol, Jan. 15, 1996, 501-8, vol. 490 (Pt 2).

Papamichael, et al., "*Ankle-Brachial Index as a Predictor of the Extent of Coronary Atherosclerosis and Cardiovascular Events in Patients with Coronary Artery Disease,*" Am J Cardiol, Sep. 15, 2000, 615-8, vol. 86 (6).

Quyyumi, "*Prognostic Value of Endothelial Function,*" Am J Cardiol, Jun. 19, 2003, 19H-24H, vol. 91 (12A).

Rozanski, et al., "*Peripheral Arterial Responses to Treadmill Exercise among Healthy Subjects and Atherosclerotic Patients,*" Circulation, Apr. 24, 2001, 2084-9, vol. 103 (16).

Rubinstein, et al., "*Skin-Surface Temperature Gradients Correlate with Fingertip Blood Flow in Humans,*" Anesthesiology, Sep. 1990, 541-5, vol. 73 (3).

Sarzynska-Dlugosz, et al., "*[Abstract] [Common Carotid Artery Intima-Media Thickness: The Role in Evaluation of Atherosclerosis Progression],*" Neurol Neurochir Pol, Nov.-Dec. 2001, 1093-102, vol. 35 (6).

Sessler, "*Skin-Temperature Gradients Are a Validated Measure of Fingertip Perfusion,*" Eur J Appl Physiol, May 2003, 401-2; author reply 03-4, vol. 89 (3-4).

Shamim-Uzzaman, et al., "*Altered Cutaneous Microvascular Responses to Reactive Hyperaemia in Coronary Artery Disease: A Comparative Study with Conduit Vessel Responses,*" Clin Sci (Lond), Sep. 2002, 267-73, vol. 103 (3).

Shusterman, et al., "*Spontaneous Skin Temperature Oscillations in Normal Human Subjects,*" Am J Physiol., Sep. 1997, R1173-81, vol. 273 (3 Pt. 2).

Stulc, et al., "*Microvascular Reactivity in Patients with Hypercholesterolemia: Effect of Lipid Lowering Treatment,*" Physiol Res, 2003, 439-45, vol. 52 (4).

Vink, et al, "*Morphometric and immunohistochemical characterization of the intimal layer throughout the arterial system of elderly humans.*" J. Anat. 200 (2002) 97-103.

Vita, et al., "*Endothelial Function: A Barometer for Cardiovascular Risk?,*" Circulation, Aug. 6, 2002, 640-42, vol. 106 (6).

Vogel, et al., "*Effect of a Single High-Fat Meal on Endothelial Function in Healthy Subjects,*" Am J Cardiol, Feb. 1, 1997, 350-4, vol. 79 (3).

Vogel, "*Heads and Hearts. The Endothelial Connection.*" [Editorial] Circulation 2003; 107:2766-2768.

Wigley, et al., "*The Post-Occlusive Hyperemic Response in Patients with Systemic Sclerosis,*" Arthritis Rheum, Nov. 1990, 1620-5, vol. 33 (11).

Willerson, et al., "*Reserpine in Raynaud's Disease and Phenomenon. Short-Term Response to Intra-Arterial Injection,*" Ann Intern Med, Jan. 1970, 17-27, vol. 72 (1).

Wilson, et al. (1998). "Prediction of coronary heart disease using risk factor categories." Circulation 97(18): 1837-47.

International Search Report received in application No. PCT/US03/26238 dated May 7, 2004.

International Search Report received in application No. PCT/US05/18437 dated Jul. 3, 2008.

\* cited by examiner

METHOD AND APPARATUS FOR DETERMINING VASCULAR HEALTH CONDITIONS

CROSS REFERENCE TO RELATED APPLICATIONS

This application is a continuation-in-part of, and claims priority to, U.S. application Ser. No. 10/525,255, filed Feb. 23, 2005 now abandoned, which claims priority under 35 USC §120 to PCT application PCT/US2003/026238, filed Aug. 22, 2003 (published as WO04/17905) and which claimed priority under 35 USC §119 to U.S. Provisional Application No. 60/405,352, filed Aug. 23, 2002, the disclosures of which are incorporated herein by reference. This application is also a continuation of and claims priority to U.S. application Ser. No. 11/563,676, filed Nov. 27, 2006 now abandoned, which is in turn a continuation-in-part of PCT/US2005/018437, filed May 25, 2005, and which claims priority under 35 USC §119 to U.S. Provisional Application No. 60/585,773, filed Jul. 6, 2004; U.S. Provisional Application No. 60/574,255, filed May 26, 2004; U.S. Provisional Application No. 60/626,006, filed Nov. 8, 2004, and U.S. Provisional Application No. 60/628,173, filed Nov. 15, 2004, the disclosures of which are incorporated herein by reference.

FIELD OF THE INVENTION

The present invention relates generally to the field of assessing a patient's vascular health including endothelial function by monitoring changes in hemodynamic parameters responsive to the introduction of a vasodilating stimulant. The monitored hemodynamic parameters may include blood temperature, blood flow, and/or blood oxygen content.

BACKGROUND

Cardiovascular disease and its sequalae account for a significant percentage of the morbidity or mortality in industrialized countries. It is known that cardiovascular disease may be caused and/or enhanced by an impairment of tissue perfusion.

The endothelium has many important functions in maintaining the patency and integrity of the arterial system. The endothelium can reduce and inactivate toxic super-oxides which may be present in diabetics and in smokers. The endothelium is the source of nitric oxide, a local hormone that relaxes the adjacent smooth muscle cells in the media, and is a powerful vasodilator.

The endothelium regulates vascular homeostasis by elaborating a variety of paracrine factors that act locally in the blood vessel wall and lumen. Under normal conditions, these aspects of the endothelium, hereinafter referred to as "endothelial factors", maintain normal vascular tone, blood fluidity, and limit vascular inflammation and smooth muscle cell proliferation.

When coronary risk factors are present, the endothelium may adopt a phenotype that facilitates inflammation, thrombosis, vasoconstriction, and atherosclerotic lesion formation. In human patients, the maladaptive endothelial phenotype manifests itself prior to the development of frank atherosclerosis and is associated with traditional risk factors such as hypercholesterolemia, hypertension, and diabetes mellitus. The maladaptive endothelial phenotype is further identified with emerging risk factors such as hyperhomocysteinemia, obesity, and systemic inflammation.

Prior art means for estimating endothelial dysfunction include the use of cold pressure tests by invasive quantitative coronary angiography and the injection of radioactive material and subsequent tracking of radiotracers in the blood. These invasive methods are costly, inconvenient, and must be administered by highly trained medical practitioners.

Noninvasive prior art methods for measuring endothelial dysfunction include, the measurement of the percent change and the diameter of the left main trunk induced by cold pressure test with two dimensional echo cardiography, the Dundee step test, laser doppler perfusion imaging and iontophoresis, and high resolution lo-mode ultrasound.

SUMMARY OF THE INVENTION

The disclosures herein relate generally to vascular health and neurovascular conditions and more particularly to a method and apparatus for determining one or more health conditions.

In an embodiment, vascular function may be assessed by providing a vasodilating stimulant to a patient to stimulate hemodynamic activity in a selected region of the patient's body; monitoring a change in a hemodynamic parameter at the selected region; and assessing the patient's vascular function based upon said monitoring.

In one aspect, the method for measuring vascular reactivity includes the steps of initiating monitoring of a hemodynamic parameter such as blood flow and/or blood oxygen content on a digit such as a finger and/or a toe, providing a vasodilating stimulant to the extremity to which the digit is affixed to stimulate hemodynamic activity in the digit while continuously monitoring the hemodynamic parameter, continuing monitoring until a time after the hemodynamic parameter affected by the vasodilating stimulant has stabilized, and assessing the patient's vascular reactivity based upon the monitoring. In a preferred embodiment, blood flow is measured by skin temperature on a fingertip of the patient and vascular reactivity is assessed by monitoring the changes in skin temperature on the fingertip during and after the vasodilating stimulant. A suitable vasodilating stimulant can be provided by compressing an artery ultimately feeding the fingertip for a predetermined period of time and ceasing compression after the predetermined period of time. In one embodiment, the vasodilating stimulant is compression and subsequent release of compression of the brachial artery of the arm where measurements are taken on the fingertip.

In alternate embodiments, the monitoring is accomplished by assessing blood flow by photoplethysmography, while in other embodiments the monitoring is accomplished by assessing blood flow by ultrasound Doppler. Whether measured by skin temperature, photoplethysmography, ultrasound Doppler, or pulse oximetry, the hemodynamic activity plotted as a function of time.

In a preferred embodiment, a method for measuring vascular reactivity in a patient is provided including the steps of initiating monitoring of temperature on a fingertip of an arm of the patient, occluding blood flow to the arm for a predetermined period of time to stimulate hemodynamic activity, and ceasing the occlusion after the predetermined period of time, continuing monitoring of the temperature on the fingertip until blood flow has stabilized after ceasing the occlusion; and assessing the patient's vascular reactivity based upon changes in the temperature during the monitoring. The temperature changes are plotted as a function of time.

In a further embodiment, endothelial function may be measured by providing a vasodilating stimulant to a patient to stimulate hemodynamic activity in a selected region of the patient's body; monitoring a change in blood oxygen content at the selected region; and assessing the patient's endothelial function based upon said monitoring.

In yet a further embodiment, endothelial function may be measured by providing a vasodilating stimulant to a patient to stimulate hemodynamic activity in a selected region of the patient's body; monitoring a change in blood flow rate at the selected region; and assessing the patient's endothelial function based upon said monitoring.

According to one aspect of the present disclosure, a thermal energy measurement apparatus is provided comprising a thermal energy sensor and means for coupling the thermal energy sensor to a skin surface on a body part, the coupling means operable to couple the thermal energy sensor to the skin surface on the body part while not substantially changing the skin surface temperature of the body part.

According to one aspect of the present disclosure, a method for determining one or more health conditions is provided comprising providing a subject, measuring the skin temperature of a body part on the subject, providing a vasostimulant to the subject, measuring the skin temperature changes of the body part during and subsequent to the provision of the vasostimulant, and determining one or more health conditions for the subject based upon at least one of the skin temperature changes measured.

According to one aspect of the present disclosure, a method for determining one or more health conditions is provided comprising providing a subject, measuring the skin temperature of a first body part on the subject, placing a second body part of the subject in water, measuring the skin temperature changes of the first body part during and subsequent to the placing of the second body part in water, and determining one or more health conditions for the subject based upon at least one of the skin temperature changes measured.

According to one aspect of the present disclosure, a method for determining one or more health conditions is provided comprising providing a subject, providing a volume of a medium, placing a body part of the subject in the volume of the medium, measuring the temperature of the volume of the medium, providing a vasostimulant to the subject, measuring the temperature changes of the volume of the medium during and subsequent to the provision of the vasostimulant, and determining one or more health conditions for the subject based upon at least one of the temperature changes measured.

According to one aspect of the present disclosure, a database for diagnosing health conditions is provided comprising control data comprising a plurality of control temperature data points and temperature data comprising a baseline temperature, a temperature drop from the baseline temperature having a first slope, a lowest temperature achieved, a temperature rise from the lowest temperature achieved having a second slope, a peak temperature, and a stabilization temperature.

According to one aspect of the present disclosure, a method for determining one or more health conditions is provided comprising providing a subject, measuring the baseline skin temperature of a body part on the subject, providing a vasostimulant to the subject, measuring the lowest skin temperature of the body part during and subsequent to the provision of the vasostimulant, measuring the highest skin temperature of the body part, and determining one or more health conditions for the subject based upon at least one of the skin temperature changes measured.

According to one aspect of the present disclosure, a computer program for determining one or more health conditions is provided comprising a retrieval engine adapted to retrieve a plurality of temperature data from a database, the temperature data comprising a baseline temperature, a temperature drop from the baseline temperature having a first slope, a lowest temperature achieved, a temperature rise from the lowest temperature achieved having a second slope, a peak temperature, and a stabilization temperature; a processing engine adapted to process data retrieved by the retrieval engine, and a diagnosis engine operable to determine one or more health conditions based upon the retrieved temperature data.

According to one aspect of the present disclosure a method for determining one or more health conditions is provided comprising providing a subject, measuring the blood flow rate of the subject, providing a vasostimulant to the subject, measuring the blood flow rate changes of the subject during and subsequent to the provision of the vasostimulant, and determining one or more health conditions for the subject based upon at least one of the blood flow rate changes measured.

According to one aspect of the present disclosure a method for determining one or more health conditions is provided comprising providing a subject, measuring the skin temperature of a finger on the arm of the subject, detecting an equilibrium in the skin temperature of the finger of the subject, automatically providing a vasostimulant to the subject to substantially cease blood flow to the finger, measuring the skin temperature changes of the finger after provision of the vasostimulant, automatically removing the vasostimulant to allow blood flow to the finger, measuring the skin temperature changes of the finger after the removal of the vasostimulant, and determining one or more health conditions for the subject based upon at least one of the skin temperature changes measured.

According to one aspect of the present disclosure a method for selecting a medication for the treatment of a medical condition in a subject is provided which includes administering a medication to one or more subjects, determining the health condition of the one or more subjects using the method of: measuring the skin temperature of a body part on the one or more subjects, providing a vasostimulant to the one or more subjects, measuring the skin temperature changes of the body part during and subsequent to the provision of the vasostimulant; and determining one or more health conditions for the one or more subjects based upon at least one of the skin temperature changes measured; determining whether the medication is effective in the treatment of the one or more subjects, and selecting the medication for use in treating the medical condition in other subjects if the medication is determined to be effective in the treatment of the one or more subjects.

According to one aspect of the present disclosure a method for selecting a nutritional program for a subject is provided which includes administering a nutritional program to one or more subjects, determining the health condition of the one or more subjects using the method of: measuring the skin temperature of a body part on the one or more subjects, providing a vasostimulant to the one or more subjects, measuring the skin temperature changes of the body part during and subsequent to the provision of the vasostimulant, and determining one or more health conditions for the one or more subjects based upon at least one of the skin temperature changes measured; determining whether the nutritional program is effective for the one or more subjects, and selecting the nutritional program for other subjects if the nutritional program is determined to be effective for the one or more subjects.

According to one aspect of the present disclosure a method for selecting a medication, chemical substance, medical procedure, health intervention program, and/or nutritional program for the treatment of a medical condition in a subject is provided which includes administering a medication, chemical substance, medical procedure, health intervention program, and/or nutritional program to one or more subjects, determining the health condition of the one or more subjects using the method of: measuring the skin temperature of a body part on the one or more subjects, providing a vasostimulant to the one or more subjects, measuring the skin temperature changes of the body part during and subsequent to the provision of the vasostimulant, and determining one or more health conditions for the one or more subjects based upon at least one of the skin temperature changes measured; determining whether the medication, chemical substance, medical procedure, health intervention program, and/or nutritional program is effective in the treatment of the one or more subjects, and selecting the medication, chemical substance, medical procedure, health intervention program, and/or nutritional program for use in treating the medical condition in other subjects if the medication is determined to be effective in the treatment of the one or more subjects.

It is emphasized that this summary is not to be interpreted as limiting the scope of these inventions which are limited only by the claims herein.

BRIEF DESCRIPTION OF THE DRAWINGS

FIG. 9b is a cross sectional view illustrating an exemplary embodiment of a thermal energy sensor used with the apparatus of FIG. 9a.

FIG. 33b is a cross sectional view illustrating an exemplary embodiment of the thermal energy sensor of FIG. 33a.

FIG. 34b is a cross sectional view illustrating an exemplary embodiment of the thermal energy sensor of FIG. 34a.

FIG. 36b is a cross sectional view illustrating an exemplary embodiment of the thermal energy sensor of FIG. 36a.

FIG. 37a is a flow chart illustrating an exemplary embodiment of a portion of a method for determining one or more health conditions using the apparatus of FIG. 36a.

FIG. 37b is a flow chart illustrating an exemplary embodiment of a portion of a method for determining one or more health conditions using the apparatus of FIG. 36a.

DETAILED DESCRIPTION

Figure 1:
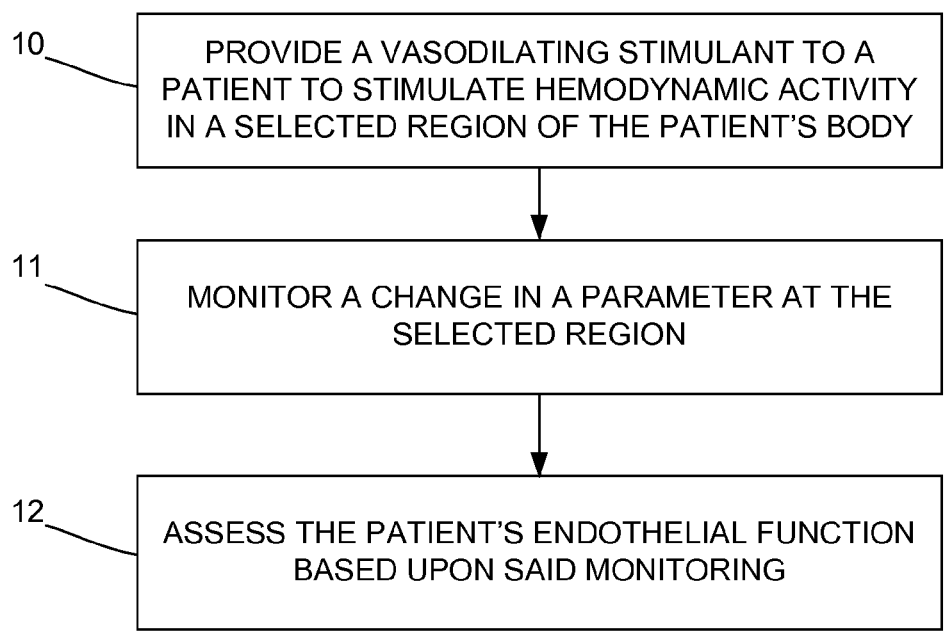
FIG. 1 is a flowchart of an embodiment of a method of endothelial function assessment/measurement.

Referring now to FIG. 1, a method for assessing endothelial function is provided that comprises providing a vasodilating stimulant to a patient to stimulate hemodynamic activity in a selected region of the patient's body, illustrated at block 10 in FIG. 1, monitoring a change in a hemodynamic parameter at the selected region, illustrated at block 11 in FIG. 1, and assessing the patient's endothelial function based upon said monitoring, illustrated at block 12 in FIG. 1. In a one embodiment, the monitored hemodynamic parameter may be a parameter such as blood temperature, blood oxygen content, blood flow rate, or the like, or a combination thereof.

Providing a vasodilating stimulant may further comprise compressing the patient's brachial artery for a predetermined period of time and ceasing the compression after that predetermined period of time. Providing a vasodilating stimulant may also comprise occluding blood flow in the patient's arm.

Additionally, the change in temperature at one of the patient's fingertips may be monitored as may the change in temperature in the patient's arm. Monitoring the change in temperature may be accomplished by placing at least two temperature sensors, for example piezoelectric sensors, proximate, e.g. on, the patient's forearm. The temperature sensors may be separated by a known distance.

Providing a vasodilating stimulant may comprise occluding blood flow in the patient's leg.

In one embodiment, a preferred method for measuring endothelial function comprises providing a vasodilating stimulant to a patient to stimulate hemodynamic activity in a selected region of the patient's body, monitoring a change in blood oxygen content at the selected region, and assessing the patient's endothelial function based upon said monitoring.

Monitoring may be accomplished by taking measurements with a pulse oximeter. The pulse oximeter may be placed proximate, e.g. on the tip of one of the patient's fingers.

In one embodiment, a second preferred method for measuring endothelial function comprises providing a vasodilating stimulant to a patient to stimulate hemodynamic activity in a selected region of the patient's body, monitoring a change in blood flow rate at the selected region, and assessing the patient's endothelial function based upon said monitoring.

Monitoring may be accomplished by taking measurements with a photoplethysmograph placed proximate, e.g. on one of the patient's fingers. Monitoring may also be accomplished by taking an ultrasound Doppler measurement. Monitoring may occur from a time prior to the beginning of the compression until a time after ceasing, e.g. when blood flow has stabilized.

Providing a vasodilating stimulant may comprise compressing one of the patient's arteries located in an outer extremity of the patient's body for a predetermined period of time and ceasing the compression after said predetermined period of time. The outer extremity may be a leg, an arm, a wrist, and/or a finger.

The second preferred method for measuring endothelial function may further comprise plotting measured blood flow as a function of time and/or plotting the change in blood flow as a function of time.

In one embodiment, a method is provided for assessing endothelial function, comprising a providing a vasodilating stimulant to a patient to stimulate hemodynamic activity in a selected region of the patient's body; monitoring a change in a hemodynamic parameter at the selected region; and assessing the patient's endothelial function based upon said monitoring. In one such embodiment, the hemodynamic parameter is at least one of (i) blood temperature, (ii) blood oxygen content, or (iii) blood flow rate. The vasodilating stimulant may comprise compressing the patient's brachial artery or occluding blood flow in the patient's arm for a predetermined period of time, and ceasing said compression after the predetermined period of time. The monitoring may further comprise monitoring a change in temperature at one of the patient's fingertips. The vasodilating stimulant may comprise occluding blood flow in the patient's leg.

In one embodiment, the monitoring comprises monitoring a change in temperature in the patient's arm. In one embodiment, the monitoring the change in temperature in the patient's arm is accomplished by placing at least two temperature sensors proximate the patient's forearm.

In one embodiment, the temperature sensors are piezoelectric sensors.

In another embodiment, the vasodilating stimulant comprises occluding blood flow in the patients' leg.

In one embodiment, a method for measuring endothelial function is provided, comprising: a) providing a vasodilating stimulant to a patient to stimulate hemodynamic activity in a selected region of the patient's body; b) monitoring a change in blood oxygen content at the selected region; and c) assessing the patient's endothelial function based upon said monitoring. In one such embodiment, the monitoring is accomplished by taking measurements with a pulse oximeter. In one such embodiment, the pulse oximeter is placed proximate the tip of one of the patient's fingers.

In one embodiment, a method is provided for measuring endothelial function, comprising: a) providing a vasodilating stimulant to a patient to stimulate hemodynamic activity in a selected region of the patient's body; b) monitoring a change in blood flow rate at the selected region; and c) assessing the patient's endothelial function based upon said monitoring. In one such embodiment, the monitoring is accomplished by taking measurements with a photoplethysmograph placed proximate the tip of one of the patient's fingers. Alternatively, monitoring is accomplished by taking an ultrasound Doppler measurement. The vasodilating stimulant may comprise compressing one of the patient's arteries located in an outer extremity of the patient's body for a predetermined period of time; and ceasing compression after said predetermined period of time. In one embodiment, the extremity is at least one of (i) a leg, (ii) an arm, (iii) a wrist, or (iv) a finger. In one embodiment, the monitoring occurs from a time prior to the beginning of said compression until a time after said ceasing when said blood flow has stabilized. In one embodiment the measured blood flow is plotted as a function of time. In another embodiment, the change in blood flow is plotted as a function of time.

Figure 2:
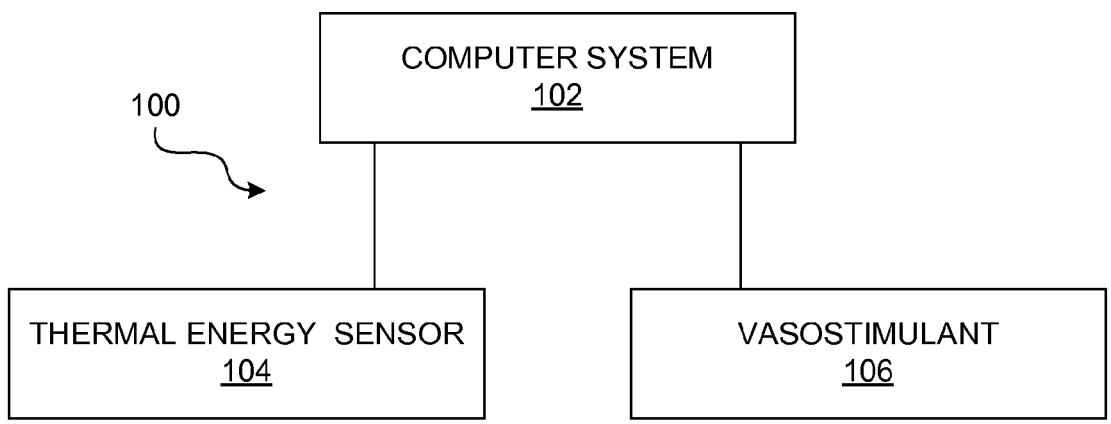
FIG. 2 is a schematic view illustrating an exemplary embodiment of an apparatus for determining one or more health conditions.

Referring now to FIG. 2, in an exemplary embodiment, an apparatus for determining one or more health conditions 100 includes a computer system 102 which is operably coupled to a thermal energy sensor 104 and a vasostimulant 106. In an exemplary embodiment, the computer system 102 may be, for example, a conventional computer system known in the art. In an exemplary embodiment, the thermal energy sensor 104 may be, for example, a conventional thermal energy sensor known in the art. In an exemplary embodiment, the thermal energy sensor 104 may be, for example, a thermocouple, a thermister, a resistance temperature detector, a heat flux sensor, a liquid crystal sensor, an infrared sensor, a thermopile, or a variety of other thermal energy sensors known in the art. In an exemplary embodiment, the thermal energy sensor is an infrared sensor that measures the thermal energy of a point on a surface. In an exemplary embodiment, thermal energy sensor is an infrared sensor that measures the thermal energy of an area on a surface. In an exemplary embodiment, the thermal energy sensor 104 may be disposable. In an exemplary embodiment, the vasostimulant 106 may be, for example, conventional vasostimulants known in the art including mechanical vasostimulants such as cuffs for compressing arteries, chemical vasostimulants such as nitroglycerin or transdermal substances, sympathetic mimetic agents, parasympathetic mimetic agents, acetylcholine, vasodilating nitrates such as, for example, nitroprusside or glyceryl trinitrate, inhibitors of endothelium-derived contracting factors such as, for example, ACE inhibitors or angiotensin II receptor antagonists, cytoprotective agents such as, for example, free radical scavengers such as superoxide dismutase endothelium dependent agents such as, for example, acetylcholine, and/or endothelium independent agents such as, for example, nitroprosside or glycerin trinitrate, psychological vasostimulants such as aptitude tests, mental arithmetic, visual stimulation, physiological vasostimulants such as the Valsalva maneuver, a tilting test, physical exercise, whole body warming, whole body cooling, local warming, local cooling, contralateral handgrip, contralateral hand cooling, and painful stimuli such as, for example, nailbed compression, and a variety of others. In an exemplary embodiment, the chemical vasostimulants may stimulate the vessel either through the endothelium or bypass the endothelium and directly affect the muscular part of the vessel wall, which is endothelium independent. In an exemplary embodiment, the vasostimulant 106 may be, for example, a neuro-vasostimulant, a neurostimulant, a vasoconstrictor, a vasodilator, an endothermal layer stimulant, or a smooth muscle cell or medial layer stimulant. In an exemplary embodiment, a neuro-vasostimulant may include, for example, having the subject drink a glass of ice water. In an exemplary embodiment, the thermal energy sensor 104 and the vasostimulant 106 are coupled to, monitored by, and/or controlled by the computer system 102 through a wireless connection such as, for example, a wireless connection including Bluetooth technology. In an exemplary embodiment, the computer system 102 may be coupled to a variety of convention medical devices known in the art such as, for example, a conventional pulse oximeter or a conventional blood pressure monitoring device.

Figure 3:
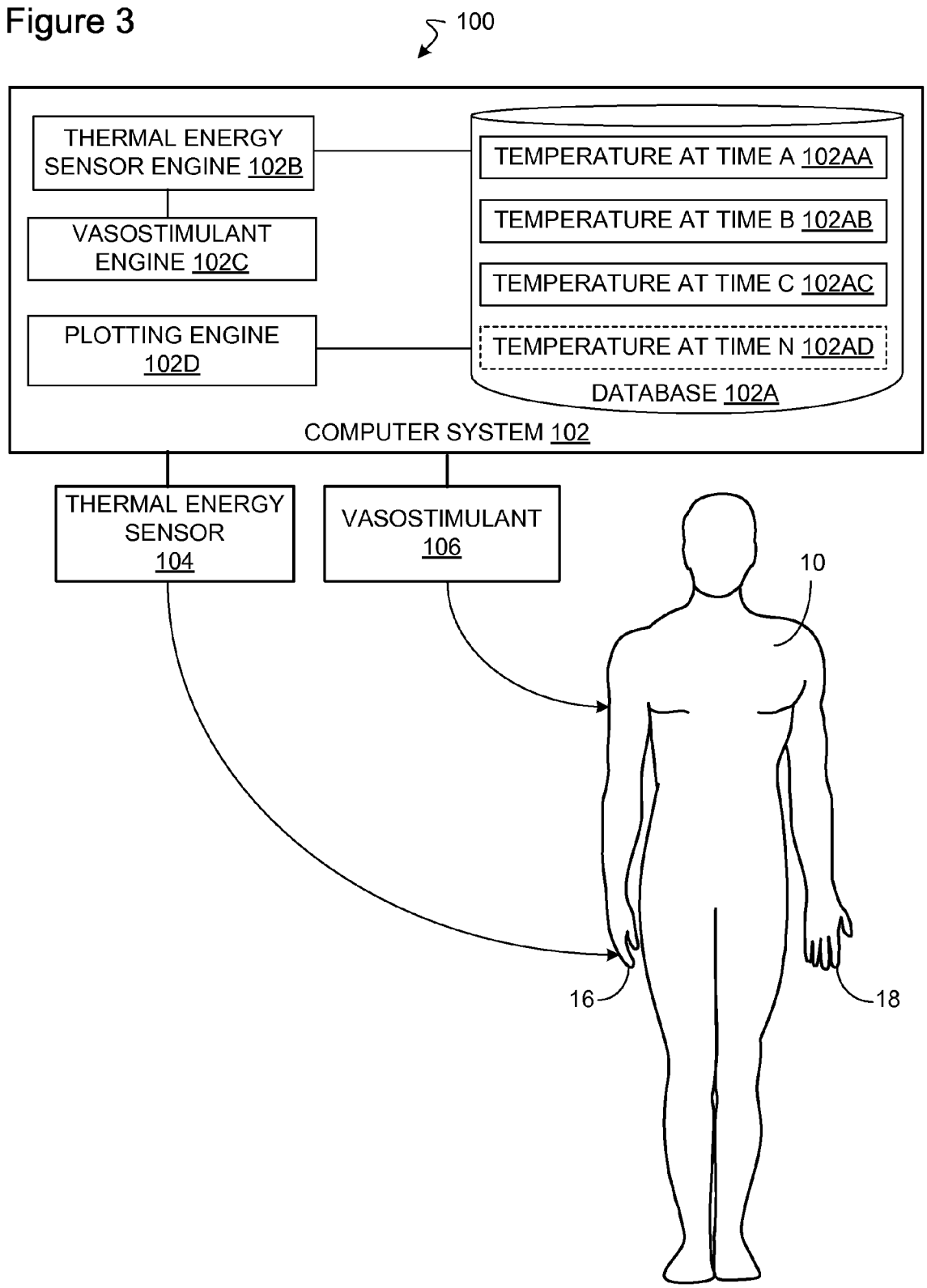
FIG. 3 is a schematic view illustrating an exemplary embodiment of a computer system used with the apparatus of FIG. 2.

Referring now to FIG. 3, in an exemplary embodiment, the computer system 102 includes a database 102a. A thermal energy sensor engine 102b is operably coupled to the database 102a. A vasostimulant engine 102c is operably coupled to the database 102a and the thermal energy sensor engine 102b. A plotting engine 102d is operably coupled to the database 102a. In an exemplary embodiment, the thermal energy sensor engine 102b, vasostimulant engine 102c, and the plotting engine 102d may be, for example, a variety of conventional software engines known in the art. In several exemplary embodiment, the thermal energy sensor engine 102b is adapted to control a thermal energy sensor such as, for example, the thermal energy sensor 104 illustrated in FIG. 3, which is operably coupled to the computer system 102. In several exemplary embodiments, the vasostimulant engine 102c is adapted to control a vasostimulant such as, for example, the vasostimulant 106 illustrated in FIG. 1, which is operably coupled to the computer system 102. In several exemplary embodiments, the plotting engine 102d is adapted to retrieve data in database 102a and manipulate the data in a variety of ways including, but not limited to, sorting the data, plotting the data, and displaying the data. In an exemplary embodiment, the computer system 102 is coupled to a therapeutic device which may be operable to perform a therapeutic function such as, for example, releasing oxygen. In an exemplary embodiment, the computer system 102 is coupled to an alerting device which may be, for example, operable to contact emergency medical services.

Referring now to FIG. 3, in an exemplary embodiment, the database 102a includes a plurality of data such as, for example, a temperature at time A 102aa, a temperature at time B 102ab, a temperature at time C 102ac, up to a temperature at time n 102ad. In an exemplary embodiment, the temperature data may include temperatures taken from one thermal energy sensor such as, for example, the thermal energy sensor 104 illustrated in FIG. 3, or from a plurality of thermal energy sensors.

Figures 4A, 4B:
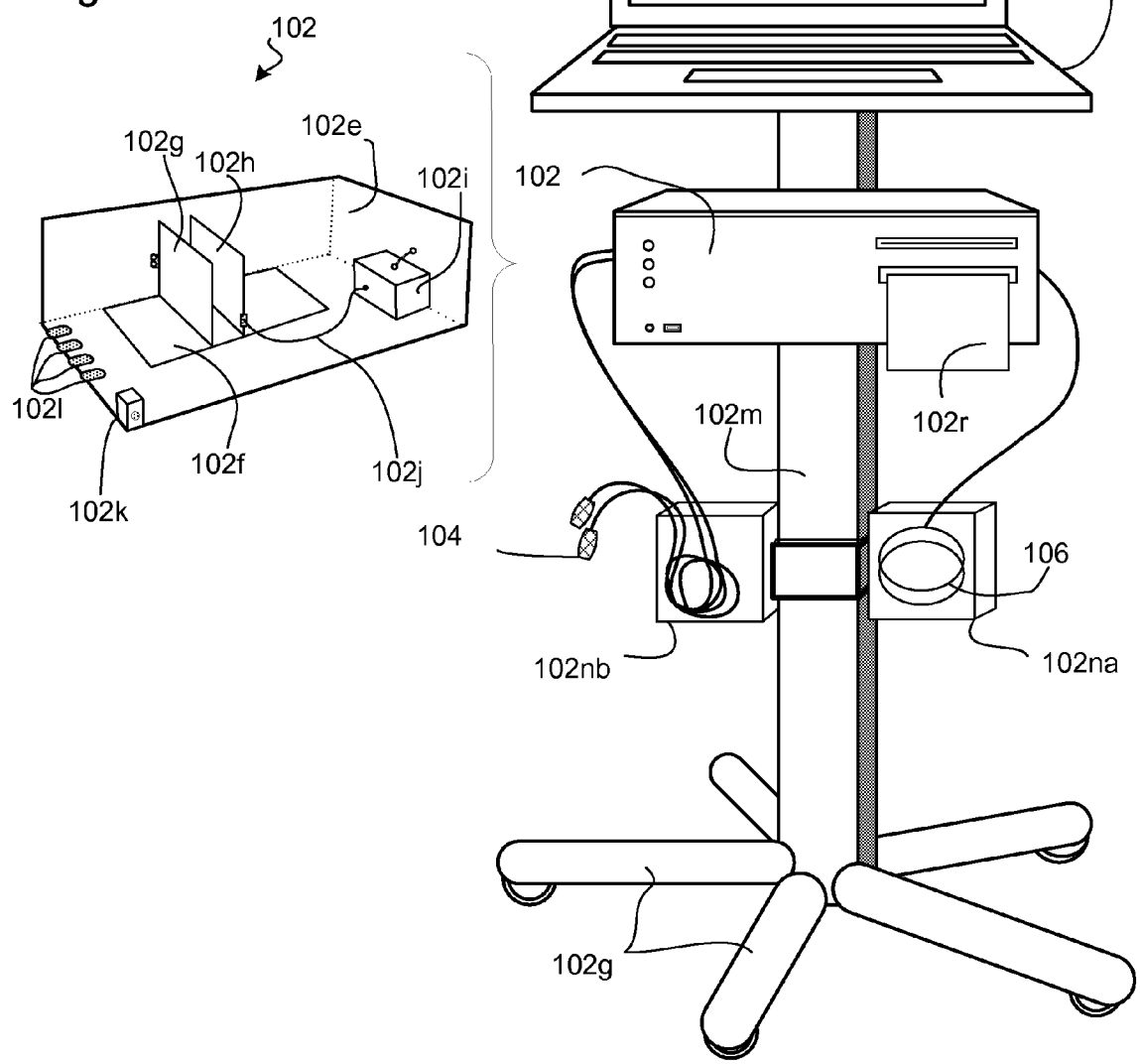
FIG. 4a is a cut away perspective view illustrating an exemplary embodiment of a computer system used with the apparatus of FIG. 2.
FIG. 4b is a perspective view illustrating an exemplary embodiment of a computer system used with the apparatus of FIG. 2.

Referring now to FIG. 4a, in an exemplary embodiment, the computer system 102 includes a chassis 102e. A computer board 102f is mounted to the chassis 102e and includes a thermal energy sensor card 102g and a vasostimulant card 102h coupled to and extending from the computer board 102f. A pump 102i is coupled to the vasostimulant card 102h by a wire 102j. In an exemplary embodiment, the chassis 102e may include wireless interface 102k for allowing wireless communication to the computer board 102f. In an exemplary embodiment, the chassis may include a plurality of communications ports 102l mounted to a surface for allowing communication with the computer board 102f. In an exemplary embodiment, the thermal energy sensor card 102g is coupled to the thermal energy sensor 104, illustrated in FIG. 2. In an exemplary embodiment, the vasostimulant card 102h is coupled to the vasostimulant 106, illustrated in FIG. 2, through the pump 102i.

Referring now to FIG. 4b, in an exemplary embodiment, the computer system 102 is positioned on a chassis 102m. A plurality of storage units 102na and 102nb extend from opposite sides of the chassis 102m with the storage unit 102na providing storage for the vasostimulant 106, described above with reference to FIG. 2, and the storage unit 102nb providing storage for the thermal energy sensor 104, described above with reference to FIG. 2. A display 102o is mounted to and positioned on top of the chassis 102m and coupled to the computer system 102 in order to display data collected by the computer system 102. An input device 102p is mounted to the chassis 102m to provide input the computer system 102 and manipulate information displayed on the display 102o. In an exemplary embodiment, the chassis 102m includes a plurality of wheels 102q which are operable to allow moving of the chassis 102m. In an exemplary embodiment, the computer system 102 is operable to produce an output 102r which includes data collected by the computer system 102.

Figure 5:
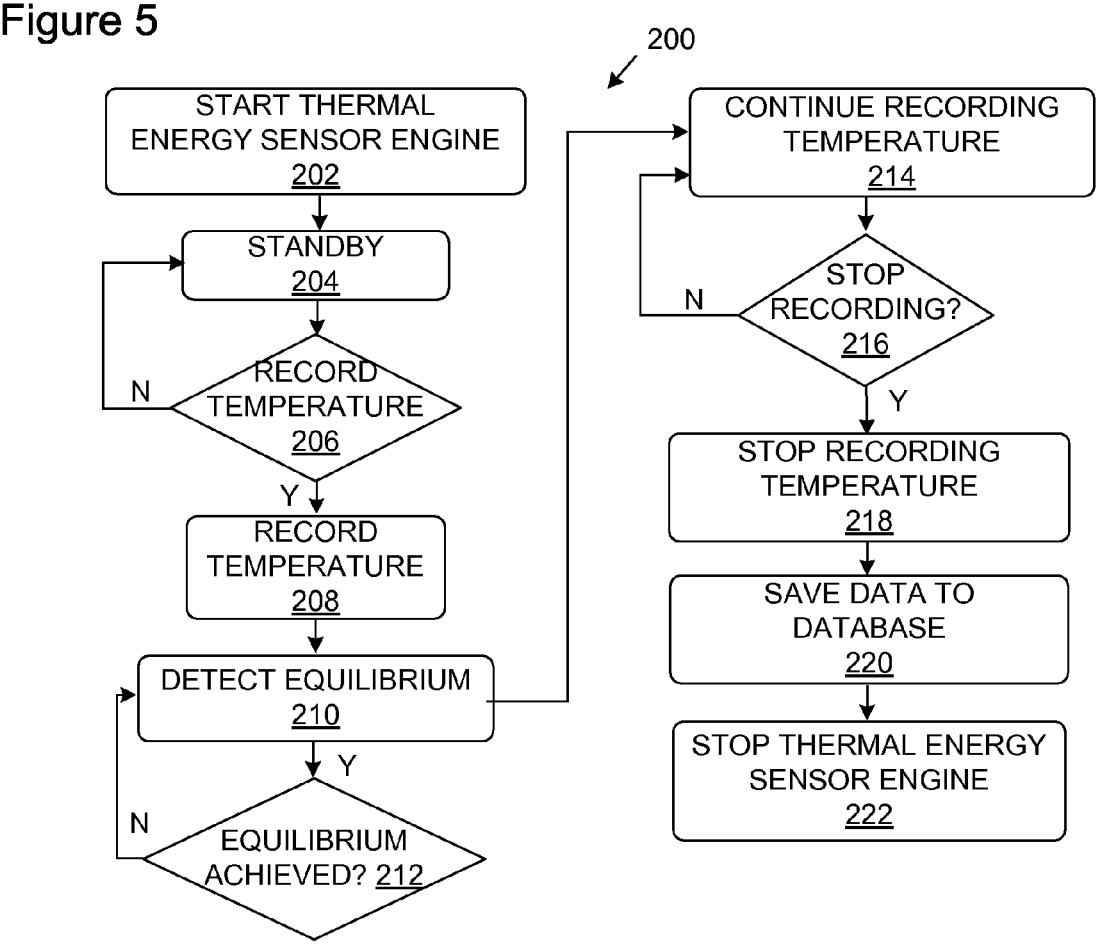
FIG. 5 is a flow chart illustrating an exemplary embodiment of the function of a thermal energy sensor engine used in the computer system of FIG. 3.

Referring now to FIG. 5, in an exemplary embodiment, a method for controlling a thermal energy sensor 200 is illustrated in which a thermal energy sensor engine such as, for example, the thermal energy sensor engine 102b illustrated in FIG. 3, is started in step 202. Starting the thermal energy sensor engine 102b at step 202 allows the thermal energy sensor engine 102b to enter a standby mode at step 204. At decision block 206, the thermal energy sensor engine 102b determines whether it is time to start recording temperature with a thermal energy sensor such as, for example, the thermal energy sensor 104 illustrated in FIG. 2. If it is not time to start recording temperature, the method 200 returns to step 204 where the thermal energy sensor engine 102b remains on standby.

If it is time to start recording temperature, the thermal energy sensor engine 102b begins recording temperature at step 206 with the thermal energy sensor 104. The method 200 then proceeds to step 208 where the thermal energy sensor engine 102b begins to detect for temperature equilibrium in step 210. In an exemplary embodiment, at step 210, the thermal energy sensor engine begins comparing successive temperature measurements made by the thermal energy sensor 104. At decision block 212, the thermal energy sensor engine 102b determines whether temperature equilibrium has been achieved. In an exemplary embodiment, temperature equilibrium is achieved when temperature changes recorded by the thermal energy sensor 104 are less than 0.1 degrees C. If the equilibrium has not been achieved, the method 200 returns to step 210 where the thermal energy sensor engine 102b detects for temperature equilibrium.

If equilibrium has been achieved, the method 200 proceeds to step 214 where the thermal energy sensor engine 102b continues recording temperature measurements made by the thermal energy sensor 104. At decision block 216, the thermal energy sensor engine 102b determines whether to stop recording. In an exemplary embodiment, the thermal energy sensor engine 102b will stop recording when temperature measurements from the thermal energy sensor 104 have stabilized. If it is not time to stop recording, the method 200 returns to step 214 where the thermal energy sensor engine 102b continues recording temperature measurements made by the thermal energy sensor 104.

If it is time to stop recording, the method 200 proceeds to step 218 where the thermal energy sensor engine 102b stops recording temperature measurements made by the thermal energy sensor 104. The method then proceeds to step 220 where the temperature measurements recorded by the thermal energy sensor engine 102*b* are saved to a database such as, for example, the database 102 illustrated in FIG. 3. The method 200 then proceeds to step 222 where the thermal energy sensor engine 200 is stopped.

Figure 6:
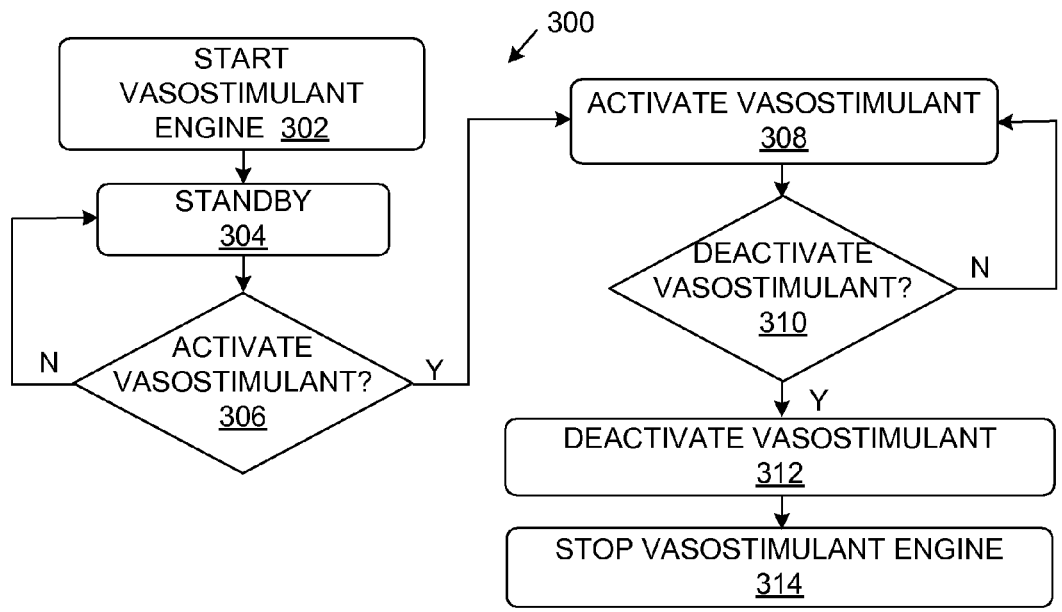
FIG. 6 is a flow chart illustrating an exemplary embodiment of the function of a vasostimulant engine used in the computer system of FIG. 3.

Referring now to FIG. 6, in an exemplary embodiment, a method for controlling a vasostimulant engine 300 is illustrated in which a vasostimulant engine such as, for example, the vasostimulant engine 102*c* illustrated in FIG. 3, is started in step 302. Starting the vasostimulant engine 102*c* at step 302 allows the vasostimulant engine 102*c* to enter a standby mode at step 304. At decision block 306, the vasostimulant engine 102*c* determines whether to activate a vasostimulant such as, for example, the vasostimulant 106 illustrated in FIG. 3. If it is not time to activate the vasostimulant 106, the method 300 returns to step 304 where the vasostimulant engine 300 remains on standby.

If it is time to activate the vasostimulant 106, the method 300 proceeds to step 308 where the vasostimulant engine 102*c* activates the vasostimulant 106. At decision block 310, the vasostimulant engine 102*c* determines whether it is time to deactivate the vasostimulant 106. If it is not time to deactivate the vasostimulant 106, the method 300 returns to step 308 where the vasostimulant engine 102*c* keeps the vasostimulant 106 activated.

If it is time to deactivate the vasostimulant 106, the method 300 proceeds to step 312 where the vasostimulant engine 102*c* deactivates the vasostimulant 106. The method 300 then proceeds to step 314 where the vasostimulant engine 102*c* is stopped.

Figure 7:
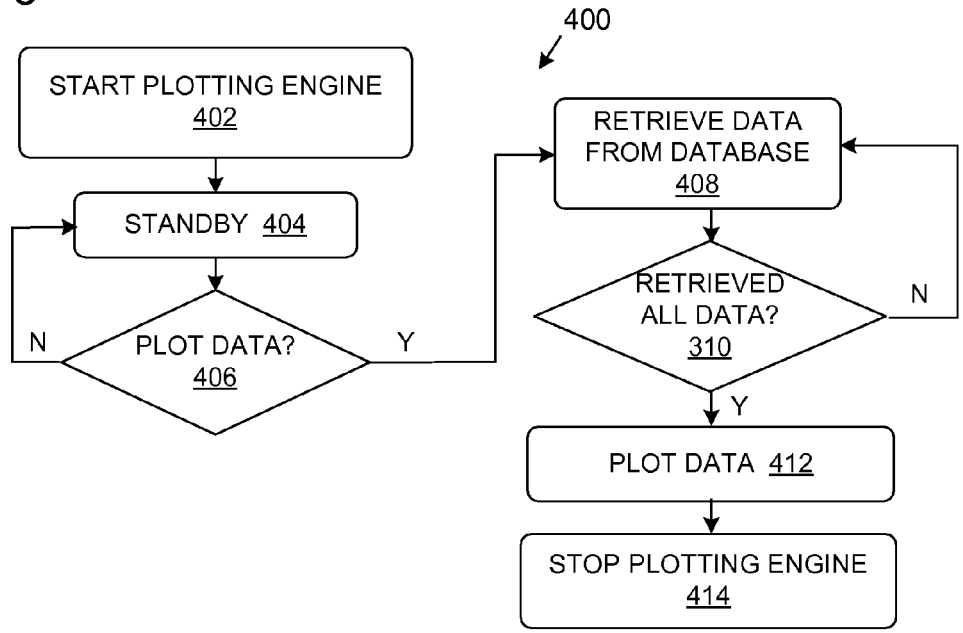
FIG. 7 is a flow chart illustrating an exemplary embodiment of the function of a plotting engine used in the computer system of FIG. 3.

Referring now to FIG. 7, in an exemplary embodiment, a method for controlling a plotting engine 400 is illustrated in which a plotting engine such as, for example, the plotting engine 102*d* illustrated in FIG. 3, is started in step 402. Starting the plotting engine 102*d* at step 402 allows the plotting engine 102*d* to enter a standby mode at step 404. At decision block 406, the plotting engine 102*d* determines whether it is time to plot data. If it is not time to plot data, the method 400 returns to step 404 where the plotting engine 102*d* remains on standby.

If it is time to plot data, the method 400 proceeds to step 408 where the plotting engine 102*d* retrieves data from a database such as, for example, the database 102*a* illustrated in FIG. 3. At decision block 410, the plotting engine 102*d* determines whether all of the data needed has been retrieved from database 102*a*. If all the data has not been retrieved, the method 400 returns to step 408 where the plotting engine 102*d* continues to retrieve data from database 102*a*.

If all the data needed has been retrieved from database 102*a*, the method proceeds to step 412 where the plotting engine 102*d* plots the data. The method 400 then proceeds to step 414 where the plotting engine 102*d* is stopped.

Figure 8:
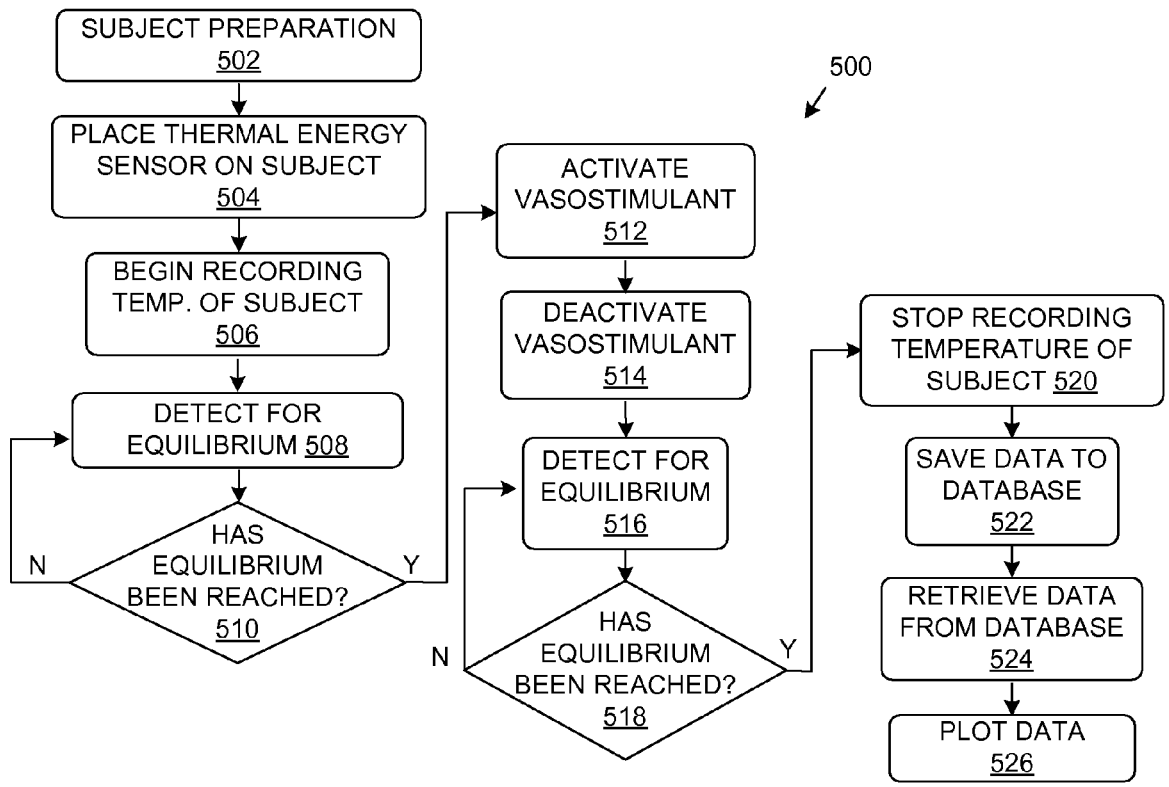
FIG. 8 is a flow chart illustrating an exemplary embodiment of a method for determining one or more health conditions.

Referring now to FIGS. 8*a* and 8*b*, in an exemplary embodiment, a method for determining one or more health conditions 500 is illustrated which begins with a subject preparation at step 502. Subject preparation at step 502 may include, for example, having a subject such as, for example, the subject 10 illustrated in FIG. 3, refrain from eating before carrying out the method 500, having the subject 10 refrain from smoking before carrying out the method 500, having the subject 10 refrain from ingesting alcohol or caffeine before carrying out the method 500, or having the subject 10 refrain from taking any vascular medications before carrying out the method 500, having the subject 10 refrain from exposure to cold weather before carrying out the method 500, ensuring the subject 10 is not experiencing urinary urgency or full bladder before carrying out the method 500, having the subject 10 refrain from physical or mental exercise before carrying out the method 500, and a variety of other factors that may temporarily affect vascular function known in the art. In an exemplary embodiment, the subject preparation at step 502 may begin at least 12 hours prior to the method 500 proceeding to step 504.

At step 504, a thermal energy sensor such as, for example, the thermal energy sensor 104 illustrated in FIG. 3, may be placed on the subject 10. In an exemplary embodiment, the thermal energy sensor 104 may be a conventional thermal energy sensor known in the art. In an exemplary embodiment, the thermal energy sensor 104 is designed such that there is a minimal area of contact between the sensor and the subject 10. In an exemplary embodiment, when placed on the subject 10, the thermal energy sensor 104 provides a minimal pressure to the subject 10. In an exemplary embodiment, in operation, the thermal energy sensor 104 measures thermal energy only and does not introduce any signals into the subject 10. In an exemplary embodiment, thermal energy measured by the thermal energy sensor 104 is not effected by insulation or perspiration. In an exemplary embodiment, the thermal energy sensor 104 does not alter the microcapillary flow in the subject 10. In an exemplary embodiment, the thermal energy sensor 104 does not restrict movement of the subject 10 and thermal energy measurements are not effected by subject 10 movement. In an exemplary embodiment, a plurality of thermal energy sensor 104 may be positioned at different locations on the subject 10. In an exemplary embodiment, the thermal energy sensor 104 is positioned on a body part of the subject 10 such as, for example, the finger 16, forearm, toe, leg, an earlobe, a rectum, or a nose. In an exemplary embodiment, the thermal energy sensor 104 may be placed on the subject 10 in order to measure the thermal energy of distal resistant vessels on the subject 10. In an exemplary embodiment, the thermal energy sensor 104 may allow the visualization of thermal response by infrared thermal energy measuring devices such as, for example, cameras, thermosensors, and/or thermocouples. In an exemplary embodiment, the thermal energy sensor 104 minimizes the temperature changes associated with the contact of the skin surface and thermal energy sensor 104 and allows the thermal energy sensor 104 to be minimally effected by factors and conditions that change skin temperature but are not associated with changes in blood flow, subcutaneous blood flow, tissue heat generation, and/or tissue heat transduction. In an exemplary embodiment, the method 500 may be carried out invasively and the thermal energy sensor 104 may placed beneath the surface of the skin such as, for example, in the subcutaneous region, the intramuscular region, the intravascular region, within the surrounding tissue, and/or inside the body.

At step 506, a thermal energy sensor engine such as, for example, the thermal energy sensor engine 102*b* illustrated in FIG. 3, activates a thermal energy sensor such as, for example, the thermal energy sensor 104 illustrated in FIG. 3, to begin recording the temperature of the subject 10. In an exemplary embodiment, temperature data begins being recorded continuously. In an exemplary embodiment, the thermal energy sensor 102*b* measures the skin temperature of the subject's body on which it is placed such as, for example, the hand, forearm, foot, leg, earlobe, rectum, or nose. In an exemplary embodiment, the thermal energy sensor 102*b* engages the skin of the subject 10 in order to measure temperature. In an exemplary embodiment, the thermal energy sensor 102*b* measures the skin temperature of the subject 10 without engaging the skin of the subject 10. In an exemplary embodiment, the ambient temperature is held constant around the thermal energy sensor 104. In an exemplary embodiment, the fluid flow such as, for example, the airflow, around the thermal energy sensor 104 is kept to a minimum. In an exemplary embodiment, the thermal energy sensor 104 includes an infrared thermal energy measurement device which measures the thermal response of the face or other highly vascular areas.

At step 508, the thermal energy sensor engine 102b begins to detect for equilibrium in the temperature of subject 10. In an exemplary embodiment, at step 508, the thermal energy sensor engine 102b retrieves successive temperature measurements from the thermal energy sensor 104.

At decision block 510, the thermal energy sensor engine 102b determines whether the temperature of the subject 10 has reached equilibrium. If the temperature of the subject 10 has not reached equilibrium, the temperature sensor engine proceeds back to step 508 to detect for equilibrium. In an exemplary embodiment, determining whether the temperature of the subject 10 has reached equilibrium in step 510 may include, for example, determining whether the temperature changes of a subject 10 are less than 0.1 degree C.

If the temperature changes in the subject 10 have reached equilibrium, the method proceeds to step 512 where a vasostimulant engine such as, for example, the vasostimulant engine 102c illustrated in FIG. 3, activates a vasostimulant such as, for example, the vasostimulant 106 illustrated in FIG. 3. In an exemplary embodiment, the vasostimulant 106 may be an inflatable cuff, and activating the vasostimulant 106 at step 512 may include, for example inflating the cuff to 200 mm Hg systolic BP. In an exemplary embodiment, the vasostimulant 106 may be a chemical such as, for example, nitroglycerin, and activating the vasostimulant 106 at step 512 may include administering a predetermined amount of the chemical to the subject 10. Further methods of providing a chemical vasostimulant 106 include injecting it into a vein or artery of the subject 10, having the subject 10 orally inject the chemical vasostimulant 106, having the subject 10 inhale the chemical vasostimulant 106, having the subject 10 sublingually absorb the chemical vasostimulant 106, and/or having the subject 10 diffuse the chemical vasostimulant 106 through their skin such as, for example, by having the subject diffuse 1% acetylcholine chloride for endothelium dependent assessment and 1% sodium nitroprusside for endothelium independent response. In an exemplary embodiment, the vasostimulant 106 may be an aptitude test, and activating the vasostimulant 106 at step 512 may include having the subject 10 begin the aptitude test. In an exemplary embodiment, providing the vasostimulant 106 may include rubbing a vasodilator cream such as, for example, a 1% topical acetylcholine cream on the skin of the subject 10 where significant subcutaneous fat exists such as, for example, the abdominal area. The continued recording of temperature may then include visualizing the thermal response of the subject 10 with an infrared thermal measurement device. In an exemplary embodiment, the provision of the vasostimulant 106 may include provision of modifiers of vasostimulators such as, for example, LNAME, which stops production of nitric oxide, or L-Arginine, which increases the nitric oxide level of endothelial cells.

At step 514, the vasostimulant engine 102c may deactivate the vasostimulant 106. In an exemplary embodiment, the vasostimulant 106 may be an inflatable cuff, and deactivating the vasostimulant 106 at step 514 may include deflating the cuff. In an exemplary embodiment, the vasostimulant 106 may be a chemical such as, for example, nitroglycerin, and deactivating the vasostimulant 106 at step 514 may include providing an amount of the chemical in step 512 such that the effects of the chemical on the subject 10 wear off in a predetermined amount of time. In an exemplary embodiment, deactivating the vasostimulant 106 at step 514 may include providing additional chemicals to the subject 10 to reverse the effects of the vasostimulant chemicals provided in step 512. In an exemplary embodiment, the vasostimulant 106 may be an aptitude test, and deactivating the vasostimulant 106 at step 514 may include having the subject 10 cease taking the aptitude test. In an exemplary embodiment, the vasostimulant is deactivated anywhere from 2 to 5 minutes after activation in step 512. In an exemplary embodiment, the vasostimulant is deactivated less than 5 minutes after activation in step 512, which is less than the conventional deactivation time for tests involving vasostimulation and provides a method which reduces the pain sometimes associated with vasostimulants. In an exemplary embodiment, the vasostimulant is deactivated less than 4 minutes after activation in step 512, which is less than the conventional deactivation time for tests involving vasostimulation and provides a method which reduces the pain sometimes associated with vasostimulants. In an exemplary embodiment, the vasostimulant is deactivated less than 3 minutes after activation in step 512, which is less than the conventional deactivation time for tests involving vasostimulation and provides a method which reduces the pain sometimes associated with vasostimulants. In an exemplary embodiment, the vasostimulant is deactivated approximately 2 minutes after activation in step 512, which is less than the conventional deactivation time for tests involving vasostimulation and provides a method which reduces the pain sometimes associated with vasostimulants. In an exemplary embodiment, the subject 10 may be asked to exercise the body part on which thermal energy is being detected, which allows the method 500 to simulate a longer vasostimulation in a shorter amount of time, which can also reduce the pain sometimes associated with vasostimulants.

At step 516, the thermal energy sensor engine 102b begins to detect for equilibrium in the temperature of subject 10. In an exemplary embodiment, at step 516, the thermal energy sensor engine 102b retrieves successive temperature measurement from the thermal energy sensor.

At decision block 518, the thermal energy sensor engine 102b determines whether the temperature of the subject 10 has reached equilibrium. If the temperature of the subject 10 has not reached equilibrium, the temperature sensor engine proceeds back to step 516 to detect for equilibrium. In an exemplary embodiment, determining whether the temperature of the subject 10 has reached equilibrium in step 518 may include, for example, determining whether the temperature changes of a subject 10 are less than 0.1 degree C.

If the temperature changes in the subject 10 have reached equilibrium, the method proceeds to step 520 where the temperature sensor engine 102b stops recording the temperature of the subject 10.

At step 522, data acquired from measuring and recording temperature changes which began at step 506 and continued throughout the method 500 is saved by the temperature sensor engine 102b to a database such as, for example, the database 102a illustrated in FIG. 3.

At step 524, a plotting engine such as, for example, the plotting engine 102d illustrated in FIG. 3, may retrieve data from the database 102a.

At step 526, the plotting engine 102d may plot out the data retrieved. In an exemplary embodiment, the data may be plotted out as temperature vs. time. In an exemplary embodiment, the plotting engine 102d may plot out data obtained from the temperature measurements concurrent with the data being obtained. In an exemplary embodiment, the plotting engine 102d may retrieve data taken from multiple positions on subject 10 and plot out an average of that data over time. In an exemplary embodiment, the plotting engine 102*d* may retrieve data taken from subject 10 at different times and plot out an average of that data.

Figure 9A:
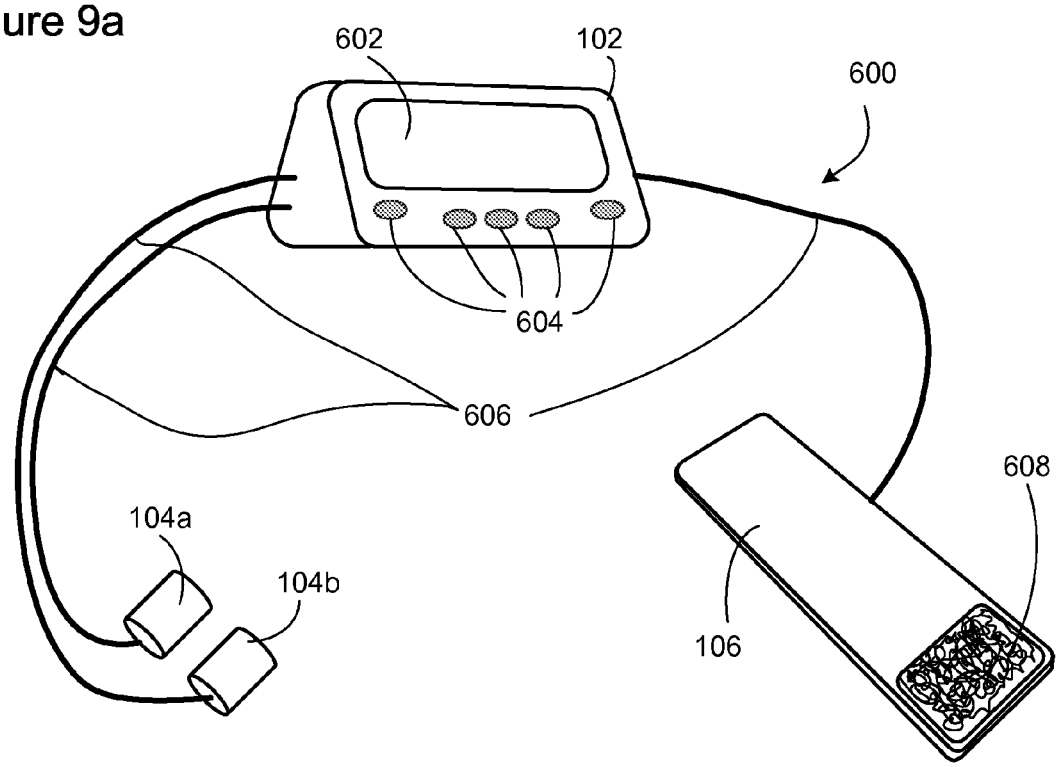
FIG. 9a is a perspective view illustrating an exemplary embodiment of an apparatus for determining one or more health conditions.
Figure 9B:
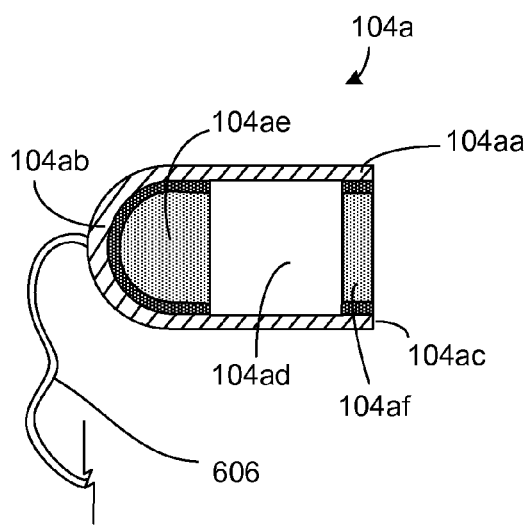
Figure 10A:
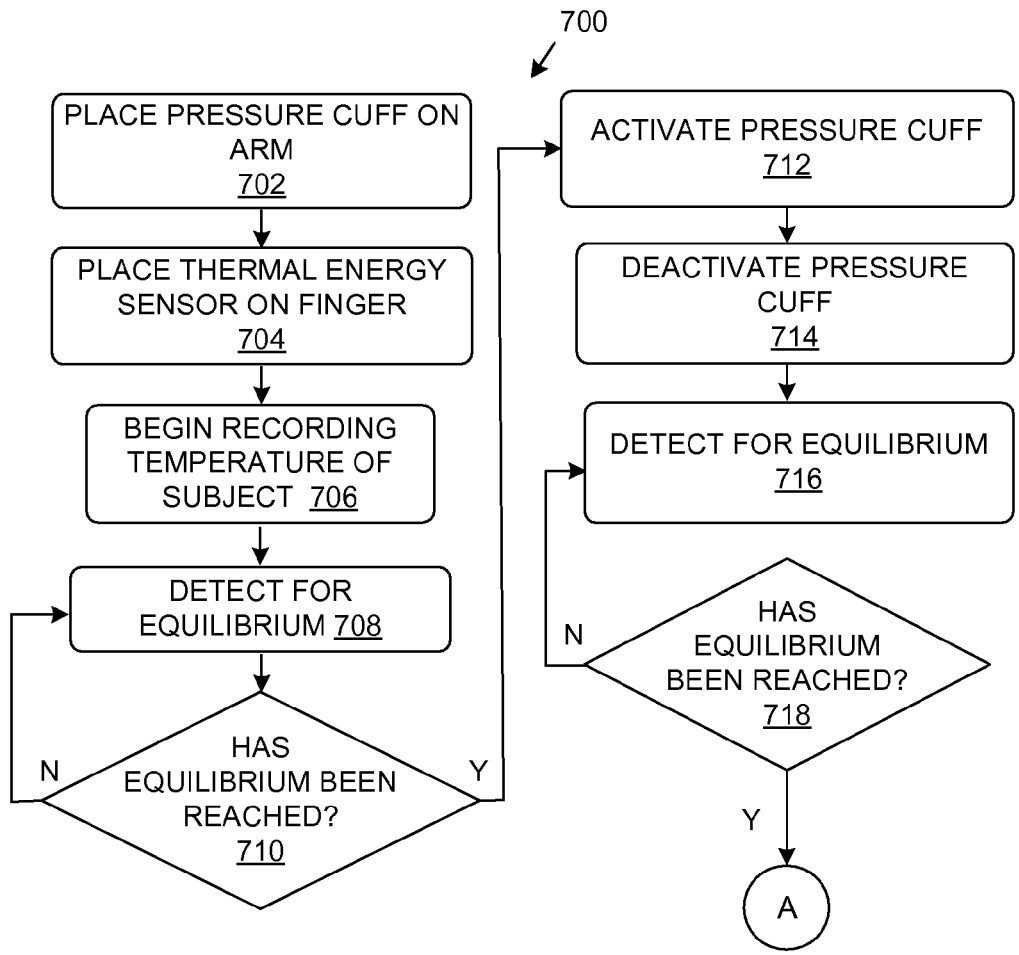
FIG. 10a is a flow chart illustrating an exemplary embodiment of a method for determining one or more health conditions using the apparatus of FIGS. 9a and 9b.
Figure 10B:
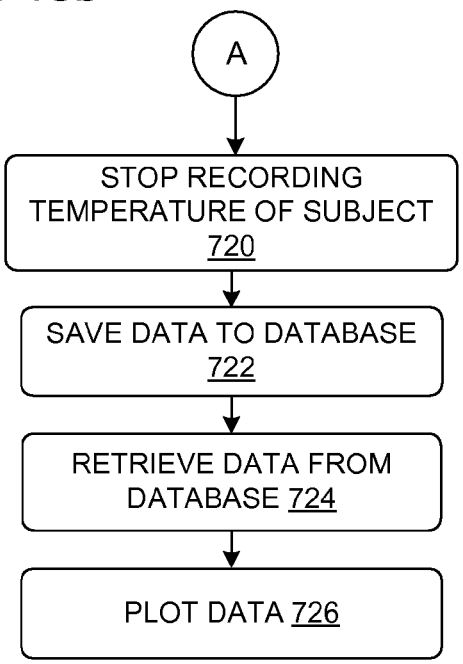
FIG. 10b is a flow chart illustrating an exemplary embodiment of a method for determining one or more health conditions using the apparatus of FIGS. 9a and 9b.
Figure 10C:
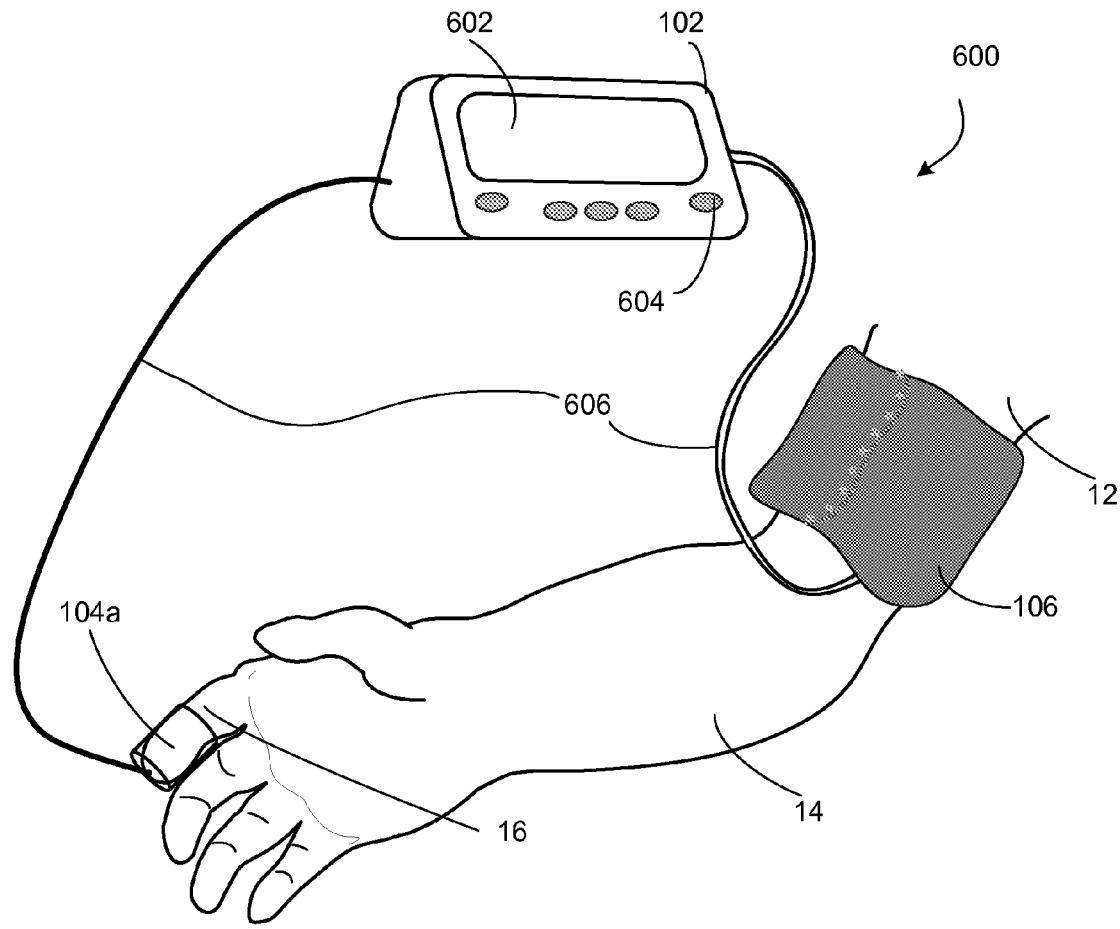
FIG. 10c is a perspective view illustrating an exemplary embodiment of the subject of FIG. 1 coupled to the apparatus of FIGS. 9a and 9b.
Figure 10D:
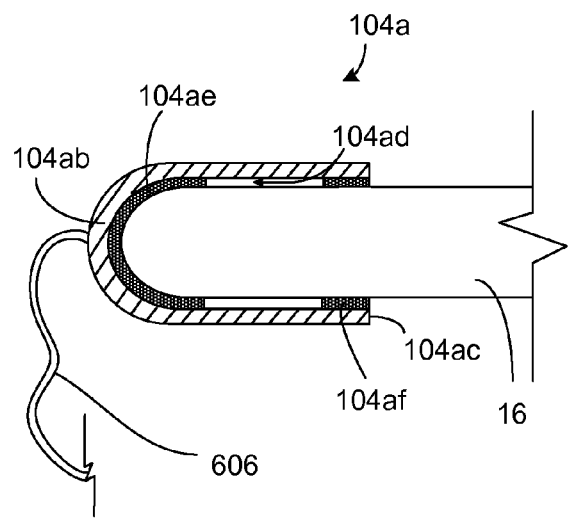
FIG. 10d is a perspective view illustrating an exemplary embodiment of the subject of FIG. 1 coupled to the apparatus of FIGS. 9a and 9b.
Figure 11A:
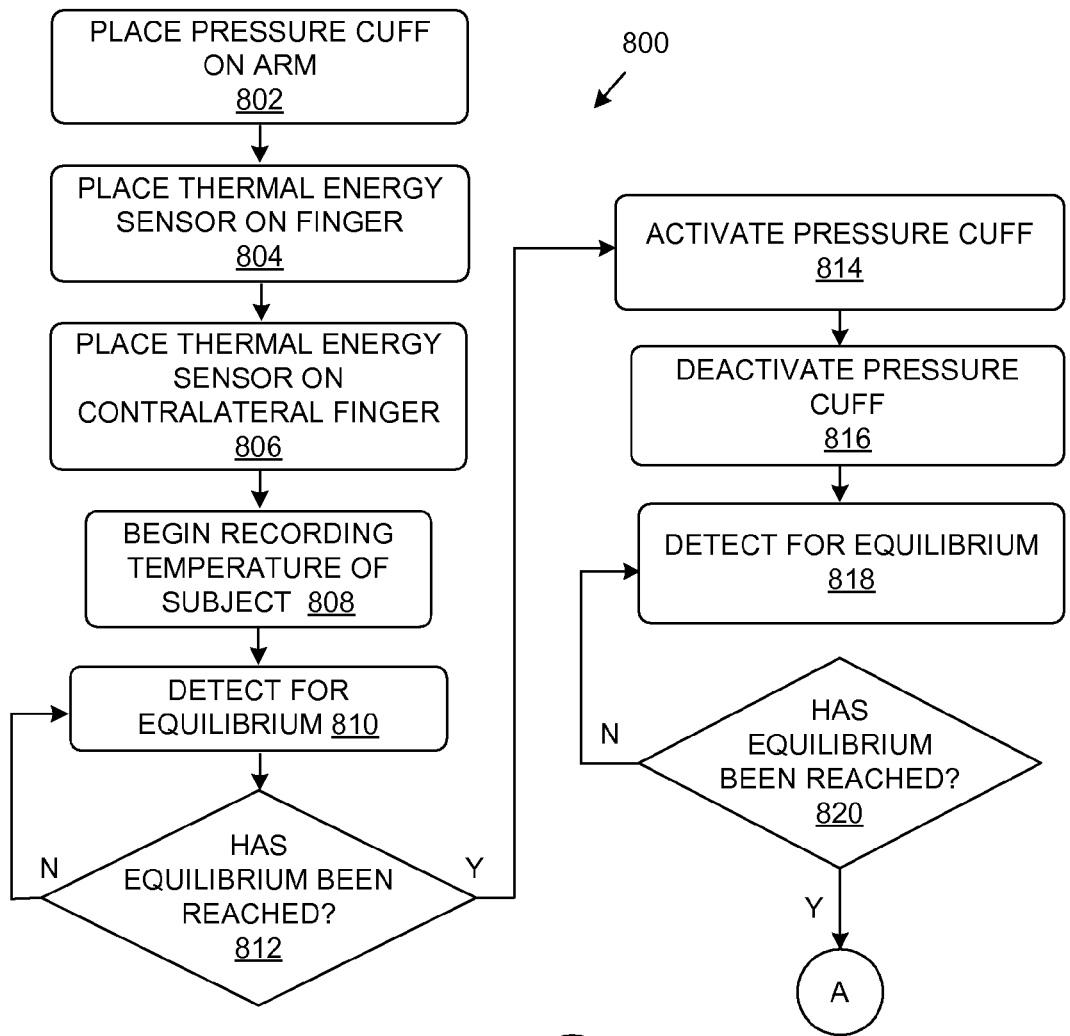
FIG. 11a is a flow chart illustrating an exemplary embodiment of a method for determining one or more health conditions using the apparatus of FIGS. 9a and 9b.
Figure 11B:
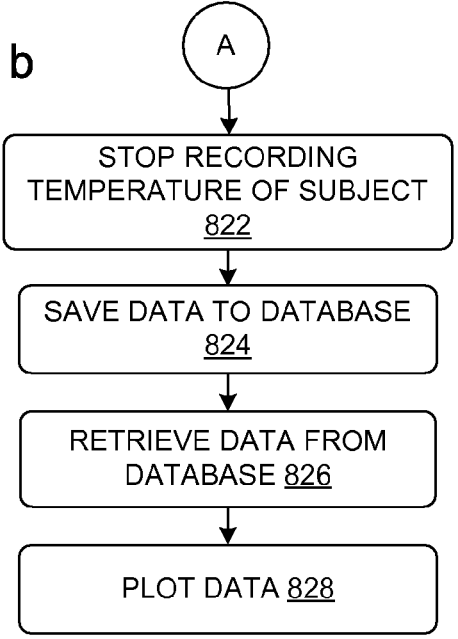
FIG. 11b is a flow chart illustrating an exemplary embodiment of a method for determining one or more health conditions using the apparatus of FIGS. 9a and 9b.
Figure 11C:
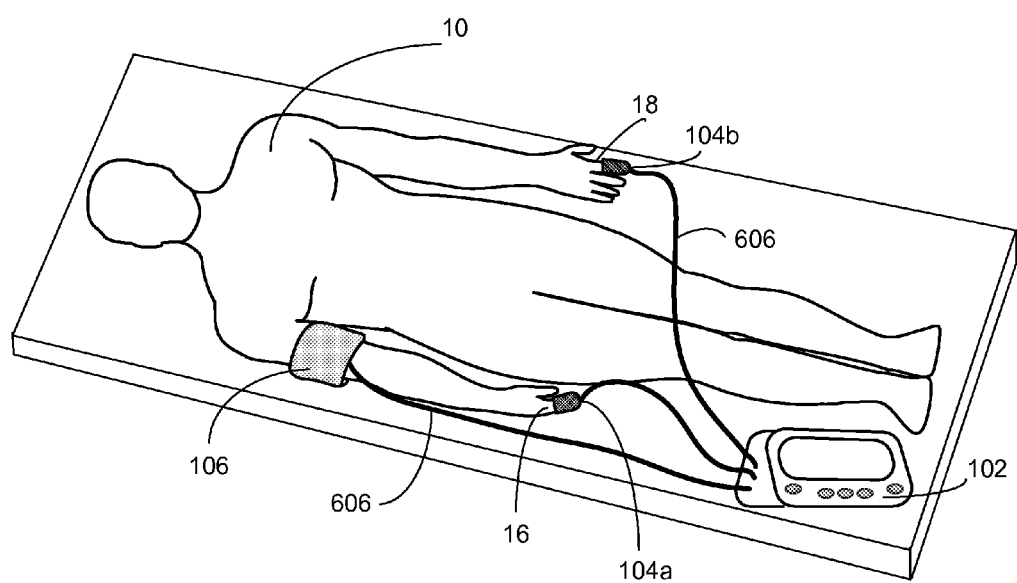
FIG. 11c is a perspective view illustrating an exemplary embodiment of the subject of FIG. 1 coupled to the apparatus of FIGS. 9a and 9b.
Figure 12A:
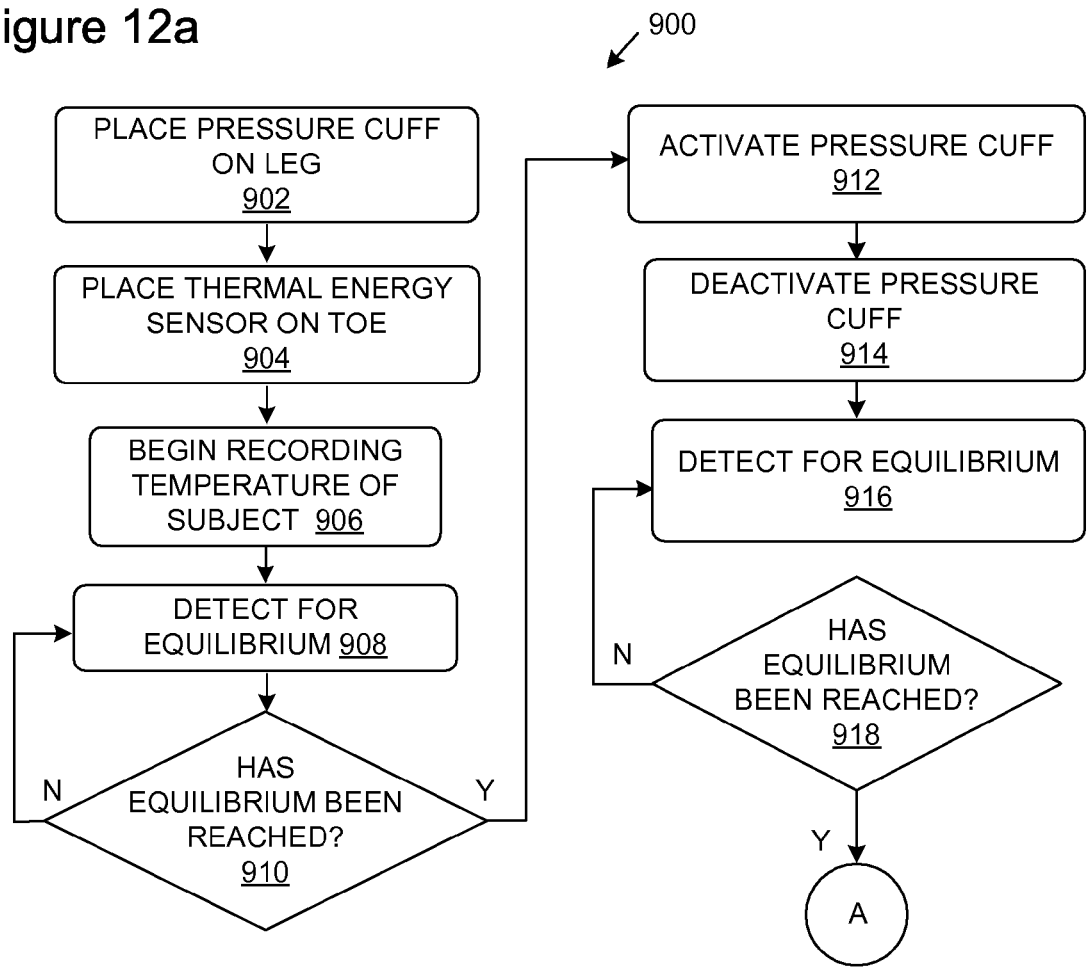
FIG. 12a is a flow chart illustrating an exemplary embodiment of a method for determining one or more health conditions using the apparatus of FIGS. 9a and 9b.
Figure 12B:
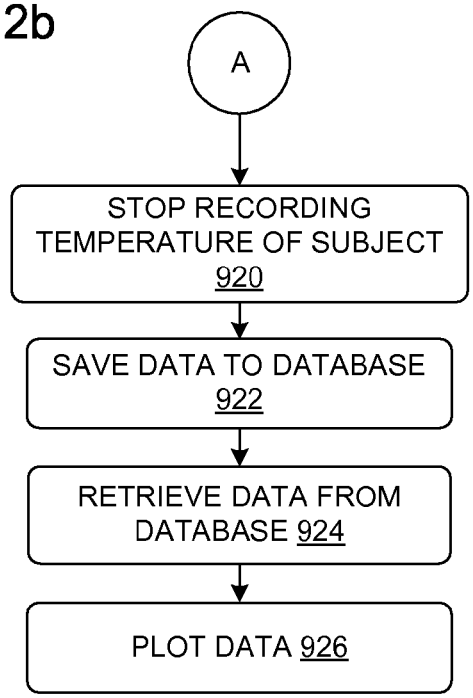
FIG. 12b is a flow chart illustrating an exemplary embodiment of a method for determining one or more health conditions using the apparatus of FIGS. 9a and 9b.
Figure 12C:
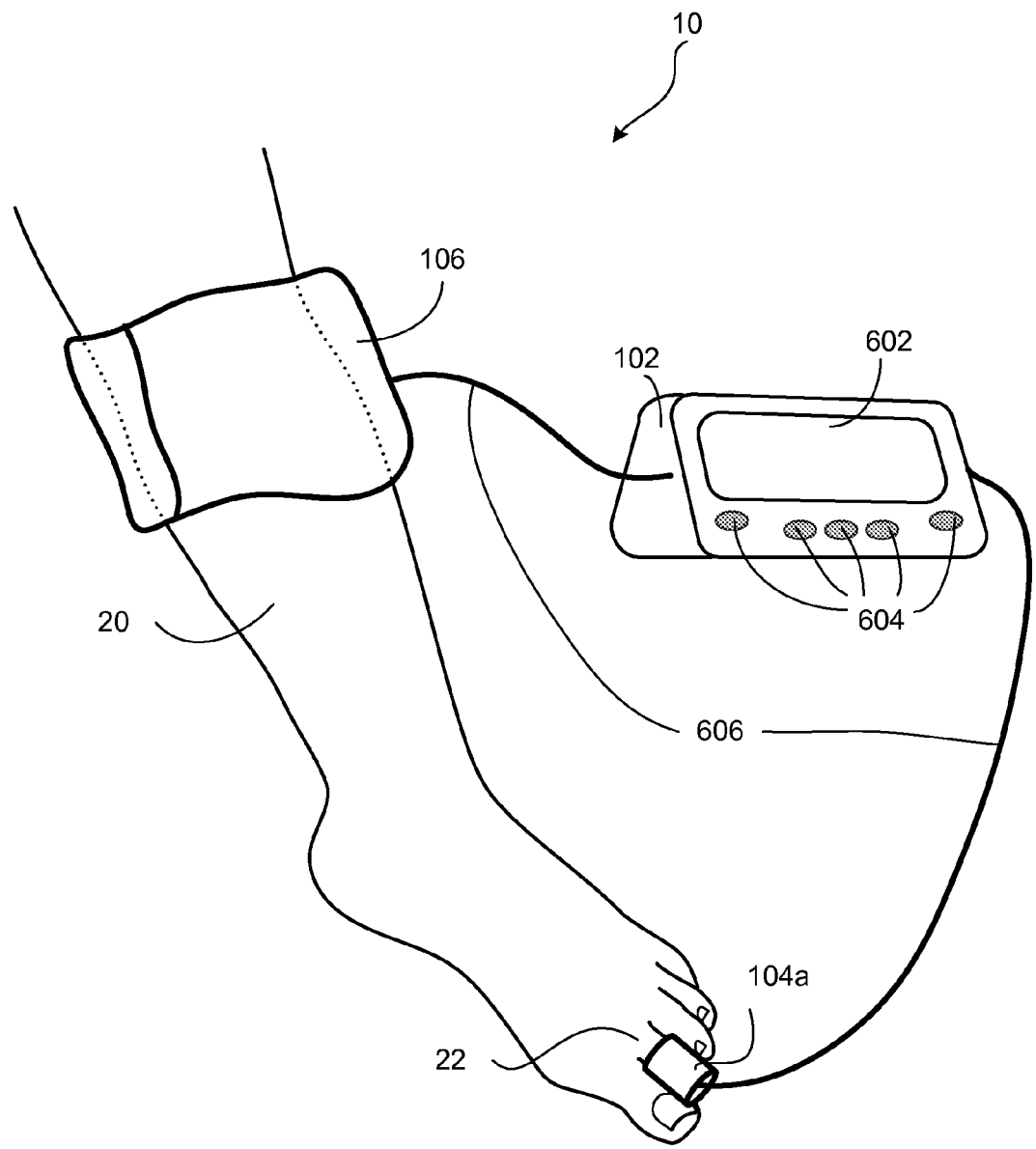
FIG. 12c is a perspective view illustrating an exemplary embodiment of the subject of FIG. 1 coupled to the apparatus of FIGS. 9a and 9b.

Referring now to FIGS. 9*a* and 9*b*, an alternative embodiment of an apparatus for determining one or more health conditions 600 is substantially identical in design and operation to apparatus 100 described above with reference to FIGS. 1, 2, 3, 4, 5, 6, 7, 8*a* and 8*b* with the addition of a display 602, a plurality of output buttons 604, a plurality of coupling wires 606, and vasostimulant coupling member 608. Computer system 102 includes the display 602 and the plurality of display output buttons 604 on a surface. A plurality of the thermal energy sensors 104*a* and 104*b* are coupled to the computer system 102 by respective coupling wires 606. The vasostimulator 106 is a pressure cuff and is coupled to the computer system 102 by coupling wire 606. The pressure cuff vasostimulator 106 includes a vasostimulant coupling member 608 along an edge of its length. In an exemplary embodiment, the pressure cuff vasostimulator 106 may be adapted to measure a subject's blood pressure. Thermal energy sensor 104*a* is substantially similar to thermal energy sensor 104*b* and includes a tubular housing 104*aa* with a hemispherical closed end 104*ab* and an open end 104*ac* opposite the closed end 104*ab*. The housing 104*aa* defines a passageway 104*ad* therein, and includes a thermal energy measurement device 104*ae* positioned in the passageway 104*ad* and adjacent the closed end 104*ab*. A coupling member 104*af* is positioned in the passageway 104*ad* adjacent the open end 104*ac*.

Referring now to FIGS. 10*a*, 10*b*, 10*c*, and 10*d*, in an exemplary embodiment, a method for determining one or more health conditions 700 using the apparatus 600 illustrated in FIGS. 9*a* and 9*b* is illustrated which begins with placing the pressure cuff vasostimulant 106 on arm 12 of subject 10 at step 702. Pressure cuff vasostimulant 106 may be secured to arm 12 by vasostimulant coupling member 608 which may include a variety of adhesive materials known in the art. In an exemplary embodiment, the subject 10 may be in a seated position during method 700.

At step 704, thermal energy sensor 104*a* may be placed on finger 16 of the subject 10. Finger 16 is placed in passageway 104*ad* of thermal energy sensor 104*a* such that a distal end of the finger 16 is coupled to thermal energy measurement device 104*ae*. With finger 16 coupled to thermal energy measurement device 104*ae*, coupling member 104*af* secures finger 16 in thermal energy sensor 104*a*.

At step 706, a thermal energy sensor engine such as, for example, the thermal energy sensor engine 102*b* illustrated in FIG. 3, activates the thermal energy sensor 104*a* to begin recording the skin temperature of the finger 16 of subject 10. In an exemplary embodiment, temperature data begins being recorded continuously. In an exemplary embodiment, the thermal energy sensor 104*a* engages the skin of the finger 16 of subject 10 in order to measure temperature. In an exemplary embodiment, the thermal energy sensor 104*a* measures the skin temperature of the finger 16 of subject 10 without engaging the skin of the finger 16 of subject 10. In an exemplary embodiment, the ambient temperature is held constant around the thermal energy sensor 104*a*. In an exemplary embodiment, the fluid flow such as, for example, the airflow, around the thermal energy sensor 104*a* is kept to a minimum.

At step 708, the thermal energy sensor engine 102*b* begins to detect for equilibrium in the skin temperature of the finger 16 of subject 10. In an exemplary embodiment, at step 508, the thermal energy sensor engine 102*b* retrieves successive temperature measurement from the thermal energy sensor 104*a*.

At decision block 710, the thermal energy sensor engine 102*b* determines whether the skin temperature of finger 106 of subject 10 has reached equilibrium. If the skin temperature of finger 16 has not reached equilibrium, the temperature sensor engine 102*b* proceeds back to step 708 to detect for equilibrium. In an exemplary embodiment, determining whether the skin temperature of the finger 16 has reached equilibrium in step 710 may include, for example, determining whether the temperature changes of the finger 16 are less than 0.1 degree C.

If the temperature changes in the finger 16 have reached equilibrium, the method proceeds to step 712 where a vasostimulant engine such as, for example, the vasostimulant engine 102*c* illustrated in FIG. 3, activates the pressure cuff vasostimulant 106. In an exemplary embodiment, activating the pressure cuff vasostimulant 106 at step 712 may include, for example, inflating the cuff to 200 mm Hg systolic BP.

At step 714, the vasostimulant engine 102*c* may deactivate the pressure cuff vasostimulant 106. In an exemplary embodiment, deactivating the pressure cuff vasostimulant 106 at step 714 may include deflating the cuff. In an exemplary embodiment, the pressure cuff vasostimulant 106 is deactivated anywhere from 2 to 5 minutes after activation in step 712. In an exemplary embodiment, the vasostimulant is deactivated less than 5 minutes after activation in step 712, which is less than the conventional deactivation time for tests involving vasostimulation and provides a method which reduces the pain sometimes associated with vasostimulants. In an exemplary embodiment, the vasostimulant is deactivated less than 4 minutes after activation in step 712, which is less than the conventional deactivation time for tests involving vasostimulation and provides a method which reduces the pain sometimes associated with vasostimulants. In an exemplary embodiment, the vasostimulant is deactivated less than 3 minutes after activation in step 712, which is less than the conventional deactivation time for tests involving vasostimulation and provides a method which reduces the pain sometimes associated with vasostimulants. In an exemplary embodiment, the vasostimulant is deactivated approximately 2 minutes after activation in step 712, which is less than the conventional deactivation time for tests involving vasostimulation and provides a method which reduces the pain sometimes associated with vasostimulants. In an exemplary embodiment, the subject 10 may be asked to exercise the body part on which thermal energy is being detected, which allows the method 700 to simulate a longer vasostimulation in a shorter amount of time, which can also reduce the pain sometimes associated with vasostimulants.

At step 716, the thermal energy sensor engine 102*b* begins to detect for equilibrium in the skin temperature of the finger 16 of subject 10. In an exemplary embodiment, at step 716, the thermal energy sensor engine 102*b* retrieves successive temperature measurement from the thermal energy sensor 104*a*.

At decision block 718, the thermal energy sensor engine 102*b* determines whether the skin temperature of the finger 16 of subject 10 has reached equilibrium. If the skin temperature of the finger 16 has not reached equilibrium, the temperature sensor engine 102*b* proceeds back to step 716 to detect for equilibrium. In an exemplary embodiment, determining whether the skin temperature of the finger 16 has reached equilibrium in step 718 may include, for example, determining whether the temperature changes of the finger 16 are less than 0.1 degree C.

If the temperature changes in the finger 16 have reached equilibrium, the method proceeds to step 720 where the temperature sensor engine 102b stops recording the skin temperature of the finger 16 of subject 10.

At step 722, data acquired from measuring and recording temperature changes of finger 16 which began at step 706 and continued throughout the method 700 is saved by the temperature sensor engine 102b to a database such as, for example, the database 102a illustrated in FIG. 3.

At step 724, a plotting engine such as, for example, the plotting engine 102d illustrated in FIG. 3, may retrieve data from the database 102a.

At step 726, the plotting engine 102d may plot out the data retrieved. In an exemplary embodiment, the data may be plotted out as temperature vs. time. In an exemplary embodiment, the plotting engine 102d may plot out data obtained from the temperature measurements concurrent with the data being obtained.

Referring now to FIGS. 9a, 9b, 11a, 11b, and 11c, in an exemplary embodiment, a method for determining one or more health conditions 800 using the apparatus 600 illustrated in FIGS. 9a and 9b is illustrated which begins with placing the pressure cuff vasostimulant 106 on arm 12 of subject 10 at step 802. Pressure cuff vasostimulant 106 may be secured to arm 12 by vasostimulant coupling member 608 which may include a variety of adhesive materials known in the art. In an exemplary embodiment, the subject 10 may be in a seated position during method 700.

At step 804, thermal energy sensor 104a may be placed on finger 16 of the subject 10. Finger 16 is placed in passageway 104ad of thermal energy sensor 104a such that a distal end of the finger 16 is coupled to thermal energy measurement device 104ae. With finger 16 coupled to thermal energy measurement device 104ae, coupling member 104af secures finger 16 in thermal energy sensor 104a.

At step 806, thermal energy sensor 104b may be placed on contralateral finger 18 of the subject. Contralateral finger 18 is placed in thermal energy sensor 104b in substantially the same manner as finger 16 is place in thermal energy sensor 104a described above with reference to FIGS. 9a, 9b, 10c and 10d. In an exemplary embodiment, a plurality of thermal energy sensors similar to thermal energy sensor 104, illustrated in FIG. 3, may be placed on a plurality of contralateral body parts. In an exemplary embodiment, a contralateral body part includes any body part on the subject which is not directly affected by the vasostimulant activated in step 814 such as, for example, any body part on the subject which is not distal to the vasostimulant. In an exemplary embodiment, the thermal energy sensor 104b may be placed on the toe 22 of the subject.

At step 808, a thermal energy sensor engine such as, for example, the thermal energy sensor engine 102b illustrated in FIG. 3, activates the thermal energy sensors 104 to begin recording the skin temperature of the finger 16 and contralateral finger 18 of subject. In an exemplary embodiment, temperature data begins being recorded continuously. In an exemplary embodiment, the thermal energy sensors 104a and 104b engage the skin of the finger 16 and contralateral finger 18 of subject in order to measure temperature. In an exemplary embodiment, the thermal energy sensor 104a and 104b measure the skin temperature of the finger 16 and contralateral finger 18 of subject 10 without engaging the skin of the finger 16 and contralateral finger 18 of subject. In an exemplary embodiment, the ambient temperature is held constant around the thermal energy sensor 104a and 104b. In an exemplary embodiment, the fluid flow such as, for example, the airflow, around the thermal energy sensor 104a and 104b is kept to a minimum.

At step 810, the thermal energy sensor engine 102b begins to detect for equilibrium in the skin temperature of the finger 16 of subject. In an exemplary embodiment, at step 810, the thermal energy sensor engine 102b retrieves successive temperature measurement from the thermal energy sensor 104a.

At decision block 812, the thermal energy sensor engine 102b determines whether the skin temperature of finger 16 of subject has reached equilibrium. If the skin temperature of finger 16 has not reached equilibrium, the temperature sensor engine 102b proceeds back to step 810 to detect for equilibrium. In an exemplary embodiment, determining whether the skin temperature of the finger 16 has reached equilibrium in step 812 may include, for example, determining whether the temperature changes of the finger 16 are less than 0.1 degree C.

If the temperature changes in the finger 16 have reached equilibrium, the method proceeds to step 814 where a vasostimulant engine such as, for example, the vasostimulant engine 102c illustrated in FIG. 3, activates the pressure cuff vasostimulant 106. In an exemplary embodiment, activating the pressure cuff vasostimulant 106 at step 814 may include, for example, inflating the cuff to 200 mm Hg systolic BP.

At step 816, the vasostimulant engine 102c may deactivate the pressure cuff vasostimulant 106. In an exemplary embodiment, deactivating the pressure cuff vasostimulant 106 at step 816 may include deflating the cuff. In an exemplary embodiment, the pressure cuff vasostimulant 106 is deactivated anywhere from 2 to 5 minutes after activation in step 814. In an exemplary embodiment, the vasostimulant is deactivated less than 5 minutes after activation in step 814, which is less than the conventional deactivation time for tests involving vasostimulation and provides a method which reduces the pain sometimes associated with vasostimulants. In an exemplary embodiment, the vasostimulant is deactivated less than 4 minutes after activation in step 814, which is less than the conventional deactivation time for tests involving vasostimulation and provides a method which reduces the pain sometimes associated with vasostimulants. In an exemplary embodiment, the vasostimulant is deactivated less than 3 minutes after activation in step 814, which is less than the conventional deactivation time for tests involving vasostimulation and provides a method which reduces the pain sometimes associated with vasostimulants. In an exemplary embodiment, the vasostimulant is deactivated approximately 2 minutes after activation in step 814, which is less than the conventional deactivation time for tests involving vasostimulation and provides a method which reduces the pain sometimes associated with vasostimulants. In an exemplary embodiment, the subject 10 may be asked to exercise the body part on which thermal energy is being detected, which allows the method 800 to simulate a longer vasostimulation in a shorter amount of time, which can also reduce the pain sometimes associated with vasostimulants.

At step 818, the thermal energy sensor engine 102b begins to detect for equilibrium in the skin temperature of the finger 16 of subject 10. In an exemplary embodiment, at step 818, the thermal energy sensor engine 102b retrieves successive temperature measurement from the thermal energy sensor 104a. At decision block 820, the thermal energy sensor engine 102b determines whether the skin temperature of the finger 16 of subject 10 has reached equilibrium. If the skin temperature of the finger 16 has not reached equilibrium, the temperature sensor engine 102b proceeds back to step 818 to detect for equilibrium. In an exemplary embodiment, determining whether the skin temperature of the finger 16 has reached equilibrium in step 820 may include, for example, determining whether the temperature changes of the finger 16 are less than 0.1 degree C.

If the temperature changes in the finger 16 have reached equilibrium, the method proceeds to step 822 where the temperature sensor engine 102b stops recording the skin temperature of the finger 16 of subject 10. At step 824, data acquired from measuring and recording temperature changes of finger 16 and contralateral finger 18 which began at step 808 and continued throughout the method 800 is saved by the temperature sensor engine 102b to a database such as, for example, the database 102a illustrated in FIG. 3. At step 826, a plotting engine such as, for example, the plotting engine 102d illustrated in FIG. 3, may retrieve data from the database 102a.

At step 828, the plotting engine 102d may plot out the data retrieved. In an exemplary embodiment, the data may be plotted out as temperature vs. time. In an exemplary embodiment, the data for the finger 16 and contralateral finger 18 may be plotted on the same graph. In an exemplary embodiment, the plotting engine 102d may plot out data obtained from the temperature measurements concurrent with the data being obtained. In an exemplary embodiment, the temperature changes measured in the finger 16 may be adjusted based on the temperature changes measured in the contralateral finger 18. For example, the adjustment may include subtracting the temperature changes measured in the contralateral finger 18 from the temperature changes measured in the finger 16, or vice versa.

Referring now to FIGS. 9a, 9b, 12a, 12b, and 12c, in an exemplary embodiment, a method for determining one or more health conditions 900 using the apparatus 600 illustrated in FIGS. 9a and 9b is illustrated which begins with placing the pressure cuff vasostimulant 106 on a leg of subject 10 at step 902. Pressure cuff vasostimulant 106 may be secured to a leg by vasostimulant coupling member 608 which may include a variety of adhesive materials known in the art. At step 904, thermal energy sensor 104a may be placed on a toe of the subject 10. A toe is placed in thermal energy sensor 104b in substantially the same manner as finger 16 is place in thermal energy sensor 104a described above with reference to FIGS. 9a, 9b, 10c and 10d.

At step 906, a thermal energy sensor engine such as, for example, the thermal energy sensor engine 102b illustrated in FIG. 3, activates the thermal energy sensor 104a to begin recording the skin temperature of the toe of a subject. In an exemplary embodiment, temperature data begins being recorded continuously. In an exemplary embodiment, the thermal energy sensor 104a engages the skin of the toe in order to measure temperature. In an exemplary embodiment, the thermal energy sensor 104a measures the skin temperature of the toe without engaging the skin of the toe. In an exemplary embodiment, the ambient temperature is held constant around the thermal energy sensor 104a. In an exemplary embodiment, the fluid flow such as, for example, the airflow, around the thermal energy sensor 104a is kept to a minimum.

At step 908, the thermal energy sensor engine 102b begins to detect for equilibrium in the skin temperature of the toe. In an exemplary embodiment, at step 908, the thermal energy sensor engine 102b begins comparing successive temperature measurement from the thermal energy sensor 104a.

At decision block 910, the thermal energy sensor engine 102b determines whether the skin temperature of toe has reached equilibrium. If the skin temperature of toe has not reached equilibrium, the temperature sensor engine 102b proceeds back to step 908 to detect for equilibrium. In an exemplary embodiment, determining whether the skin temperature of the toe has reached equilibrium in step 812 may include, for example, determining whether the temperature changes of the toe are less than 0.1 degree C.

If the temperature changes in the toe have reached equilibrium, the method proceeds to step 912 where a vasostimulant engine such as, for example, the vasostimulant engine 102c illustrated in FIG. 3, activates the pressure cuff vasostimulant 106. In an exemplary embodiment, activating the pressure cuff vasostimulant 106 at step 912 may include, for example, inflating the cuff to 200 mm Hg systolic BP.

At step 914, the vasostimulant engine 102c may deactivate the pressure cuff vasostimulant 106. In an exemplary embodiment, deactivating the pressure cuff vasostimulant 106 at step 914 may include deflating the cuff. In an exemplary embodiment, the pressure cuff vasostimulant 106 is deactivated anywhere from 2 to 5 minutes after activation in step 912. In an exemplary embodiment, the vasostimulant is deactivated less than 5 minutes after activation in step 912, which is less than the conventional deactivation time for tests involving vasostimulation and provides a method which reduces the pain sometimes associated with vasostimulants. In an exemplary embodiment, the vasostimulant is deactivated less than 4 minutes after activation in step 912, which is less than the conventional deactivation time for tests involving vasostimulation and provides a method which reduces the pain sometimes associated with vasostimulants. In an exemplary embodiment, the vasostimulant is deactivated less than 3 minutes after activation in step 912, which is less than the conventional deactivation time for tests involving vasostimulation and provides a method which reduces the pain sometimes associated with vasostimulants. In an exemplary embodiment, the vasostimulant is deactivated approximately 2 minutes after activation in step 912, which is less than the conventional deactivation time for tests involving vasostimulation and provides a method which reduces the pain sometimes associated with vasostimulants. In an exemplary embodiment, the subject may be asked to exercise the body part on which thermal energy is being detected, which allows the method 900 to simulate a longer vasostimulation in a shorter amount of time, which can also reduce the pain sometimes associated with vasostimulants.

At step 916, the thermal energy sensor engine 102b begins to detect for equilibrium in the skin temperature of the toe. In an exemplary embodiment, at step 916, the thermal energy sensor engine 102b retrieves successive temperature measurement from the thermal energy sensor 104a. At decision block 918, the thermal energy sensor engine 102b determines whether the skin temperature of the toe has reached equilibrium. If the skin temperature of the toe has not reached equilibrium, the temperature sensor engine 102b proceeds back to step 916 to detect for equilibrium. In an exemplary embodiment, determining whether the skin temperature of the toe has reached equilibrium in step 918 may include, for example, determining whether the temperature changes of the toe are less than 0.1 degree C.

If the temperature changes in the toe has reached equilibrium, the method proceeds to step 920 where the temperature sensor engine 102b stops recording the skin temperature of the toe. At step 922, data acquired from measuring and recording temperature changes of toe 22 which began at step 906 and continued throughout the method 900 is saved by the temperature sensor engine 102b to a database such as, for example, the database 102a illustrated in FIG. 3. At step 924, a plotting engine such as, for example, the plotting engine 102d illustrated in FIG. 3, may retrieve data from the database 102a. At step 926, the plotting engine 102d may plot out the data retrieved. In an exemplary embodiment, the data may be plotted out as temperature vs. time. In an exemplary embodiment, the plotting engine 102d may plot out data obtained from the temperature measurements concurrent with the data being obtained.

Figure 13:
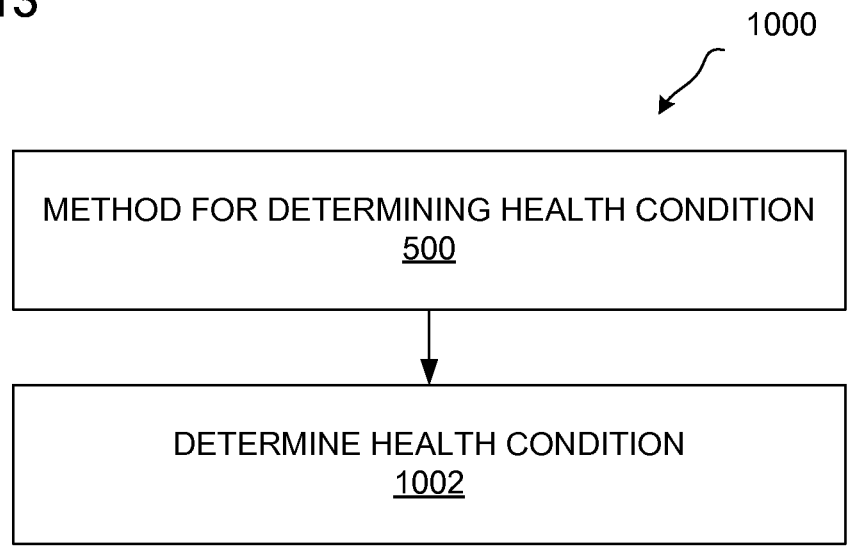
FIG. 13 is a flow chart illustrating an exemplary embodiment of a method for determining one or more health conditions using the apparatus of FIG. 2.

Referring now to FIG. 13, an alternative embodiment of a method for determining one or more health conditions 1000 is substantially identical in design and operation to method 500 described above with reference to FIGS. 8a and 8b, with the addition of determining health condition at step 1002. In an exemplary embodiment, determining health condition at step 1002 may involved a health care professional analyzing the temperature data in order to diagnose a variety of health conditions for the subject 10. In an several exemplary embodiments, determining a health condition at step 1002 includes, for example, assessing the risk of atherosclerotic cardiovascular disorder, monitoring the progression of heart failure, managing obesity, screening for high sympathetic reactivity, screening for high blood pressure, screening for white coat hypertension, screening for smooth muscle cell dysfunction, predicting the development of diabetes, determining a fitness level, assessing the vascular effects of a rheumatologic disorder, screening for Raynauld's phenomenon, predicting the risk of connective tissue disorders, determining the risk for pulmonary hypertension, monitoring a smoking cessation program, and monitoring sleep disorders such as, for example, sleep apnea.

Figure 14:
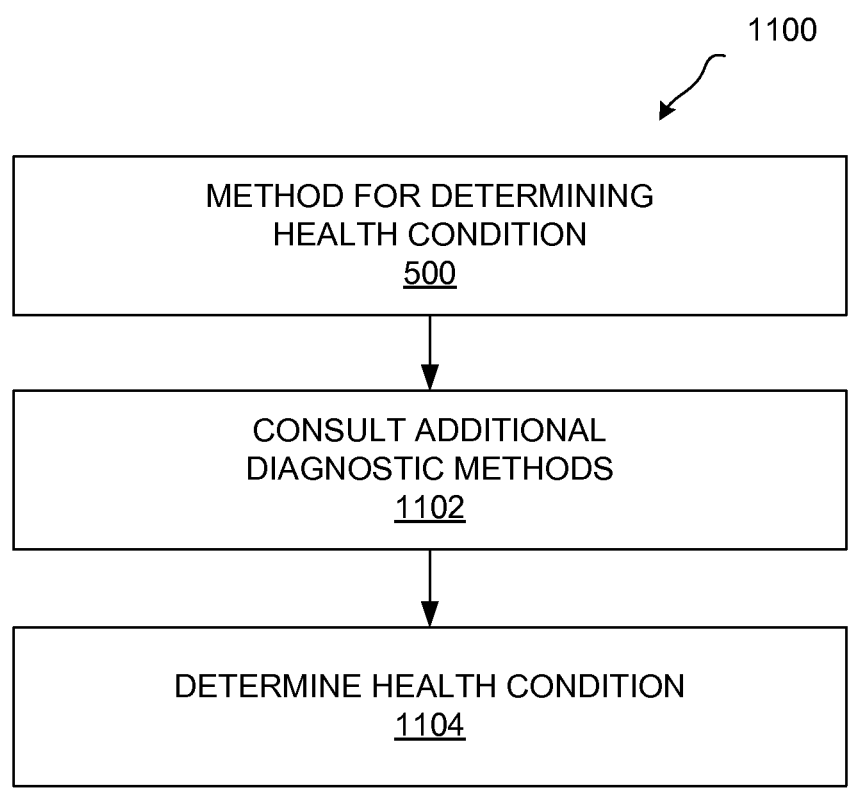
FIG. 14 is a flow chart illustrating an exemplary embodiment of a method for determining one or more health conditions using the apparatus of FIG. 2.

Referring now to FIG. 14, an alternative embodiment of a method for determining one or more health conditions 1100 is substantially identical in design and operation to method 500 described above with reference to FIGS. 8a and 8b, with the addition of consulting additional diagnosis methods at step 1102 and determining health condition at step 1104. In an exemplary embodiment, consulting additional diagnosis methods at step 1102 may involve measuring other parameters of subject 10 such as, for example, blood pressure, glucose level, internal temperature, and a variety of others. In an exemplary embodiment, determining health condition at step 1104 may involved a health care professional analyzing the temperature data along with data obtained from additional diagnosis methods in order to diagnose a variety of health conditions for the subject. In an several exemplary embodiments, determining a health condition at step 1002 includes, for example, assessing the risk of atherosclerotic cardiovascular disorder, monitoring the progression of heart failure, managing obesity, screening for high sympathetic reactivity, screening for high blood pressure, screening for white coat hypertension, screening for smooth muscle cell dysfunction, predicting the development of diabetes, determining a fitness level, assessing the vascular effects of a rheumatologic disorder, screening for Raynauld's phenomenon, predicting the risk of connective tissue disorders, determining the risk for pulmonary hypertension, monitoring a smoking cessation program, and monitoring sleep disorders such as, for example, sleep apnea.

Figure 15:
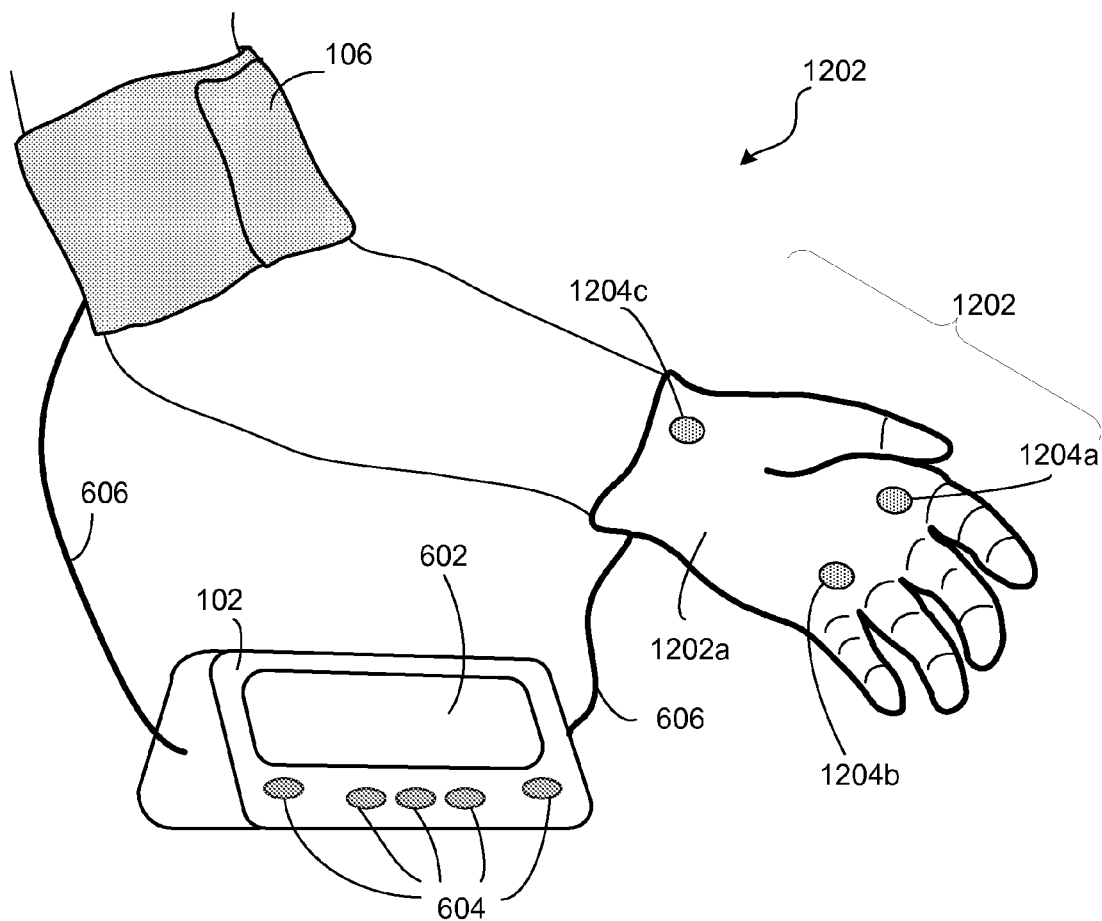
FIG. 15 is a perspective view illustrating an exemplary embodiment of an apparatus for determining one or more health conditions.

Referring now to FIG. 15, an alternative embodiment of an apparatus for determining one or more health conditions 1200 is substantially identical in design and operation to apparatus 600 described above with reference to FIGS. 9a, 9b, 10a, 10b, 10c, and 10d, with the addition of a thermal energy sensor 1202. Thermal energy sensor 1202 is coupled to computer system 102 by wire 606 and includes a glove 1202a including a plurality of thermal energy measurement devices 1204a, 1204b, and 1204c, which are positioned at different locations on the glove 1202a. Having the thermal energy measurement devices 1204a, 1204b, and 1204c positioned at different locations on the glove 1202a allows blood flow rate from device to device to be calculated. In an exemplary embodiment, glove 1202a may extend and cover the skin surface up to the vasostimulant 106.

Figure 16:
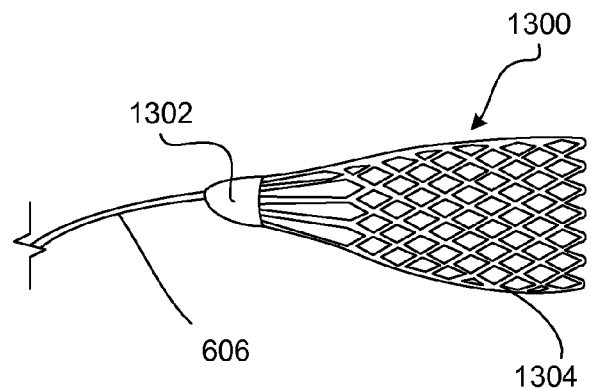
FIG. 16 is a side view illustrating an exemplary embodiment of a thermal energy sensor.

Referring now to FIG. 16, an alternative embodiment of an apparatus for determining one or more health conditions 1300 is substantially identical in design and operation to apparatus 600 described above with reference to FIGS. 9a, 9b, 10a, 10b, 10c, and 10d, with the addition of a thermal energy sensor 1302. Thermal energy sensor 1302 is coupled to computer system 102 by wire 606 and includes a coupler 1304 operable to couple the thermal energy sensor 1302 to subject 10 without substantially changing the temperature of the subject 10. In an exemplary embodiment, the coupler 1304 may be a mesh material or other similar materials that limit thermal insulation of the subject 10. In an exemplary embodiment, the coupler 1304 is operable to keep the thermal energy sensor 1302 in contact with the skin surface with minimal pressure, contact area, and insulation.

Figure 17:
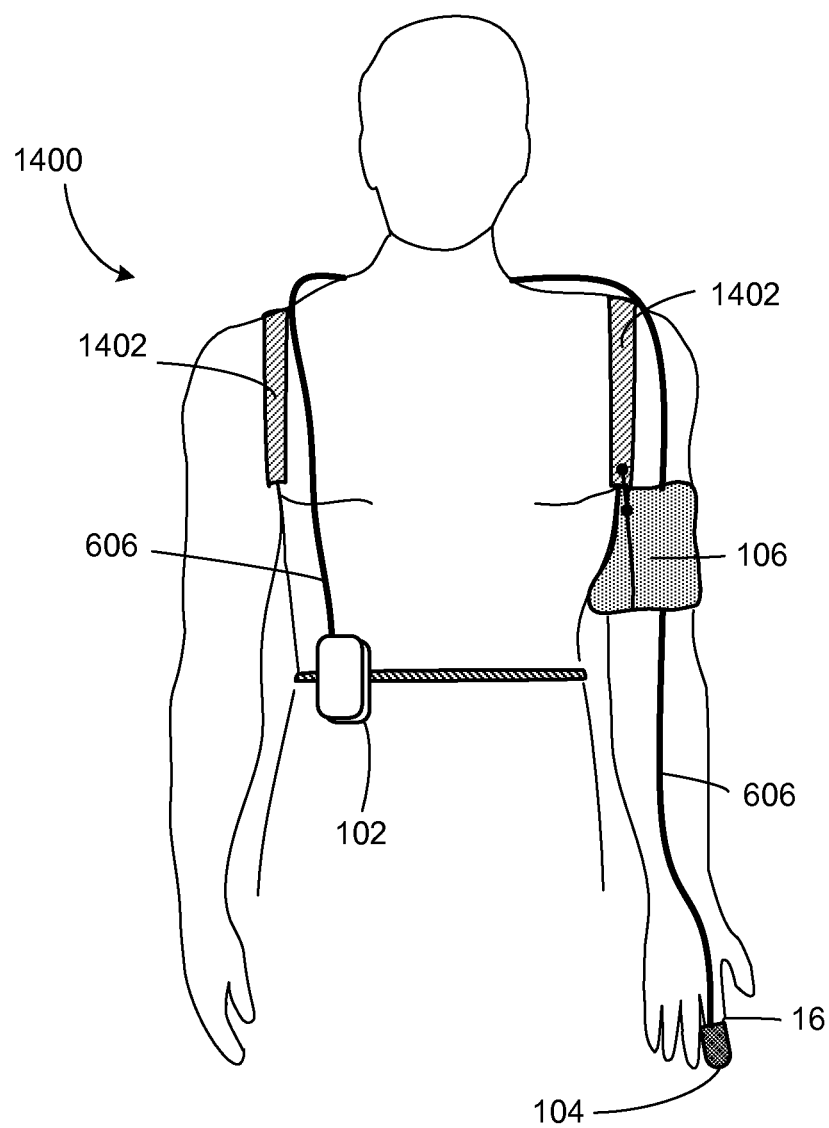
FIG. 17 is a front view illustrating an exemplary embodiment of an apparatus for determining one or more health conditions.
Figure 18A:
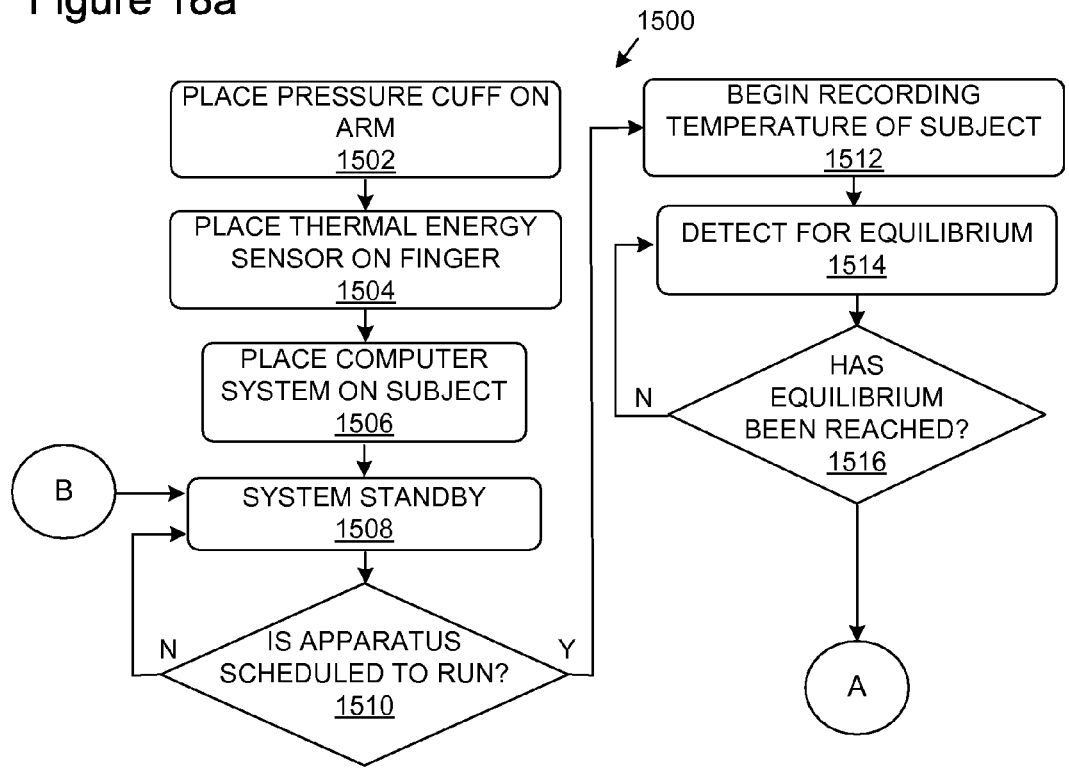
FIG. 18a is a flow chart illustrating an exemplary embodiment of a method for determining one or more health conditions using the apparatus of FIG. 17.
Figure 18B:
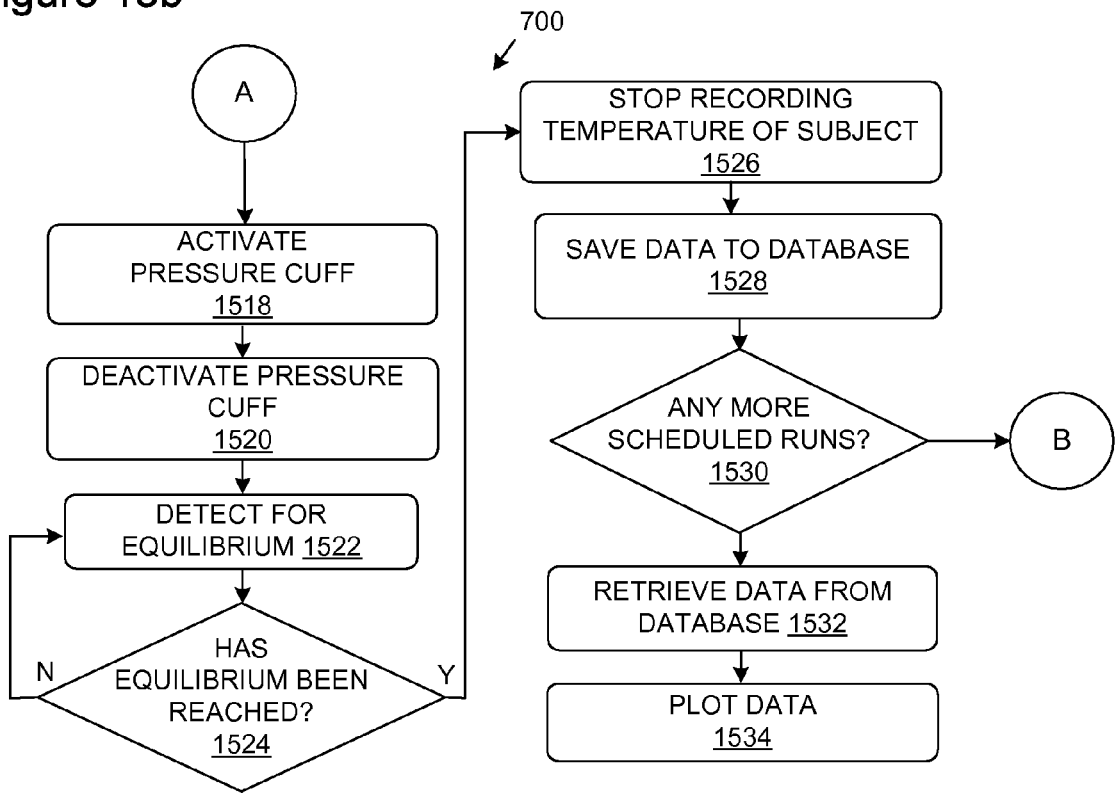
FIG. 18b is a flow chart illustrating an exemplary embodiment of a method for determining one or more health conditions using the apparatus of FIG. 17.

Referring now to FIG. 17, an alternative embodiment of an apparatus for determining one or more health conditions 1400 is substantially identical in design and operation to apparatus 600 described above with reference to FIGS. 9a, 9b, 10a, 10b, 10c, and 10d, with the addition of a support strap 1402. The support strap 1402 allows the apparatus 1400 to be coupled to the subject for repeated use of the apparatus throughout a predetermined time period such as, for example, 24 hours. In an exemplary embodiment, support strap 902 allows ambulatory measurements to be taken of the subject.

Referring now to FIGS. 9a, 9b, 17, 18a, and 18b, in an exemplary embodiment, a method for determining one or more health conditions 1500 using the apparatus 1400 illustrated in FIG. 17 is illustrated which begins with placing the pressure cuff vasostimulant 106 on arm 12 of subject 10 at step 1502. Pressure cuff vasostimulant 106 may be secured to arm 12 by vasostimulant coupling member 608 and with securing strap 1402, which keeps pressure cuff vasostimulant 102 positioned properly on arm 12.

At step 1504, thermal energy sensor 104 may be placed on finger 16 of the subject 10. Finger 16 is placed in passageway 104d of thermal energy sensor 104 such that a distal end of the finger 16 is coupled to thermal energy measurement device 104e. With finger 16 coupled to thermal energy measurement device 104e, coupling member 104f secures finger 16 in thermal energy sensor 104.

At step 1506, computer system 102 may be positioned on subject 10. In an exemplary embodiment, computer system 102 may be positioned on subject 10 by coupling it to a belt, waistband, or other article of clothing on subject 10.

At step 1508, the computer system 102 is placed on standby. In an exemplary embodiment, when computer system 102 is on standby at step 1508, the computer system 102 is powered on but not running as to save power in the computer system 102.

At decision block 1510, the computer system 102 checks whether the apparatus 1400 is scheduled to run. If the apparatus 1400 is not scheduled to run, the computer system is returned to standby at step 1508. In an exemplary embodiment, the apparatus may be scheduled to run periodically through a predetermined time period such as, for example, 24 hours.

If the apparatus 1400 is scheduled to run, the method 1500 proceeds to step 1512 where a thermal energy sensor engine such as, for example, the thermal energy sensor engine 102b illustrated in FIG. 3, activates the thermal energy sensor 104 to begin recording the skin temperature of the finger 16 of subject 10. In an exemplary embodiment, temperature data begins being recorded continuously. In an exemplary embodiment, the thermal energy sensor 104 engages the skin of the finger 16 of subject 10 in order to measure temperature. In an exemplary embodiment, the thermal energy sensor 104 measures the skin temperature of the finger 16 of subject 10 without engaging the skin of the finger 16 of subject 10. In an exemplary embodiment, the ambient temperature is held constant around the thermal energy sensor 104. In an exemplary embodiment, the fluid flow such as, for example, the airflow, around the thermal energy sensor 104 is kept to a minimum.

At step 1514, the thermal energy sensor engine 102b begins to detect for equilibrium in the skin temperature of the finger 16 of subject 10. In an exemplary embodiment, at step 1514, the thermal energy sensor engine 102b retrieves successive temperature measurement from the thermal energy sensor 104.

At decision block 1516, the thermal energy sensor engine 102b determines whether the skin temperature of finger 106 of subject 10 has reached equilibrium. If the skin temperature of finger 16 has not reached equilibrium, the temperature sensor engine 102b proceeds back to step 1514 to detect for equilibrium. In an exemplary embodiment, determining whether the skin temperature of the finger 16 has reached equilibrium in step 1516 may include, for example, determining whether the temperature changes of the finger 16 are less than 0.1 degree C.

If the temperature changes in the finger 16 have reached equilibrium, the method proceeds to step 1518 where a vasostimulant engine such as, for example, the vasostimulant engine 102c illustrated in FIG. 2, activates the pressure cuff vasostimulant 106. In an exemplary embodiment, activating the pressure cuff vasostimulant 106 at step 1518 may include, for example, inflating the cuff to 200 mm Hg systolic BP.

At step 1520, the vasostimulant engine 102c may deactivate the pressure cuff vasostimulant 106. In an exemplary embodiment, deactivating the pressure cuff vasostimulant 106 at step 1520 may include deflating the cuff. In an exemplary embodiment, the pressure cuff vasostimulant 106 is deactivated anywhere from 2 to 5 minutes after activation in step 1518. In an exemplary embodiment, the vasostimulant is deactivated less than 5 minutes after activation in step 1518, which is less than the conventional deactivation time for tests involving vasostimulation and provides a method which reduces the pain sometimes associated with vasostimulants. In an exemplary embodiment, the vasostimulant is deactivated less than 4 minutes after activation in step 1518, which is less than the conventional deactivation time for tests involving vasostimulation and provides a method which reduces the pain sometimes associated with vasostimulants. In an exemplary embodiment, the vasostimulant is deactivated less than 3 minutes after activation in step 1518, which is less than the conventional deactivation time for tests involving vasostimulation and provides a method which reduces the pain sometimes associated with vasostimulants. In an exemplary embodiment, the vasostimulant is deactivated approximately 2 minutes after activation in step 1518, which is less than the conventional deactivation time for tests involving vasostimulation and provides a method which reduces the pain sometimes associated with vasostimulants. In an exemplary embodiment, the subject may be asked to exercise the body part on which thermal energy is being detected, which allows the method 1500 to simulate a longer vasostimulation in a shorter amount of time, which can also reduce the pain sometimes associated with vasostimulants.

At step 1522, the thermal energy sensor engine 102b begins to detect for equilibrium in the skin temperature of the finger 16 of subject 10. In an exemplary embodiment, at step 1522, the thermal energy sensor engine 102b retrieves successive temperature measurement from the thermal energy sensor 104.

At decision block 1524, the thermal energy sensor engine 102b determines whether the skin temperature of the finger 16 of subject 10 has reached equilibrium. If the skin temperature of the finger 16 has not reached equilibrium, the temperature sensor engine 102b proceeds back to step 1522 to detect for equilibrium. In an exemplary embodiment, determining whether the skin temperature of the finger 16 has reached equilibrium in step 1524 may include, for example, determining whether the temperature changes of the finger 16 are less than 0.1 degree C.

If the temperature changes in the finger 16 have reached equilibrium, the method proceeds to step 1526 where the temperature sensor engine 102b stops recording the skin temperature of the finger 16 of subject 10. At step 1528, data acquired from measuring and recording temperature changes of finger 16 which began at step 1512 and continued throughout the method 1500 is saved by the temperature sensor engine 102b to a database such as, for example, the database 102a illustrated in FIG. 3.

At decision block 1530, the computer system 102 checks whether there are any more scheduled runs for apparatus 1400. If there are more scheduled runs for apparatus 1400, the method 1500 returns to step 1508 where the computer system 102 goes on standby. In an exemplary embodiment, the apparatus may be scheduled to run periodically through a predetermined time period such as, for example, 24 hours.

If there are no more scheduled runs for apparatus 1400, the method proceeds to step 1532 where a plotting engine such as, for example, the plotting engine 102d illustrated in FIG. 3, may retrieve data from the database 102a.

At step 1534, the plotting engine 102d may plot out the data retrieved. In an exemplary embodiment, the data may be plotted out as temperature vs. time. In an exemplary embodiment, the plotting engine 102d may plot out data obtained from the temperature measurements concurrent with the data being obtained.

Figure 19:
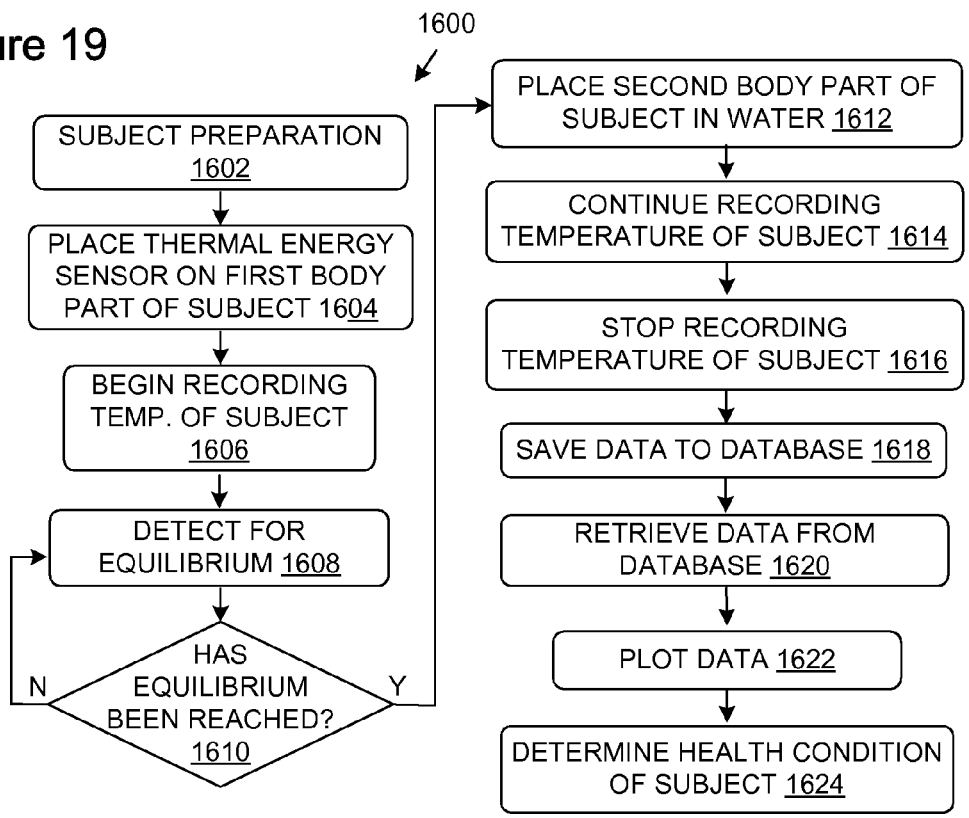
FIG. 19 is a flow chart illustrating an exemplary embodiment of a method for determining one or more health conditions.

Referring now to FIG. 19, in an exemplary embodiment, a method for determining one or more health conditions 1600 is illustrated which begins with a subject preparation at step 1602. Subject preparation at step 1602 may include, for example, having a subject refrain from eating before undergoing the method 1600, having the subject refrain from smoking before undergoing the method 1600, having the subject refrain from ingesting alcohol or caffeine before undergoing the method 1600, or having the subject refrain from taking any vascular medications before undergoing the method 1600.

At step 1604, a thermal energy sensor such as, for example, the thermal energy sensor 104 illustrated in FIG. 3, may be placed on the subject. In an exemplary embodiment, the thermal energy sensor 104 may be a conventional thermal energy sensor known in the art. In an exemplary embodiment, the thermal energy sensor 104 is designed such that there is a minimal area of contact between the sensor and the subject. In an exemplary embodiment, when placed on the subject, the thermal energy sensor 104 provides a minimal pressure to the subject. In an exemplary embodiment, in operation, the thermal energy sensor 104 measures thermal energy only and does not introduce any signals into the subject. In an exemplary embodiment, thermal energy measured by the thermal energy sensor 104 is not effected by insulation or perspiration. In an exemplary embodiment, the thermal energy sensor 104 does not alter the microcapillary flow in the subject. In an exemplary embodiment, the thermal energy sensor 104 does not restrict movement of the subject and thermal energy measurements are not effected by subject movement. In an exemplary embodiment, a plurality of thermal energy sensor 104 may be positioned at different locations on the subject. In an exemplary embodiment, the thermal energy sensor 104 is positioned on a body part of the subject such as, for example, a finger, forearm, toe, leg, earlobe, or nose. In an exemplary embodiment, the thermal energy sensor 104 may be placed on the subject in order to measure the thermal energy of distal resistant vessels on the subject.

At step 1606, a thermal energy sensor engine such as, for example, the thermal energy sensor engine 102b illustrated in FIG. 3, activates a thermal energy sensor such as, for example, the thermal energy sensor 104 illustrated in FIG. 3, to begin recording the temperature of the subject. In an exemplary embodiment, temperature data begins being recorded continuously. In an exemplary embodiment, the thermal energy sensor 104 measures the skin temperature of the subjects body on which it is placed such as, for example, the hand, forearm, foot, leg, earlobe, or nose. In an exemplary embodiment, the thermal energy sensor 104 engages the skin of the subject in order to measure temperature. In an exemplary embodiment, the thermal energy sensor 104 measures the skin temperature of the subject without engaging the skin of the subject. In an exemplary embodiment, the ambient temperature is held constant around the thermal energy sensor 104. In an exemplary embodiment, the fluid flow such as, for example, the airflow, around the thermal energy sensor 104 is kept to a minimum.

At step 1608, the thermal energy sensor engine 102b begins to detect for equilibrium in the subject. In an exemplary embodiment, at step 1608, the thermal energy sensor engine 102b retrieves successive temperature measurement from the thermal energy sensor.

At decision block 1610, the thermal energy sensor engine 102b determines whether the subject has reached equilibrium. If the subject has not reached equilibrium, the temperature sensor engine proceeds back to step 1608 to detect for equilibrium. In an exemplary embodiment, determining whether the subject 10 has reached equilibrium in step 1610 may include, for example, determining whether the temperature changes of a subject are less than 0.1 degree C.

If the temperature changes in the subject have reached equilibrium, the method proceeds to step 1612 where a second body part of subject is placed in water. In an exemplary embodiment, the water may be ice water.

At step 1614, the thermal energy sensor engine 102b continues recording the temperature of the subject.

At step 1616, the thermal energy sensor engine 102b stops recording the temperature of the subject after a predetermined amount of time.

At step 1618, data acquired from measuring and recording temperature changes which began at step 1606 and continued throughout the method 1600 is saved by the temperature sensor engine 102b to a database such as, for example, the database 102a illustrated in FIG. 3.

At step 1620, a plotting engine such as, for example, the plotting engine 102d illustrated in FIG. 3, may retrieve data from the database 102a.

At step 1622, the plotting engine 102d may plot out the data retrieved. In an exemplary embodiment, the data may be plotted out as temperature vs. time. In an exemplary embodiment, the plotting engine 102d may plot out data obtained from the temperature measurements concurrent with the data being obtained.

At step 1624, a health professional may analyze the data acquired through method 1600 in order to diagnose a variety of health conditions in subject.

Figure 20:
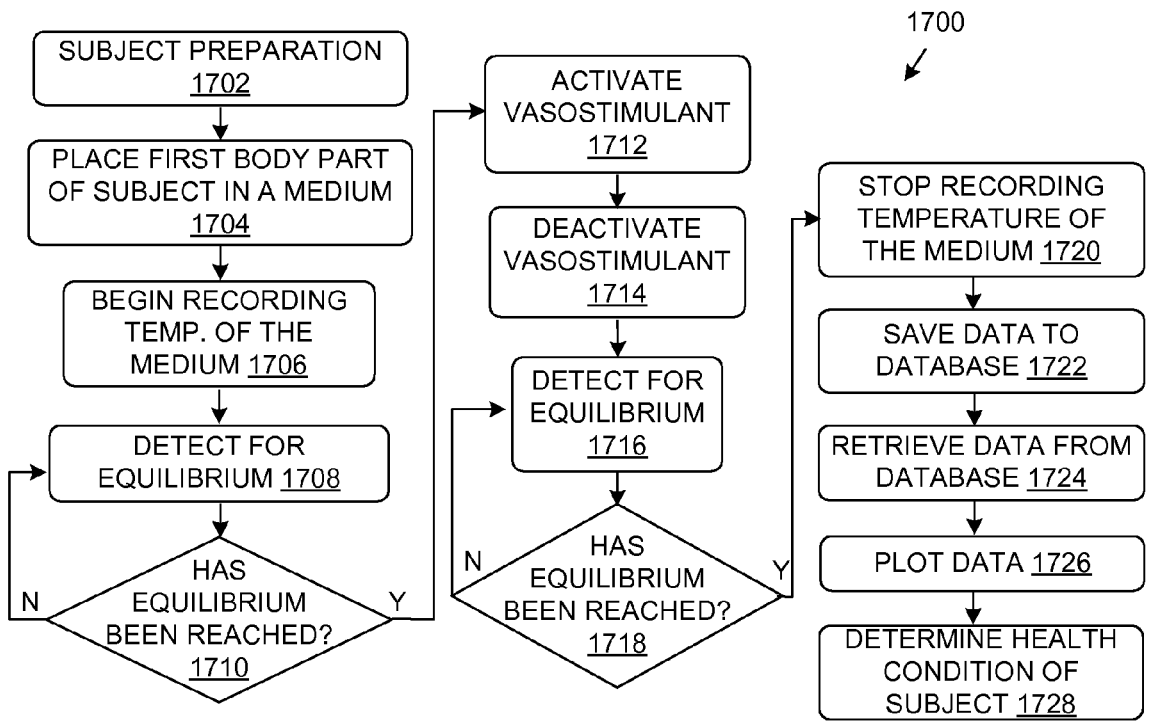
FIG. 20 is a flow chart illustrating an exemplary embodiment of a method for determining one or more health conditions.

Referring now to FIGS. 20a and 20b, in an exemplary embodiment, a method for determining one or more health conditions 1700 is illustrated which begins with a subject preparation at step 1702. Subject preparation at step 1702 may include, for example, having a subject refrain from eating before undergoing the method 1700, having the subject refrain from smoking before undergoing the method 1700, having the subject refrain from ingesting alcohol or caffeine before undergoing the method 1700, or having the subject refrain from taking any vascular medications before undergoing the method 1700.

At step 1704, a first body part of the subject is placed in a medium. In an exemplary embodiment, the medium may be a medium which has a minimum specific heat capacity and/or a maximum heat conductivity in order to provide maximum heat transfer between the body part of the subject and a thermal energy sensor such as, for example, the thermal energy sensor 104 illustrated in FIG. 2.

At step 1706, a thermal energy sensor engine such as, for example, the thermal energy sensor engine 102b illustrated in FIG. 2, activates a thermal energy sensor such as, for example, the thermal energy sensor 104 illustrated in FIG. 3, to begin recording the temperature of the medium.

At step 1708, the thermal energy sensor engine 102b begins to detect for equilibrium in the medium. In an exemplary embodiment, at step 1708, the thermal energy sensor engine 102b retrieves successive temperature measurement from the thermal energy sensor.

At decision block 1710, the thermal energy sensor engine 102b determines whether the medium has reached equilibrium. If the medium has not reached equilibrium, the temperature sensor engine 102b proceeds back to step 1708 to detect for equilibrium. In an exemplary embodiment, determining whether the medium has reached equilibrium in step 1710 may include, for example, determining whether the temperature changes of the medium are less than 0.1 degree C.

If the temperature changes in the medium have reached equilibrium, the method proceeds to step 1712 where a vasostimulant engine such as, for example, the vasostimulant engine 102c illustrated in FIG. 3, activates a vasostimulant such as, for example, the vasostimulant 106 illustrated in FIG. 2. In an exemplary embodiment, the vasostimulant 106 may be an inflatable cuff, and activating the vasostimulant 106 at step 1712 may include, for example inflating the cuff to 200 mm Hg systolic BP. In an exemplary embodiment, the vasostimulant 106 may be a chemical such as, for example, nitroglycerin, and activating the vasostimulant 106 at step 1712 may include administering a predetermined amount of the chemical to the subject. In an exemplary embodiment, the vasostimulant 106 may be an aptitude test, and activating the vasostimulant 106 at step 1712 may include having the subject begin the aptitude test.

At step 1714, the vasostimulant engine 102c may deactivate the vasostimulant 106. In an exemplary embodiment, the vasostimulant 106 may be an inflatable cuff, and deactivating the vasostimulant 106 at step 1714 may include deflating the cuff. In an exemplary embodiment, the vasostimulant 106 may be a chemical such as, for example, nitroglycerin, and deactivating the vasostimulant 106 at step 1714 may include providing an amount of the chemical in step 1712 such that the effects of the chemical on the subject wear off in a predetermined amount of time. In an exemplary embodiment, deactivating the vasostimulant 106 at step 1714 may include providing additional chemicals to the subject to reverse the effects of the vasostimulant chemicals provided in step 1712. In an exemplary embodiment, the vasostimulant 106 may be an aptitude test, and deactivating the vasostimulant 106 at step 1714 may include having the subject cease taking the aptitude test. In an exemplary embodiment, the vasostimulant is deactivated anywhere from 2 to 5 minutes after activation in step 1714. In an exemplary embodiment, the vasostimulant is deactivated less than 5 minutes after activation in step 1714, which is less than the conventional deactivation time for tests involving vasostimulation and provides a method which reduces the pain sometimes associated with vasostimulants. In an exemplary embodiment, the vasostimulant is deactivated less than 4 minutes after activation in step 1714, which is less than the conventional deactivation time for tests involving vasostimulation and provides a method which reduces the pain sometimes associated with vasostimulants. In an exemplary embodiment, the vasostimulant is deactivated less than 3 minutes after activation in step 1714, which is less than the conventional deactivation time for tests involving vasostimulation and provides a method which reduces the pain sometimes associated with vasostimulants. In an exemplary embodiment, the vasostimulant is deactivated approximately 2 minutes after activation in step 1714, which is less than the conventional deactivation time for tests involving vasostimulation and provides a method which reduces the pain sometimes associated with vasostimulants. In an exemplary embodiment, the subject 10 may be asked to exercise the body part on which thermal energy is being detected, which allows the method 1700 to simulate a longer vasostimulation in a shorter amount of time, which can also reduce the pain sometimes associated with vasostimulants.

At step 1716, the thermal energy sensor engine 102b begins to detect for equilibrium in the temperature of the medium. In an exemplary embodiment, at step 1716, the thermal energy sensor engine 102b retrieves successive temperature measurement from the thermal energy sensor.

At decision block 1718, the thermal energy sensor engine 102b determines whether the temperature of the medium has reached equilibrium. If the temperature of the medium has not reached equilibrium, the temperature sensor engine proceeds back to step 1716 to detect for equilibrium. In an exemplary embodiment, determining whether the temperature of the medium has reached equilibrium in step 1718 may include, for example, determining whether the temperature changes of medium are less than 0.1 degree C.

If the temperature changes in the medium have reached equilibrium, the method proceeds to step 1720 where the temperature sensor engine 102b stops recording the temperature of the medium.

At step 1722, data acquired from measuring and recording temperature changes which began at step 1706 and continued throughout the method 1700 is saved by the temperature sensor engine 102b to a database such as, for example, the database 102a illustrated in FIG. 3. At step 1724, a plotting engine such as, for example, the plotting engine 102d illustrated in FIG. 3, may retrieve data from the database 102a. At step 1726, the plotting engine 102d may plot out the data retrieved. In an exemplary embodiment, the data may be plotted out as temperature vs. time. In an exemplary embodiment, the plotting engine 102d may plot out data obtained from the temperature measurements concurrent with the data being obtained.

At step 1728, a health professional may analyze the data acquired through method 1700 in order to diagnose a variety of health conditions in subject 10.

Figure 21:
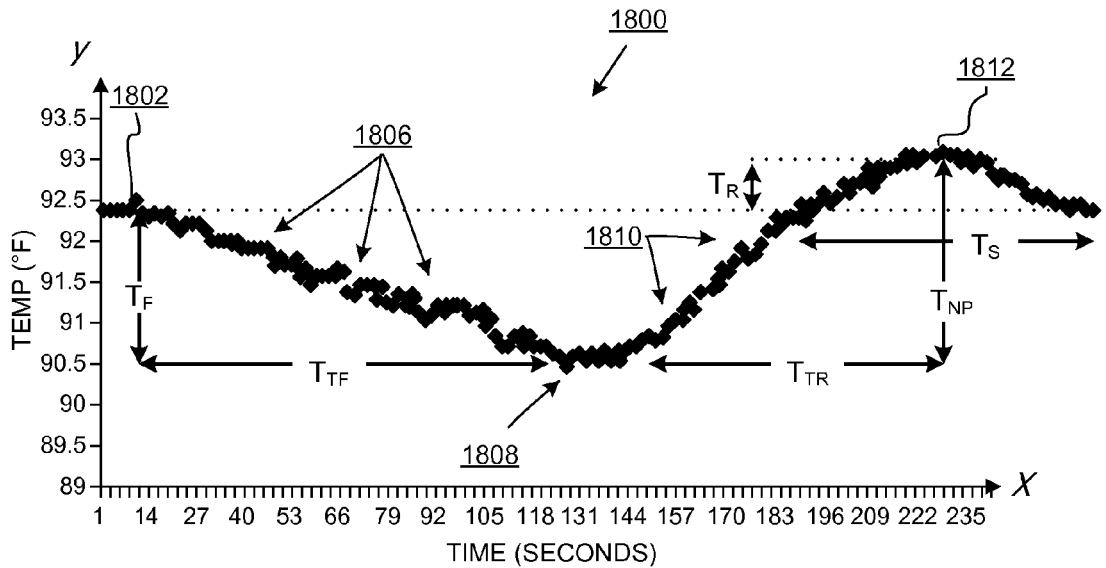
FIG. 21 is a graph illustrating an exemplary embodiment of temperature vs. time data obtained using the apparatus of FIGS. 2, 3, and 4 using the methods of FIGS. 8a and 8b.

Referring now to FIG. 21, a representative experimental graph 1800 of temperature vs. time is illustrated for a healthy subject during the methods 500, 700, 800, 900, 1000, 1100, 1500, 1600, or 1700. In an exemplary embodiment, the graph 1800 may be produced by the plotting engine 102d, illustrated in FIG. 3. A baseline temperature 1802 is achieved when the subject reaches a steady temperature after having a thermal energy sensor such as, for example, the thermal energy sensor 104 illustrated in FIG. 3, coupled to them. At time 1804, the vasostimulant is activated, causing the temperature of the subject to drop, resulting in a slope 1806. At time 1808, the vasostimulant is deactivated, causing the temperature of the subject to rise, resulting in a slope 1810. The temperature of the subject crosses the baseline temperature 1802 and reaches a peak temperature 1812, after which the temperature returns back to the baseline temperature 1802. A number of measurements can be made from the data shown in graph 1800 including, but not limited to, the fall temperature change TF between the baseline temperature 1802 and the temperature recorded at time 1808, the rebound temperature change TR between the baseline temperature 1802 and the peak temperature 1812, the nadir to peak temperature change TNP between the temperature recorded at time 1808 and the peak temperature 1812, the time to fall temperature TTF, the time to rebound temperature TTR, the time to stabilized temperature TS, the steepness of the slopes 1806 and 1810, the area under the temperature curve bounded by the temperature curve and the temperature reached at time 1808 and between time equal zero and time 1808, the area under the temperature curve bounded by the temperature curve and the temperature reached at time 1808 and between time 1808 and the time at peak temperature 1812, and the area under the temperature curve bounded by the temperature curve and the temperature reached at time 1808 and between time 1808 and the time at which the temperature stabilizes.

In an exemplary embodiment, healthy vascular reactivity may be indicated by a value of TNP which is greater than TF. In an exemplary embodiment, unhealthy vascular reactivity may be indicated by a value of TNP which is less than TF. In an exemplary embodiment, unhealthy vascular reactivity may be indicated by a negative value of TR. In an exemplary embodiment, several graphs similar to graph 1800 may be taken from a subject and then averaged to get an average graph for the subject which may indicate the average response for the subject over a period of time.

In an exemplary embodiment, the value of TR may be normalized using thermodynamic equations for calculating heat flow based on the following parameters: baseline temperature 1802, fall temperature change TF, ambient room temperature, core temperature, tissue heat capacity, tissue metabolism rate, tissue heat conduction, the mass of the testing volume, the location the method is conducted, blood flow rate, the position of the subject during the method, and a variety of other physical and/or physiological factors that may effect the value of TR. In an experimental embodiment of the method 500 described above with respect to FIGS. 8a and 8b, an ambient temperature of 22 degrees C. was measured. A first subject was tested and found to have a baseline temperature of 35 degrees C., a TF of 2 degrees C. and a TR of 0.5 degrees. A subject like first subject has a baseline temperature which is significantly greater than the ambient temperature, and it is expected that such a subject will experience a higher than normal TF and a lower than normal TR. Furthermore, a subject having a baseline temperature which is significantly greater than the subject's core temperature is expected to experience a higher than normal TF and a lower than normal TR. A second subject was tested and found to have a baseline temperature of 25 degrees C., a TF of 1 degrees C. and a TR of 3 degrees. A subject like second subject has a baseline temperature which is close to the ambient temperature, and it is expected that such a subject will experience a lower than normal TF and a higher than normal TR. Furthermore, a subject having a baseline temperature which is close to the subject's core temperature is expected to experience a lower than normal TF and a higher than normal TR.

Figure 22:
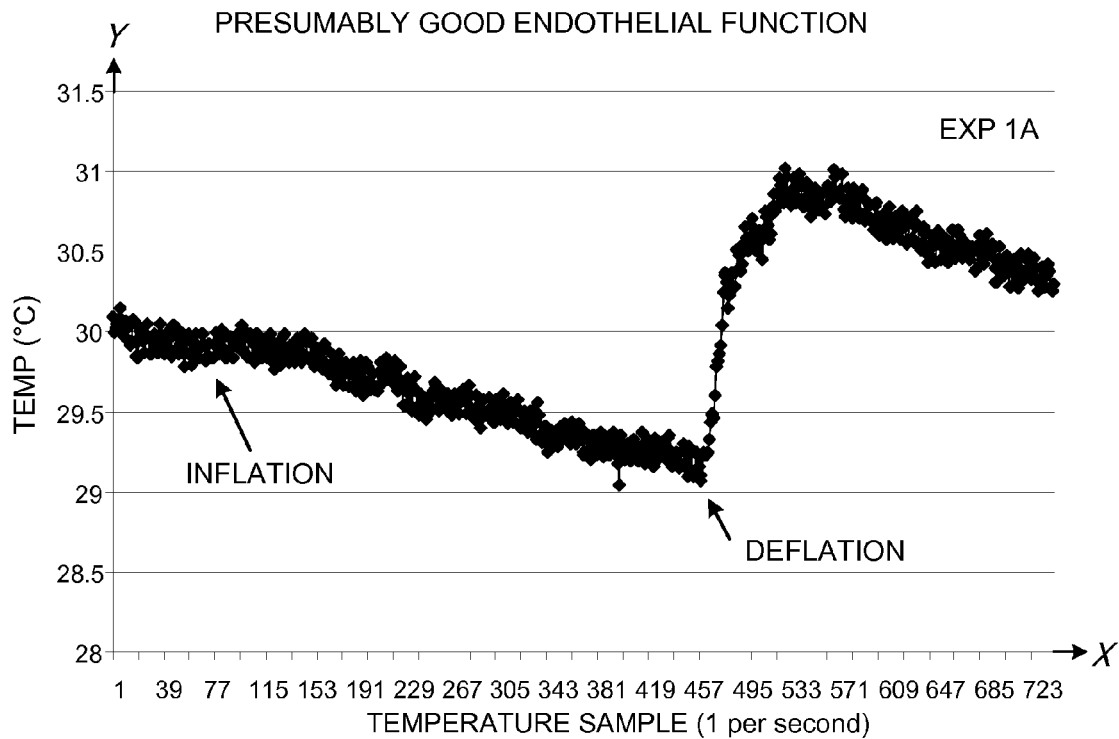
FIG. 22 is a graph illustrating an exemplary experimental embodiment of temperature vs. time data obtained using the apparatus of FIGS. 2, 3, and 4 using the methods of FIGS. 8a and 8b.

Referring now to FIG. 22, in an exemplary experimental embodiment EXP1, the method 500 was carried out on a subject, and a graph EXP1A was obtained of data relating to temperature changes of the skin on a finger of the subject. A pressure cuff was provided as the vasostimulant, and vasostimulant activation at time 1804 and deactivation at time 1808 was provided by inflating and deflating the pressure cuff. The subject exhibited a baseline temperature 1802 of approximately 30 degrees C., a temperature at time 1808 of approximately 29.1 degrees C., a peak temperature 1812 of approximately 31 degrees C., and a rebound temperature change TR of approximately 1 degree C. The subject showed presumably good endothelial function due to, for example, the positive value of rebound temperature change TR.

Figure 23:
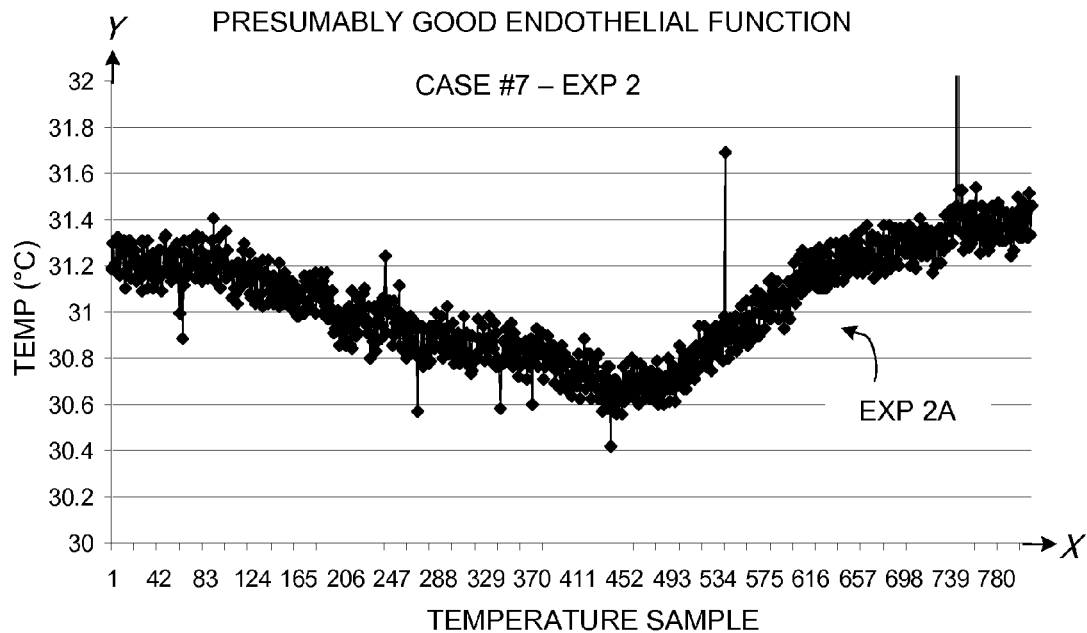
FIG. 23 is a graph illustrating an exemplary experimental embodiment of temperature vs. time data obtained using the apparatus of FIGS. 2, 3, and 4 using the methods of FIGS. 8a and 8b.

Referring now to FIG. 23, in an exemplary experimental embodiment EXP2, the method 500 was carried out on a subject, and a graph EXP2A was obtained of data relating to temperature changes of the skin on a finger of the subject. A pressure cuff was provided as the vasostimulant, and vasostimulant activation at time 1804 and deactivation at time 1808 was provided by inflating and deflating the pressure cuff. The subject exhibited a baseline temperature 1802 of approximately 31.2 degrees C., a temperature at time 1808 of approximately 30.6 degrees C., a peak temperature 1812 of approximately 31.4 degrees C., and a rebound temperature change TR of approximately 0.2 degree C. The subject showed presumably good endothelial function due to, for example, the positive value of rebound temperature change TR.

Figure 24:
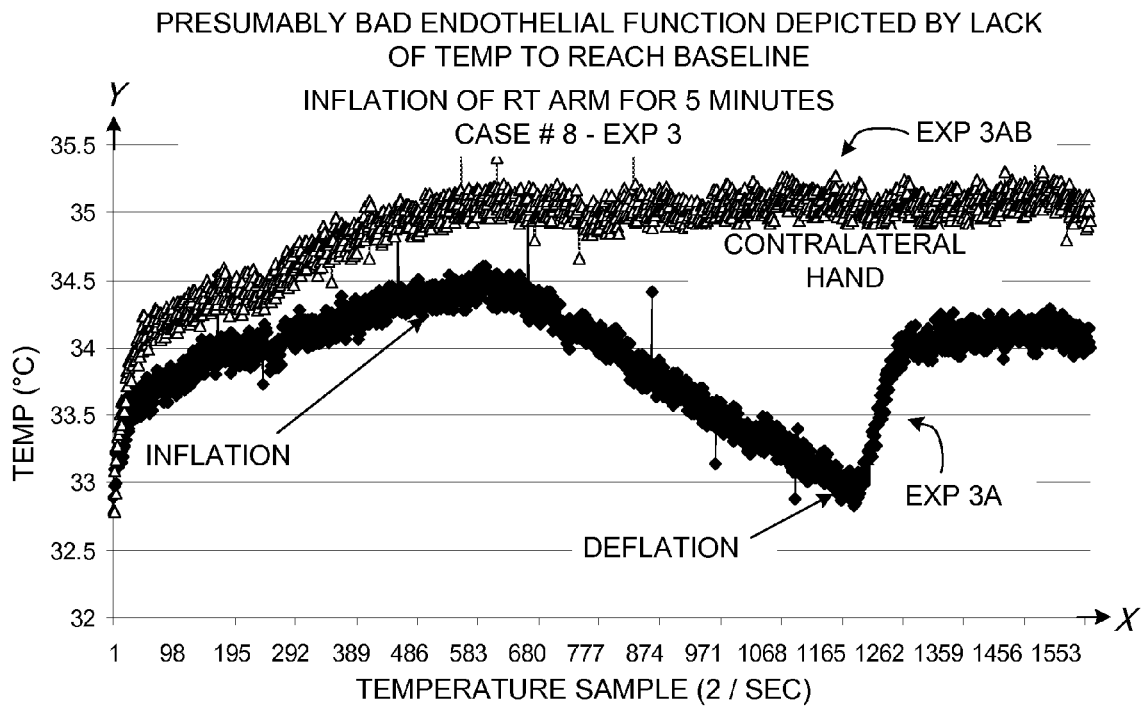
FIG. 24 is a graph illustrating an exemplary experimental embodiment of temperature vs. time data obtained using the apparatus of FIGS. 2, 3, and 4 using the methods of FIGS. 8a and 8b.

Referring now to FIG. 24, in an exemplary experimental embodiment EXP3, the method 500 was carried out on a subject, and a graph EXP3A was obtained of data EXP3AA relating to temperature changes of the skin on a finger of the subject and including data EXP3AB relating to the temperature of a contralateral finger for use as a control. A pressure cuff was provided as the vasostimulant, and vasostimulant activation at time 1804 and deactivation at time 1808 was provided by inflating and deflating the pressure cuff. Data EXP3AA exhibited a baseline temperature 1802 of approximately 34.5 degrees C., a temperature at time 1808 of approximately 33 degrees C., a peak temperature 1812 of approximately 34 degrees C., and a rebound temperature change TR of approximately negative 0.5 degrees C. Data EXP3AB exhibited a control temperature of approximately 35 decrees C. The subject showed presumably bad endothelial function due to, for example, the negative value of rebound temperature change TR.

Figure 25:
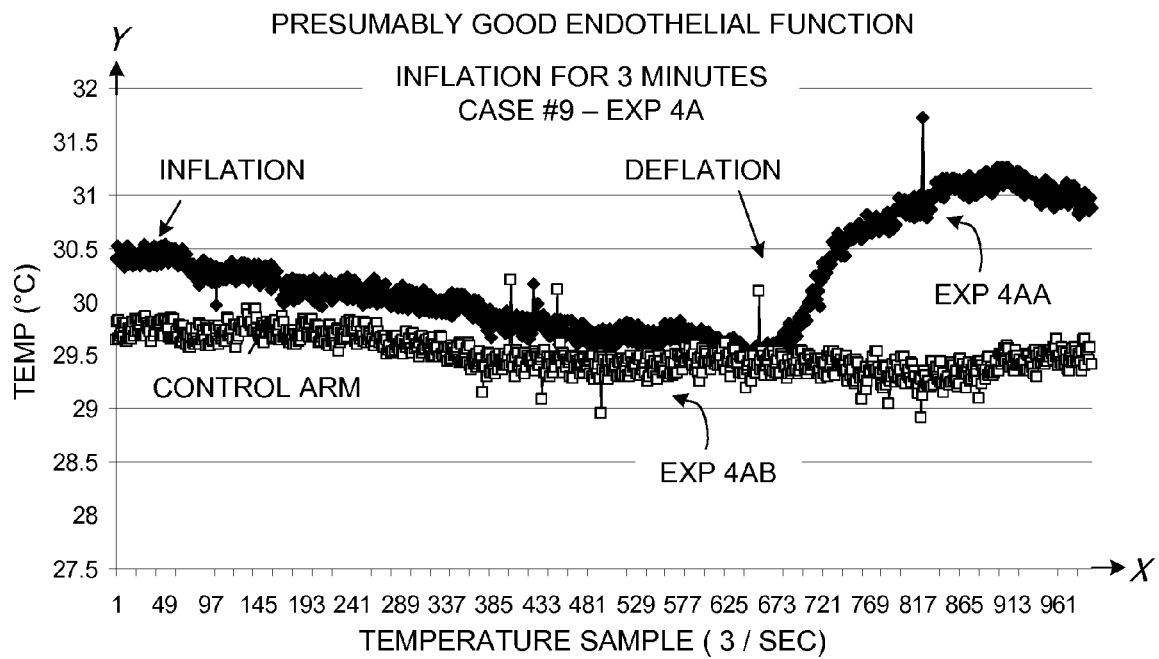
FIG. 25 is a graph illustrating an exemplary experimental embodiment of temperature vs. time data obtained using the apparatus of FIGS. 2, 3, and 4 using the methods of FIGS. 8a and 8b.

Referring now to FIG. 25, in an exemplary experimental embodiment EXP4, the method 500 was carried out on a subject, and a graph EXP4A was obtained of data EXP4AA relating to temperature changes of the skin on a finger of the subject and including data EXP4AB relating to the temperature of a contralateral finger for use as a control. A pressure cuff was provided as the vasostimulant, and vasostimulant activation at time 1804 and deactivation at time 1808 was provided by inflating and deflating the pressure cuff. Data EXP4AA exhibited a baseline temperature 1802 of approximately 30.5 degrees C., a temperature at time 1808 of approximately 29.5 degrees C., a peak temperature 1812 of approximately 31.2 degrees C., and a rebound temperature change TR of approximately 0.7 degrees C. Data EXP4AB exhibited a control temperature of approximately 29.5 degrees C. The subject showed presumably good endothelial function due to, for example, the positive value of rebound temperature change TR.

Figure 26:
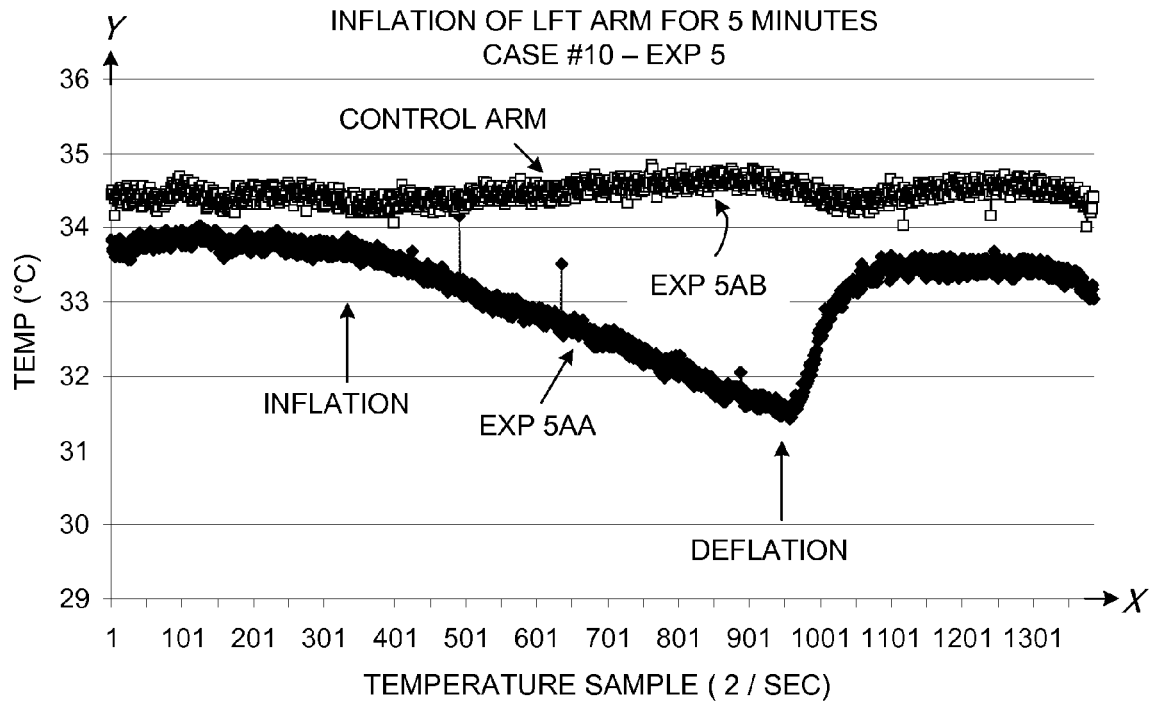
FIG. 26 is a graph illustrating an exemplary experimental embodiment of temperature vs. time data obtained using the apparatus of FIGS. 2, 3, and 4 using the methods of FIGS. 8a and 8b.

Referring now to FIG. 26, in an exemplary experimental embodiment EXP5, the method 500 was carried out on a subject, and a graph EXP5A was obtained of data EXP5AA relating to temperature changes of the skin on a finger of the subject and including data EXP5AB relating to the temperature of a contralateral finger for use as a control. A pressure cuff was provided as the vasostimulant, and vasostimulant activation at time 1804 and deactivation at time 1808 was provided by inflating and deflating the pressure cuff. Data EXP5AA exhibited a baseline temperature 1802 of approximately 34 degrees C., a temperature at time 1808 of approximately 31.5 degrees C., a peak temperature 1812 of approximately 33.5 degrees C., and a rebound temperature change TR of approximately negative 0.5 degree C. Data EXP5AB exhibited a control temperature of approximately 34.5 degrees C. The subject showed presumably bad endothelial function due to, for example, the negative value of rebound temperature change TR.

Figure 27:
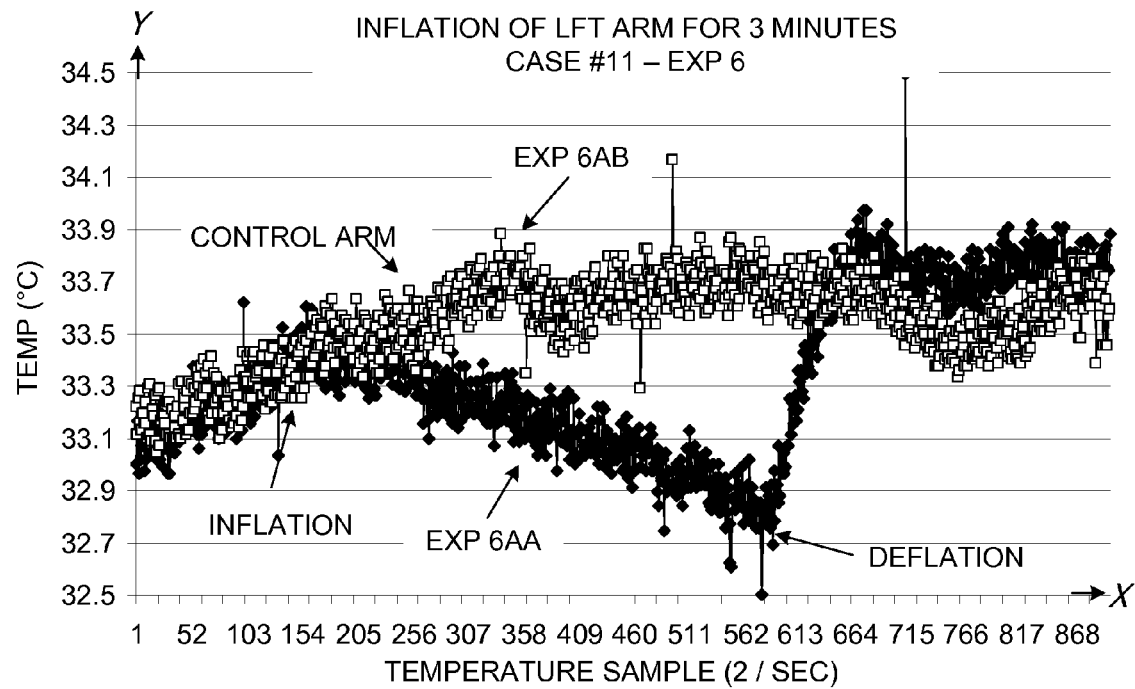
FIG. 27 is a graph illustrating an exemplary experimental embodiment of temperature vs. time data obtained using the apparatus of FIGS. 2, 3, and 4 using the methods of FIGS. 8a and 8b.

Referring now to FIG. 27, in an exemplary experimental embodiment EXP6, the method 500 was carried out on a subject, and a graph EXP6A was obtained of data EXP6AA relating to temperature changes of the skin on a finger of the subject and including data EXP6AB relating to the temperature of a contralateral finger for use as a control. A pressure cuff was provided as the vasostimulant, and vasostimulant activation at time 1804 and deactivation at time 1808 was provided by inflating and deflating the pressure cuff. Data EXP6AA exhibited a baseline temperature 1802 of approximately 33.4 degrees C., a temperature at time 1808 of approximately 32.8 degrees C., a peak temperature 1812 of approximately 33.8 degrees C., and a rebound temperature change TR of approximately 0.4 degree C. Data EXP6AA exhibited a control temperature of approximately 33.7 degrees C. The subject showed presumably good endothelial function due to, for example, the positive value of rebound temperature change TR.

Figure 28:
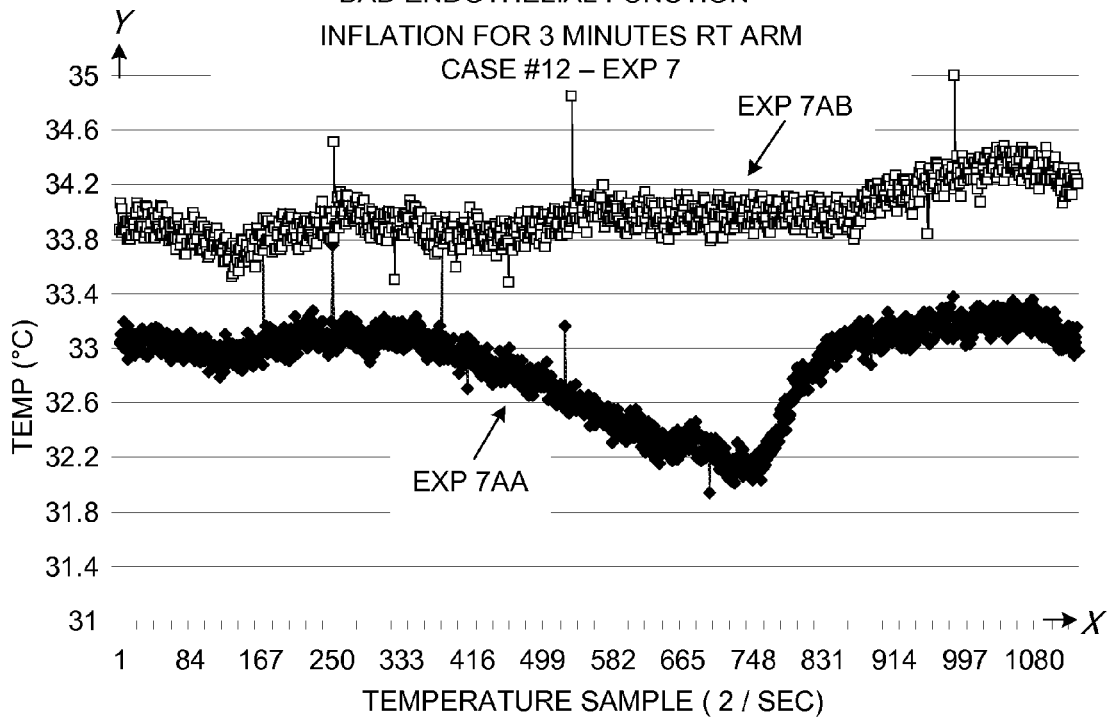
FIG. 28 is a graph illustrating an exemplary experimental embodiment of temperature vs. time data obtained using the apparatus of FIGS. 2, 3, and 4 using the methods of FIGS. 8a and 8b.

Referring now to FIG. 28, in an exemplary experimental embodiment EXP7, the method 500 was carried out on a subject, and a graph EXP7A was obtained of data EXP7AA relating to temperature changes of the skin on a finger of the subject and including data EXP7AB relating to the temperature of a contralateral finger for use as a control. A pressure cuff was provided as the vasostimulant, and vasostimulant activation at time 1804 and deactivation at time 1808 was provided by inflating and deflating the pressure cuff. Data EXP7AA exhibited a baseline temperature 1802 of approximately 33.1 degrees C., a temperature at time 1808 of approximately 32.1 degrees C., a peak temperature 1812 of approximately 33.1 degrees C., and a rebound temperature change TR of approximately 0.0 degree C. Data EXP7AB exhibited a control temperature of approximately 34 degrees C. The subject showed presumably bad endothelial function due, for example, to the 0.0 degree value of rebound temperature change TR.

Figure 29:
FIG. 29 is a graph illustrating an exemplary experimental of data obtained using the apparatus of FIGS. 2, 3, and 4 using the methods of FIGS. 8a and 8b correlated to percentage change in brachial artery diameter.
Figure 29:
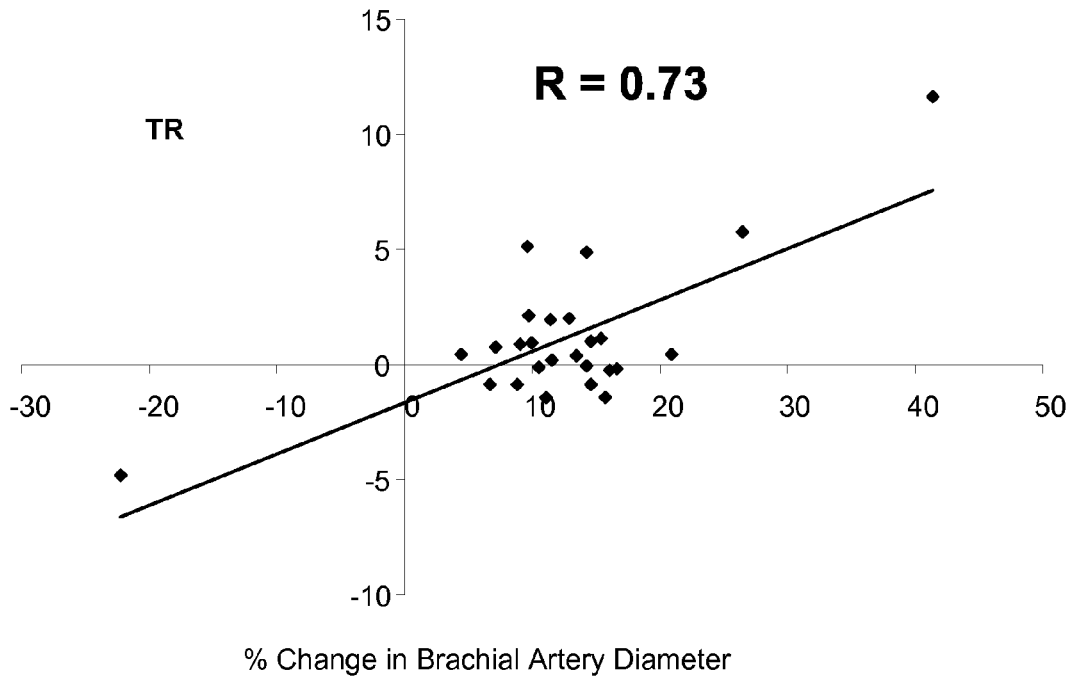

Referring now to FIG. 29, in an exemplary experimental embodiment EXP8, the method 500 was carried out on a subject by occluding the brachial artery of the subject and measuring the temperature changes on the skin of the subjects finger before and after occlusion. While carrying out the method 500, a conventional endothelial function test was conducted which measure the percentage change in brachial artery diameter before and after occlusion of the brachial artery. A correlation graph was created plotting rebound temperature change TR against the percentage change in brachial artery diameter. A correlation factor R of 0.73 was found between rebound temperature change TR and percentage change in brachial artery diameter, indicating that the method 500 can provide a diagnosis equivalent to the more expensive and subjective brachial artery diameter test.

Figure 30:
FIG. 30 is a graph illustrating an exemplary experimental embodiment of data obtained using the apparatus of FIGS. 2, 3, and 4 using the methods of FIGS. 8a and 8b correlated to percentage change in brachial artery diameter.
Figure 30:
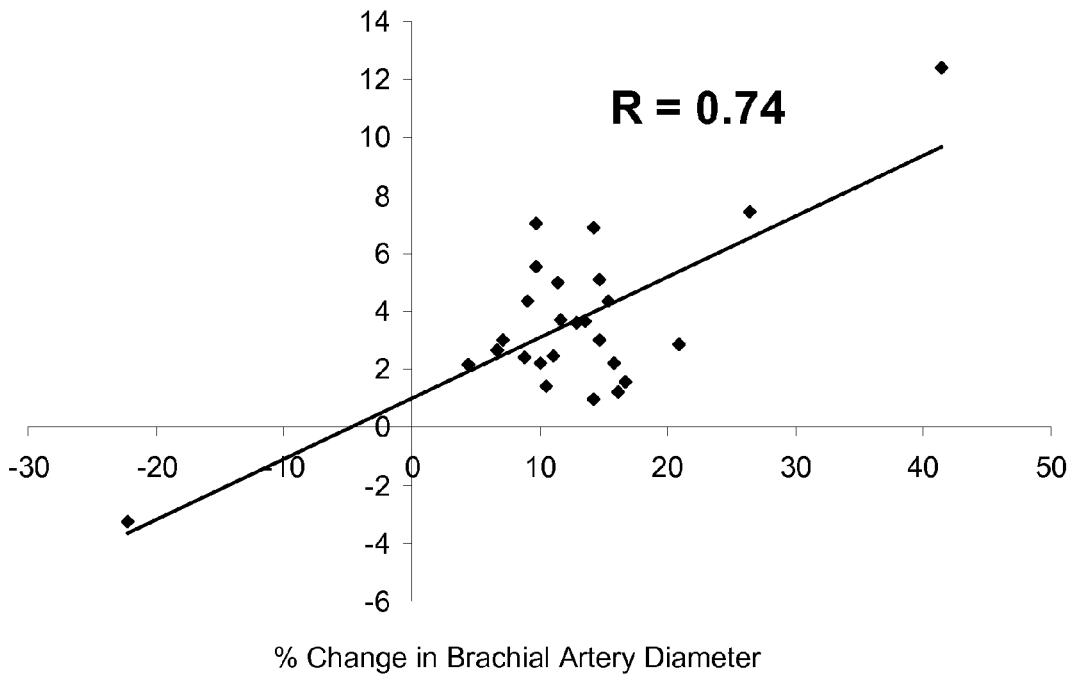

Referring now to FIG. 30, in an exemplary experimental embodiment EXP9, the method 500 was carried out on a subject by occluding the brachial artery of the subject and measuring the temperature changes on the skin of the subjects finger before and after occlusion. While carrying out the method 500, a conventional endothelial function test was conducted which measure the percentage change in brachial artery diameter before and after occlusion of the brachial artery. A correlation graph was created plotting nadir to peak temperature change TNP against percentage change in brachial artery diameter. A correlation factor R of 0.74 was found between nadir to peak temperature change TNP and percentage change in brachial artery diameter, indicating that the method 500 can provide a diagnosis equivalent to the more expensive and subjective brachial artery diameter test.

Figure 31:
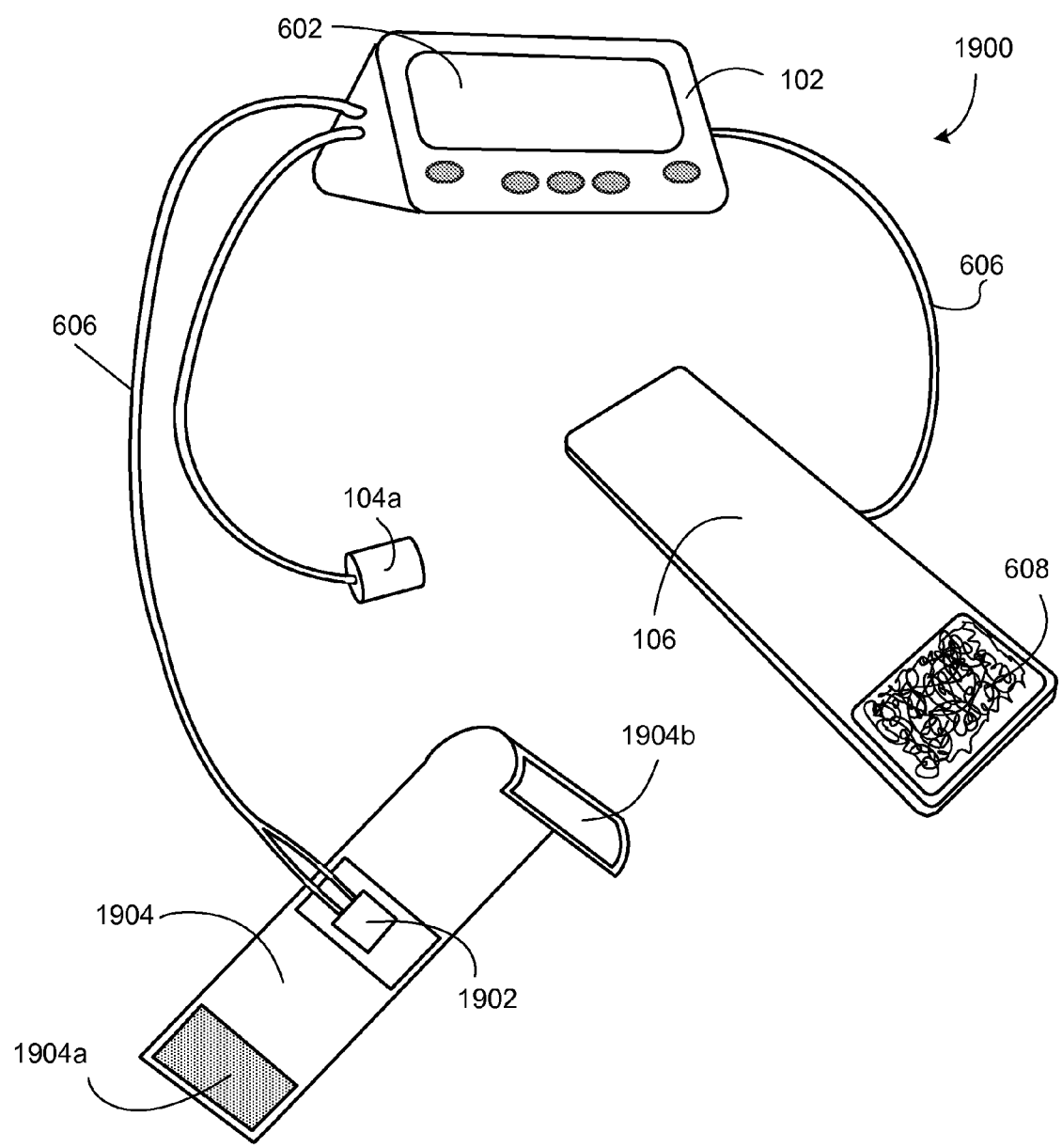
FIG. 31 is a perspective view illustrating an exemplary embodiment of an apparatus for determining one or more health conditions.

Referring now to FIG. 31, an alternative embodiment of an apparatus for determining one or more health conditions 1900 is substantially identical in design and operation to apparatus 600 described above with reference to FIGS. 9a and 9b, with the provision of a Doppler probe 1902 replacing the thermal energy sensor 104b. The Doppler probe 1902 is coupled to a wristband 1904 which includes a plurality of adhesive members 1904 and 1904b on either end of the wristband 1904. In an exemplary embodiment, the thermal probe 104b, illustrated in FIG. 9a, may be included on the apparatus 1900 and the Doppler probe 1902 may be coupled to the computer system 102 by an additional coupling wire 606.

Figure 32A:
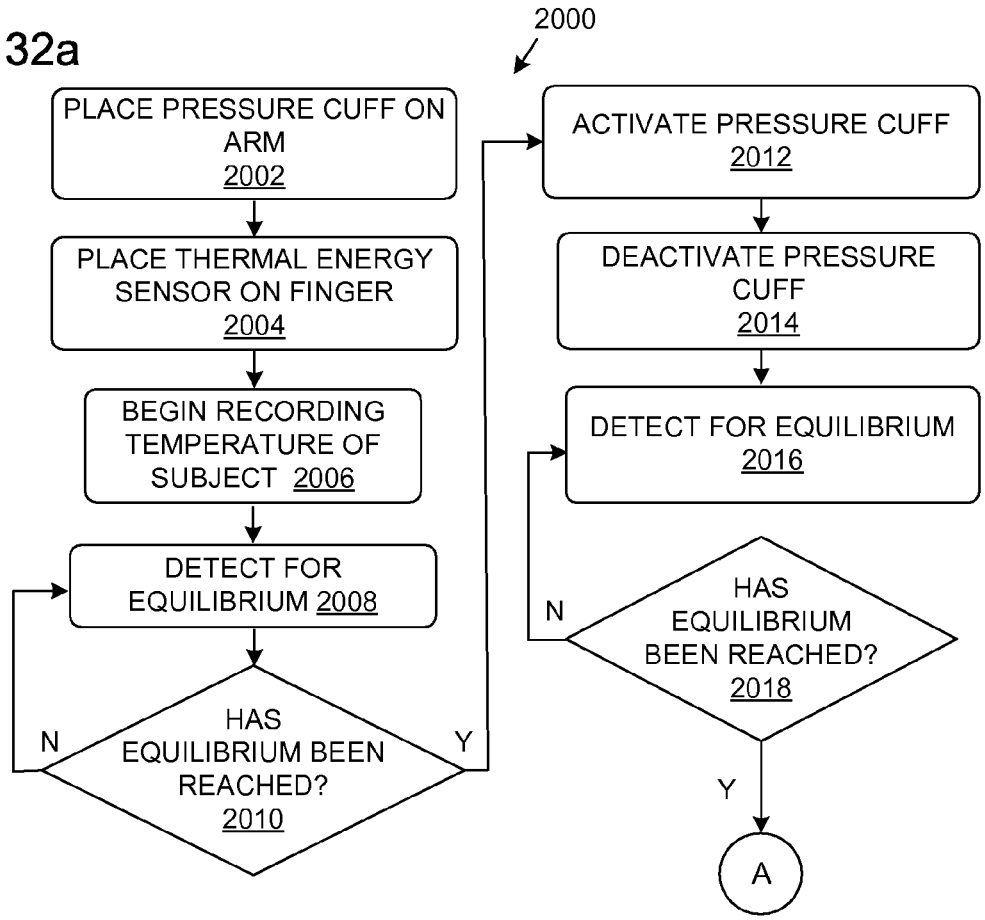
FIG. 32a is a flow chart illustrating an exemplary embodiment of a portion of a method for determining one or more health conditions using the apparatus of FIG. 31.
Figure 32B:
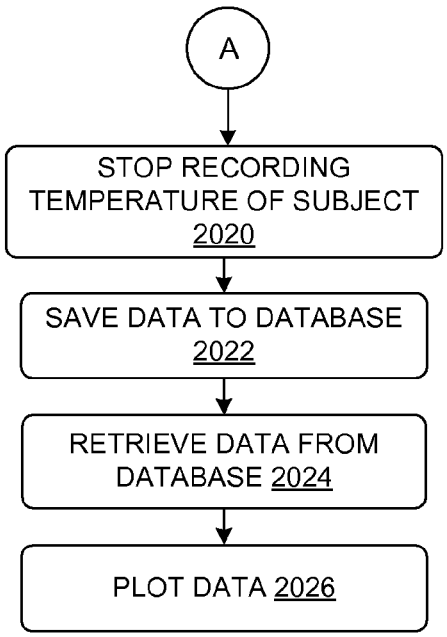
FIG. 32b is a flow chart illustrating an exemplary embodiment of a portion of a method for determining one or more health conditions using the apparatus of FIG. 31.
Figure 32C:
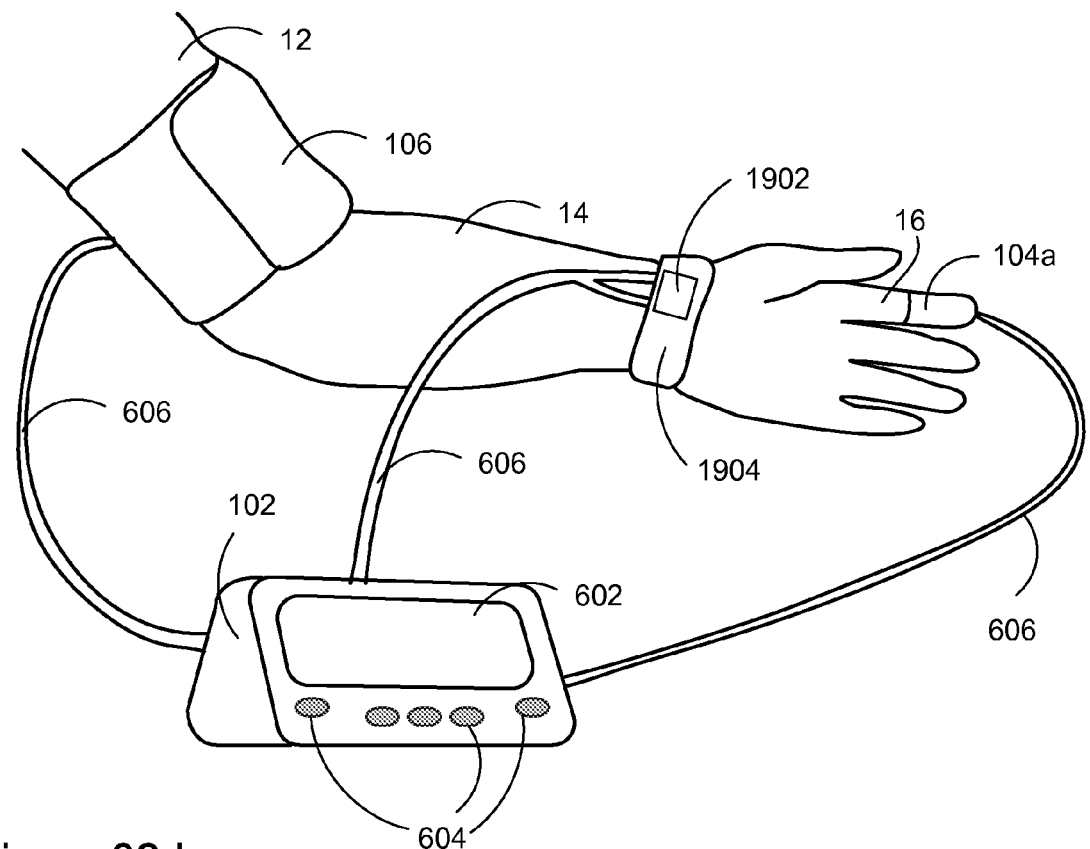
FIG. 32c is a perspective view illustrating an exemplary embodiment of the apparatus of FIG. 31 being used on the subject of FIG. 3 during the method of FIGS. 32a and 32b.
Figure 32D:
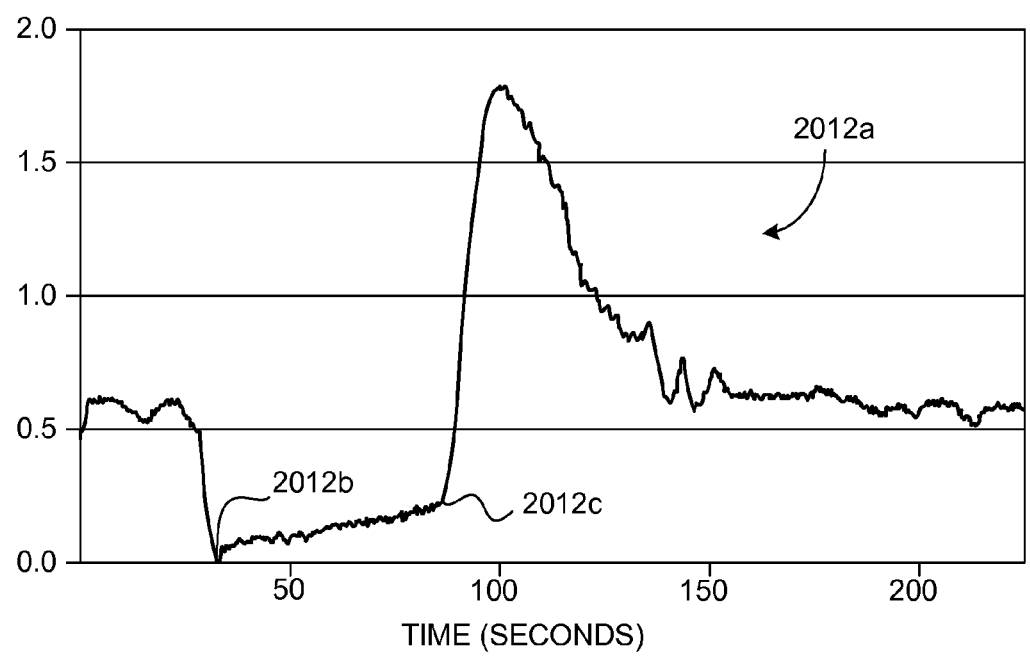
FIG. 32d is a graph illustrating an experimental embodiment of the apparatus of FIG. 31 being used on the subject of FIG. 3 during the method of FIGS. 32a and 32b.
Figure 33A:
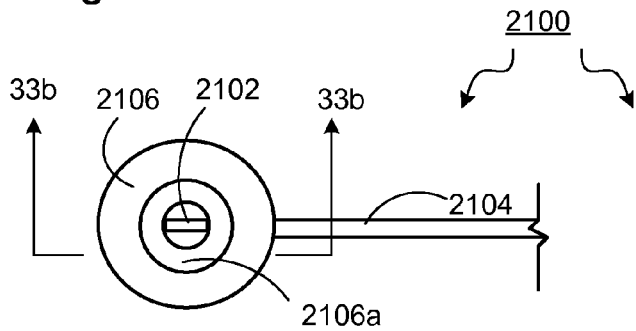
FIG. 33a is a top view illustrating an exemplary embodiment of a thermal energy sensor.
Figure 33B:
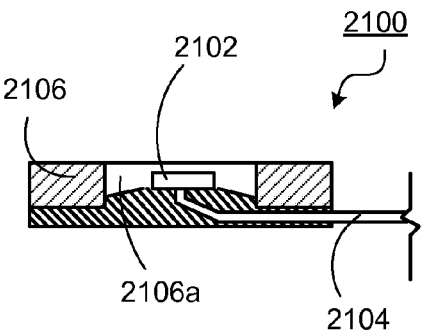
Figure 33C:
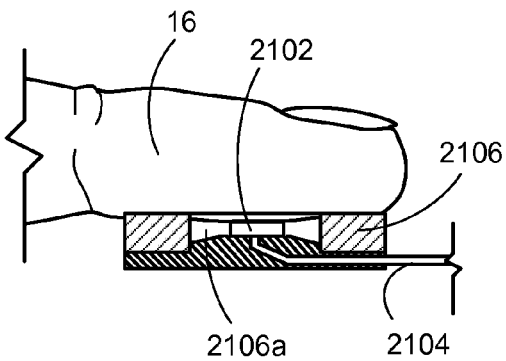
FIG. 33c is a cross sectional view illustrating an exemplary embodiment of operation of the thermal energy sensor of FIG. 33b.
Figure 34A:
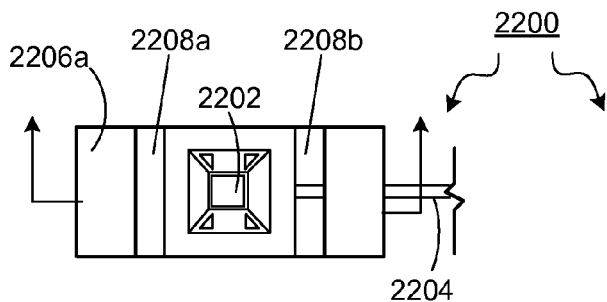
FIG. 34a is a top view illustrating an exemplary embodiment of a thermal energy sensor.
Figure 34B:
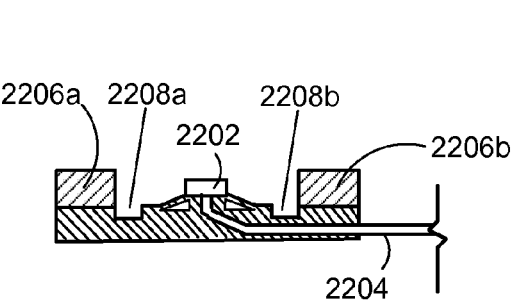
Figure 34C:
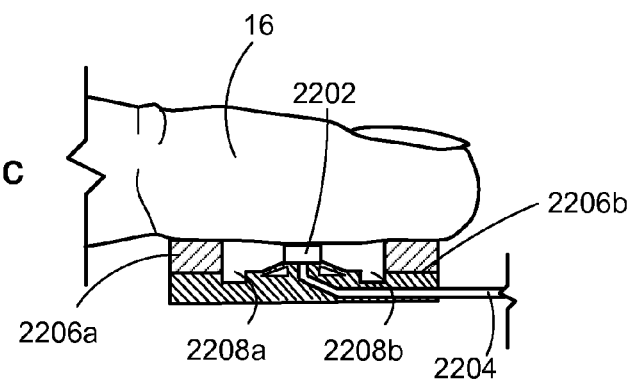
FIG. 34c is a cross sectional view illustrating an exemplary embodiment of operation of the thermal energy sensor of FIG. 34b.

Referring now to FIGS. 3, 32a, 32b, 32c, 32d, and 32e, in an exemplary embodiment, a method for determining one or more health conditions 2000 using the apparatus 1900 illustrated in FIG. 31 is illustrated which begins with placing the pressure cuff vasostimulant 106 on arm 12 of subject 10 at step 2002. Pressure cuff vasostimulant 106 may be secured to arm 12 by vasostimulant coupling member 608 which may include a variety of adhesive materials known in the art. The wristband 1904 including Doppler probe 1902 is placed on a distal portion of the forearm 14 and may be secured to the forearm 14 using adhesive members 1904a and 1904b. The Doppler probe 1902 is positioned such that it is immediately adjacent an artery in forearm 14, as illustrated in FIG. 32c.

At step 2004, thermal energy sensor 104a may be placed on finger 16 of the subject 10. Finger 16 is placed in passageway 104ad of thermal energy sensor 104a such that a distal end of the finger 16 is coupled to thermal energy measurement device 104ae. With finger 16 coupled to thermal energy measurement device 104ae, coupling member 104af secures finger 16 in thermal energy sensor 104a.

At step 2006, a thermal energy sensor engine such as, for example, the thermal energy sensor engine 102b illustrated in FIG. 3, activates the thermal energy sensor 104a to begin recording the skin temperature of finger 16. In an exemplary embodiment, temperature data begins being recorded continuously. In an exemplary embodiment, the thermal energy sensor 104a engages the skin of finger 16 in order to measure temperature. In an exemplary embodiment, the thermal energy sensor 104a measures the skin temperature of finger 16 without engaging the skin of finger 16.

At step 2008, the thermal energy sensor engine 102b begins to detect for equilibrium in the skin temperature of the finger 16 of subject 10. In an exemplary embodiment, at step 2008, the thermal energy sensor engine 102b retrieves successive temperature measurement from the thermal energy sensor 104a.

At decision block 2010, the thermal energy sensor engine 102b determines whether the skin temperature of finger 16 of subject 10 has reached equilibrium. If the skin temperature of finger 16 has not reached equilibrium, the temperature sensor engine 102b proceeds back to step 2008 to detect for equilibrium. In an exemplary embodiment, determining whether the skin temperature of the finger has reached equilibrium in step 2010 may include, for example, determining whether the temperature changes of the finger 16 are less than 0.1 degree C.

If the temperature changes in the finger 16 have reached equilibrium, the method proceeds to step 2012 where a vasostimulant engine such as, for example, the vasostimulant engine 102c illustrated in FIG. 2, activates the pressure cuff vasostimulant 106. In an exemplary embodiment, activating the pressure cuff vasostimulant 106 at step 2012 may include, for example, inflating the cuff to 200 mm Hg systolic BP. The Doppler probe 1902 measures the speed of the blood in an artery in the forearm 14, and, in an exemplary embodiment, the readings from the Doppler probe 1902 may be used to determine when the appropriate pressure is being applied by the pressure cuff vasostimulant 106 by determining when blood flow has substantially ceased flowing in the artery in forearm 14. In an experimental embodiment 2012a, illustrated in FIG. 32d, the Doppler probe 1902 showed that blood substantially ceased flowing through the artery in forearm 14 at data point 2012b. In an exemplary embodiment, the Doppler probe 1902 can aid in ensuring that the pressure applied by the pressure cuff vasostimulant 106 is no more than is necessary to conduct the method 2000, and prevents the method 2000 from being interrupted due to pain in the subject.

At step 2014, the vasostimulant engine 102c may deactivate the pressure cuff vasostimulant 106. In an exemplary embodiment, deactivating the pressure cuff vasostimulant 106 at step 2014 may include deflating the cuff. In an exemplary embodiment, the pressure cuff vasostimulant 106 is deactivated anywhere from 2 to 5 minutes after activation in step 2012. In an exemplary embodiment, the vasostimulant is deactivated less than 5 minutes after activation in step 2012, which is less than the conventional deactivation time for tests involving vasostimulation and provides a method which reduces the pain sometimes associated with vasostimulants. In an exemplary embodiment, the vasostimulant is deactivated less than 4 minutes after activation in step 2012, which is less than the conventional deactivation time for tests involving vasostimulation and provides a method which reduces the pain sometimes associated with vasostimulants. In an exemplary embodiment, the vasostimulant is deactivated less than 3 minutes after activation in step 2012, which is less than the conventional deactivation time for tests involving vasostimulation and provides a method which reduces the pain sometimes associated with vasostimulants. In an exemplary embodiment, the vasostimulant is deactivated approximately 2 minutes after activation in step 2012, which is less than the conventional deactivation time for tests involving vasostimulation and provides a method which reduces the pain sometimes associated with vasostimulants. In an exemplary embodiment, the subject may be asked to exercise the body part on which thermal energy is being detected, which allows the method 2000 to simulate a longer vasostimulation in a shorter amount of time, which can also reduce the pain sometimes associated with vasostimulants. In an experimental embodiment 2012a, illustrated in FIG. 32d, the Doppler probe 1902 showed that blood substantially increased in flow rate through the artery in forearm 14 at data point 2012c.

At step 2016, the thermal energy sensor engine 102b begins to detect for equilibrium in the skin temperature of the finger 16 of subject 10. In an exemplary embodiment, at step 2016, the thermal energy sensor engine 102b retrieves successive temperature measurement from the thermal energy sensor 104a.

At decision block 2018, the thermal energy sensor engine 102b determines whether the skin temperature of the finger 16 of subject 10 has reached equilibrium. If the skin temperature of the finger 16 has not reached equilibrium, the temperature sensor engine 102b proceeds back to step 2016 to detect for equilibrium. In an exemplary embodiment, determining whether the skin temperature of the finger 16 has reached equilibrium in step 2018 may include, for example, determining whether the temperature changes of the finger 16 are less than 0.1 degree C.

If the temperature changes in the finger 16 have reached equilibrium, the method proceeds to step 2020 where the temperature sensor engine 102b stops recording the skin temperature of the finger 16 of subject 10.

At step 2022, data acquired from measuring and recording temperature changes of finger 16 which began at step 2006 and continued throughout the method 2000 is saved by the temperature sensor engine 102b to a database such as, for example, the database 102a illustrated in FIG. 3.

At step 2024, a plotting engine such as, for example, the plotting engine 102d illustrated in FIG. 3, may retrieve data from the database 102a.

At step 2026, the plotting engine 102d may plot out the data retrieved. In an exemplary embodiment, the data may be plotted out as temperature vs. time. In an exemplary embodiment, the plotting engine 102d may plot out data obtained from the temperature measurements concurrent with the data being obtained.

Referring now to FIGS. 3, 9a, 33a, 33b, and 33c, an alternative embodiment of an apparatus for determining one or more health conditions 2100 is substantially identical in design and operation to apparatus 600 described above with reference to FIGS. 9a, 9b, 10a, 10b, 10c, and 10d, with the addition of a thermal energy sensor 2102 replacing the thermal energy sensors 104a and 104b. Thermal energy sensor 2102 is mounted to a lead 2104 which electrically couples the thermal energy sensor 2102 to the computer system 102. A circular adhesive 2106 defines a circular channel 2106a centrally located on the circular adhesive 2106 and is positioned adjacent the thermal heat sensor 2102 such that the thermal heat sensor 2102 is located in the circular channel 2106a on the circular adhesive 2106. In operation, the finger 16 of subject 10 is coupled to the apparatus 2100 by engaging the finger 16 with the circular adhesive 2106. With the finger 16 engaging the circular adhesive 2106, there is contact between the skin surface of the finger 16 and the thermal energy sensor 2102, which allows the skin temperature of the finger 16 to be measured and recorded. In an embodiment, the circular adhesive 2106 is positioned adjacent the thermal heat sensor 2102 such that with the finger 16 engaging the thermal energy sensor 2102, a minimum pressure is applied across the finger 16 in order to not substantially change the skin surface temperature of the finger 16. In an exemplary embodiment, a minimum pressure is a pressure which is sufficient to couple the thermal heat sensor 2102 to the skin surface of the finger 16 in order to obtain accurate temperature measurements without impeding underlying microcapillary circulation. In an embodiment, the circular adhesive 2106 is designed such that with the finger 16 engaging the thermal energy sensor 2102, a minimum surface area of the finger 16 is covered in order to not substantially change the skin surface temperature of the finger 16. In an exemplary embodiment, a minimum surface area is a surface area which is sufficient to couple the thermal heat sensor 2102 to the skin surface of the finger 16 in order to obtain accurate temperature measurements without impeding the exchange of heat flow between the ambient and the skin surface.

Referring now to FIGS. 3, 9a, 34a, 34b, and 34c, an alternative embodiment of an apparatus for determining one or more health conditions 2200 is substantially identical in design and operation to apparatus 600 described above with reference to FIGS. 9a, 9b, 10a, 10b, 10c, and 10d, with the addition of a thermal energy sensor 2202 replacing the thermal energy sensors 104a and 104b. Thermal energy sensor 2202 is mounted to a lead 2204 which electrically couples the thermal energy sensor 2202 to the computer system 102. A plurality of spaced apart rectangular adhesive members 2206a and 2206b are positioned adjacent the thermal heat sensor 2202 and on opposite sides of the thermal energy sensor 2202 such that a plurality of airflow channels 2208a and 2208b are located on opposite sides of the thermal energy sensor 2202. In operation, the finger 16 of subject 10 is coupled to the apparatus 2200 by engaging the finger 16 with the plurality of rectangular adhesive members 2206a and 2206b. With the finger 16 engaging the rectangular adhesive members 2206a and 2206b, there is contact between the skin surface of the finger 16 and the thermal energy sensor 2202 while allowing air to flow through the airflow channels 2208a and 2208b on either side of the thermal energy sensor 2202, which allows the skin temperature of the finger 16 to be measured and recorded while allowing air circulation past the finger 16 such that the apparatus 2200 does not substantially change the skin temperature of the finger 16. In an embodiment, the rectangular adhesive members 2206a and 2206b are positioned adjacent the thermal heat sensor 2202 such that with the finger 16 engaging the thermal energy sensor 2202, a minimum pressure is applied across the finger 16 in order to not substantially change the skin surface temperature of the finger 16. In an exemplary embodiment, a minimum pressure is a pressure which is sufficient to couple the thermal heat sensor 2202 to the skin surface of the finger 16 in order to obtain accurate temperature measurements without impeding underlying microcapillary circulation. In an embodiment, the rectangular adhesive members 2206a and 2206b are designed such that with the finger 16 engaging the thermal energy sensor 2202, a minimum surface area of the finger 16 is covered in order to not substantially change the skin surface temperature of the finger 16. In an exemplary embodiment, a minimum surface area is a surface area which is sufficient to couple the thermal heat sensor 2202 to the skin surface of the finger 16 in order to obtain accurate temperature measurements without impeding the exchange of heat flow between the ambient and the skin surface.

Figure 35:
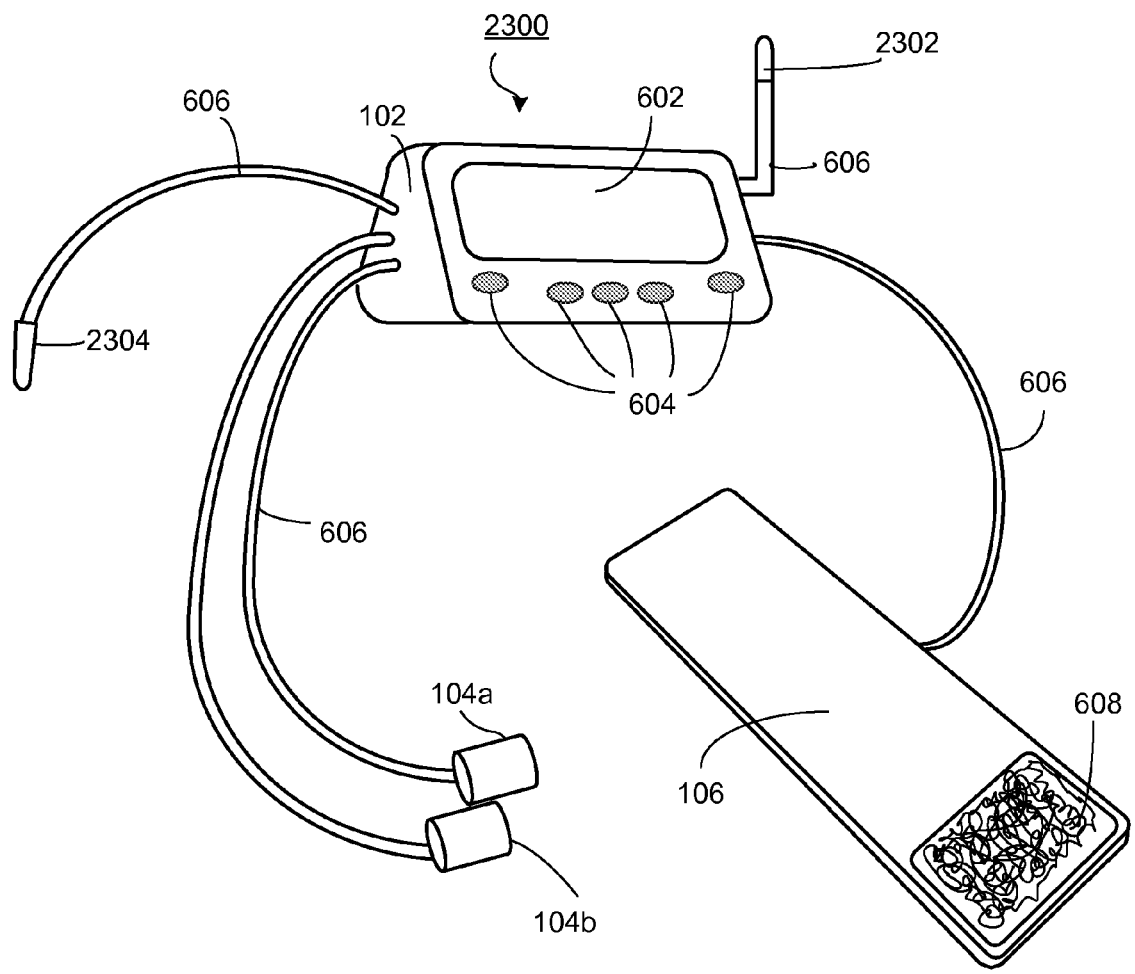
FIG. 35 is a perspective view illustrating an exemplary embodiment of an apparatus for determining one or more health conditions.

Referring now to FIGS. 6a and 35, an alternative embodiment of an apparatus for determining one or more health conditions 2300 is substantially identical in design and operation to apparatus 600 described above with reference to FIGS. 9a, 9b, 10a, 10b, 10c, and 10d, with the addition of a room temperature measurement device 2302 which is coupled to the computer system 102 by a coupling wire 606 and a core temperature measurement device 2304 which is coupled to the computer system 102 by a coupling wire 606. In operation, the room temperature measurement device 2302 may be a conventional room temperature measurement device 2302 known in the art and is used to measure the ambient temperature in a room where the apparatus 2300 is being used. The core temperature measurement device 2304 may be a conventional core temperature measurement device 2304 such as, for example, a conventional thermometer, and is used to measure the core temperature of the subject by, for example, placing the thermometer in the mouth, under the arm, and/or in the rectum of the subject 10.

Figure 36A:
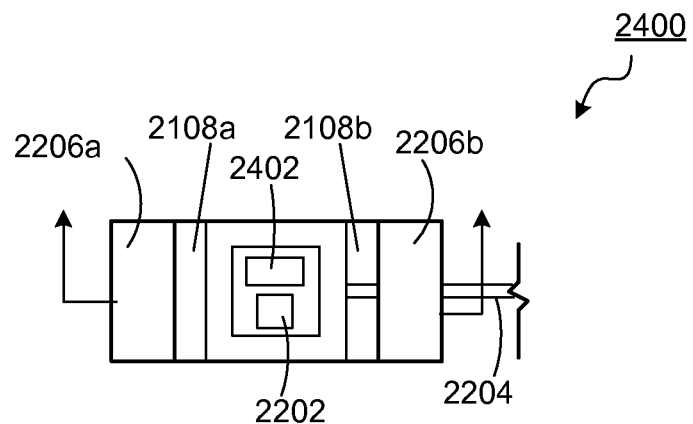
FIG. 36a is a top view illustrating an exemplary embodiment of a thermal energy sensor.
Figure 36B:
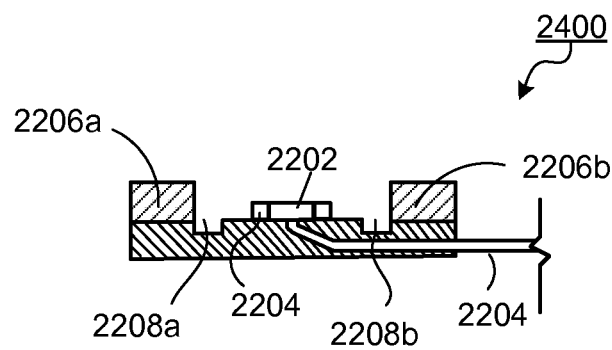
Figure 36C:
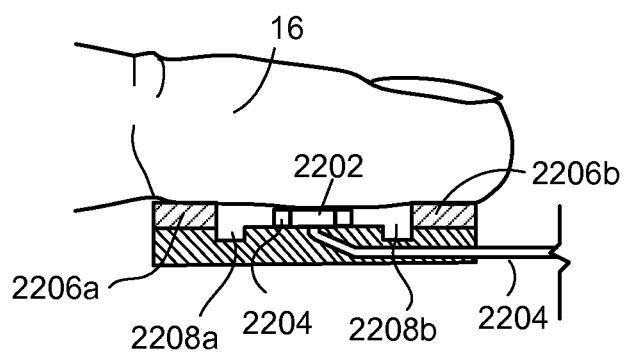
FIG. 36c is a cross sectional view illustrating an exemplary embodiment of the operation of the thermal energy sensor of FIG. 36b.

Referring now to FIGS. 3, 9a, 36a, and 36b, an alternative embodiment of an apparatus for determining one or more health conditions 2400 is substantially identical in design and operation to apparatus 2200 described above with reference to FIGS. 3, 9a, 34a, 34b, and 34c, with the addition of a thermal device 2402. Thermal device 2402 is operable to heat up or cool down using conventional heating and cooling elements known in the art.

Figure 37A:
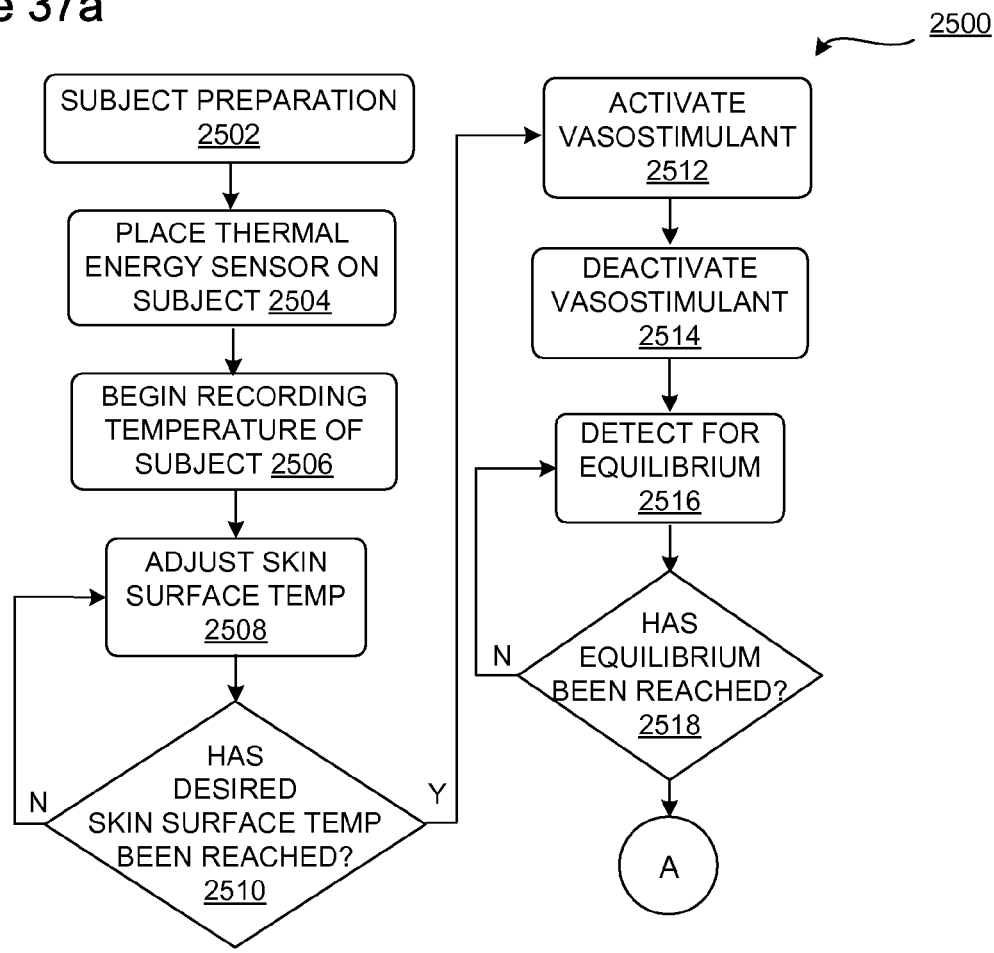
Figure 37B:
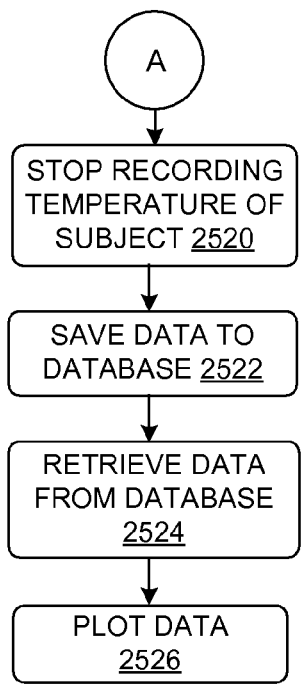

Referring now to FIGS. 37a, 37b, and 37c, in an exemplary embodiment, a method for determining one or more health conditions 2500 is illustrated which begins with a subject preparation at step 2502. Subject preparation at step 2502 may include, for example, having a subject refrain from eating before carrying out the method 2500, having the subject refrain from smoking, ingesting alcohol or caffeine, or taking any vascular medications before carrying out the method 2500.

At step 2504, a thermal energy sensor such as, for example, the thermal energy sensor 2202 on apparatus 200, illustrated in FIGS. 36a and 36b, may be placed on the subject. The finger 16 is coupled to the apparatus 2200 by engaging the finger 16 with the plurality of rectangular adhesive members 2206a and 2206b. With the finger 16 engaging the rectangular adhesive members 2206a and 2206b, there is contact between the skin surface of the finger 16 and the thermal energy sensor 2202 while allowing air to flow through the airflow channels 2208a and 2208b on either side of the thermal energy sensor 2202, which allows the skin temperature of the finger 16 to be measured and recorded while allowing air circulation past the finger 16 such that the apparatus 2200 does not substantially change the skin temperature of the finger 16. With the finger 16 engaging the rectangular adhesive members 2206a and 2206b, there is also contact between the thermal device 2402 and the finger 16, as illustrated in FIG. 37c. In an embodiment, the rectangular adhesive members 2206a and 2206b are positioned adjacent the thermal heat sensor 2202 such that with the finger 16 engaging the thermal energy sensor 2202, a minimum pressure is applied across the finger 16 in order to not substantially change the skin surface temperature of the finger 16. In an exemplary embodiment, a minimum pressure is a pressure which is sufficient to couple the thermal heat sensor 2202 to the skin surface of the finger 16 in order to obtain accurate temperature measurements without impeding underlying microcapillary circulation. In an embodiment, the rectangular adhesive members 2206a and 2206b are designed such that with the finger 16 engaging the thermal energy sensor 2202, a minimum surface area of the finger 16 is covered in order to not substantially change the skin surface temperature of the finger 16. In an exemplary embodiment, a minimum surface area is a surface area which is sufficient to couple the thermal heat sensor 2202 to the skin surface of the finger 16 in order to obtain accurate temperature measurements without impeding the exchange of heat flow between the ambient and the skin surface.

At step 2506, a thermal energy sensor engine such as, for example, the thermal energy sensor engine 102b illustrated in FIG. 3, activates a thermal energy sensor 2402 to begin recording the temperature of the subject. In an exemplary embodiment, temperature data begins being recorded continuously. In an exemplary embodiment, the thermal energy sensor 102b measures the skin temperature of the subject's body on which it is placed such as, for example, the hand, forearm, foot, leg, earlobe, rectum, or nose.

At step 2508, the thermal energy sensor engine 102b activates the thermal device 2402 in order to adjust the skin surface temperature on the finger. The thermal device 2402 may be activated to either heat or cool the skin surface of the finger in order to adjust the skin surface temperature of the finger 16. In an exemplary embodiment, at step 2508, the thermal energy sensor engine 102b retrieves successive temperature measurements from the thermal energy sensor 2202 to adjust the skin surface temperature of the finger 16.

At decision block 2510, the thermal energy sensor engine 102b determines whether the desired skin surface temperature of the finger 16 has been reached. If the desired temperature has not been reached, the temperature sensor engine 102b proceeds back to step 2508 to adjust the skin temperature. In an exemplary embodiment, determining whether the desired temperature of the subject has been reached in step 2510 may include, for example, determining whether the temperature changes of a subject are less than 0.1 degree C.

If the desired temperature in the subject has been reached, the method proceeds to step 2512 where a vasostimulant engine such as, for example, the vasostimulant engine 102c illustrated in FIG. 3, activates a vasostimulant such as, for example, the vasostimulant 106 illustrated in FIG. 3. In an exemplary embodiment, the vasostimulant 106 may be an inflatable cuff, and activating the vasostimulant 106 at step 2512 may include, for example inflating the cuff to 200 mm Hg systolic BP. In an exemplary embodiment, the vasostimulant 106 may be a chemical such as, for example, nitroglycerin, and activating the vasostimulant 106 at step 2512 may include administering a predetermined amount of the chemical to the subject. In an exemplary embodiment, the vasostimulant 106 may be an aptitude test, and activating the vasostimulant 106 at step 2512 may include having the subject begin the aptitude test.

At step 2514, the vasostimulant engine 102c may deactivate the vasostimulant 106. In an exemplary embodiment, the vasostimulant 106 may be an inflatable cuff, and deactivating the vasostimulant 106 at step 2514 may include deflating the cuff. In an exemplary embodiment, the vasostimulant 106 may be a chemical such as, for example, nitroglycerin, and deactivating the vasostimulant 106 at step 2514 may include providing an amount of the chemical in step 2512 such that the effects of the chemical on the subject wear off in a predetermined amount of time. In an exemplary embodiment, deactivating the vasostimulant 106 at step 2514 may include providing additional chemicals to the subject to reverse the effects of the vasostimulant chemicals provided in step 2512. In an exemplary embodiment, the vasostimulant 106 may be an aptitude test, and deactivating the vasostimulant 106 at step 2514 may include having the subject cease taking the aptitude test. In an exemplary embodiment, the vasostimulant is deactivated anywhere from 2 to 5 minutes after activation in step 2512. In an exemplary embodiment, the vasostimulant is deactivated less than 5 minutes after activation in step 2512, which is less than the conventional deactivation time for tests involving vasostimulation and provides a method which reduces the pain sometimes associated with vasostimulants. In an exemplary embodiment, the vasostimulant is deactivated less than 4 minutes after activation in step 2512, which is less than the conventional deactivation time for tests involving vasostimulation and provides a method which reduces the pain sometimes associated with vasostimulants. In an exemplary embodiment, the vasostimulant is deactivated less than 3 minutes after activation in step 2512, which is less than the conventional deactivation time for tests involving vasostimulation and provides a method which reduces the pain sometimes associated with vasostimulants. In an exemplary embodiment, the vasostimulant is deactivated approximately 2 minutes after activation in step 2512, which is less than the conventional deactivation time for tests involving vasostimulation and provides a method which reduces the pain sometimes associated with vasostimulants. In an exemplary embodiment, the subject may be asked to exercise the body part on which thermal energy is being detected, which allows the method 2500 to simulate a longer vasostimulation in a shorter amount of time, which can also reduce the pain sometimes associated with vasostimulants.

At step 2516, the thermal energy sensor engine 102b begins to detect for equilibrium in the temperature of subject. In an exemplary embodiment, at step 2516, the thermal energy sensor engine 102b retrieves successive temperature measurement from the thermal energy sensor.

At decision block 2518, the thermal energy sensor engine 102b determines whether the temperature of the subject has reached equilibrium. If the temperature of the subject has not reached equilibrium, the temperature sensor engine proceeds back to step 2516 to detect for equilibrium. In an exemplary embodiment, determining whether the temperature of the subject has reached equilibrium in step 2518 may include, for example, determining whether the temperature changes of a subject are less than 0.1 degree C.

If the temperature changes in the subject have reached equilibrium, the method proceeds to step 2520 where the temperature sensor engine 102b stops recording the temperature of the subject.

At step 2522, data acquired from measuring and recording temperature changes which began at step 2506 and continued throughout the method 2500 is saved by the temperature sensor engine 102b to a database such as, for example, the database 102a illustrated in FIG. 3.

At step 2524, a plotting engine such as, for example, the plotting engine 102d illustrated in FIG. 2, may retrieve data from the database 102a.

At step 2526, the plotting engine 102d may plot out the data retrieved. In an exemplary embodiment, the data may be plotted out as temperature vs. time. In an exemplary embodiment, the plotting engine 102d may plot out data obtained from the temperature measurements concurrent with the data being obtained. In an exemplary embodiment, the plotting engine 102d may retrieve data taken from multiple positions on subject and plot out an average of that data over time. In an exemplary embodiment, the plotting engine 102d may retrieve data taken from subject at different times and plot out an average of that data.

Figure 38A:
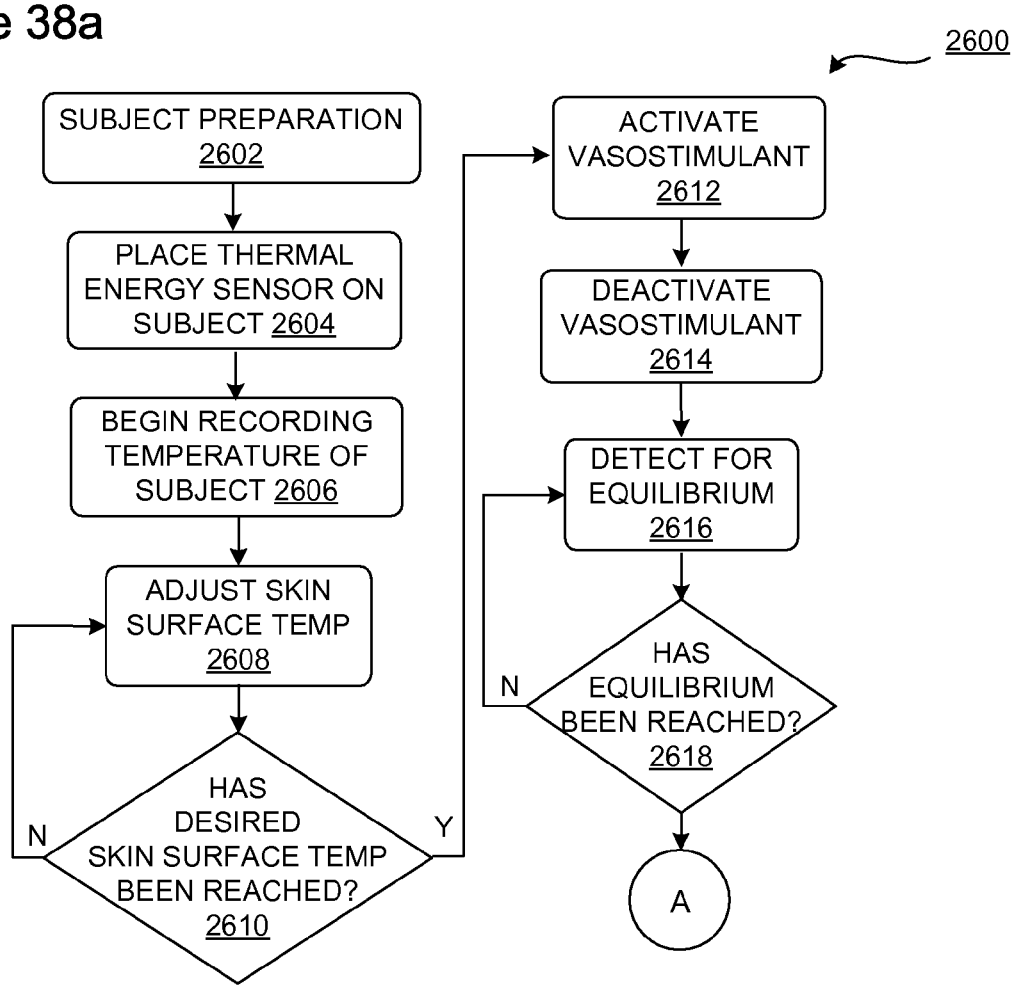
FIG. 38a is a flow chart illustrating an exemplary embodiment of a portion of a method for determining one or more health conditions.
Figure 38B:
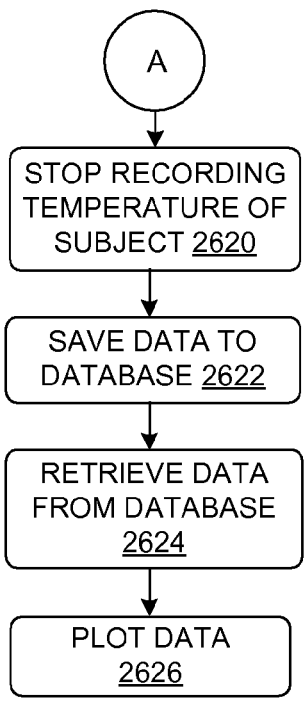
FIG. 38b is a flow chart illustrating an exemplary embodiment of a portion of a method for determining one or more health conditions.

Referring now to FIGS. 38a and 38b, in an exemplary embodiment, a method for determining one or more health conditions 2600 is illustrated which begins with a subject preparation at step 2602. Subject preparation at step 2602 may include, for example, having a subject refrain from eating before carrying out the method 2600, having the subject refrain from smoking before carrying out the method 2600, having the subject refrain from ingesting alcohol or caffeine before carrying out the method 2600, or having the subject refrain from taking any vascular medications before carrying out the method 2600.

At step 2604, a thermal energy sensor such as, for example, the thermal energy sensor 104a on apparatus 600, illustrated in FIGS. 9a and 9b, may be placed on the finger 16 of subject and the thermal energy sensor 104b may be placed on the contralateral finger 18 of subject.

At step 2606, a thermal energy sensor engine such as, for example, the thermal energy sensor engine 102b illustrated in FIG. 3, activates the thermal energy sensors 104a and 104b to begin recording the skin temperature of the finger 16 and the contralateral finger 18 of the subject. In an exemplary embodiment, temperature data begins being recorded continuously.

Figure 38C:
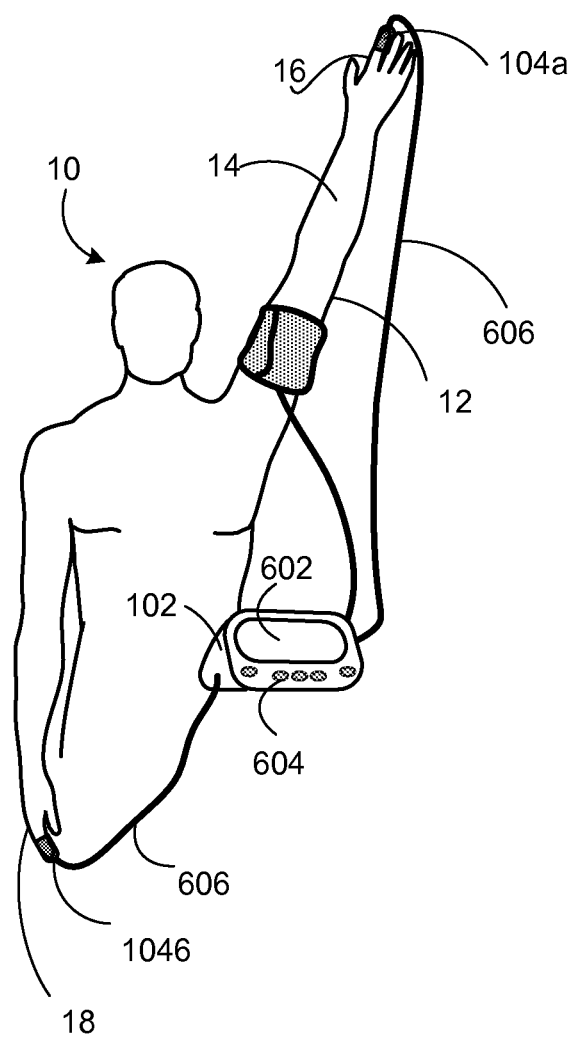
FIG. 38c is a perspective view illustrating an exemplary embodiment of the subject of FIG. 3 during the method of FIGS. 38a and 38b.
Figure 38D:
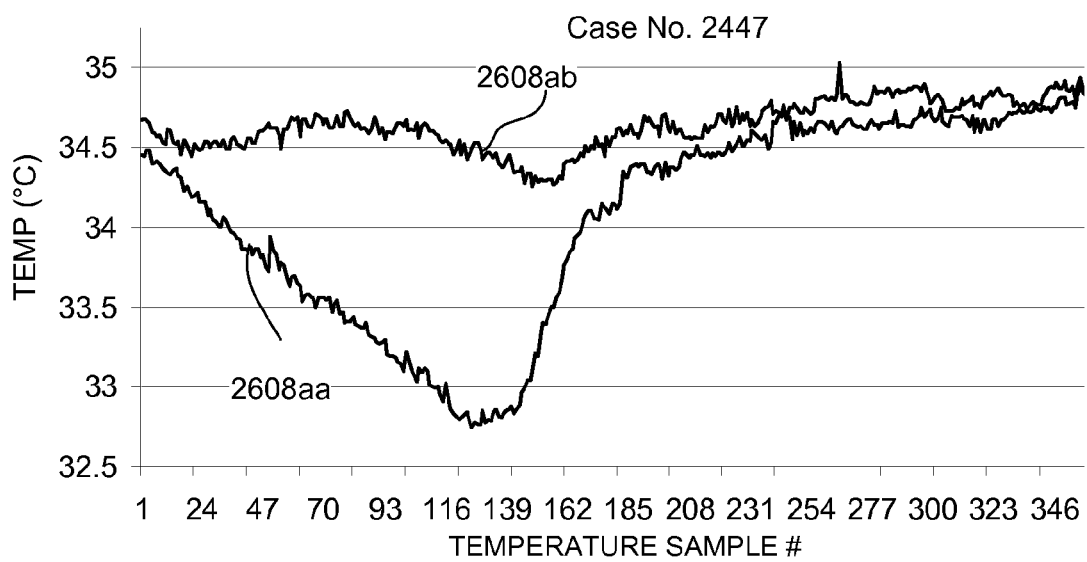
FIG. 38d is a graph illustrating an experimental embodiment of the subject not undergoing the method of FIGS. 38a and 38b.
Figure 38E:
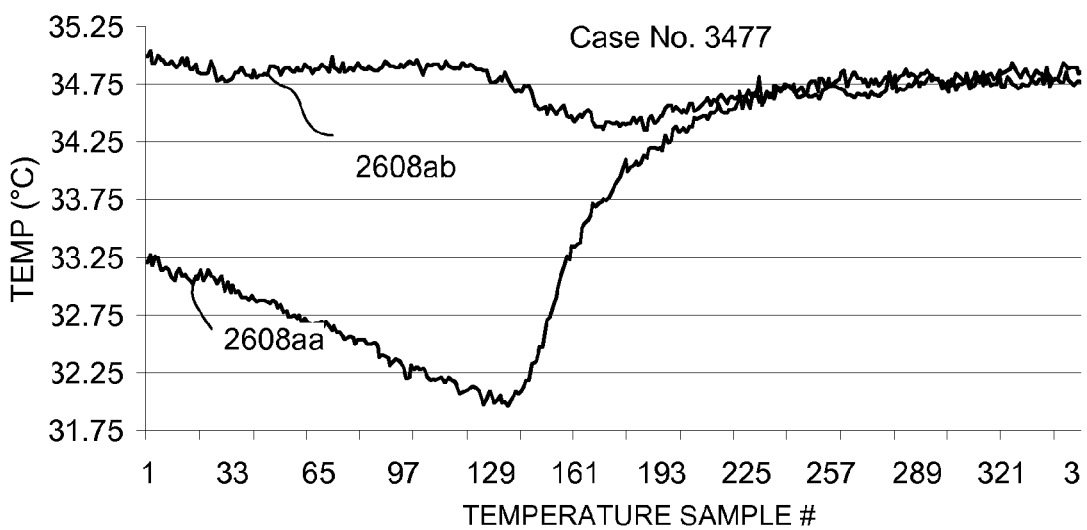
FIG. 38e is a graph illustrating an experimental embodiment of the subject undergoing the method of FIGS. 38a and 38b.

At step 2608, the skin surface temperature on the finger 16 of subject is adjusted. The finger 16 of the subject is elevated, as illustrated in FIG. 38c, such that blood flow to the finger 16 is decreased and the temperature of the skin surface of the finger 16 decreases. In an experimental embodiment 2608a, illustrated in FIG. 38d, the subject did not elevate the finger 16 or the contralateral finger 18 and the finger temperature 2608aa and the contralateral finger temperature 2608ab both began the method 2600 at approximately 34.4 to 34.7 degrees Celsius. In an experimental embodiment 2608b, illustrated in FIG. 38e, the subject elevated the finger 16 and the finger temperature 2608aa was allowed to drop such that it began the method 2600 at approximately 33.2 degrees Celsius while the contralateral finger temperature 2608ab began the method 2600 at approximately 35 degrees Celsius. The experimental embodiments 2608a and 2608b show that the skin temperature of the finger 16 may be adjusted by elevating the finger 16 of the subject.

At decision block 2610, the thermal energy sensor engine 102b determines whether the desired skin surface temperature of the finger 16 of subject has been reached. If the desired temperature of the subject has not been reached, the temperature sensor engine 102b proceeds back to step 2608 to detect whether the desired temperature has been reached. In an exemplary embodiment, determining whether the desired temperature of the subject has been reached in step 2610 may include, for example, determining whether the temperature changes of a subject are less than 0.1 degree C.

If the desired temperature in the subject has been reached, the method proceeds to step 2612 where a vasostimulant engine such as, for example, the vasostimulant engine 102c illustrated in FIG. 2, activates a vasostimulant such as, for example, the vasostimulant 106 illustrated in FIG. 1. In an exemplary embodiment, the vasostimulant 106 may be an inflatable cuff, and activating the vasostimulant 106 at step 2612 may include, for example inflating the cuff to 200 mm Hg systolic BP. In an exemplary embodiment, the vasostimulant 106 may be a chemical such as, for example, nitroglycerin, and activating the vasostimulant 106 at step 2612 may include administering a predetermined amount of the chemical to the subject. In an exemplary embodiment, the vasostimulant 106 may be an aptitude test, and activating the vasostimulant 106 at step 2612 may include having the subject begin the aptitude test.

At step 2614, the vasostimulant engine 102c may deactivate the vasostimulant 106. In an exemplary embodiment, the vasostimulant 106 may be an inflatable cuff, and deactivating the vasostimulant 106 at step 2614 may include deflating the cuff. In an exemplary embodiment, the vasostimulant 106 may be a chemical such as, for example, nitroglycerin, and deactivating the vasostimulant 106 at step 2614 may include providing an amount of the chemical in step 2612 such that the effects of the chemical on the subject wear off in a predetermined amount of time. In an exemplary embodiment, deactivating the vasostimulant 106 at step 2614 may include providing additional chemicals to the subject to reverse the effects of the vasostimulant chemicals provided in step 2612. In an exemplary embodiment, the vasostimulant 106 may be an aptitude test, and deactivating the vasostimulant 106 at step 2614 may include having the subject cease taking the aptitude test. In an exemplary embodiment, the vasostimulant is deactivated anywhere from 2 to 5 minutes after activation in step 2612. In an exemplary embodiment, the vasostimulant is deactivated less than 5 minutes after activation in step 2612, which is less than the conventional deactivation time for tests involving vasostimulation and provides a method which reduces the pain sometimes associated with vasostimulants. In an exemplary embodiment, the vasostimulant is deactivated less than 4 minutes after activation in step 2612, which is less than the conventional deactivation time for tests involving vasostimulation and provides a method which reduces the pain sometimes associated with vasostimulants. In an exemplary embodiment, the vasostimulant is deactivated less than 3 minutes after activation in step 2612, which is less than the conventional deactivation time for tests involving vasostimulation and provides a method which reduces the pain sometimes associated with vasostimulants. In an exemplary embodiment, the vasostimulant is deactivated approximately 2 minutes after activation in step 2612, which is less than the conventional deactivation time for tests involving vasostimulation and provides a method which reduces the pain sometimes associated with vasostimulants. In an exemplary embodiment, the subject may be asked to exercise the body part on which thermal energy is being detected, which allows the method 2600 to simulate a longer vasostimulation in a shorter amount of time, which can also reduce the pain sometimes associated with vasostimulants.

At step 2616, the thermal energy sensor engine 102b begins to detect for equilibrium in the temperature of subject. In an exemplary embodiment, at step 2616, the thermal energy sensor engine 102b retrieves successive temperature measurement from the thermal energy sensor.

At decision block 2618, the thermal energy sensor engine 102b determines whether the temperature of the subject has reached equilibrium. If the temperature of the subject has not reached equilibrium, the temperature sensor engine proceeds back to step 2616 to detect for equilibrium. In an exemplary embodiment, determining whether the temperature of the subject has reached equilibrium in step 2618 may include, for example, determining whether the temperature changes of a subject are less than 0.1 degree C.

If the temperature changes in the subject have reached equilibrium, the method proceeds to step 2620 where the temperature sensor engine 102b stops recording the temperature of the subject.

At step 2622, data acquired from measuring and recording temperature changes which began at step 2606 and continued throughout the method 2600 is saved by the temperature sensor engine 102b to a database such as, for example, the database 102a illustrated in FIG. 3.

At step 2624, a plotting engine such as, for example, the plotting engine 102d illustrated in FIG. 3, may retrieve data from the database 102a.

At step 2626, the plotting engine 102d may plot out the data retrieved. In an exemplary embodiment, the data may be plotted out as temperature vs. time. In an exemplary embodiment, the plotting engine 102d may plot out data obtained from the temperature measurements concurrent with the data being obtained. In an exemplary embodiment, the plotting engine 102d may retrieve data taken from multiple positions on subject and plot out an average of that data over time. In an exemplary embodiment, the plotting engine 102d may retrieve data taken from subject at different times and plot out an average of that data.

Figure 39:
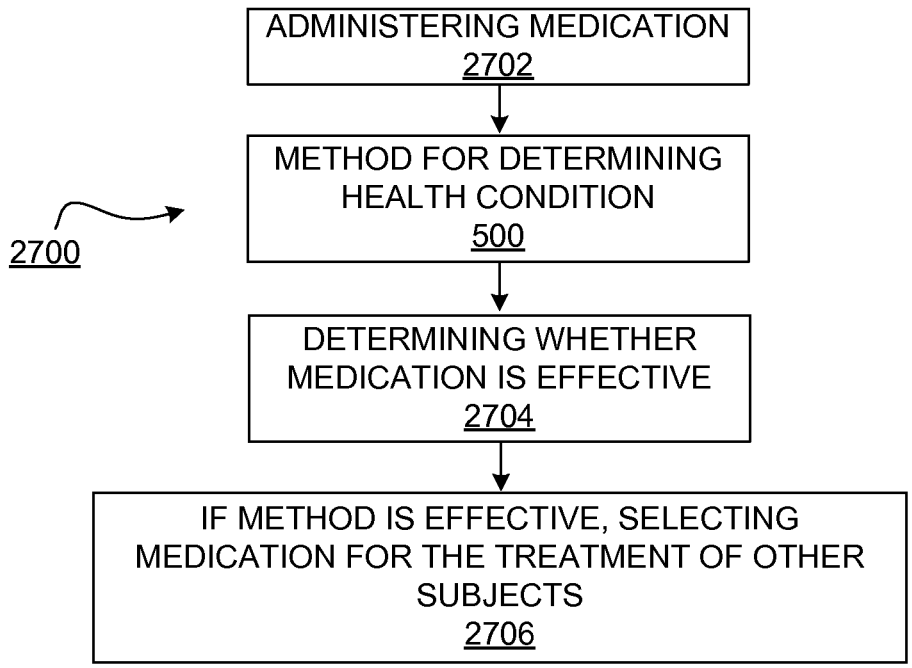
FIG. 39 is a flow chart illustrating an embodiment of a method for determining the effectiveness of a medication.

Referring now to FIG. 39, an embodiment of a method 2700 for selecting a medication for the treatment of a medical condition in a subject is substantially identical in design and operation to method 500 described above with reference to FIGS. 8a and 8b, with the addition of administering a medication to one or more subjects at step 2702, determining whether the medication is effective in treatment of the medical condition of the subject at step 2704, and, if the medication is effective in treatment of the medical condition of the subject, selecting the medication for use in treating the medical condition in other subjects at step 2706. The method 2700 begins as step 2702 where medication is administered to one or more subjects at step 2702. In an exemplary embodiment, the medication may be a drug which is being evaluated or screened to determine its effectiveness in treating a medical condition of the subjects. The method 2700 then proceeds to follow the method 500 where the health condition of the subject is determined as described above with reference to FIGS. 8a and 8b. The method then proceeds to step 2704 where it is determined whether the medication is effective in treatment of the medical condition of the subject at step 2704. The method 2700 then proceeds to step 2706 where, if the medication is effective in treatment of the medical condition of the subject, the medication is selected for use in treating the medical condition in other subjects. In an exemplary embodiment, the method 2700 may be used to evaluate the effectiveness of any treatment given to a subject such as, for example, drugs, surgery, physical therapy, exercise, cancer treatments, non-invasive treatments, invasive treatments, nutritional regimens, and/or combinations of the foregoing.

Figure 40:
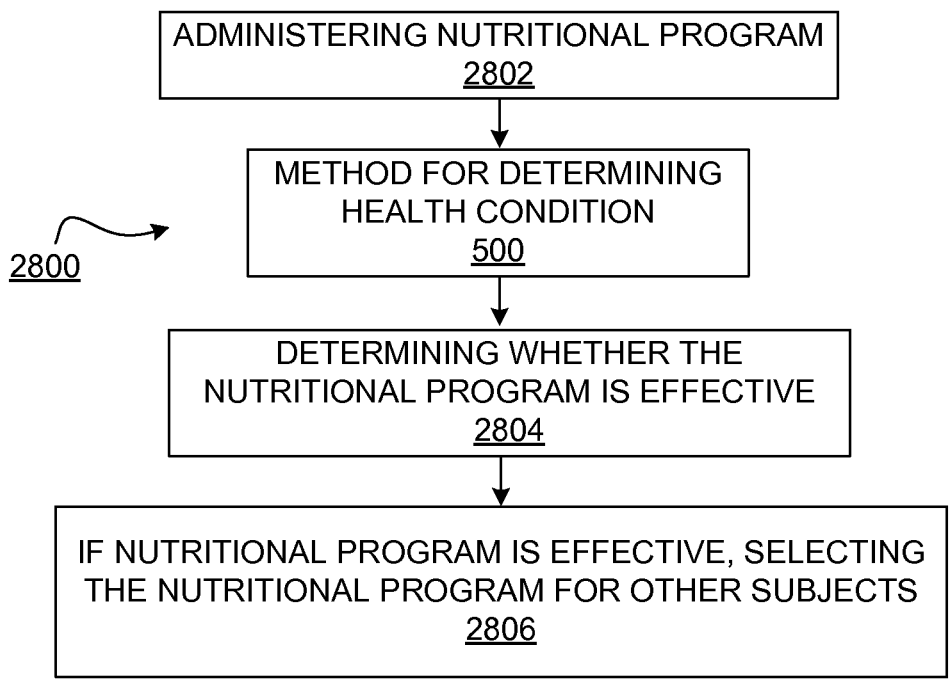
FIG. 40 is a flow chart illustrating an embodiment of a method for determining the effectiveness of a nutritional program.

Referring now to FIG. 40, an embodiment of a method 2800 for selecting a nutritional program for a subject is substantially identical in design and operation to method 500 described above with reference to FIGS. 8a and 8b, with the addition of administering a nutritional program to one or more subjects at step 2802, determining whether the nutritional program is effective for the subject at step 2804, and, if the nutritional program is effective for the subject, selecting the nutritional program for other subjects at step 2806. The method 2800 begins as step 2802 where a nutritional program is administered to one or more subjects at step 2802. In an exemplary embodiment, the nutritional program may a variety of diet and/or exercise programs which are being evaluated or screened to determine their effectiveness for subjects for example, to deal with general nutritional concerns or in obesity management. The method 2800 then proceeds to follow the method 500 where the health condition of the subject is determined as described above with reference to FIGS. 8a and 8b. The method then proceeds to step 2804 where it is determined whether the nutritional program is effective for the subject at step 2804. In an exemplary embodiment, the nutritional program may be determined to be effective if the subject achieves a desired physical condition such as, for example, a lower body weight, a lower body fat percentage, a higher muscle mass, or a variety of other physical conditions known in the art. The method then proceeds to step 2806 where, if the nutritional program is effective for the subject, the nutritional program is used for other subjects. In an exemplary embodiment, the method 2800 may be used to evaluate the effectiveness of any treatment given to a subject such as, for example, drugs, surgery, physical therapy, exercise, cancer treatments, non-invasive treatments, invasive treatments, nutritional regimens, and/or combinations of the foregoing.

Figure 41:
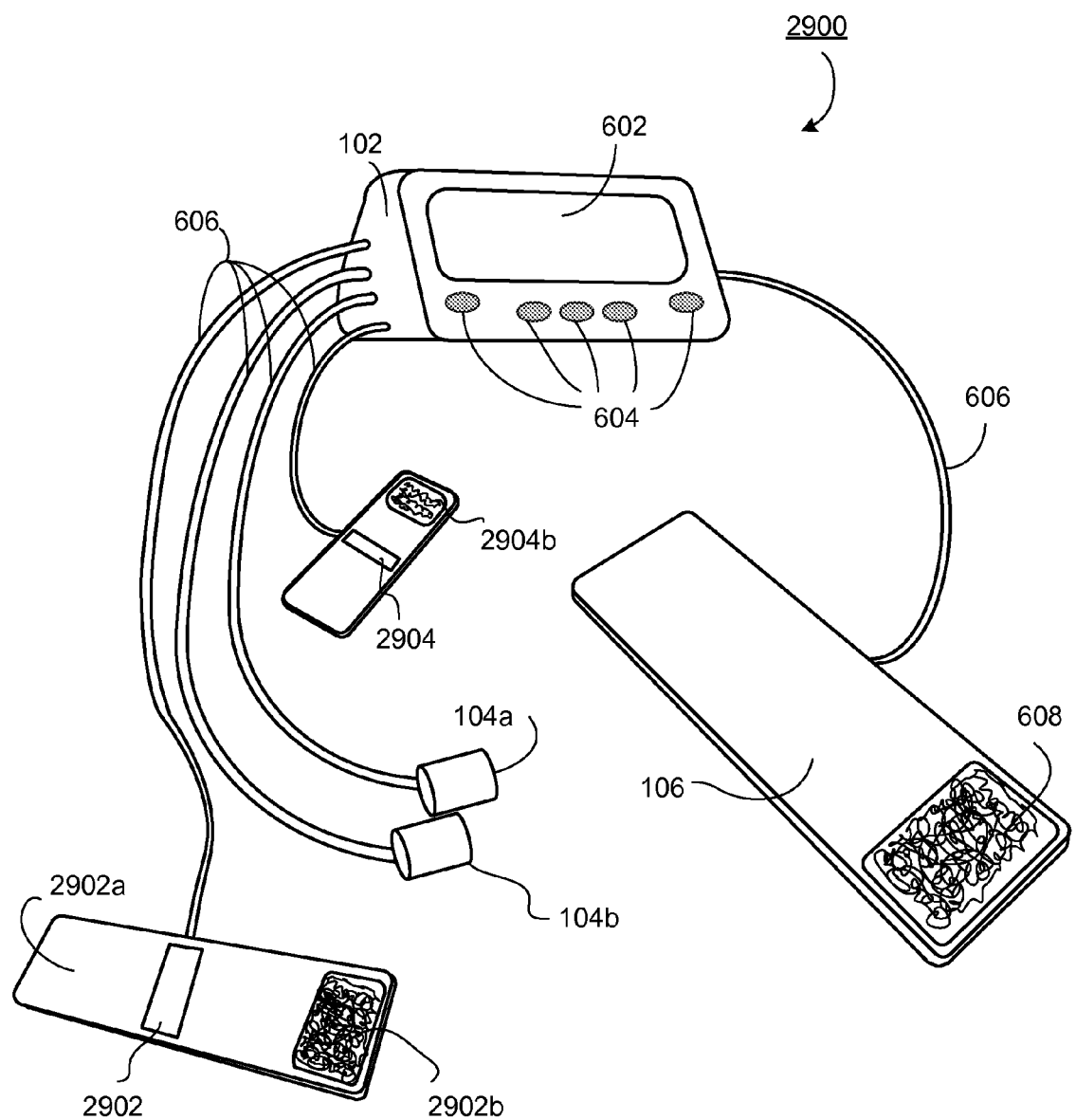
FIG. 41 is a perspective view illustrating an embodiment of apparatus for determining health condition.

Referring now to FIG. 41, an alternative embodiment of an apparatus for determining one or more health conditions 2900 is substantially identical in design and operation to apparatus 600 described above with reference to FIGS. 3, 4, 5, 6, 7, 8a, 8b, 9a, and 9b with the addition of a wrist thermal energy sensor 2902 and an additional finger thermal energy sensor 2904. The wrist thermal energy sensor 2902 is coupled to the computer system 102 by a coupling wire 606 and includes a wrist coupler 2902a having an adhesive member 2902b on a distal end of the wrist coupler 2902a which may adhere to the wrist coupler 2902a. The finger thermal energy sensor 2904 is coupled to the computer system 102 by a coupling wire 606 and includes a finger coupler 2904a having an adhesive member 2904b on a distal end of the finger coupler 2904a which may adhere to the finger coupler 2904a.

Figure 42A:
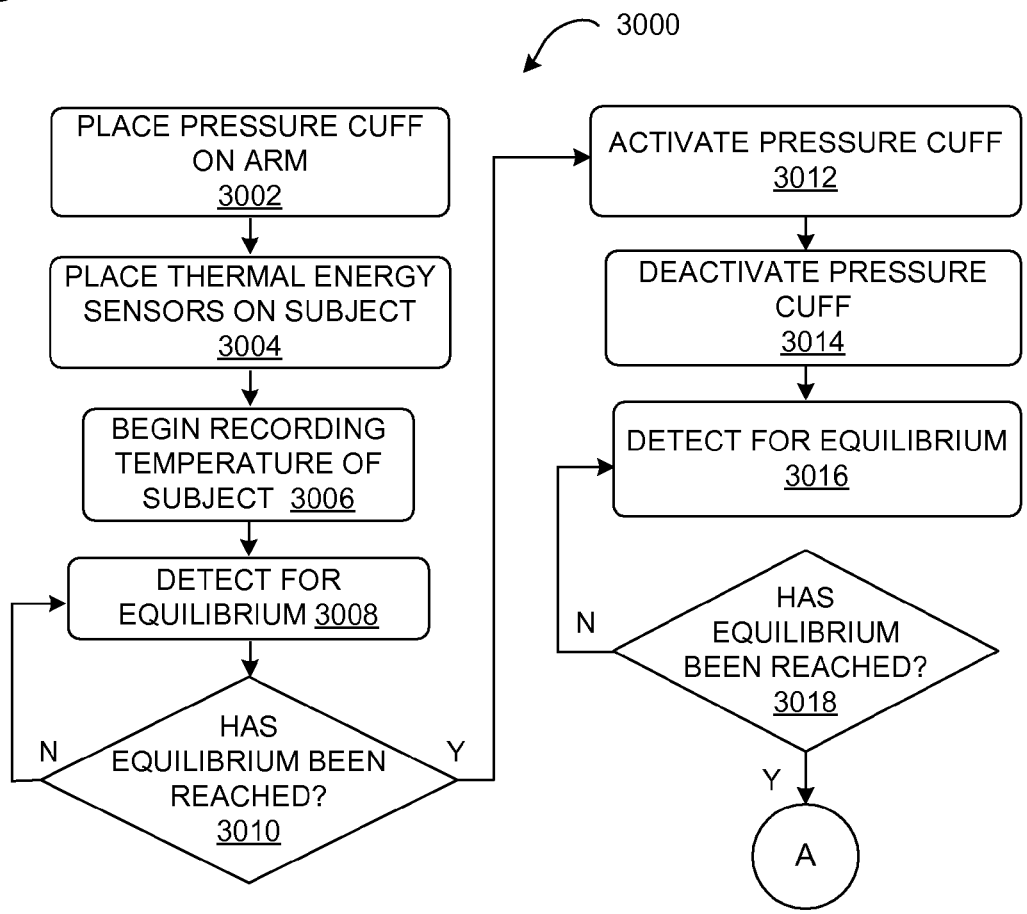
FIG. 42a is a flow chart illustrating an embodiment of a portion of a method for determining health condition using the apparatus of FIG. 41.
Figure 42B:
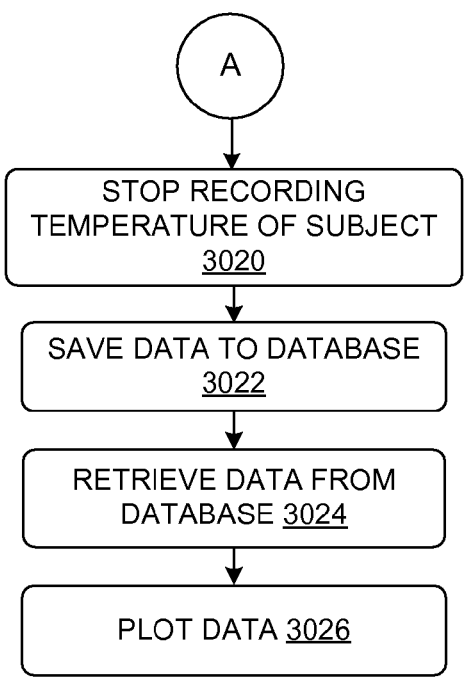
FIG. 42b is a flow chart illustrating an embodiment of a portion of a method for determining health condition using the apparatus of FIG. 41.
Figure 42C:
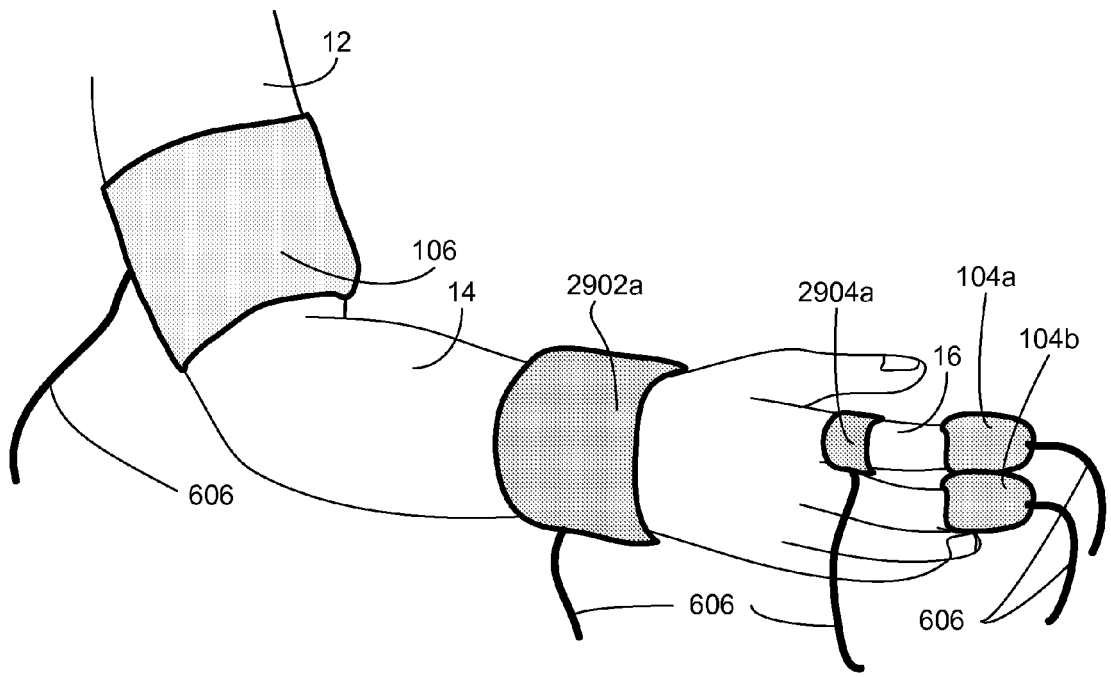
FIG. 42c is a perspective view illustrating an embodiment of the apparatus of FIG. 41 on the subject of FIG. 1 during the method of FIGS. 42a and 42b.

Referring now to FIGS. 42a, 42b, and 42c, in an exemplary embodiment, a method 3000 for determining one or more health conditions using the apparatus 2900 illustrated in FIG. 41 is illustrated which begins with placing the pressure cuff vasostimulant 106 on arm 12 of subject at step 3002. Pressure cuff vasostimulant 106 may be secured to arm 12 by vasostimulant coupling member 608 which may include a variety of adhesive materials known in the art. In an exemplary embodiment, the subject may be in a seated position during method 3000.

At step 3004, the thermal energy sensor 104a may be placed on finger 16 of the subject. The thermal energy sensor 104b may be placed on a finger adjacent finger 16 of subject. The finger thermal energy sensor 2904a may be also placed on finger 16 of subject by adhering adhesive member 2904c to finger coupler 2904b, as illustrated in FIG. 42c. The wrist thermal energy sensor 2902a may be placed on the wrist of subject between the forearm 14 and the finger 16 of subject by adhering adhesive member 2902c to wrist coupler 2902b, as illustrated in FIG. 42c.

At step 3006, a thermal energy sensor engine such as, for example, the thermal energy sensor engine 102b illustrated in FIG. 3, activates the thermal energy sensor 104a to begin recording the skin temperature of the finger 16, the finger adjacent the finger 16, and the wrist between the forearm 14 and the finger 16, of subject. In an exemplary embodiment, temperature data begins being recorded continuously. In an exemplary embodiment, the thermal energy sensor 104a engages the skin of the finger 16 of subject in order to measure temperature. In an exemplary embodiment, the thermal energy sensor 104a measures the skin temperature of the finger 16 of subject without engaging the skin of the finger 16 of subject. In an exemplary embodiment, the ambient temperature is held constant around the thermal energy sensor 104a. In an exemplary embodiment, the fluid flow such as, for example, the airflow, around the thermal energy sensor 104a is kept to a minimum.

At step 3008, the thermal energy sensor engine 102b begins to detect for equilibrium in the skin temperature of the finger 16, the finger adjacent the finger 16, and the wrist between the forearm 14 and the finger 16, of subject. In an exemplary embodiment, at step 3008, the thermal energy sensor engine 102b retrieves successive temperature measurement from the thermal energy sensor 104a.

At decision block 3010, the thermal energy sensor engine 102b determines whether the skin temperature of finger 16, the finger adjacent the finger 16, and the wrist between the forearm 14 and the finger 16, of subject 10 has reached equilibrium. If the skin temperature of finger 16, the finger adjacent the finger 16, and the wrist between the forearm 14 and the finger 16, has not reached equilibrium, the temperature sensor engine 102b proceeds back to step 3008 to detect for equilibrium. In an exemplary embodiment, determining whether the skin temperature of the finger 16, the finger adjacent the finger 16, and the wrist between the forearm 14 and the finger 16, has reached equilibrium in step 710 may include, for example, determining whether the temperature changes of the finger 16, the finger adjacent the finger 16, and the wrist between the forearm 14 and the finger 16, are less than 0.1 degree C.

If the temperature changes in the finger 16, the finger adjacent the finger 16, and the wrist between the forearm 14 and the finger 16, have reached equilibrium, the method proceeds to step 3012 where a vasostimulant engine such as, for example, the vasostimulant engine 102c illustrated in FIG. 3, activates the pressure cuff vasostimulant 106. In an exemplary embodiment, activating the pressure cuff vasostimulant 106 at step 3012 may include, for example, inflating the cuff to 200 mm Hg systolic BP.

At step 3014, the vasostimulant engine 102c may deactivate the pressure cuff vasostimulant 106. In an exemplary embodiment, deactivating the pressure cuff vasostimulant 106 at step 3014 may include deflating the cuff. In an exemplary embodiment, the pressure cuff vasostimulant 106 is deactivated anywhere from 2 to 5 minutes after activation in step 3012. In an exemplary embodiment, the vasostimulant is deactivated less than 5 minutes after activation in step 3012, which is less than the conventional deactivation time for tests involving vasostimulation and provides a method which reduces the pain sometimes associated with vasostimulants. In an exemplary embodiment, the vasostimulant is deactivated less than 4 minutes after activation in step 3012, which is less than the conventional deactivation time for tests involving vasostimulation and provides a method which reduces the pain sometimes associated with vasostimulants. In an exemplary embodiment, the vasostimulant is deactivated less than 3 minutes after activation in step 3012, which is less than the conventional deactivation time for tests involving vasostimulation and provides a method which reduces the pain sometimes associated with vasostimulants. In an exemplary embodiment, the vasostimulant is deactivated approximately 2 minutes after activation in step 3012, which is less than the conventional deactivation time for tests involving vasostimulation and provides a method which reduces the pain sometimes associated with vasostimulants. In an exemplary embodiment, the subject may be asked to exercise the body part on which thermal energy is being detected, which allows the method 3000 to simulate a longer vasostimulation in a shorter amount of time, which can also reduce the pain sometimes associated with vasostimulants.

At step 3016, the thermal energy sensor engine 102b begins to detect for equilibrium in the skin temperature of the finger 16, the finger adjacent the finger 16, and the wrist between the forearm 14 and the finger 16, of subject 10. In an exemplary embodiment, at step 3016, the thermal energy sensor engine 102b retrieves successive temperature measurement from the thermal energy sensor 104a.

At decision block 3018, the thermal energy sensor engine 102b determines whether the skin temperature of the finger 16, the finger adjacent the finger 16, and the wrist between the forearm 14 and the finger 16, of subject 10 has reached equilibrium. If the skin temperature of the finger 16, the finger adjacent the finger 16, and the wrist between the forearm 14 and the finger 16, has not reached equilibrium, the temperature sensor engine 102b proceeds back to step 3016 to detect for equilibrium. In an exemplary embodiment, determining whether the skin temperature of the finger 16, the finger adjacent the finger 16, and the wrist between the forearm 14 and the finger 16, has reached equilibrium in step 3018 may include, for example, determining whether the temperature changes of the finger 16 are less than 0.1 degree C.

If the temperature changes in the finger 16, the finger adjacent the finger 16, and the wrist between the forearm 14 and the finger 16, have reached equilibrium, the method proceeds to step 3020 where the temperature sensor engine 102*b* stops recording the skin temperature of the finger 16, the finger adjacent the finger 16, and the wrist between the forearm 14 and the finger 16, of subject 10.

At step 3022, data acquired from measuring and recording temperature changes of finger 16, the finger adjacent the finger 16, and the wrist between the forearm 14 and the finger 16, which began at step 3006 and continued throughout the method 3000 is saved by the temperature sensor engine 102*b* to a database such as, for example, the database 102*a* illustrated in FIG. 3.

At step 3024, a plotting engine such as, for example, the plotting engine 102*d* illustrated in FIG. 3, may retrieve data from the database 102*a*.

At step 3026, the plotting engine 102*d* may plot out the data retrieved. In an exemplary embodiment, the data may be plotted out as temperature vs. time. In an exemplary embodiment, the plotting engine 102*d* may plot out data obtained from the temperature measurements concurrent with the data being obtained.

Figure 43A:
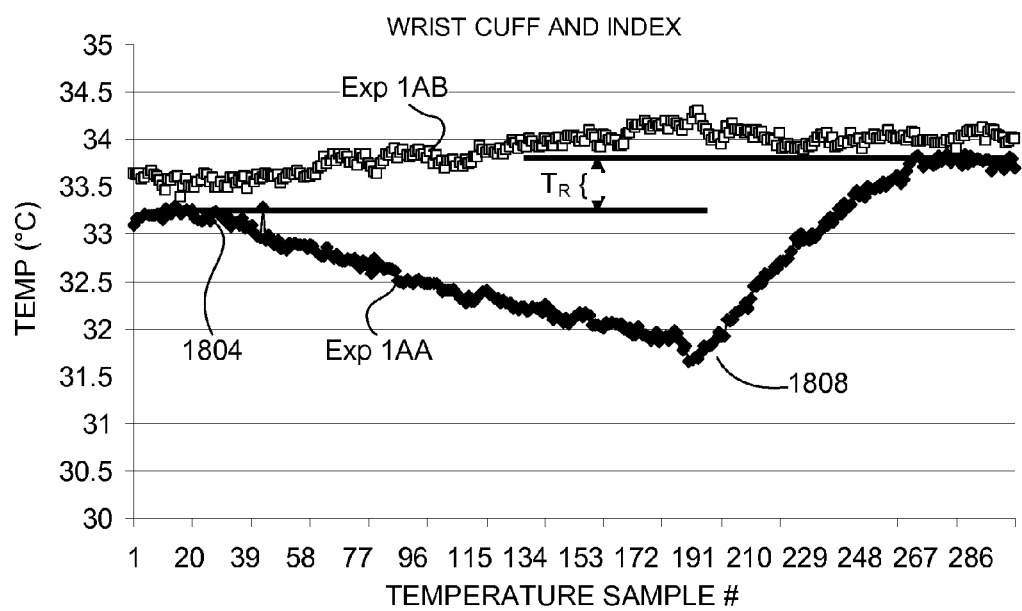
FIG. 43a is a graph illustrating an experimental embodiment of the subject undergoing the method of FIGS. 42a and 42b.
Figure 43B:
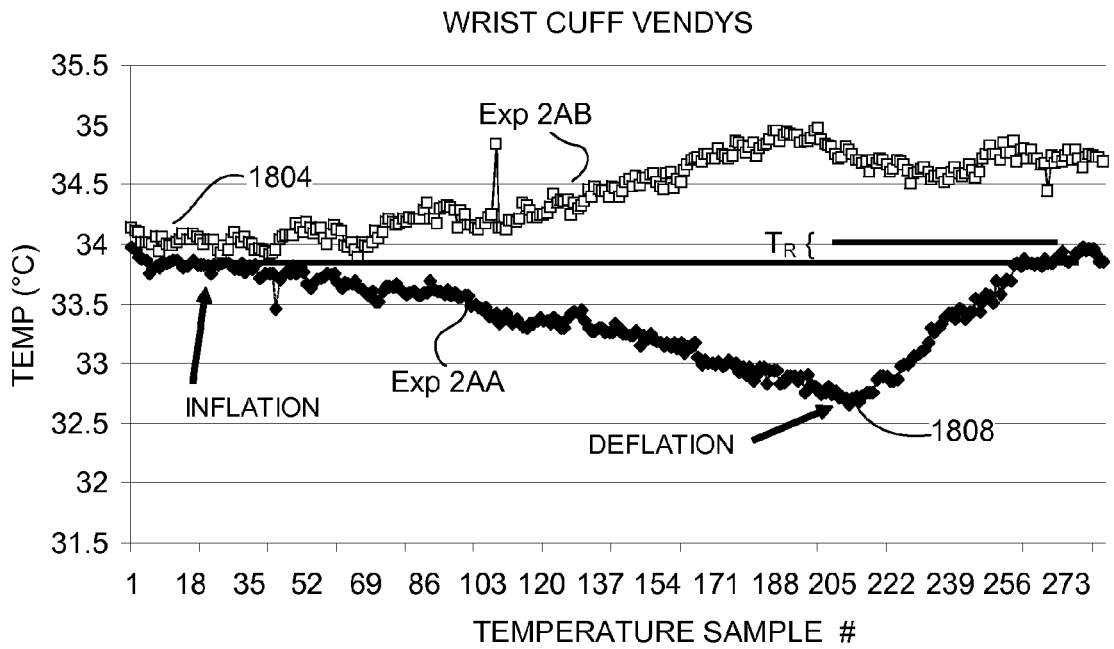
FIG. 43b is a graph illustrating an experimental embodiment of the subject undergoing the method of FIGS. 42a and 42b.
Figure 43C:
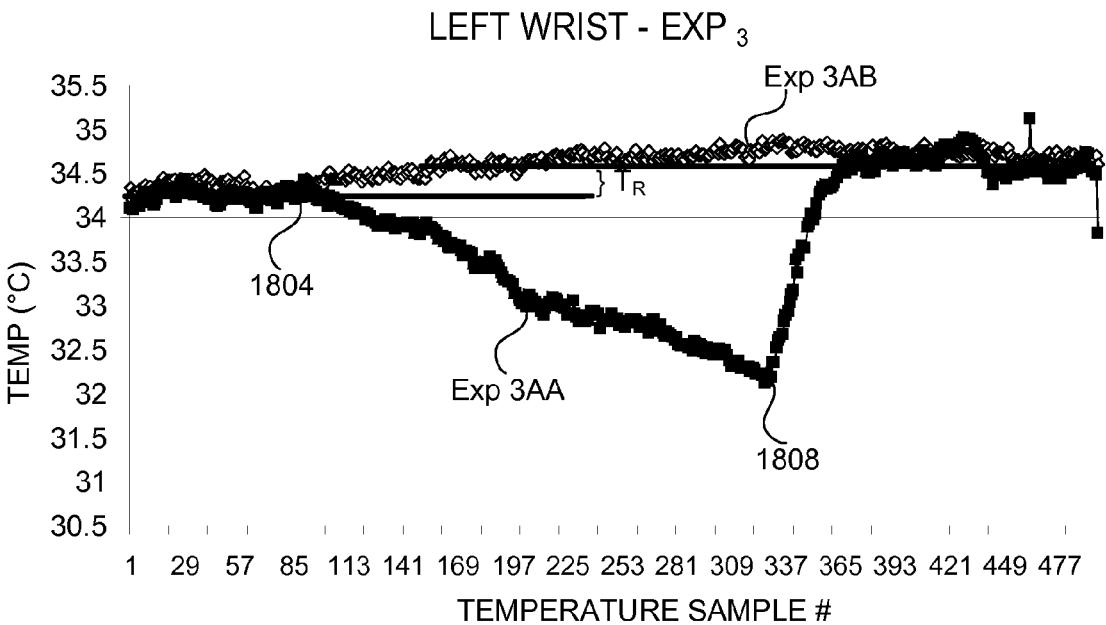
FIG. 43c is a graph illustrating an experimental embodiment of the subject undergoing the method of FIGS. 42a and 42b.

Referring now to FIGS. 43*a*, 43*b*, and 43*c*, in a plurality of exemplary experimental embodiments EXP1, EXP2, and EXP3, the method 3000 was carried out on a subject, and a plurality of graphs EXP1A, EXP2A, and EXP3A, were obtained of data relating to temperature changes of the skin on a wrist of the subject. A pressure cuff was provided as the vasostimulant, and vasostimulant activation at time 1804 and deactivation at time 1808 was provided by inflating and deflating the pressure cuff. In graph EXP1A, the temperature in a wrist EXP1AA distal to the pressure cuff and the temperature in a finger EXP1AB which was not distal to the pressure cuff were measured. The temperature in the wrist EXP1AA distal to the pressure cuff dropped as expected between times 1804 and 1808 and a positive TR was measured after time 1808. In graph EXP2A, the temperature in a wrist EXP2AA distal to the pressure cuff and the temperature in a finger EXP2AB which was not distal to the pressure cuff were measured. The temperature in the wrist EXP2AA distal to the pressure cuff dropped as expected between times 1804 and 1808 and a positive TR was measured after time 1808. In graph EXP3A, the temperature in a wrist EXP3AA distal to the pressure cuff and the temperature in a finger EXP3AB which was not distal to the pressure cuff were measured. The temperature in the wrist EXP3AA distal to the pressure cuff dropped as expected between times 1804 and 1808 and a positive TR was measured after time 1808. The experimental embodiments EXP1, EXP2, and EXP3, show that temperature data such as that obtained from the methods 500, 700, 800, 900, 1000, 1100, 1500, 1600, 1700, 2000, 2500, or 2600 and/or the apparatus 100, 600, 1200, 1300, 1400, 1900, 2100, 2200, 2300, or 2400 may be obtained which is substantially similar to the temperature data described above with reference to FIGS. 22, 23, 24, 25, 26, 27, and 28, by obtaining such temperature data from temperature measurements made at the wrist of the subject rather than at the finger of the subject.

In several exemplary embodiment, the methods 500, 700, 800, 900, 1000, 1100, 1500, 1600, 1700, 2000, 2500, 2600, 2700, 2800, and 3000 may be carried out along with a variety of other diagnostic techniques known in the art in order to improve diagnostic ability to assess cardiovascular health condition. For example, magnetic resonance imaging may be carried out on the subject. Intravascular diagnostic tools such as, for example, intravascular ultrasound, may be used on the subject to diagnose cardiovascular health condition of the subject. The blood flow rate in the skin of the subject or the skin perfusion of the subject may be measured using, for example, optical spectroscopy, near infrared spectroscopy, and/or Doppler flowmetry. In an exemplary embodiment, an optical spectroscopy tracer may be administered to subject before using optical spectroscopy on the subject. In an exemplary embodiment, the blood flow rate of the subject may be measured in place of the skin temperature measurements of the subject. The blood pressure of the subject may be measured and recorded using methods such as, for example, Korotkoff sounds or oscillometric methods, measuring the blood pressure at the fingertip, and/or measuring the blood pressure at the wrist. In an exemplary embodiment, the blood pressure of the subject may be taken before the provision of the vasostimulant in methods 500, 700, 800, 900, 1000, 1100, 1500, 1600, 1700, 2000, 2500, 2600, 2700, 2800, and 3000. In an exemplary embodiment, the blood pressure of the subject may be taken after the provision of the vasostimulant in methods 500, 700, 800, 900, 1000, 1100, 1500, 1600, 1700, 2000, 2500, 2600, 2700, 2800, and 3000. In an exemplary embodiment, the blood pressure of the subject may be taken before, after, and during the provision of the vasostimulant in methods 500, 700, 800, 900, 1000, 1100, 1500, 1600, 1700, 2000, 2500, 2600, 2700, 2800, and 3000. Determining the blood pressure of the subject before and after the provision of the vasostimulant such as, for example, a vasodilative stimulant, allows for the determination of a vasodilative index or vasoconstrictive index for the subject. A vasodilative index for a subject results from a blood pressure drop after the provision of the vasodilative stimulant which indicates dilation in the artery after provision of the vasodilative stimulant and is indicative of a healthy response in the subject. A vasoconstrictive index for a subject results from a blood pressure rise and/or lack of change in blood pressure after the provision of the vasodilative stimulant which indicates no dilation in the artery after provision of the vasodilative stimulant and is indicative of a unhealthy response in the subject. In an exemplary embodiment, an ankle-brachial blood pressure index test may be administered to the subject. A blood marker of endothelial function may be used on the subject along with the methods 500, 700, 800, 900, 1000, 1100, 1500, 1600, 1700, 2000, 2500, 2600, 2700, 2800, and 3000. The stiffness of the artery supplying blood to the finger may be measured and recorded, for example, using arterial pulse waveform analysis during the methods 500, 700, 800, 900, 1000, 1100, 1500, 1600, 1700, 2000, 2500, 2600, 2700, 2800, and 3000. In an exemplary embodiment, stiffness of the artery may be measured and recorded before provision of the vasostimulant in methods 500, 700, 800, 900, 1000, 1100, 1500, 1600, 1700, 2000, 2500, 2600, 2700, 2800, and 3000. In an exemplary embodiment, stiffness of the artery may be measured and recorded after provision of the vasostimulant in methods 500, 700, 800, 900, 1000, 1100, 1500, 1600, 1700, 2000, 2500, 2600, 2700, 2800, and 3000. In an exemplary embodiment, stiffness of the artery may be measured and recorded before, during, and after provision of the vasostimulant in methods 500, 700, 800, 900, 1000, 1100, 1500, 1600, 1700, 2000, 2500, 2600, 2700, 2800, and 3000.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of atherosclerotic cardiovascular disorder in the subject may be determined. It is well known that deficiencies in endothelial function are indicative of atherosclerotic cardiovascular disorder. Use of the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, permits a health care professional to acquire temperature data which may be analyzed to determine endothelial dysfunction. In an exemplary embodiment, determining the status of atherosclerotic cardiovascular disorder includes assessing the risk of atherosclerotic cardiovascular disorder in the subject. In an exemplary embodiment, determining the status of atherosclerotic cardiovascular disorder includes monitoring the subject's response to atherosclerotic cardiovascular disorder therapies. In an exemplary embodiment, determining the status of atherosclerotic cardiovascular disorder includes using conventional methods such as, for example, a coronary calcium score, a Framingham risk score, or a carotid intima-media thickness test, along with methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900 to assess the risk of atherosclerotic cardiovascular disorder.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of heart failure in the subject may be determined. It is well known that deficiencies in endothelial function are indicative of heart failure. Use of the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900 permits a health care professional to acquire temperature data which may be analyzed to determine endothelial dysfunction. In an exemplary embodiment, determining the status of heart failure includes monitoring the progression of heart failure in the subject. In an exemplary embodiment, determining the status of heart failure includes monitoring the subject's response to heart failure therapies. In an exemplary embodiment, determining the status of heart failure includes using conventional methods such as, for example, a cardiac function test, along with methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900 to monitor the progression of heart failure in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of obesity in the subject may be determined. It is well known that deficiencies in endothelial function are indicative of obesity. Use of the above methods and/or apparatus permits a health care professional to acquire temperature data which may be analyzed to determine endothelial dysfunction. In an exemplary embodiment, determining the status of obesity includes managing the subject's obesity by determining the likelihood of the subject regaining lost weight. In an exemplary embodiment, determining the status of obesity includes using conventional methods along with the methods and/or the apparatus of the present invention to monitor the progression of obesity in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of high sympathetic reactivity in the subject may be determined. It is well known that deficiencies in endothelial function are indicative of high sympathetic reactivity. Use of these methods and/or apparatus permits a health care professional to acquire temperature data which may be analyzed to determine endothelial dysfunction. In an exemplary embodiment, determining the status of high sympathetic reactivity includes identifying whether the subject has high sympathetic reactivity. In an exemplary embodiment, determining the status of high sympathetic reactivity includes monitoring the subject's response to hypersympathetic therapies. In an exemplary embodiment, determining the status of heart failure includes using conventional methods along with methods and/or the apparatus of the present invention to identify whether the subject has high sympathetic reactivity.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of high blood pressure in the subject may be determined. It is well known that deficiencies in endothelial function are indicative of high blood pressure. Use of these methods and/or apparatus permits a health care professional to acquire temperature data which may be analyzed to determine endothelial dysfunction. In an exemplary embodiment, determining the status of high blood pressure includes screening the subject for high blood pressure. In an exemplary embodiment, determining the status of high blood pressure includes monitoring the subject's response to high blood pressure therapies. In an exemplary embodiment, determining the status of high blood pressure includes using conventional methods along with the methods and/or the apparatus of the present invention to screen the subject for high blood pressure. In an exemplary embodiment, determining the status of high blood pressure includes identifying whether the subject is resistant to high blood pressure therapies. In an exemplary embodiment, determining the status of high blood pressure includes screening the subject for white coat hypertension. In an exemplary embodiment, determining the status of high blood pressure includes measuring the blood pressure of a subject and distinguishing between the different stages of hypertensive vascular disease.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of smooth muscle cell dysfunction in the subject may be determined. It is well known that deficiencies in endothelial function are indicative of smooth muscle cell dysfunction. Use of these methods and/or apparatus permits a health care professional to acquire temperature data which may be analyzed to determine endothelial dysfunction. In an exemplary embodiment, determining the status of smooth muscle cell dysfunction includes screening the subject for smooth muscle cell dysfunction. In an exemplary embodiment, determining the status of smooth muscle cell dysfunction includes monitoring the subject's response to smooth muscle cell dysfunction therapies. In an exemplary embodiment, determining the status of smooth muscle cell dysfunction includes using conventional methods along with methods and/or the apparatus of the present invention to screen the subject for smooth muscle cell dysfunction.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of diabetes in the subject may be determined. It is well known that deficiencies in endothelial function are indicative of diabetes. Use of these methods and/or apparatus permits a health care professional to acquire temperature data which may be analyzed to determine endothelial dysfunction. In an exemplary embodiment, determining the status of diabetes includes predicting whether the subject will develop diabetes. In an exemplary embodiment, determining the status of diabetes includes monitoring the status and progression of diabetes in the subject. In an exemplary embodiment, determining the status of diabetes includes monitoring the subject's response to diabetes therapies. In an exemplary embodiment, determining the status of diabetes includes using conventional methods such as, for example, a hemoglobin A1C test or measuring the subjects glucose level, along with methods and/or the apparatus of the present invention to monitor the status and progression of diabetes in the subject. In an exemplary embodiment, determining the status of diabetes in the subject includes determining the status of type-2 diabetes in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of fitness level in the subject may be determined. It is well known that deficiencies in endothelial function are indicative of fitness level. Use of these methods and/or apparatus permits a health care professional to acquire temperature data which may be analyzed to determine endothelial dysfunction. In an exemplary embodiment, determining the status of fitness level includes identifying the fitness level of the subject. In an exemplary embodiment, determining the status of fitness level includes monitoring the subject's response to fitness program. In an exemplary embodiment, determining the status of smooth muscle cell dysfunction includes using conventional methods along with methods and/or the apparatus of the present invention to identify the fitness level of the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of rheumatologic and/or connective tissue disorders in the subject may be determined. It is well known that deficiencies in endothelial function are indicative of rheumatologic and/or connective tissue disorders. Use of these methods and/or apparatus permits a health care professional to acquire temperature data which may be analyzed to determine endothelial dysfunction. In an exemplary embodiment, determining the status of rheumatologic and/or connective tissue disorders includes assessing the subject for vascular effects due to rheumatologic and/or connective tissue disorders. In an exemplary embodiment, determining the status of rheumatologic and/or connective tissue disorders includes monitoring the subject's response to rheumatologic and/or connective tissue disorder therapies. In an exemplary embodiment, determining the status of rheumatologic and/or connective tissue disorders includes using conventional methods along with methods and/or the apparatus of the present invention to assess the subject for vascular effects due to rheumatologic and/or connective tissue disorders.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of pulmonary hypertension in the subject may be determined. It is well known that deficiencies in endothelial function are indicative of pulmonary hypertension. Use of these methods and/or apparatus permits a health care professional to acquire temperature data which may be analyzed to determine endothelial dysfunction. In an exemplary embodiment, determining the status of pulmonary hypertension includes assessing whether the subject is at risk for pulmonary hypertension. In an exemplary embodiment, determining the status of pulmonary hypertension includes monitoring the status and progression of pulmonary hypertension in the subject. In an exemplary embodiment, determining the status of pulmonary hypertension includes monitoring the subject's response to pulmonary hypertension therapies. In an exemplary embodiment, determining the status of pulmonary hypertension includes using conventional methods along with methods and/or the apparatus of the present invention to monitor the status and progression of pulmonary hypertension in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of smoking cessation in the subject may be determined. It is well known that deficiencies in endothelial function are indicative of smoking. Use of these methods and/or apparatus permits a health care professional to acquire temperature data which may be analyzed to determine endothelial dysfunction. In an exemplary embodiment, determining the status of smoking cessation includes assessing whether the subject would respond positively to a smoking cessation program. In an exemplary embodiment, determining the status of smoking cessation includes monitoring the subject's success with a smoking cessation program. In an exemplary embodiment, determining the status of smoking cessation includes using conventional methods along with methods and/or the apparatus of the present invention to assess whether the subject would response positively to a smoking cessation program.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of vascular stress in the subject may be determined without subjecting the subject to physical activity. It is well known that deficiencies in endothelial function are indicative of vascular stress. Use of these methods and/or apparatus permits a health care professional to acquire temperature data which may be analyzed to determine endothelial dysfunction. In an exemplary embodiment, determining the status of vascular stress includes monitoring the progression of vascular stress in the subject. In an exemplary embodiment, determining the status of vascular stress includes monitoring the subject's response to vascular stress therapies. In an exemplary embodiment, determining the status of vascular stress includes using conventional methods along with methods and/or the apparatus of the present invention to monitor the progression of vascular stress in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of sleep disorders such as, for example, sleep apnea, in the subject may be determined. It is well known that deficiencies in endothelial function are indicative of sleep disorders.

Use of these methods and/or apparatus permits a health care professional to acquire temperature data which may be analyzed to determine endothelial dysfunction. In an exemplary embodiment, determining the status of sleep disorders includes monitoring the progression of sleep disorders in the subject. In an exemplary embodiment, determining the status of sleep disorders includes monitoring the subject's response to sleep disorder therapies. In an exemplary embodiment, determining the status of sleep disorders includes using conventional methods along with methods and/or the apparatus of the present invention to monitor the progression of sleep disorder in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of metabolic syndrome in the subject may be determined. It is well known that deficiencies in endothelial function are indicative of metabolic syndrome. Use of these methods and/or apparatus permits a health care professional to acquire temperature data which may be analyzed to determine endothelial dysfunction. In an exemplary embodiment, determining the status of metabolic syndrome includes monitoring the progression of metabolic syndrome in the subject. In an exemplary embodiment, determining the status of metabolic syndrome includes monitoring the subject's response to metabolic syndrome therapies. In an exemplary embodiment, determining the status of metabolic syndrome includes using conventional methods along with methods and/or the apparatus of the present invention to monitor whether the subject is at risk for metabolic syndrome.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of subclinical hypothyroidism in the subject may be determined. It is well known that deficiencies in endothelial function are indicative of subclinical hypothyroidism. Use of these methods and/or apparatus permits a health care professional to acquire temperature data which may be analyzed to determine endothelial dysfunction. In an exemplary embodiment, determining the status of subclinical hypothyroidism includes detecting subclinical hypothyroidism in the subject. In an exemplary embodiment, determining the status of subclinical hypothyroidism includes monitoring the subject's response to subclinical hypothyroidism therapies. In an exemplary embodiment, determining the status of subclinical hypothyroidism includes using conventional methods along with methods and/or the apparatus of the present invention to detect subclinical hypothyroidism in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of vascular dementia and/or Alzheimer's disease in the subject may be determined. It is well known that deficiencies in endothelial function are indicative of vascular dementia and/or Alzheimer's disease. Use of these methods and/or apparatus permits a health care professional to acquire temperature data which may be analyzed to determine endothelial dysfunction. In an exemplary embodiment, determining the status of vascular dementia and/or Alzheimer's disease includes screening for vascular dementia and/or Alzheimer's disease in the subject. In an exemplary embodiment, determining the status of vascular dementia and/or Alzheimer's disease includes monitoring the subject's response to vascular dementia and/or Alzheimer's disease therapies. In an exemplary embodiment, determining the status of vascular dementia and/or Alzheimer's disease includes using conventional methods along with methods and/or the apparatus of the present invention to screen for vascular dementia and/or Alzheimer's disease in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of endothelial function in the subject may be determined. Use of these methods and/or apparatus, permits a health care professional to acquire temperature data which may be analyzed to determine endothelial dysfunction. In an exemplary embodiment, determining the status of endothelial function includes using others tests related to endothelial function such as, for example, an endothelial driven microparticles test, a VCAM1 test, an ICAM1 test, a SELECTIN test, a VWF test, a TF test, and/or a CD54 test, along with methods and/or the apparatus of the present invention to assess endothelial function.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of autonomic nervous system function in the subject may be determined. It is well known that deficiencies in endothelial function are indicative of autonomic nervous system function. Use of these methods and/or apparatus permits a health care professional to acquire temperature data which may be analyzed to determine endothelial dysfunction. In an exemplary embodiment, determining the status of autonomic nervous system function includes screening for autonomic nervous system function in the subject. In an exemplary embodiment, determining the status of autonomic nervous system function includes using conventional methods along with methods and/or the apparatus of the present invention to screen for autonomic nervous system function in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of portal hypertension in the subject may be determined. It is well known that deficiencies in endothelial function are indicative of portal hypertension. Use of these methods and/or apparatus permits a health care professional to acquire temperature data which may be analyzed to determine endothelial dysfunction. In an exemplary embodiment, determining the status of portal hypertension includes determining whether the subject will develop portal hypertension. In an exemplary embodiment, determining the status of portal hypertension includes determining the status and progression of portal hypertension in the subject. In an exemplary embodiment, determining the status of portal hypertension includes determining the response of the subject to portal hypertension disease therapies. In an exemplary embodiment, determining the status of portal hypertension includes using conventional methods along with methods and/or the apparatus of the present invention to screen for portal hypertension in the subject.

In several exemplary embodiments, after acquiring and/or plotting the temperature data obtained using the methods 500,

700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of cancer in the subject may be determined. It is well known that deficiencies in endothelial function are indicative of cancer. Use of these methods and/or apparatus permits a health care professional to acquire temperature data which may be analyzed to determine endothelial dysfunction. In an exemplary embodiment, determining the status of cancer includes determining whether the subject will develop cancer. In an exemplary embodiment, determining the status of cancer includes determining the status and progression of cancer in the subject. In an exemplary embodiment, determining the status of cancer includes determining the response of the subject to cancer disease therapies. In an exemplary embodiment, determining the status of cancer includes using conventional methods along with methods and/or the apparatus of the present invention to screen for cancer in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of renal function in the subject may be determined. It is well known that deficiencies in endothelial function are indicative of renal function. Use of these methods and/or apparatus permits a health care professional to acquire temperature data which may be analyzed to determine endothelial dysfunction. In an exemplary embodiment, determining the status of renal function includes determining whether the subject will develop renal function. In an exemplary embodiment, determining the status of renal function includes determining the status and progression of renal function in the subject. In an exemplary embodiment, determining the status of renal function includes determining the response of the subject to renal function disease therapies. In an exemplary embodiment, determining the status of renal function includes using conventional methods along with methods and/or the apparatus of the present invention to screen for renal function in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of hypertension in the subject may be determined. It is well known that deficiencies in endothelial function are indicative of hypertension. Use of these methods and/or apparatus permits a health care professional to acquire temperature data which may be analyzed to determine endothelial dysfunction. In an exemplary embodiment, determining the status of hypertension includes determining whether the subject will develop hypertension. In an exemplary embodiment, determining the status of hypertension includes determining the status and progression of hypertension in the subject. In an exemplary embodiment, determining the status of hypertension includes determining the response of the subject to hypertension disease therapies. In an exemplary embodiment, determining the status of hypertension includes using conventional methods along with methods and/or the apparatus of the present invention to screen for hypertension in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of cerebral vascular disease in the subject may be determined. It is well known that deficiencies in endothelial function are indicative of cerebral vascular disease. Use of these methods and/or the apparatus permits a health care professional to acquire temperature data which may be analyzed to determine endothelial dysfunction. In an exemplary embodiment, determining the status of cerebral vascular disease includes determining whether the subject will develop cerebral vascular disease. In an exemplary embodiment, determining the status of hypertension includes determining the status and progression of cerebral vascular disease in the subject. In an exemplary embodiment, determining the status of cerebral vascular disease includes determining the response of the subject to stroke therapies. In an exemplary embodiment, determining the status of cerebral vascular disease includes using conventional methods along with methods and/or the apparatus of the present invention to screen for cerebral vascular disease in the subject. In an embodiment, cerebral vascular disease may include, for example, strokes.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of dementia and/or memory loss in the subject may be determined. It is well known that deficiencies in endothelial function are indicative of dementia and/or memory loss. Use of these methods and/or the apparatus permits a health care professional to acquire temperature data which may be analyzed to determine endothelial dysfunction. In an exemplary embodiment, determining the status of dementia and/or memory loss includes determining whether the subject will develop dementia and/or memory loss. In an exemplary embodiment, determining the status of dementia includes determining the status and progression of dementia and/or memory loss in the subject. In an exemplary embodiment, determining the status of dementia and/or memory loss includes determining the response of the subject to dementia and/or memory loss disease therapies. In an exemplary embodiment, determining the status of dementia and/or memory loss includes using conventional methods along with methods and/or the apparatus of the present invention to screen for dementia and/or memory loss in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of vision loss in the subject may be determined. It is well known that deficiencies in endothelial function are indicative of vision loss. Use of these methods and/or the apparatus permits a health care professional to acquire temperature data which may be analyzed to determine endothelial dysfunction. In an exemplary embodiment, determining the status of vision loss includes determining whether the subject will develop vision loss. In an exemplary embodiment, determining the status of vision loss includes determining the status and progression of vision loss in the subject. In an exemplary embodiment, determining the status of vision loss includes determining the response of the subject to vision loss disease therapies. In an exemplary embodiment, determining the status of vision loss includes using conventional methods along with methods and/or the apparatus of the present invention to screen for vision loss in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of heart attack and/or angina in the subject may be determined. It is well known that deficiencies in endothelial function are indicative of heart attack and/or angina. Use of these methods and/or the apparatus permits a health care professional to acquire temperature data which may be analyzed to determine endothelial dysfunction. In an exemplary embodiment, determining the status of heart attack and/or angina includes determining whether the subject will develop heart attacks and/or angina. In an exemplary embodiment, determining the status of heart attack and/or angina includes determining the status and progression of heart attacks and/or angina in the subject. In an exemplary embodiment, determining the status of heart attack and/or angina includes determining the response of the subject to heart attack and/or angina therapies. In an exemplary embodiment, determining the status of heart attack and/or angina includes using conventional methods along with methods and/or the apparatus of the present invention to screen for heart attacks and/or angina in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of erectile dysfunction in the subject may be determined. It is well known that deficiencies in endothelial function are indicative of erectile dysfunction. Use of these methods and/or the apparatus permits a health care professional to acquire temperature data which may be analyzed to determine endothelial dysfunction. In an exemplary embodiment, determining the status of erectile dysfunction includes determining whether the subject will develop erectile dysfunction. In an exemplary embodiment, determining the status of erectile dysfunction includes determining the status and progression of erectile dysfunction in the subject. In an exemplary embodiment, determining the status of erectile dysfunction includes determining the response of the subject to erectile dysfunction therapies. In an exemplary embodiment, determining the status of erectile dysfunction includes using conventional methods along with methods and/or the apparatus of the present invention to screen for erectile dysfunction in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of peripheral artery disease in the subject may be determined. It is well known that deficiencies in endothelial function are indicative of peripheral artery disease. Use of these methods and/or the apparatus permits a health care professional to acquire temperature data which may be analyzed to determine endothelial dysfunction. In an exemplary embodiment, determining the status of peripheral artery disease includes determining whether the subject will develop peripheral artery disease. In an exemplary embodiment, determining the status of peripheral artery disease includes determining the status and progression of peripheral artery disease in the subject. In an exemplary embodiment, determining the status of peripheral artery disease includes determining the response of the subject to peripheral artery disease therapies. In an exemplary embodiment, determining the status of peripheral artery disease includes using conventional methods along with methods and/or the apparatus of the present invention to screen for peripheral artery disease in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of pregnancy in the subject may be determined. It is well known that deficiencies in endothelial function are indicative of pregnancy. Use of these methods and/or the apparatus permits a health care professional to acquire temperature data which may be analyzed to determine endothelial dysfunction. In an exemplary embodiment, determining the status of pregnancy includes determining the status and progression of pregnancy in the subject. In an exemplary embodiment, determining the status of pregnancy includes determining the status of preeclampsia in the subject. In an exemplary embodiment, determining the status of pregnancy includes using conventional methods along with methods and/or the apparatus of the present invention to screen for pregnancy in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of migraine headaches in the subject may be determined. It is well known that deficiencies in endothelial function are indicative of migraine headaches. Use of these methods and/or the apparatus permits a health care professional to acquire temperature data which may be analyzed to determine endothelial dysfunction. In an exemplary embodiment, determining the status of migraine headaches includes determining whether the subject will develop migraine headaches. In an exemplary embodiment, determining the status of migraine headaches includes determining the status and progression of migraine headaches in the subject. In an exemplary embodiment, determining the status of migraine headaches includes determining the response of the subject to migraine headaches therapies. In an exemplary embodiment, determining the status of migraine headaches includes using conventional methods along with methods and/or the apparatus of the present invention to screen for migraine headaches in the subject. In an exemplary embodiment, a migraine headache may include headaches such as, for example, vascular headaches, migraine variants, and a variety of other headaches known in the art.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of Prinzmetal's angina in the subject may be determined. It is well known that deficiencies in endothelial function are indicative of Prinzmetal's angina. Use of these methods and/or the apparatus permits a health care professional to acquire temperature data which may be analyzed to determine endothelial dysfunction. In an exemplary embodiment, determining the status of Prinzmetal's angina includes determining whether the subject will develop Prinzmetal's angina. In an exemplary embodiment, determining the status of Prinzmetal's angina includes determining the status and progression of Prinzmetal's angina in the subject. In an exemplary embodiment, determining the status of Prinzmetal's angina includes determining the response of the subject to Prinzmetal's angina therapies. In an exemplary embodiment, determining the status of Prinzmetal's angina includes using conventional methods along with methods and/or the apparatus of the present invention to screen for Prinzmetal's angina in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of HIV in the subject may be determined. It is well known that deficiencies in endothelial function are indicative of HIV. Use of these methods and/or the apparatus permits a health care professional to acquire temperature data which may be analyzed to determine endothelial dysfunction. In an exemplary embodiment, determining the status of HIV includes determining whether the subject has contracted HIV. In an exemplary embodiment, determining the status of HIV includes determining the status and progression of HIV in the subject. In an exemplary embodiment, determining the status of HIV includes determining the response of the subject to HIV therapies. In an exemplary embodiment, determining the status of HIV includes using conventional methods along with methods and/or the apparatus of the present invention to screen for HIV in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the status of diabetic foot in the subject may be determined. It is well known that deficiencies in endothelial function are indicative of diabetic foot. Use of these methods and/or the apparatus permits a health care professional to acquire temperature data which may be analyzed to determine endothelial dysfunction. In an exemplary embodiment, determining the status of diabetic foot includes determining whether the subject has diabetic foot. In an exemplary embodiment, determining the status of diabetic foot includes determining the status and progression of diabetic foot in the subject. In an exemplary embodiment, determining the status of diabetic foot includes determining the response of the subject to diabetic foot therapies. In an exemplary embodiment, determining the status of diabetic foot includes using conventional methods along with methods and/or the apparatus of the present invention to screen for diabetic foot in the subject. In an exemplary embodiment, determining the status of diabetic foot includes measuring the autonomic nervous systemic function in the subject such as, for example, by looking at the changes in temperature in the contralateral finger 18 on subject 10 after provision of the vasostimulant. In an exemplary embodiment, an increase in temperature in the contralateral finger 18 of subject 10 indicates a healthy autonomic nervous system function in the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, the effectiveness of cholesterol lowering medications in the subject may be determined. It is well known that deficiencies in endothelial function are indicative of the effectiveness of cholesterol lowering medications. Use of these methods and/or the apparatus permits a health care professional to acquire temperature data which may be analyzed to determine endothelial dysfunction. In an exemplary embodiment, determining the effectiveness of cholesterol lowering medications includes determining the effectiveness of cholesterol lowering medications from the family of statins such as, for example, Lipitor and/or mevalonate.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, additional diagnosis techniques such as, for example, determining a coronary calcium score, determining a Framingham risk score, determining a carotid intima media thickness, conducting a c-reactive protein test, determining a Lp-PLA2 level, and/or a variety of other techniques which may be used to provide a comprehensive determination of health condition with the methods of the present invention in order to determine the health condition of the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, additional diagnosis techniques such as, for example, change in oxygen saturation in the body part in which temperature is being measured, change in Doppler flow in the body part in which temperature is being measured, change in pressure in the body part in which temperature is being measured, and/or change in blood flow measured by near infrared spectroscopy in the body part in which temperature is being measured, may be used to provide a comprehensive determination of health condition with the methods of the present invention in order to determine the health condition of the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, additional risk assessment methods such as, for example, intravascular optical coherent tomography, coronary fractional flow reserve, intravascular ultrasound radiofrequency backscatter analysis or Virtual Histology, urinary albumin, serum fibrinogen, IL6, CD40/CD40L, serum amyloid A, ankle brachial index, MRI, coronary calcium score, carotid intima thickness, Framingham risk score, C-reactive protein tests, waist circumference, blood insulin level, PAI-1 test, t-PA test, glucose tolerance tests, fasting plasma glucose level, HDL cholesterol level, fasting plasma insulin test, homeostasis model assessment, BMI, body fat level, visceral fat test, subcutaneous fat test, white blood cell count, Neutrophil/lymphocyte ratio, platelet function test, combinations thereof, and/or a variety of other cardiovascular risk assessment methods may be used to provide a comprehensive determination of health condition with the methods of the present invention in order to determine the health condition of the subject. In an exemplary embodiment, ankle-brachial index is the blood pressure measured at the ankle level over the blood pressure measured at the arm level. A ratio of 0.9 or less is considered unhealthy and an indication of peripheral artery disease. Using the methods and/or the apparatus of the present invention, temperature measurements at the ankle level and the arm level can be used to create a ration substantially similar to the ankle brachial index. Furthermore, multiple temperature measurements of a subject using the methods and/or the apparatus of the present invention at different body parts on the subject may provide a more comprehensive assessment of health condition.

In several exemplary embodiments, after acquiring and/or plotting the temperature data obtained using the methods 500, 700, 800, 900, 1000, 1100, 1500, 1600, 1700, 2000, 2500,

2600, 2700, 2800, and 3000 and/or the apparatus 100, 600, 1200, 1300, 1400, 1900, 2100, 2200, 2300, 2400, or 2900, additional diagnostic methods which include factors or markers related to endothelial function, endothelial activation, or endothelial damage, such as, for example, plasma and urinary level of asymmetrical (ADMA) and symmetrical (SDMA) dimethylarginine, exhaled nitric oxide, serum homocysteine, an endothelial driven microparticles test, a VCAM1 test, an ICAM1 test, a SELECTIN test, a VWF test, a TF test, and/or a CD54 test, endothelial progenitor cells, myelo-peroxidase (MPO), increased neutrophil/lymphocyte ratio, endothelin-1, thrombomodulin, tissue factor and tissue factor pathway inhibitor, markers of inflammation such as, for example, granulocyte-macrophage colony-stimulating factor (GM-CSF) and macrophage chemoattractant protein-1 (MCP-1) nitric oxide and its metabolites nitrates and nitrites, almost nitrosylated proteins, a selectin such as, for example, soluble endothelium, leukocyte, and platelet selectins, markers of oxidative stress including but not limited to free radical measurements of the blood or through the skin, TBAR, and/or extra cellular super oxide dismutase activity, vascular stiffness or compliance, combinations thereof, and/or a variety of other endothelial related techniques may be used to provide a comprehensive determination of health condition with the methods of the present invention in order to determine the health condition of the subject.

In several exemplary embodiments, after acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, additional diagnostic methods which measure parameters which change in the subject during these methods along with temperature such as, for example, skin color, nail capilloroscopy, ultrasound brachial artery imaging, forearm plethysmography, fingertip plethysmography, oxygen saturation change, pressure change, near-infrared spectroscopy measurements, Doppler flow change, peripheral arterial tomometry, combinations thereof, and/or a variety of other endothelial related techniques may be used to provide a comprehensive determination of health condition with the methods of the present invention in order to determine the health condition of the subject.

In several exemplary embodiments, additional diagnosis techniques may be used to acquire a measure of endothelium independent vascular reactivity along with the measure of endothelium dependent vascular reactivity which may be acquired by the methods 500, 700, 800, 900, 1000, 1100, 1500, 1600, 1700, 2000, 2500, 2600, 2700, 2800, and 3000, and a ratio of the endothelium dependent vascular reactivity over the endothelium independent vascular reactivity or a composite index of the endothelium dependent vascular reactivity and the endothelium independent vascular reactivity may be calculated to determine the health condition of the subject. Additional diagnosis techniques may also be used to acquire a measure of parameters which change in the subject during these methods along with temperature along with the measure of endothelium dependent vascular reactivity which may be acquired by the methods, and a ratio of the parameters which change in the subject during the methods along with temperature over the endothelium dependent vascular reactivity or a composite index of the parameters which change in the subject during the methods along with temperature and the endothelium dependent vascular reactivity may be calculated to determine the health condition of the subject. In an exemplary embodiment, a ratio or composite index may include variables determined using the methods 500, 700, 800, 900, 1000, 1100, 1500, 1600, 1700, 2000, 2500, 2600, 2700, 2800, and 3000 on a variety of body parts on the subject. In an exemplary embodiment, a ratio or composite index may include variables determined using these methods and a variety of additional diagnostic methods such as the diagnostic methods described above. In an exemplary embodiment, a composite index is the operation of a plurality of factors using any mathematical operator.

In several exemplary embodiments, along with acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, a medication may be administered to the subject for the treatment of a medical condition. These methods and/or the apparatus help to determine whether the medication is effective in the treatment of the medical condition and, if the medication is determined to be effective, the medication may be selected in treating that medical condition in other subjects.

In several exemplary embodiments, along with acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, a nutritional program may be administered to the subject. The methods and/or the apparatus of the present invention help to determine whether the nutritional program is effective for the subject and, if the nutritional program is determined to be effective, the nutritional program may be selected for other subjects.

In several exemplary embodiments, along with acquiring and/or plotting the temperature data obtained using the methods 500, 700, 800, 900, 1000, 1100, 1500, 1600, 1700, 2000, 2500, 2600, 2700, 2800, and 3000 and/or the apparatus 100, 600, 1200, 1300, 1400, 1900, 2100, 2200, 2300, 2400, or 2900, a chemical agent, medical procedure, or health intervention program may be administered to the subject for the treatment of a medical condition. The methods and/or the apparatus of the present invention help to study the effects of the chemical agent, medical procedure and or health intervention program in treating the subject for the medical condition. In an exemplary embodiment, a health intervention program includes, but is not limited to, a program of smoking cessation, a program of drinking cessation, a dietary program, and/or an exercise program.

A thermal energy measurement apparatus has been described that includes a thermal energy sensor and means for coupling the thermal energy sensor to a skin surface of a body part, the coupling means operable to couple the thermal energy sensor to the skin surface of the body part while not substantially changing the skin temperature of the body part. In an exemplary embodiment, the means for coupling the thermal energy sensor to the skin surface of the body part comprises a mesh. In an exemplary embodiment, the means for coupling the thermal energy sensor to the skin surface of the body part comprises a non-insulating material. In an exemplary embodiment, the thermal energy sensor is adapted to measure skin temperature. In an exemplary embodiment, the means for coupling the thermal energy sensor to the skin surface of the body part is operable to hold the thermal energy sensor in contact with skin surface on the body part. In an exemplary embodiment, the thermal energy sensor comprises a plurality of thermal energy sensors.

In an exemplary embodiment, a computer system is coupled to the thermal energy sensor. In an exemplary embodiment, the computer system is coupled to the thermal energy sensor by a wireless connection. In an exemplary embodiment, the wireless connection comprises Bluetooth technology. In an exemplary embodiment, the computer system is chosen from the group consisting of a cellular phone, a PDA, a personal computing device, and combinations thereof.

In an exemplary embodiment, the computer system is coupled to a therapeutic device, the therapeutic device operable to perform a therapeutic function. In an exemplary embodiment, the therapeutic function includes the release of oxygen. In an exemplary embodiment, the computer system is coupled to an alerting device. In an exemplary embodiment, the alerting device is operable to contact emergency medical services. In an exemplary embodiment, the computer system is coupled to a pulse oximeter. In an exemplary embodiment, the computer system is coupled to a blood pressure monitoring device. In an exemplary embodiment, the computer system is coupled to a Doppler probe. In an exemplary embodiment, the computer system is coupled to a room temperature measurement device. In an exemplary embodiment, the computer system is coupled to a core temperature measurement device.

In an exemplary embodiment, the means for coupling the thermal energy sensor to the body part comprises a ring. In an exemplary embodiment, the means for coupling the thermal energy sensor to the body part comprises a watch. In an exemplary embodiment, the means for coupling the thermal energy sensor to the body part comprises a bracelet. In an exemplary embodiment, the thermal energy sensor comprises a probe operable to measure thermal energy of the skin surface of the body part without contacting the body part. In an exemplary embodiment, the means for coupling the thermal energy sensor to the body part comprises an article of clothing. In an exemplary embodiment, the means for coupling the thermal energy sensor to the body part comprises an adhesive. In an exemplary embodiment, the means for coupling the thermal energy sensor to the body part is disposable. In an exemplary embodiment, the thermal energy sensor is operable to measure thermal energy over a time period. In an exemplary embodiment, the means for coupling the thermal energy sensor to a skin surface of a body part comprises an adhesive. In an exemplary embodiment, the apparatus further comprises an airflow channel defined by the means for coupling the thermal energy sensor to a skin surface of a body part located between the thermal energy sensor and the adhesive. In an exemplary embodiment, the means for coupling the thermal energy sensor to a skin surface of a body part is operable to apply a minimum pressure across a body part in order to not substantially change the skin surface temperature of the body part. In an exemplary embodiment, the means for coupling the thermal energy sensor to a skin surface of a body part is operable to couple to a minimum surface area of the body part in order to not substantially change the skin surface temperature of the body part.

In an exemplary embodiment, the apparatus further comprises a second thermal energy sensor and a means for coupling the second thermal energy sensor to a contralateral body part. In an exemplary embodiment, the means for coupling the thermal energy sensor to the skin surface of the body part comprises a glove. In an exemplary embodiment, the means for coupling the thermal energy sensor to the skin surface of the body part does not substantially change a microcapillary blood flow underlying the skin surface. In an exemplary embodiment, the apparatus further comprises a thermal device operable to adjust the skin surface temperature of the body part.

In an exemplary embodiment, the thermal energy sensor comprises a thermocouple. In an exemplary embodiment, the thermal energy sensor comprises a thermister. In an exemplary embodiment, the thermal energy sensor comprises a resistance temperature detector. In an exemplary embodiment, the thermal energy sensor comprises a heat flux detector. In an exemplary embodiment, the thermal energy sensor comprises a liquid crystal sensor. In an exemplary embodiment, the thermal energy sensor comprises a thermopile. In an exemplary embodiment, the thermal energy sensor comprises a infrared sensor. In an exemplary embodiment, the infrared sensor measures thermal energy of a point on a surface. In an exemplary embodiment, the infrared sensor measures thermal energy of an area on a surface.

A method for determining one or more health conditions has been described that includes providing a subject, measuring the skin temperature of a body part on the subject, providing a vasostimulant to the subject, measuring the skin temperature changes of the body part during and subsequent to the provision of the vasostimulant, and determining one or more health conditions for the subject based upon at least one of the skin temperature changes measured. In an exemplary embodiment, the measuring the skin temperature of the body part of the subject comprises coupling a thermal energy measurement apparatus to the body part.

In an exemplary embodiment, the providing a vasostimulant comprises providing a neuro-vasostimulant. In an exemplary embodiment, the neuro-vasostimulant comprises the subject consuming a glass of ice water. In an exemplary embodiment, the providing a vasostimulant comprises providing a neurostimulant. In an exemplary embodiment, the providing a vasostimulant comprises compressing an artery on the subject for a period of time followed by ceasing the compression. In an exemplary embodiment, the vasostimulant is provided for 5 minutes or less. In an exemplary embodiment, the vasostimulant is provided for 4 minutes or less. In an exemplary embodiment, the vasostimulant is provided for 3 minutes or less. In an exemplary embodiment, the vasostimulant is provided for approximately 2 minutes. In an exemplary embodiment, the method further includes having the subject exercise the body part on which thermal energy is being measured after provision of the vasostimulant.

In an exemplary embodiment, the skin temperature of the body part is measured on a distal location to the artery. In an exemplary embodiment, the artery comprises a brachial artery. In an exemplary embodiment, the providing a vasostimulant comprises administering a chemical agent to the subject which effects vascular function. In an exemplary embodiment, the chemical agent comprises a vasoconstrictor. In an exemplary embodiment, the chemical agent comprises a vasodilator. In an exemplary embodiment, the chemical agent comprises a neurostimulator. In an exemplary embodiment, the chemical agent is nitroglycerin. In an exemplary embodiment, the nitroglycerin is administered sublingually.

In an exemplary embodiment, the measuring the skin temperature changes of the body part during and subsequent to the provision of the vasostimulant comprises measuring the lowest skin temperature of the body part. In an exemplary embodiment, the measuring the skin temperature changes of the body part during and subsequent to the provision of the vasostimulant comprises measuring the time required to achieve the lowest skin temperature of the body part. In an exemplary embodiment, the measuring the skin temperature changes of the body part during and subsequent to the provision of the vasostimulant comprises measuring the highest skin temperature of the body part. In an exemplary embodiment, the measuring the skin temperature changes of the body part during and subsequent to the provision of the vasostimulant comprises measuring the temperature difference between the highest skin temperature of the body part and the skin temperature of the body part prior to the provision of the vasostimulant. In an exemplary embodiment, the difference between the highest skin temperature of the body part and the skin temperature of the body part prior to the provision of the vasostimulant is normalized based on the skin temperature of the body part prior to the provision of the vasostimulant. In an exemplary embodiment, the measuring the skin temperature changes of the body part during and subsequent to the provision of the vasostimulant comprises measuring the temperature difference between the highest skin temperature of the body part and the lowest skin temperature of the body part. In an exemplary embodiment, the measuring the skin temperature changes of the body part during and subsequent to the provision of the vasostimulant comprises measuring the time required for the skin temperature of the body part to stabilize subsequent to the provision of the vasostimulant.

In an exemplary embodiment, the determining one or more health conditions for the subject based upon at least one of the temperature changes measured comprises determining the slope of the skin temperature changes of the body part from the skin temperatures of the body part upon the provision of the vasostimulant up to the lowest skin temperature of the body part achieved. In an exemplary embodiment, the determining one or more health conditions for the subject based upon at least one of the temperature changes measured comprises determining the slope of the skin temperature changes of the body part from the lowest skin temperature of the body part achieved up to the highest skin temperature of the body part achieved. In an exemplary embodiment, the determining one or more health conditions for the subject based upon at least one of the temperature changes measured comprises plotting the temperature changes over time and measuring the area bounded by the skin temperature curve, the lowest skin temperature of the body part achieved, the time at which the vasostimulant was provided, and the time at which the lowest skin temperature of the body part was achieved.

In an exemplary embodiment, the determining one or more health conditions for the subject based upon at least one of the temperature changes measured comprises plotting the temperature changes over time and measuring the area bounded by the skin temperature curve, the lower skin temperature of the body part achieved, the time at which the lowest skin temperature of the body part was achieved, and the time at which the highest skin temperature of the body part was achieved.

In an exemplary embodiment, the determining one or more health conditions for the subject based upon at least one of the temperature changes measured comprises determining endothelial function.

In an exemplary embodiment, the determining one or more health conditions for the subject based upon at least one of the temperature changes measured comprises screening for autonomic nervous system function. In an exemplary embodiment, the determining one or more health conditions for the subject based upon at least one of the temperature changes measured comprises analyzing the temperature response to the vasostimulant in order to assess cardiovascular risk for atherosclerotic cardiovascular disorder. In an exemplary embodiment, the determining one or more health conditions for the subject based upon at least one of the temperature changes measured comprises analyzing the temperature response to the vasostimulant in order to monitor the subject's response to atherosclerotic cardiovascular disorder therapies. In an exemplary embodiment, the determining one or more health conditions for the subject based upon at least one of the temperature changes measured comprises analyzing the temperature response to the vasostimulant along with additional diagnosis techniques in order to assess cardiovascular risk for atherosclerotic cardiovascular disorder. In an exemplary embodiment, the additional diagnosis techniques comprise a coronary calcium score. In an exemplary embodiment, the additional diagnosis techniques comprise a Framingham risk score. In an exemplary embodiment, the additional diagnosis techniques comprise a carotid intima-media thickness test.

In an exemplary embodiment, the determining one or more health conditions for the subject based upon at least one of the temperature changes measured comprises analyzing the temperature response to the vasostimulant in order to monitor the progression of heart failure in the subject. In an exemplary embodiment, the determining one or more health conditions for the subject based upon at least one of the temperature changes measured comprises analyzing the temperature response to the vasostimulant in order to monitor the subject's response to heart failure therapies. In an exemplary embodiment, the determining one or more health conditions for the subject based upon at least one of the temperature changes measured comprises analyzing the temperature response to the vasostimulant along with additional diagnosis techniques in order to monitor the progression of heart failure in the subject. In an exemplary embodiment, the additional diagnosis techniques comprise a cardiac function test.

In an exemplary embodiment, the determining one or more health conditions for the subject based upon at least one of the temperature changes measured comprises analyzing the temperature response to the vasostimulant for use in obesity management of the subject. In an exemplary embodiment, the determining one or more health conditions for the subject based upon at least one of the temperature changes measured comprises analyzing the temperature response to the vasostimulant along with additional diagnosis techniques for use in obesity management of the subject.

In an exemplary embodiment, the determining one or more health conditions for the subject based upon at least one of the temperature changes measured comprises analyzing the temperature response to the vasostimulant in order to identify whether the subject has high sympathetic reactivity. In an exemplary embodiment, the determining one or more health conditions for the subject based upon at least one of the temperature changes measured comprises analyzing the temperature response to the vasostimulant in order to monitor the subject's response to hypersympathetic therapies. In an exemplary embodiment, the determining one or more health conditions for the subject based upon at least one of the temperature changes measured comprises analyzing the temperature response to the vasostimulant along with additional diagnosis techniques in order to identify whether the subject has high sympathetic reactivity. In an exemplary embodiment, the determining one or more health conditions for the subject based upon at least one of the temperature changes measured comprises analyzing the temperature response to the vasostimulant in order to screen the subject for susceptibility to high blood pressure.

In an exemplary embodiment, the determining one or more health conditions for the subject based upon at least one of the temperature changes measured comprises analyzing the temperature response to the vasostimulant in order to monitor the subject's response to high blood pressure therapies. In an exemplary embodiment, the determining one or more health conditions for the subject based upon at least one of the temperature changes measured comprises analyzing the temperature response to the vasostimulant along with additional diagnosis techniques in order to screen the subject for susceptibility to high blood pressure. In an exemplary embodiment, the determining one or more health conditions for the subject based upon at least one of the temperature changes measured comprises analyzing the temperature response to the vasostimulant in order to identify whether the subject is resistant to high blood pressure therapies.

In an exemplary embodiment, the determining one or more health conditions for the subject based upon at least one of the temperature changes measured comprises analyzing the temperature response to the vasostimulant in order to screen the subject for white coat hypertension. In an exemplary embodiment, the determining one or more health conditions for the subject based upon at least one of the temperature changes measured comprises analyzing the temperature response to the vasostimulant along with additional diagnosis techniques in order to screen the subject for white coat hypertension.

In an exemplary embodiment, the method further comprises measuring and recording the blood pressure of the subject, wherein the determining one or more health conditions for the subject based upon at least one of the temperature changes measured comprises distinguishing between different stages of hypertensive vascular disease. In an exemplary embodiment, the determining one or more health conditions for the subject based upon at least one of the temperature changes measured comprises analyzing the temperature response to the vasostimulant along with additional diagnosis techniques in order to distinguish between different stages of hypertensive vascular disease. In an exemplary embodiment, the determining one or more health conditions for the subject based upon at least one of the temperature changes measured comprises screening the subject for smooth muscle cell (SMC) dysfunction.

In an exemplary embodiment, the determining one or more health conditions for the subject based upon at least one of the temperature changes measured comprises monitoring the subject's response to smooth muscle cell (SMC) dysfunction therapies. In an exemplary embodiment, the determining one or more health conditions for the subject based upon at least one of the temperature changes measured comprises analyzing the temperature response to the vasostimulant along with additional diagnosis techniques in order to screen the subject smooth muscle cell (SMC) dysfunction.

In an exemplary embodiment, the determining one or more health conditions for the subject based upon at least one of the temperature changes measured comprises analyzing the temperature response to the vasostimulant in order to predict whether the subject will develop diabetes. In an exemplary embodiment, the determining one or more health conditions for the subject based upon at least one of the temperature changes measured comprises analyzing the temperature response to the vasostimulant in order to monitor the status and progression of the subject's diabetes. In an exemplary embodiment, the determining one or more health conditions for the subject based upon at least one of the temperature changes measured comprises analyzing the temperature response to the vasostimulant in order to monitor the subject's response to diabetes therapies. In an exemplary embodiment, the determining one or more health conditions for the subject based upon at least one of the temperature changes measured comprises analyzing the temperature response to the vasostimulant along with additional diagnosis techniques in order to monitor the status and progression of the subject's diabetes. In an exemplary embodiment, the additional diagnosis techniques comprise a hemoglobin A1C test. In an exemplary embodiment, the additional diagnosis techniques comprise measuring the subjects glucose level.

In an exemplary embodiment, the determining one or more health conditions for the subject based upon at least one of the temperature changes measured comprises analyzing the temperature response to the vasostimulant in order to determine a fitness level in the subject. In an exemplary embodiment, the determining one or more health conditions for the subject based upon at least one of the temperature changes measured comprises analyzing the temperature response to the vasostimulant in order to determine a the subject's response to a fitness program. In an exemplary embodiment, the determining one or more health conditions for the subject based upon at least one of the temperature changes measured comprises analyzing the temperature response to the vasostimulant along with additional diagnosis techniques in order to determine a fitness level in the subject.

In an exemplary embodiment, the determining one or more health conditions for the subject based upon at least one of the temperature changes measured comprises assessing the subject for vascular effects due to a rheumatologic disorder. In an exemplary embodiment, the determining one or more health conditions for the subject based upon at least one of the temperature changes measured comprises monitoring the subject's response to treatment for a rheumatologic disorder. In an exemplary embodiment, the determining one or more health conditions for the subject based upon at least one of the temperature changes measured comprises analyzing the temperature response to the vasostimulant along with additional diagnosis techniques in order to assess the subject for vascular effects due to a rheumatologic disorder. In an exemplary embodiment, the body part is a finger, whereby the determining one or more health conditions for the subject based upon at least one of the temperature changes measured comprises screening the subject for Raynauld's phenomenon. In an exemplary embodiment, the determining one or more health conditions for the subject based upon at least one of the temperature changes measured comprises analyzing the temperature response to the vasostimulant along with additional diagnosis techniques in order to screen the subject for Raynauld's phenomenon.

In an exemplary embodiment, the determining one or more health conditions for the subject based upon at least one of the temperature changes measured comprises predicting whether the subject is at risk for a connective tissue disorder. In an exemplary embodiment, the connective tissue disorder is presclerodema. In an exemplary embodiment, the determining one or more health conditions for the subject based upon at least one of the temperature changes measured comprises monitoring the subject's response to treatment for presclerodema. In an exemplary embodiment, the determining one or more health conditions for the subject based upon at least one of the temperature changes measured comprises analyzing the temperature response to the vasostimulant along with additional diagnosis techniques in order to predict whether the subject is at risk for a connective tissue disorder.

In an exemplary embodiment, the determining one or more health conditions for the subject based upon at least one of the temperature changes measured comprises analyzing the temperature response to the vasostimulant in order to determine whether the subject is at risk for pulmonary hypertension. In an exemplary embodiment, the determining one or more health conditions for the subject based upon at least one of the temperature changes measured comprises analyzing the temperature response to the vasostimulant in order to monitor the status and progression of the subject's pulmonary hypertension. In an exemplary embodiment, the determining one or more health conditions for the subject based upon at least one of the temperature changes measured comprises analyzing the temperature response to the vasostimulant in order to monitor the subject's response to pulmonary hypertension therapies. In an exemplary embodiment, the determining one or more health conditions for the subject based upon at least one of the temperature changes measured comprises analyzing the temperature response to the vasostimulant along with additional diagnosis techniques in order to monitor the status and progression of the subject's pulmonary hypertension.

In an exemplary embodiment, the determining one or more health conditions for the subject based upon at least one of the temperature changes measured comprises analyzing the temperature response to the vasostimulant in order to determine whether the subject would respond positively to a smoking cessation program. In an exemplary embodiment, the determining one or more health conditions for the subject based upon at least one of the temperature changes measured comprises analyzing the temperature response to the vasostimulant in order to monitor the subject's smoking cessation. In an exemplary embodiment, the determining one or more health conditions for the subject based upon at least one of the temperature changes measured comprises analyzing the temperature response to the vasostimulant in order to monitor the subject's success with a smoking cessation program. In an exemplary embodiment, the determining one or more health conditions for the subject based upon at least one of the temperature changes measured comprises analyzing the temperature response to the vasostimulant along with additional diagnosis techniques in order to determine whether the subject would respond positively to a smoking cessation program.

In an exemplary embodiment, the determining one or more health conditions for the subject based upon at least one of the temperature changes measured comprises analyzing the temperature response to the vasostimulant in order to monitor vascular stress of the subject without subjecting the subject to physical activity.

In an exemplary embodiment, the determining one or more health conditions for the subject based upon at least one of the temperature changes measured comprises analyzing the temperature response to the vasostimulant in order to monitor the progression of sleep disorder in the subject. In an exemplary embodiment, the determining one or more health conditions for the subject based upon at least one of the temperature changes measured comprises analyzing the temperature response to the vasostimulant in order to monitor the subject's response to sleep disorder therapy. In an exemplary embodiment, the determining one or more health conditions for the subject based upon at least one of the temperature changes measured comprises analyzing the temperature response to the vasostimulant along with additional diagnosis techniques in order to monitor the progression of sleep disorder in the subject. In an exemplary embodiment, the method further comprises measuring the heart rate of the subject, wherein the measuring the heart rate and the measuring the skin temperature changes of the body part are performed at least partially while the subject is sleeping in order to detect sleep disorders.

In an exemplary embodiment, the method is carried out a plurality of times over a designated time interval. In an exemplary embodiment, the method further comprises administering a magnetic resonance imaging test to the subject. In an exemplary embodiment, the method further comprises diagnosing an intravascular property of the subject using intravascular diagnostic tools. In an exemplary embodiment, the intravascular diagnostic tools comprise intravascular ultrasound. In an exemplary embodiment, the method further comprises measuring and recording a blood flow rate of the subject. In an exemplary embodiment, the blood flow rate is measured using optical spectroscopy. In an exemplary embodiment, the blood flow rate is measured using near infrared spectroscopy. In an exemplary embodiment, the method further comprises measuring and recording a room temperature. In an exemplary embodiment, the method further comprises measuring and recording a core temperature of the subject. In an exemplary embodiment, the method further comprises measuring and recording a tissue heat capacity of the subject. In an exemplary embodiment, the method further comprises measuring and recording a tissue metabolic rate of the subject.

In an exemplary embodiment, the method further comprises measuring and recording the blood pressure of the subject. In an exemplary embodiment, the blood pressure of the subject is measured using Korotkoff sounds or oscillometric methods. In an exemplary embodiment, the blood pressure of the subject is measured using fingertip blood pressure. In an exemplary embodiment, the blood pressure of the subject is measured using wrist blood pressure. In an exemplary embodiment, the method further comprises determining a vasodilative index for the subject. In an exemplary embodiment, the method further comprises determining a vasoconstrictive index for the subject. In an exemplary embodiment, the blood pressure of the subject is measured before the provision of the vasostimulant. In an exemplary embodiment, the blood pressure of the subject is measured after the provision of the vasostimulant. In an exemplary embodiment, the blood pressure of the subject is measured before, during, and after the provision of the vasostimulant.

In an exemplary embodiment, the determining one or more health conditions for the subject based upon at least one of the temperature changes measured comprises analyzing the temperature response to the vasostimulant in order to monitor the subject's response to mental stress. In an exemplary embodiment, the monitoring the subject's response to mental stress comprises detecting whether or not the subject is telling the truth. In an exemplary embodiment, the determining one or more health conditions for the subject based upon at least one of the temperature changes measured comprises analyzing the temperature response to the vasostimulant along with additional diagnosis techniques in order to monitor the subject's response to mental stress.

In an exemplary embodiment, the method further comprises providing a thermal measuring device operable to measure and record the skin temperature of a body part. In an exemplary embodiment, the thermal measuring device comprises a ring. In an exemplary embodiment, the thermal measuring device comprises a watch. In an exemplary embodiment, the thermal measuring device comprises a bracelet.

In an exemplary embodiment, the method further comprises measuring the skin temperature changes on a contralateral body part of the subject. In an exemplary embodiment, the contralateral body part comprises a plurality of contralateral body parts. In an exemplary embodiment, the body part is a first hand on the subject, and the contralateral body part is a second hand on the subject. In an exemplary embodiment, the body part is a first foot on the subject, and the contralateral body part is a second foot on the subject. In an exemplary embodiment, the body part is a finger on the subject, and the contralateral body part is a toe on the subject.

In an exemplary embodiment, the determining one or more health conditions for the subject based upon at least one of the temperature changes measured comprises analyzing the temperature response to the vasostimulant in order to monitor the progression of metabolic syndrome in the subject. In an exemplary embodiment, the determining one or more health conditions for the subject based upon at least one of the temperature changes measured comprises analyzing the temperature response to the vasostimulant in order to monitor the subject's response to metabolic syndrome therapy. In an exemplary embodiment, the determining one or more health conditions for the subject based upon at least one of the temperature changes measured comprises analyzing the temperature response to the vasostimulant along with additional indicative criteria in order to detect whether the subject is at risk for metabolic syndrome.

In an exemplary embodiment, the body part comprises a finger. In an exemplary embodiment, the body part comprises a hand. In an exemplary embodiment, the body part comprises a forearm. In an exemplary embodiment, the body part comprises a leg. In an exemplary embodiment, the body part comprises a foot. In an exemplary embodiment, the body part comprises an earlobe. In an exemplary embodiment, the body part comprises a nose. In an exemplary embodiment, the measuring and recording the skin temperature of a body part comprises multiple temperature measurement at different points on the body part.

In an exemplary embodiment, the determining one or more health conditions for the subject based upon at least one of the temperature changes measured comprises analyzing the temperature response to the vasostimulant to detect subclinical hypothyroidism in the subject. In an exemplary embodiment, the determining one or more health conditions for the subject based upon at least one of the temperature changes measured comprises analyzing the temperature response to the vasostimulant in order to monitor the subject's response to subclinical hypothyroidism therapy. In an exemplary embodiment, the determining one or more health conditions for the subject based upon at least one of the temperature changes measured comprises analyzing the temperature response to the vasostimulant along with additional indicative criteria in order to detect subclinical hypothyroidism in the subject.

In an exemplary embodiment, the determining one or more health conditions of the subject based upon at least one of the temperature changes measured comprises a software program which diagnoses the subject based on the temperature changes measured.

In an exemplary embodiment, the determining one or more health conditions of the subject based upon at least one of the temperature changes measured comprises analyzing the temperature response to the vasostimulant in order to screen the subject for vascular dementia. In an exemplary embodiment, the determining one or more health conditions of the subject based upon at least one of the temperature changes measured comprises analyzing the temperature response to the vasostimulant in order to monitor the subject's response to treatment for vascular dementia. In an exemplary embodiment, the determining one or more health conditions of the subject based upon at least one of the temperature changes measured comprises analyzing the temperature response to the vasostimulant along with other diagnostic methods in order to screen the subject for vascular dementia.

In an exemplary embodiment, the determining one or more health conditions of the subject based upon at least one of the temperature changes measured comprises analyzing the temperature response to the vasostimulant in order to screen the subject for Alzheimer's disease. In an exemplary embodiment, the determining one or more health conditions of the subject based upon at least one of the temperature changes measured comprises analyzing the temperature response to the vasostimulant along with other diagnostic methods in order to screen the subject for Alzheimer's disease.

In an exemplary embodiment, the determining one or more health conditions of the subject based upon at least one of the temperature changes measured comprises determining whether the subject will develop portal hypertension. In an exemplary embodiment, the determining one or more health conditions of the subject based upon at least one of the temperature changes measured comprises determining the status and progression of portal hypertension in the subject. In an exemplary embodiment, the determining one or more health conditions of the subject based upon at least one of the temperature changes measured comprises determining the response of the subject to portal hypertension disease therapies. In an exemplary embodiment, the determining one or more health conditions of the subject based upon at least one of the temperature changes measured comprises analyzing the temperature response to the vasostimulant along with additional diagnosis techniques in order to diagnose the subject for portal hypertension.

In an exemplary embodiment, the determining one or more health conditions of the subject based upon at least one of the temperature changes measured comprises determining whether the subject will develop cancer. In an exemplary embodiment, the determining one or more health conditions of the subject based upon at least one of the temperature changes measured comprises determining the status and progression of cancer in the subject. In an exemplary embodiment, the determining one or more health conditions of the subject based upon at least one of the temperature changes measured comprises determining the response of the subject to cancer disease therapies. In an exemplary embodiment, the determining one or more health conditions of the subject based upon at least one of the temperature changes measured comprises analyzing the temperature response to the vasostimulant along with additional diagnosis techniques in order to diagnose the subject for cancer.

In an exemplary embodiment, the determining one or more health conditions of the subject based upon at least one of the temperature changes measured comprises determining whether the subject will develop renal function. In an exemplary embodiment, the determining one or more health conditions of the subject based upon at least one of the temperature changes measured comprises determining the status and progression of renal function in the subject. In an exemplary embodiment, the determining one or more health conditions of the subject based upon at least one of the temperature changes measured comprises determining the response of the subject to renal function therapies. In an exemplary embodiment, the determining one or more health conditions of the subject based upon at least one of the temperature changes measured comprises analyzing the temperature response to the vasostimulant along with additional diagnosis techniques in order to diagnose the subject for renal function.

In an exemplary embodiment, the determining one or more health conditions of the subject based upon at least one of the temperature changes measured comprises determining whether the subject will develop hypertension. In an exemplary embodiment, the determining one or more health conditions of the subject based upon at least one of the temperature changes measured comprises determining the status and progression of hypertension in the subject. In an exemplary embodiment, the determining one or more health conditions of the subject based upon at least one of the temperature changes measured comprises determining the response of the subject to hypertension therapies. In an exemplary embodiment, the determining one or more health conditions of the subject based upon at least one of the temperature changes measured comprises analyzing the temperature response to the vasostimulant along with additional diagnosis techniques in order to diagnose the subject for hypertension.

In an exemplary embodiment, the determining one or more health conditions of the subject based upon at least one of the temperature changes measured comprises determining whether the subject is at risk for cerebral vascular disease. In an exemplary embodiment, the determining one or more health conditions of the subject based upon at least one of the temperature changes measured comprises determining the response of the subject to stroke therapies. In an exemplary embodiment, the determining one or more health conditions of the subject based upon at least one of the temperature changes measured comprises analyzing the temperature response to the vasostimulant along with additional diagnosis techniques in order to determine whether the subject is at risk for cerebral vascular disease.

In an exemplary embodiment, the determining one or more health conditions of the subject based upon at least one of the temperature changes measured comprises determining whether the subject will develop dementia. In an exemplary embodiment, the determining one or more health conditions of the subject based upon at least one of the temperature changes measured comprises determining the status and progression of dementia in the subject. In an exemplary embodiment, the determining one or more health conditions of the subject based upon at least one of the temperature changes measured comprises determining the response of the subject to dementia therapies. In an exemplary embodiment, the determining one or more health conditions of the subject based upon at least one of the temperature changes measured comprises analyzing the temperature response to the vasostimulant along with additional diagnosis techniques in order to diagnose the subject for dementia.

In an exemplary embodiment, the determining one or more health conditions of the subject based upon at least one of the temperature changes measured comprises determining whether the subject will develop memory loss. In an exemplary embodiment, the determining one or more health conditions of the subject based upon at least one of the temperature changes measured comprises determining the status and progression of memory loss in the subject. In an exemplary embodiment, the determining one or more health conditions of the subject based upon at least one of the temperature changes measured comprises determining the response of the subject to memory loss therapies. In an exemplary embodiment, the determining one or more health conditions of the subject based upon at least one of the temperature changes measured comprises analyzing the temperature response to the vasostimulant along with additional diagnosis techniques in order to diagnose the subject for memory loss.

In an exemplary embodiment, the determining one or more health conditions of the subject based upon at least one of the temperature changes measured comprises determining whether the subject will develop vision loss. In an exemplary embodiment, the determining one or more health conditions of the subject based upon at least one of the temperature changes measured comprises determining the status and progression of vision loss in the subject. In an exemplary embodiment, the determining one or more health conditions of the subject based upon at least one of the temperature changes measured comprises determining the response of the subject to vision loss therapies. In an exemplary embodiment, the determining one or more health conditions of the subject based upon at least one of the temperature changes measured comprises analyzing the temperature response to the vasostimulant along with additional diagnosis techniques in order to diagnose the subject for vision loss.

In an exemplary embodiment, the determining one or more health conditions of the subject based upon at least one of the temperature changes measured comprises determining whether the subject is at risk for heart attack. In an exemplary embodiment, the determining one or more health conditions of the subject based upon at least one of the temperature changes measured comprises determining the response of the subject to heart attack therapies. In an exemplary embodiment, the determining one or more health conditions of the subject based upon at least one of the temperature changes measured comprises analyzing the temperature response to the vasostimulant along with additional diagnosis techniques in order to determine whether the subject is at risk for heart attack.

In an exemplary embodiment, the determining one or more health conditions of the subject based upon at least one of the temperature changes measured comprises determining whether the subject will develop angina. In an exemplary embodiment, the determining one or more health conditions of the subject based upon at least one of the temperature changes measured comprises determining the status and progression of angina in the subject. In an exemplary embodiment, the determining one or more health conditions of the subject based upon at least one of the temperature changes measured comprises determining the response of the subject to angina therapies. In an exemplary embodiment, the determining one or more health conditions of the subject based upon at least one of the temperature changes measured comprises analyzing the temperature response to the vasostimulant along with additional diagnosis techniques in order to diagnose the subject for angina.

In an exemplary embodiment, the determining one or more health conditions of the subject based upon at least one of the temperature changes measured comprises determining whether the subject will develop erectile dysfunction. In an exemplary embodiment, the determining one or more health conditions of the subject based upon at least one of the temperature changes measured comprises determining the status and progression of erectile dysfunction in the subject. In an exemplary embodiment, the determining one or more health conditions of the subject based upon at least one of the temperature changes measured comprises determining the response of the subject to erectile dysfunction therapies. In an exemplary embodiment, the determining one or more health conditions of the subject based upon at least one of the temperature changes measured comprises analyzing the temperature response to the vasostimulant along with additional diagnosis techniques in order to diagnose the subject for erectile dysfunction.

In an exemplary embodiment, the determining one or more health conditions of the subject based upon at least one of the temperature changes measured comprises determining whether the subject will develop peripheral arterial disease. In an exemplary embodiment, the determining one or more health conditions of the subject based upon at least one of the temperature changes measured comprises determining the status and progression of peripheral arterial disease in the subject. In an exemplary embodiment, the determining one or more health conditions of the subject based upon at least one of the temperature changes measured comprises determining the response of the subject to peripheral arterial disease therapies. In an exemplary embodiment, the determining one or more health conditions of the subject based upon at least one of the temperature changes measured comprises analyzing the temperature response to the vasostimulant along with additional diagnosis techniques in order to diagnose the subject for peripheral arterial disease.

In an exemplary embodiment, the determining one or more health conditions of the subject based upon at least one of the temperature changes measured comprises determining whether the subject will develop migraine headaches. In an exemplary embodiment, the determining one or more health conditions of the subject based upon at least one of the temperature changes measured comprises determining the status and progression of migraine headaches in the subject. In an exemplary embodiment, the determining one or more health conditions of the subject based upon at least one of the temperature changes measured comprises determining the response of the subject to migraine headache therapies. In an exemplary embodiment, the determining one or more health conditions of the subject based upon at least one of the temperature changes measured comprises analyzing the temperature response to the vasostimulant along with additional diagnosis techniques in order to diagnose the subject for migraine headaches.

In an exemplary embodiment, the determining one or more health conditions of the subject based upon at least one of the temperature changes measured comprises determining whether the subject will develop Prinzmetal's angina. In an exemplary embodiment, the determining one or more health conditions of the subject based upon at least one of the temperature changes measured comprises determining the status and progression of Prinzmetal's angina in the subject. In an exemplary embodiment, the determining one or more health conditions of the subject based upon at least one of the temperature changes measured comprises determining the response of the subject to Prinzmetal's angina therapies. In an exemplary embodiment, the determining one or more health conditions of the subject based upon at least one of the temperature changes measured comprises analyzing the temperature response to the vasostimulant along with additional diagnosis techniques in order to diagnose the subject for Prinzmetal's angina.

In an exemplary embodiment, the determining one or more health conditions of the subject based upon at least one of the temperature changes measured comprises determining whether the subject has contracted HIV. In an exemplary embodiment, the determining one or more health conditions of the subject based upon at least one of the temperature changes measured comprises determining the status and progression of HIV in the subject. In an exemplary embodiment, the determining one or more health conditions of the subject based upon at least one of the temperature changes measured comprises determining the response of the subject to HIV therapies. In an exemplary embodiment, the determining one or more health conditions of the subject based upon at least one of the temperature changes measured comprises analyzing the temperature response to the vasostimulant along with additional diagnosis techniques in order to diagnose the subject for HIV.

In an exemplary embodiment, the determining one or more health conditions of the subject based upon at least one of the temperature changes measured comprises determining whether the subject has diabetic foot. In an exemplary embodiment, the determining one or more health conditions of the subject based upon at least one of the temperature changes measured comprises determining the status and progression of diabetic foot in the subject. In an exemplary embodiment, the determining one or more health conditions of the subject based upon at least one of the temperature changes measured comprises determining the response of the subject to diabetic foot therapies. In an exemplary embodiment, the determining one or more health conditions of the subject based upon at least one of the temperature changes measured comprises analyzing the temperature response to the vasostimulant along with additional diagnosis techniques in order to diagnose the subject for diabetic foot.

In an exemplary embodiment, the method further comprises administering an ankle-brachial blood pressure index test to the subject. In an exemplary embodiment, the determining one or more health conditions for the subject based upon at least one of the temperature changes measured comprises analyzing the temperature response to the vasostimulant in order to assess the subjects endothelial function. In an exemplary embodiment, the determining one or more health conditions for the subject based upon at least one of the temperature changes measured comprises analyzing the temperature response to the vasostimulant along with additional diagnosis techniques in order to assess the subjects endothelial function. In an exemplary embodiment, the additional diagnosis techniques comprise using a blood marker of endothelial function. In an exemplary embodiment, the additional diagnosis techniques comprise an endothelial driven microparticles test. In an exemplary embodiment, the additional diagnosis techniques comprise a VCAM1 test. In an exemplary embodiment, the additional diagnosis techniques comprise an ICAM1 test. In an exemplary embodiment, the additional diagnosis techniques comprise a SELECTIN test. In an exemplary embodiment, the additional diagnosis techniques comprise a VWF test. In an exemplary embodiment, the additional diagnosis techniques comprise an oxygen saturation measurement at a fingertip. In an exemplary embodiment, the additional diagnosis techniques comprise a CD54 test.

In an exemplary embodiment, the determining one or more health conditions of the subject based upon at least one of the temperature changes measured comprises monitoring the pregnancy of the subject. In an exemplary embodiment, the monitoring the pregnancy of the subject comprises diagnosing the subject for preeclampsia.

In an exemplary embodiment, the method further comprises measuring the blood pressure of the subject. In an exemplary embodiment, the method further comprises changing the skin temperature of the body part. In an exemplary embodiment, the changing the skin temperature of the body part comprises heating and/or cooling the body part with a thermal device. In an exemplary embodiment, the changing the skin temperature of the body part comprises elevating the body part. In an exemplary embodiment, the method further comprises measuring a blood speed through an artery of the subject which supplies blood to the body part. In an exemplary embodiment, the blood speed is measured before, during, and after the provision of the vasostimulant. In an exemplary embodiment, the method further comprises measuring and recording the stiffness of an artery supplying blood to the body part. In an exemplary embodiment, the stiffness of the artery is measured and recorded using arterial pulse waveform analysis. In an exemplary embodiment, the stiffness of the artery is measured and recorded before providing the vasostimulant. In an exemplary embodiment, the stiffness of the artery is measured and recorded after providing the vasostimulant. In an exemplary embodiment, the stiffness of the artery is measured and recorded before, during, and after providing the vasostimulant.

In an exemplary embodiment, the ambient temperature around the thermal energy sensor is held constant. In an exemplary embodiment, the fluid flow around the thermal energy sensor is kept to a minimum. In an exemplary embodiment, the determining one or more health conditions comprises determining a coronary calcium score. In an exemplary embodiment, the determining one or more health conditions comprises determining a Framingham risk score. In an exemplary embodiment, the determining one or more health conditions comprises determining a carotid intima media thickness. In an exemplary embodiment, the determining one or more health conditions comprises conducting a c-reactive protein test. In an exemplary embodiment, the determining one or more health conditions comprises determining an Lp-PLA2 level.

In an exemplary embodiment, the method further comprises acquiring a measure of endothelium dependent vascular reactivity, using additional non-endothelial related diagnosis techniques to acquire a measure of endothelium independent vascular reactivity, calculating a ratio of the measure of endothelium dependent vascular reactivity over the measure of endothelium independent vascular reactivity, and determining a health condition of the subject. In an exemplary embodiment, the method further comprises acquiring a measure of endothelium dependent vascular reactivity, using additional diagnosis techniques to acquire a measure of parameters other than temperature that change upon provision of the vasostimulant, calculating a ratio of the measure of endothelium dependent vascular reactivity over the measure of parameters other than temperature that change upon provision of the vasostimulant, and determining a health condition of the subject. In an exemplary embodiment, the providing a vasostimulant comprises providing a modifier of vasostimulators. In an exemplary embodiment, the modifier of vasostimulators comprises an LNAME compound. In an exemplary embodiment, the modifier of vasostimulators comprises an L-Arginine compound.

In an exemplary embodiment, the determining one or more health conditions of the subject based upon at least one of the temperature changes measured comprises determining whether the effectiveness of cholesterol lowering medications in the subject. In an exemplary embodiment, the cholesterol lowering medications are from the family of statins. In an exemplary embodiment, the cholesterol lowering medications include Lipitor. In an exemplary embodiment, the cholesterol lowering medications include mevalonate.

In an exemplary embodiment, the method further includes measuring the change in oxygen saturation of the body part. In an exemplary embodiment, the method further includes measuring the change in Doppler flow of the body part. In an exemplary embodiment, the method further includes measuring the change in pressure of the body part. In an exemplary embodiment, the method further includes measuring the change in blood flow of the body part by near infrared spectroscopy. In an exemplary embodiment, the method further includes using an additional diagnostic techniques in order to determine the health condition of the patient selected from the group consisting of: intravascular optical coherent tomography, coronary fractional flow reserve, intravascular ultrasound radiofrequency backscatter analysis or Virtual Histology, urinary albumin, serum fibrinogen, IL6, CD40/CD40L, serum amyloid A, ankle brachial index, MRI, coronary calcium score, carotid intermedia thickness, vascular stiffness tests, C-reactive protein tests, waist circumference, blood insulin level, PAI-1 test, t-PA test, glucose tolerance tests, fasting plasma glucose level, HDL cholesterol level, fasting plasma insulin test, homeostasis model assessment, BMI, body fat level, visceral fat test, subcutaneous fat test, white blood cell count, Neutrophil/lymphocyte ratio, platelet function tests, and combinations thereof.

In an exemplary embodiment, the method further includes using an additional diagnostic techniques in order to determine the health condition of the patient selected from the group consisting of: plasma and urinary level of asymmetrical (ADMA) and symmetrical (SDMA) dimethylarginine, exhaled nitric oxide, serum homocysteine, an endothelial driven microparticles test, a VCAM1 test, an ICAM1 test, a SELECTIN test, a VWF test, a TF test, a CD54 test, endothelial progenitor cells, myelo-peroxidase (MPO), increased neutrophil/lymphocyte ratio, endothelin-1, thrombomodulin, tissue factor and tissue factor pathway inhibitor, markers of inflammation such as, for example, granulocyte-macrophage colony-stimulating factor (GM-CSF) and macrophage chemoattractant protein-1 (MCP-1) nitric oxide and its metabolites nitrates and nitrites, almost nitrosylated proteins, a selectin such as, for example, soluble endothelium, leukocyte, and platelet selecting, markers of oxidative stress including but not limited to free radical measurements of the blood or through the skin, TBAR, and/or extra cellular super oxide dismutase activity, vascular stiffness or compliance, and combinations thereof.

In an exemplary embodiment, the method further includes using an additional diagnostic techniques in order to determine the health condition of the patient selected from the group consisting of: skin color, nail capilloroscopy, ultrasound brachial artery imaging, forearm plethysmography, fingertip plethysmography, oxygen saturation change, pressure change, near-infrared spectroscopy measurements, Doppler flow change, peripheral artery tomometry, and combinations thereof. In an exemplary embodiment, the method further includes acquiring a measure of endothelium dependent vascular reactivity, using additional non-endothelial related diagnosis techniques to acquire a measure of endothelium independent vascular reactivity, calculating a composite index of the measure of endothelium dependent vascular reactivity and the measure of endothelium independent vascular reactivity, and determining a health condition of the subject. In an exemplary embodiment, the method further includes acquiring a measure of endothelium dependent vascular reactivity, using additional diagnosis techniques to acquire a measure of parameters other than temperature that change upon provision of the vasostimulant, calculating a composite index of the measure of endothelium dependent vascular reactivity and the measure of parameters other than temperature that change upon provision of the vasostimulant, and determining a health condition of the subject.

A method for determining one or more health conditions has been described comprising providing a subject, measuring the skin temperature of a first body part on the subject, placing a second body part of the subject in water, measuring the skin temperature changes of the first body part during and subsequent to the placing of the second body part in water, and determining one or more health conditions for the subject based upon at least one of the skin temperature changes measured.

A method for determining one or more health conditions has been described comprising providing a subject, providing a volume of a medium, placing a body part of the subject in the volume of the medium, measuring the temperature of the volume of the medium, providing a vasostimulant to the subject, measuring the temperature changes of the volume of the medium during and subsequent to the provision of the vasostimulant, and determining one or more health conditions for the subject based upon at least one of the temperature changes measured.

A database for diagnosing health conditions has been described comprising control data comprising a plurality of control temperature data points and temperature data comprising a baseline temperature, a temperature drop from the baseline temperature having a first slope, a lowest temperature achieved, a temperature rise from the lowest temperature achieved having a second slope, a peak temperature, and a stabilization temperature.

A method for determining one or more health conditions has been described comprising providing a subject, measuring the baseline skin temperature of a body part on the subject, providing a vasostimulant to the subject, measuring the lowest skin temperature of the body part during and subsequent to the provision of the vasostimulant, measuring the highest skin temperature of the body part, and determining one or more health conditions for the subject based upon at least one of the skin temperature changes measured. In an exemplary embodiment, the determining one or more health conditions for the subject based upon at least one of the skin temperature changes measured comprises diagnosing healthy vascular reactivity due to the temperature difference between the highest skin temperature measured and the lowest skin temperature measured being greater than the difference between the baseline temperature measured and the lowest skin temperature measured. In an exemplary embodiment, the determining one or more health conditions for the subject based upon at least one of the skin temperature changes measured comprises diagnosing unhealthy vascular reactivity due to temperature difference between the highest skin temperature measured and the lowest skin temperature measured being less than the difference between the baseline temperature measured and the lowest skin temperature measured. In an exemplary embodiment, the determining one or more health conditions for the subject based upon at least one of the skin temperature changes measured comprises diagnosing unhealthy vascular reactivity due to temperature difference between the highest skin temperature measured and the baseline temperature measured being negative.

A computer program for determining one or more health conditions has been described comprising a retrieval engine adapted to retrieve a plurality of temperature data from a database, the temperature data comprising a baseline temperature, a temperature drop from the baseline temperature having a first slope, a lowest temperature achieved, a temperature rise from the lowest temperature achieved having a second slope, a peak temperature, and a stabilization temperature; a processing engine adapted to process data retrieved by the retrieval engine, and a diagnosis engine operable to determine one or more health conditions based upon the retrieved temperature data. In an exemplary embodiment, the diagnosis engine may diagnose healthy vascular reactivity due to the temperature difference between the peak temperature and the lowest temperature being greater than the difference between the baseline temperature and the lowest temperature. In an exemplary embodiment, the diagnosis engine may diagnose unhealthy vascular reactivity due to temperature difference between the peak temperature and the lowest temperature being less than the difference between the baseline temperature and the lowest temperature. In an exemplary embodiment, the diagnosis engine may diagnose unhealthy vascular reactivity due to temperature difference between the peak temperature and the baseline temperature being negative.

A method for determining one or more health conditions has been described which includes providing a subject, measuring the blood flow rate of the subject, providing a vasostimulant to the subject, measuring the blood flow rate changes of the subject during and subsequent to the provision of the vasostimulant, and determining one or more health conditions for the subject based upon at least one of the blood flow rate changes measured. In an exemplary embodiment, the blood flow rate is measured using optical spectroscopy. In an exemplary embodiment, the method further comprises administering an optical spectroscopy tracer to the subject.

A method for determining one or more health conditions has been described which includes providing a subject, measuring the skin temperature of a finger on the arm of the subject, detecting an equilibrium in the skin temperature of the finger of the subject, automatically providing a vasostimulant to the subject to substantially cease blood flow to the finger, measuring the skin temperature changes of the finger after provision of the vasostimulant, automatically removing the vasostimulant to allow blood flow to the finger, measuring the skin temperature changes of the finger after the removal of the vasostimulant, and determining one or more health conditions for the subject based upon at least one of the skin temperature changes measured. In an exemplary embodiment, the providing a vasostimulant comprises inflating an inflatable cuff on an arm of the subject to a pressure which is higher than a blood pressure of the subject. In an exemplary embodiment, the blood pressure of the subject is a measured blood pressure. In an exemplary embodiment, the blood pressure of the subject is a known blood pressure. In an exemplary embodiment, the blood pressure of the subject is an estimated blood pressure. In an exemplary embodiment, the method further comprises measuring the skin temperature of a contralateral body part on the subject.

A method for selecting a medication for the treatment of a medical condition in a subject has been described which includes administering a medication to one or more subjects, determining the health condition of the one or more subjects using the method of: measuring the skin temperature of a body part on the one or more subjects, providing a vasostimulant to the one or more subjects, measuring the skin temperature changes of the body part during and subsequent to the provision of the vasostimulant; and determining one or more health conditions for the one or more subjects based upon at least one of the skin temperature changes measured; determining whether the medication is effective in the treatment of the one or more subjects, and selecting the medication for use in treating the medical condition in other subjects if the medication is determined to be effective in the treatment of the one or more subjects.

A method for selecting a nutritional program for a subject has been described which includes administering a nutritional program to one or more subjects, determining the health condition of the one or more subjects using the method of: measuring the skin temperature of a body part on the one or more subjects, providing a vasostimulant to the one or more subjects, measuring the skin temperature changes of the body part during and subsequent to the provision of the vasostimulant, and determining one or more health conditions for the one or more subjects based upon at least one of the skin temperature changes measured; determining whether the nutritional program is effective for the one or more subjects, and selecting the nutritional program for other subjects if the nutritional program is determined to be effective for the one or more subjects.

A system for selecting a medication for the treatment of a medical condition in a subject has been described which includes means for administering a medication to one or more subjects, means for determining the health condition of the one or more subjects comprising: means for measuring the skin temperature of a body part on the one or more subjects, means for providing a vasostimulant to the one or more subjects, means for measuring the skin temperature changes of the body part during and subsequent to the provision of the vasostimulant, and means for determining one or more health conditions for the one or more subjects based upon at least one of the skin temperature changes measured; means for determining whether the medication is effective in the treatment of the one or more subjects, and means for selecting the medication for use in treating the medical condition in other subjects if the medication is determined to be effective in the treatment of the one or more subjects.

A system for selecting a nutritional program for a subject has been described which includes means for administering a nutritional program to one or more subjects, means for determining the health condition of the one or more subjects comprising: means for measuring the skin temperature of a body part on the one or more subjects, means for providing a vasostimulant to the one or more subjects, means for measuring the skin temperature changes of the body part during and subsequent to the provision of the vasostimulant, and means for determining one or more health conditions for the one or more subjects based upon at least one of the skin temperature changes measured; means for determining whether the nutritional program is effective for the one or more subjects, and means for selecting the nutritional program for other subjects if the nutritional program is determined to be effective for the one or more subjects.

A method for selecting a medication lor the treatment of a medical condition in a subject has been described which includes administering a medication to one or more subjects, determining a health condition ol the one or more subjects using the apparatus of any one of the claims, determining whether the medication is effective in the treatment of the one or more subjects, and selecting the medication for use in treating a medical condition in other subjects if the medication is determined to be effective in the treatment of the one or more subjects.

A method for selecting a nutritional program for a subject has been described which includes administering a nutritional program to one or more subjects, determining a health condition of the one or more subjects using the apparatus of the present invention, determining whether the nutritional program is effective for the one or more subjects, and selecting the nutritional program for other subjects if the nutritional program is determined to be effective for the one or more subjects.

A method for selecting a chemical substance for the treatment of a medical condition has been described which includes administering a chemical substance to a subject, determining a health condition of the one or more subjects using the method of the present invention, and studying the effects of the chemical substance on the subject.

A method for selecting a medical procedure for the treatment of a medical condition has been described which includes performing a medical procedure on a subject, determining a health condition of the one or more subjects using the method of the present invention, and studying the effects of the medical procedure on the subject.

A method for selecting a health intervention program for the treatment of a subject has been described which includes administering a health intervention program on a subject, determining a health condition of the one or more subjects using the method of the present invention, and studying the effects of the health intervention program on the subject.

A method for determining one or more health conditions has been described which includes providing a subject, measuring the temperature of a body part on the subject, providing a vasostimulant to the subject, measuring the temperature changes of the body part during and subsequent to the provision of the vasostimulant, and determining one or more health conditions for the subject based upon at least one of the temperature changes measured.

It is understood that variations may be made in the foregoing without departing from the scope of the disclosed embodiments. Furthermore, the elements and teachings of the various illustrative embodiments may be combined in whole or in part some or all of the illustrated embodiments.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

We claim:

1. A method for assessing arterial reactivity in a patient, comprising:
    a) providing a vasodilating stimulant to a patient by creating an arterial occlusion at a body part of said patient using one or more pressure cuffs thereby stimulating arterial reactivity in a first region of said body part of said patient;
    b) simultaneously monitoring a patient's skin surface temperature at the first region and at a second control region before the arterial occlusion, during the arterial occlusion, and after the arterial occlusion is removed and until an equilibrium temperature is achieved using a temperature measurement device that does not substantially apply any one of thermal energy, positive pressure and negative pressure to the skin surface; wherein said second control region and said first region are located at contralateral body parts; and
    c) identifying a baseline temperature at the first region before the arterial occlusion;
    d) identifying a peak temperature at the first region after the arterial occlusion; and
    e) assessing arterial reactivity in said patient based on temperature changes at the second control region and a rebound temperature change related to said baseline temperature and said peak temperature at the first region.

2. The method of claim 1 for assessing arterial reactivity further comprising:
    a) creating the arterial occlusion for a predetermined period of time; and
    b) ceasing the occlusion after the predetermined period of time.

3. The method of claim 1, wherein providing a vasodilating stimulant comprises occluding blood flow to at least one of: (i) a leg, (ii) ankle, (iii) toe, (iv) arm, (v) wrist, and (vi) a finger.

4. The method of claim 1, wherein said monitoring occurs from a time prior to the beginning of said compression until a time after the hemodynamic activity has reached equilibrium.

5. The method of claim 1, wherein the monitoring comprises measuring changes in temperature at one of the patient's fingertips.

6. The method of claim 5, further comprising plotting the measured changes in temperature as a function of time.

7. A method for assessing arterial reactivity in a patient comprising:
    a) measuring a first equilibrium skin temperature at a first region of a body part of said patient using a temperature measurement device that does not substantially apply any one of thermal energy, positive pressure, and negative pressure to said first region of the patient;
    b) compressing arteries of said body part of the patient using a pressure cuff such that arterial blood flow in said first region of said body part is occluded;

c) simultaneously measuring skin temperature at the first region and at a second control region of said body part during cuff compression, after release of the cuff and until a second temperature equilibrium is achieved; wherein the second control region does not undergo arterial blood flow occlusion said cuff compression;

d) identifying a peak temperature at the first region after release of the cuff; and e) assessing the patient's arterial reactivity based upon temperature changes at the second control region and a rebound temperature change related to said first equilibrium temperature and said peak temperature at the first region.

8. The method of claim 7, wherein said first region is a digit.

9. The method of claim 8, wherein the digit is a finger and the temperature is measured on a fingertip.

10. The method of claim 7, comprising occluding blood flow in at least one extremity for a predetermined period of time and ceasing compression after the predetermined period of time, wherein said first region consists of one or more of: a leg, ankle, toe, arm, wrist, and a finger.

11. The method of claim 7, wherein the measuring is conducted from a time prior to the occluding blood flow with a compressing cuff until a time after a equilibrium temperature is reached after ceasing compression.

12. The method of claim 7, further comprising plotting the measured temperature as a function of time.

13. A method for determining a arterial reactivity status in a patient comprising:

a) initiating monitoring of skin surface temperature at a selected point of a selected region the patient until a first equilibrium temperature is reached using a temperature sensor that does not substantially change the skin temperature;

b) while continuing the monitoring, occluding arterial blood flow to the selected point for a predetermined period of time by providing a vasodilating stimulant using a pressure cuff and ceasing the occlusion after the predetermined period of time;

c) simultaneously with said monitoring and said occluding, monitoring skin surface temperature at a control point that does not undergo arterial flow occlusion until the skin surface temperature of the selected point has reached a second equilibrium after ceasing the occlusion;

d) identifying a peak temperature at the selected point after release of the cuff; and e) assessing the patient's arterial reactivity based upon temperature changes at the control point and a rebound temperature change related to said first equilibrium temperature and said peak temperature at the selected point.

14. The method of claim 13, further comprising plotting the monitored temperature as a function of time.

15. The method of claim 13, wherein the selected region is a finger and the temperature is measured at a point on the skin surface of a fingertip.

16. The method of claim 13, wherein the blood flow is occluded at one or more regions selected from the group consisting of: a leg, ankle, toe, arm, wrist, and a finger.

* * * * *